(12) United States Patent
Chowdhury et al.

(10) Patent No.: US 9,220,775 B2
(45) Date of Patent: Dec. 29, 2015

(54) BINDING MOLECULES SPECIFIC FOR HER3 AND USES THEREOF

(71) Applicant: MedImmune LLC, Gaithersburg, MD (US)

(72) Inventors: Partha S. Chowdhury, Gaithersburg, MD (US); David Tice, Gaithersburg, MD (US); Zhan Xiao, Boyds, MD (US); Philipp Steiner, Washington, DC (US); Krista Kinneer, Montgomery Village, MD (US); Marlon Rebelatto, Gaithersburg, MD (US)

(73) Assignee: MedImmune LLC, Gaithersburg, MD (US)

( * ) Notice: Subject to any disclaimer, the term of this patent is extended or adjusted under 35 U.S.C. 154(b) by 0 days.

(21) Appl. No.: 14/359,864

(22) PCT Filed: Nov. 20, 2012

(86) PCT No.: PCT/US2012/066038
§ 371 (c)(1),
(2) Date: May 21, 2014

(87) PCT Pub. No.: WO2013/078191
PCT Pub. Date: May 30, 2013

(65) Prior Publication Data
US 2014/0363429 A1  Dec. 11, 2014

Related U.S. Application Data

(60) Provisional application No. 61/563,092, filed on Nov. 23, 2011, provisional application No. 61/656,670, filed on Jun. 7, 2012, provisional application No. 61/722,558, filed on Nov. 5, 2012.

(51) Int. Cl.
| | |
|---|---|
| C07K 16/32 | (2006.01) |
| A61K 39/395 | (2006.01) |
| C07K 16/28 | (2006.01) |
| A61K 45/06 | (2006.01) |
| G01N 33/574 | (2006.01) |
| A61K 39/00 | (2006.01) |

(52) U.S. Cl.
CPC ........... *A61K 39/39558* (2013.01); *A61K 45/06* (2013.01); *C07K 16/2863* (2013.01); *C07K 16/32* (2013.01); *G01N 33/57492* (2013.01); *A61K 2039/505* (2013.01); *A61K 2039/507* (2013.01); *C07K 2317/21* (2013.01); *C07K 2317/33* (2013.01); *C07K 2317/55* (2013.01); *C07K 2317/56* (2013.01); *C07K 2317/565* (2013.01); *C07K 2317/567* (2013.01); *C07K 2317/73* (2013.01); *C07K 2317/76* (2013.01); *C07K 2317/77* (2013.01); *C07K 2317/92* (2013.01)

(58) Field of Classification Search
CPC .................. A61K 39/39558; A61K 2039/505; G01N 33/57492; C07K 16/32; C07K 16/2863; C07K 2317/565; C07K 2317/567; C07K 2317/76; C07K 2317/92; C07K 2317/56
USPC ........... 424/174.1; 435/320.1, 334, 375, 69.6, 435/7.23; 530/389.7, 391.1; 536/25.53
See application file for complete search history.

(56) References Cited

U.S. PATENT DOCUMENTS

| | | |
|---|---|---|
| 5,183,884 A | 2/1993 | Kraus et al. |
| 5,480,968 A | 1/1996 | Kraus et al. |
| 5,804,968 A | 9/1998 | Richard et al. |
| 5,820,859 A | 10/1998 | Kraus et al. |
| 5,916,755 A | 6/1999 | Kraus et al. |
| 5,968,511 A | 10/1999 | Akita et al. |
| 6,639,060 B1 | 10/2003 | Kraus et al. |
| 6,716,598 B2 | 4/2004 | Blank et al. |
| 6,870,034 B2 | 3/2005 | Breece et al. |
| 7,097,840 B2 | 8/2006 | Erickson et al. |
| 7,125,680 B2 | 10/2006 | Singer et al. |
| 7,247,301 B2 | 7/2007 | van de Winkel et al. |
| 7,285,649 B2 | 10/2007 | Akita et al. |
| 7,323,553 B2 | 1/2008 | Fahrner et al. |
| 7,332,580 B2 | 2/2008 | Adams et al. |
| 7,332,585 B2 | 2/2008 | Adams et al. |
| 7,390,632 B2 | 6/2008 | Maihle et al. |
| 7,402,397 B2 | 7/2008 | Chan-Hui et al. |
| 7,485,704 B2 | 2/2009 | Fahrner et al. |
| 7,527,789 B2 | 5/2009 | Loibner et al. |

(Continued)

FOREIGN PATENT DOCUMENTS

| | | |
|---|---|---|
| WO | WO 97/35885 | 10/1997 |
| WO | WO 00/78347 | 12/2000 |

(Continued)

OTHER PUBLICATIONS

Voskoglou-Nomikos (Clin. Can. Res. 9:4227-4239 (2003)).*
Dennis (Nature 442:739-741 (2006)).*
Cespdes et al. (Clin. Transl. Oncol. 8(5):318-329 (2006)).*
Talmadge et al. (Am. J. Pathol 170(3):793-804 (2007)).*
Fujimori et al. (J. Nuc. Med. 31:1191-1198 (1990)).*
Beckman et al. (Can. 109:170-179 (2007)).*
Thurber et al. (Adv. Drug Deliv. Rev. 60:1421-1434 (2008)).*

(Continued)

*Primary Examiner* — Lynn Bristol
(74) *Attorney, Agent, or Firm* — Jones Day

(57) ABSTRACT

The present invention relates to antibodies and antigen binding fragments thereof that bind the extracellular domain of the HER3 receptor and inhibit various HER3 receptor related functions via ligand-dependent and/or ligand-independent mechanisms. Also provided are compositions with increased half-life. In addition, the invention provides compositions and methods for diagnosing and treating diseases associated with HER3 mediated signal transduction.

39 Claims, 67 Drawing Sheets

(56) References Cited

U.S. PATENT DOCUMENTS

| | | |
|---|---|---|
| 7,591,994 B2 | 9/2009 | Govindan et al. |
| 7,625,558 B2 | 12/2009 | Greene et al. |
| 7,662,374 B2 | 2/2010 | Greene et al. |
| 7,705,130 B2 | 4/2010 | Rothe et al. |
| 7,718,384 B2 | 5/2010 | Maihle et al. |
| 7,744,882 B2 | 6/2010 | Maihle et al. |
| 7,825,127 B2 | 11/2010 | Ohta et al. |
| 7,829,297 B2 | 11/2010 | Spector et al. |
| 7,846,440 B2 | 12/2010 | Schoeberl et al. |
| 7,919,098 B2 | 4/2011 | Zhou |
| 7,981,418 B2 | 7/2011 | Amler et al. |
| 8,124,085 B2 | 2/2012 | Nielsen et al. |
| 8,163,287 B2 | 4/2012 | Sliwkowski et al. |
| 8,333,964 B2 | 12/2012 | Aguset et al. |
| 8,362,215 B2 | 1/2013 | Keyt et al. |
| 8,580,263 B2 | 11/2013 | Adams et al. |
| 8,592,152 B2 | 11/2013 | Mass et al. |
| 8,691,232 B2 | 4/2014 | Derynck et al. |
| 8,771,695 B2 | 7/2014 | Rothe et al. |
| 2003/0105057 A1 | 6/2003 | Fu et al. |
| 2004/0057950 A1 | 3/2004 | Waksal et al. |
| 2004/0063140 A1 | 4/2004 | Kraus et al. |
| 2004/0082510 A1 | 4/2004 | Ullrich et al. |
| 2004/0096436 A1 | 5/2004 | Carson et al. |
| 2004/0106161 A1 | 6/2004 | Bossenmaier et al. |
| 2004/0116330 A1 | 6/2004 | Naito et al. |
| 2004/0138160 A1 | 7/2004 | Naito et al. |
| 2004/0197332 A1 | 10/2004 | Ullrich et al. |
| 2004/0229293 A1 | 11/2004 | Chan-Hui et al. |
| 2004/0229299 A1 | 11/2004 | Badal et al. |
| 2004/0229380 A1 | 11/2004 | Chan-Hui et al. |
| 2004/0229494 A1 | 11/2004 | Hsu et al. |
| 2005/0101618 A1 | 5/2005 | Connell et al. |
| 2005/0147612 A1 | 7/2005 | Yayon et al. |
| 2006/0067947 A1 | 3/2006 | Yagita et al. |
| 2006/0148694 A1 | 7/2006 | Ullrich et al. |
| 2007/0009972 A1 | 1/2007 | Chao et al. |
| 2008/0138349 A1 | 6/2008 | Stavenhagen et al. |
| 2008/0153098 A1 | 6/2008 | Rimm et al. |
| 2008/0187948 A1 | 8/2008 | Chan-Hui et al. |
| 2008/0187966 A1 | 8/2008 | Simmons et al. |
| 2008/0206231 A1 | 8/2008 | Clinton et al. |
| 2008/0255027 A1 | 10/2008 | Moya et al. |
| 2009/0092617 A1 | 4/2009 | Bock et al. |
| 2009/0155259 A1 | 6/2009 | Derynck et al. |
| 2009/0214576 A1 | 8/2009 | Bacus et al. |
| 2009/0258005 A1 | 10/2009 | Gill et al. |
| 2009/0275633 A1 | 11/2009 | Esteller et al. |
| 2010/0004232 A1 | 1/2010 | Berdini et al. |
| 2010/0047829 A1 | 2/2010 | Rothe et al. |
| 2010/0056761 A1 | 3/2010 | Schoeberl et al. |
| 2010/0104586 A1 | 4/2010 | Tressler et al. |
| 2010/0196265 A1 | 8/2010 | Adams et al. |
| 2010/0255010 A1 | 10/2010 | Fuh et al. |
| 2010/0266584 A1 | 10/2010 | Schoeberl et al. |
| 2010/0310557 A1 | 12/2010 | Keyt et al. |
| 2011/0020327 A1 | 1/2011 | Moya et al. |
| 2011/0027296 A1 | 2/2011 | Almendro Navarro et al. |
| 2011/0033482 A1 | 2/2011 | Ullrich et al. |
| 2011/0039300 A1 | 2/2011 | Bayer et al. |
| 2011/0091473 A1 | 4/2011 | Golab et al. |
| 2011/0123523 A1 | 5/2011 | Schoeberl et al. |
| 2011/0171222 A1 | 7/2011 | Bossenmaier et al. |
| 2011/0229406 A1 | 9/2011 | Hettmann et al. |
| 2011/0229478 A1 | 9/2011 | Zhou et al. |
| 2011/0256154 A1 | 10/2011 | Vincent et al. |
| 2011/0280892 A1 | 11/2011 | Kinch et al. |
| 2012/0058122 A1 | 3/2012 | Rothe et al. |
| 2012/0107270 A1 | 5/2012 | Kaspar et al. |
| 2012/0107306 A1 | 5/2012 | Elis et al. |
| 2012/0156130 A1 | 6/2012 | Hettmann et al. |
| 2012/0201817 A1 | 8/2012 | Waksal |
| 2012/0225870 A1 | 9/2012 | Janne et al. |
| 2012/0328623 A1 | 12/2012 | Takahashi |
| 2013/0034548 A1 | 2/2013 | Moyo et al. |
| 2013/0039909 A1 | 2/2013 | Amler et al. |
| 2013/0084297 A1 | 4/2013 | Daly et al. |
| 2013/0156779 A1 | 6/2013 | Clarke et al. |
| 2013/0251703 A1 | 9/2013 | Elis |

FOREIGN PATENT DOCUMENTS

| | | |
|---|---|---|
| WO | WO 2007/077028 | 7/2007 |
| WO | WO 2008/081331 | 7/2008 |
| WO | WO 2008/100624 | 8/2008 |
| WO | WO 2008/119353 | 10/2008 |
| WO | WO 2009/052830 | 4/2009 |
| WO | WO 2009/082443 | 7/2009 |
| WO | WO 2009/126920 | 10/2009 |
| WO | WO 2009/157919 | 12/2009 |
| WO | WO 2010/054051 | 5/2010 |
| WO | WO 2010/097186 | 9/2010 |
| WO | WO 2010/108127 | 9/2010 |
| WO | WO 2010/127181 | 11/2010 |
| WO | WO 2011/044311 | 4/2011 |
| WO | WO 2011/047180 | 4/2011 |
| WO | WO 2011/060206 | 5/2011 |
| WO | WO 2011/136911 | 11/2011 |
| WO | WO 2012/019024 | 2/2012 |
| WO | WO 2012/022814 | 2/2012 |
| WO | WO 2012/059858 | 5/2012 |
| WO | WO 2013/071058 | 5/2013 |
| WO | WO 2013/084147 | 6/2013 |

OTHER PUBLICATIONS

Rudnick et al. (Can. Biotherp. & Radiopharm. 24: 155-162 (2009)).*

"A Phase 1 Dose Escalation Study of AV-203, an ERBB3 Inhibitory Antibody, in Subjects With Advanced Solid Tumors," ClinicalTrials. gov, accessed at http://www.clinicaltrials.gov/ct2/show/ NCT01603979?term=AV-203&rank=1, accessed on Jul. 24, 2012, 4 pages.

"A Phase 1 Study to Evaluate the Safety and Pharmacokinetics of KTN3379 in Adult Subjects With Advanced Tumors," ClinicalTrials. gov, accessed at http://www.clinicaltrials.gov/ct2/show/study/ NCT02014909?term=3379&rank=1, accessed on Oct. 7, 2014, 4 pages.

"Phase I Study of LJM716 in Combination With Trastuzumab in Patients With HER2 Overexpressing Metastatic Breast Cancer," ClinicalTrials.gov, accessed at http://clinicaltrials.gov/ct2/show/ NCT01602406, accessed on Jul. 17, 2012, 4 pages.

Addo-Yobo et al., 2006, "Paired overexpression of ErbB3 and Sox10 in pilocytic astrocytoma," J. Neuropathol. Exp. Neurol. 65:769-775.

Alimandi et al., 1995, "Cooperative signaling of ErbB3 and ErbB2 in neoplastic transformation and human mammary carcinomas," Oncogene 10:1813-1821.

Alvarado et al., 2014, "Structural basis for inhibition of ligand-dependent and -independent ErbB3 activation by KTN3379," Eur. J. Cancer 50(Suppl. 6):130, Poster 407. Board P187. Abstract. 26th EORTC-NCI-AACR Symposium on Molecular Targets and Cancer Therapeutics, Nov. 20, 2014.

Arteaga et al., 2012, "Treatment of HER2-positive breast cancer: current status and future perspectives," Nat. Rev. Clin. Oncol. 9: 16-32.

Aurisicchio et al., 2011, "Novel Anti-ErbB3 monoclonal antibodies show therapeutic efficacy in xenografted and spontaneous mouse tumors," J. Cell. Physiol. 227:3381-3388.

Baselga et al., 2009, "Novel anticancer targets: revisiting ERBB2 and discovering ERBB3," Nat. Rev. Cancer 9:463-475.

Burgess et al., 2003, "An Open-and-Shut Case? Recent Insights into the Activation of EGF/ErbB Receptors," Molecular Cell 12:541-552.

Campbell et al., 2010, "HER3 Comes of Age: New Insights into Its Functions and Role in Signaling, Tumor Biology, and Cancer Therapy," Clin. Cancer Res. 16(5):1373-1383.

Carrasco et al., 2013, "MEDI3379, a human monoclonal antibody against HER3, suppresses HER3 activity and cell proliferation in both ligand-dependent and independent cancers," AACR Annual Meeting 2013 Apr. 6-10, 2013, Abstract No. 558. Poster.

Carrasco et al., 2013, "MEDI3379, a human monoclonal antibody against HER3, suppresses HER3 activity and cell proliferation in

(56) References Cited

OTHER PUBLICATIONS both ligand-dependent and independent cancers," AACR Annual Meeting 2013, Abstract No. 558, Presentation Time Sunday Apr. 7, 2013, 1:00 PM-5:00 PM, Poster Section 24, Poster Board No. 30. Abstract.
Chakraborty et al., 2007, "Identification of genes associated with tumorigenesis of retinoblastoma by microarray analysis," Genomics 90:344-353.
Cho et al., 2002, "Structure of the Extracellular Region of HER3 Reveals an Interdomain Tether," Science 297:1330-1333.
DeFazio et al., 2000, "Expression of c-erbB receptors, heregulin and oestrogen receptor in human breast cell lines," Cancer 87:487-498.
Engelman et al., 2005, "ErbB-3 mediates phosphoinositide 3-kinase activity in gefitinib-sensitive non-small cell lung cancer cell lines," Proc. Natl. Acad. Sci. USA 102:3788-3793.
Friess et al., 1995, "Enhanced erbB-3 expression in human pancreatic cancer correlates with tumor progression," Clin. Cancer Res. 1:1413-1420.
Garner et al., 2011, "Targeting cancer with a novel anti-HER3 antibody: An anti-HER3 antibody that stabilizes the inactive conformation inhibits both HER2 and ligand driven tumor growth," San Antonio Breast Cancer Symposium Dec. 6-10, 2011, S2-5. Presentation, Daily Slide Viewer.
Garner et al., 2011, "Targeting cancer with a novel anti-HER3 antibody: An anti-HER3 antibody that stabilizes the inactive conformation inhibits both HER2 and ligand driven tumor growth," San Antonio Breast Cancer Symposium Dec. 6-10, 2011, S2-5. Presentation, Photographs.
Garner et al., 2012, "LJM716: an anti-HER3 antibody that inhibits both HER2 and NRG driven tumor growth by trapping HER3 in the inactive conformation.," Proceedings of the 103rd Annual Meeting of the American Association for Cancer Research; Mar. 31-Apr. 4, 2012; Abstract nr 2733.
Gregory et al., 2005, "Heregulin-induced activation of HER2 and HER3 increases androgen receptor transactivation and CWR-R1 human recurrent prostate cancer cell growth," Clin. Cancer Res. 11:1704-1712.
Holbro et al., 2003, "The ErbB2/ErbB3 heterodimer functions as an oncogenic unit: ErbB2 requires ErbB3 to drive breast tumor cell proliferation," Proc. Natl. Acad. Sci. USA 100:8933-8938.
International Search Report, mailed Apr. 15, 2013, for International Application No. PCT/US2012/066038, filed Nov. 20, 2012. 5 pages.
Jiang et al., 2012, "Advances in Targeting HER3 as an Anticancer Therapy," Chemotherapy Research and Practice 2012:817304, 9 pages.
Junttila et al., 2009, "Ligand-independent HER2/HER3/PI3K complex is disrupted by trastuzumab and is effectively inhibited by the PI3K inhibitor GDC-0941," Cancer Cell 15(5):429-440.
Kim et al., 1998, "Signal transduction by epidermal growth factor and heregulin via the kinase-deficient ErbB3 protein," Biochem J. 334:189-195.
Kraus et al., 1989, "Isolation and characterization of ERBB3, a third member of the ERBB/epidermal growth factor receptor family: evidence for overexpression in a subset of human mammary tumors," Proc. Natl. Acad. Sci. USA 86:9193-9197.
Kraus et al., 1993, "Demonstration of ligand-dependent signaling by the erbB-3 tyrosine kinase and its constitutive activation in human breast tumor cells," Proc. Natl. Acad. Sci. USA 90:2900-2904.
Lorusso et al., 2013, "Phase I Study of U3-1287, a Fully Human Anti-HER3 Monoclonal Antibody, in Patients With Advanced Solid Tumors," Clin. Can. Res. 19(11):3078-3087. First published online Apr. 16, 2013.
Lorusso et al., 2014, "A phase 1 study of KTN3379, a human anti-ErbB3 monoclonal antibody in patients with advanced cancers," Eur. J. Cancer 50(Suppl. 6):71, Oral Presentation 210. Abstract. 26th EORTC-NCI-AACR Symposium on Molecular Targets and Cancer Therapeutics, Nov. 20, 2014.
Mills et al., 2010, "The Rebirth of a Phoenix: Ovarian Cancers Are Addicted to ErbB3," Cancer Cell 17:217-218.

Naidu et al., 1998, "Expression of c-erbB3 protein in primary breast carcinomas," Br. J. Cancer 78:1385-1390.
Quinn et al., 1994, "c-erbB-3 protein expression in human breast cancer: comparison with other tumour variables and survival," Histopathology 25:247-252.
Rajkumar et al., 1993, "Expression of the c-erbB-3 protein in gastrointestinal tract tumours determined by monoclonal antibody RTJ1," J. Pathol. 170:271-278.
Roepstorff et al., 2008, "Endocytic downregulation of ErbB receptors: mechanisms and relevance in cancer," Histochem. Cell Biol. 129:563-578.
Sala et al., 2012, "An ErbB-3 antibody, MP-RM-1, inhibits tumor growth by blocking ligand-dependent and independent activation of ErbB-3/Akt signaling," Oncogene 31:1275-1286.
Sanidas et al., 1993, "Expression of the c-erbB-3 gene product in gastric cancer," Int. J. Cancer 54:935-940.
Schaefer et al., 2004, "Expression profiling of t(12;22) positive clear cell sarcoma of soft tissue cell lines reveals characteristic up-regulation of potential new marker genes including ERBB3," Cancer Res. 64:3395-3405.
Schaefer et al., 2006, "Constitutive activation of neuregulin/ERBB3 signaling pathway in clear cell sarcoma of soft tissue," Neoplasia 8:612-622.
Schaefer et al., 2011, "A Two-in-One Antibody against HER3 and EGFR Has Superior Inhibitory Activity Compared with Monospecific Antibodies," Cancer Cell 20:472-486.
Schlessinger, 2002, "Ligand-induced, receptor-mediated dimerization and activation of EGF receptor," Cell 110:669-672.
Schoeberl et al., 2009, "Therapeutically Targeting ErbB3: A Key Node in Ligand-Induced Activation of the ErbB Receptor-PI3K Axis," Science Signaling 2(77):ra31, 14 pages.
Schoeberl et al., 2010, "An ErbB3 Antibody, MM-121, Is Active in Cancers with Ligand-Dependent Activation," Cancer Res. 70(6):2485-2494.
Setiady et al., 2011, "huHER3-8, a novel humanized anti-HER3 antibody that inhibits exogeneous ligand-independent proliferation of tumor cells," AACR 102nd Annual Meeting, Abstract No. 4564, Presentation Time Tuesday, Apr. 5, 2011, 1:00 PM-5:00 PM, Poster Section 31, Poster Board No. 6. Abstract.
Setiady et al., 2011, "huHER3-8, a novel humanized anti-HER3 antibody that inhibits exogeneous ligand-independent proliferation of tumor cells," AACR 102nd Annual Meeting, Apr. 2-6, 2011, Abstract No. 4564. Poster.
Shintani et al., 1995, "Prognostic significance of ERBB3 overexpression in oral squamous cell carcinoma," Cancer Lett. 95:79-83.
Singer et al., 2001, "Identification of a Heregulin Binding Site in HER3 Extracellular Domain," J. Biol. Chem. 274:44266-44274.
Sithanandam et al., 2008, "The ERBB3 receptor in cancer and cancer gene therapy," Cancer Gene Therapy 15:413-448.
Sliwkowski et al., 1994, "Coexpression of erbB2 and erbB3 proteins reconstitutes a high affinity receptor for heregulin," J. Biol. Chem. 269:14661-14665.
Steiner et al., 2012, "MEDI3379, an antibody against HER3, is active in heregulin or HER2-driven human tumor models," 24th EORTC-NCI-AACR Symposium on Molecular Targets and Cancer Therapeutics, Nov. 6-9, 2012, Abstract No. 331. Poster.
Steiner et al., 2012, "MEDI3379, an Antibody Against HER3, is Active in Heregulin or HER2-driven Human Tumor Models," Eur. J. Cancer 48(Suppl. 6):101, Poster 331. Abstract.
Steiner et al., 2013, "Combined targeting of HER2 and HER3 inhibits tumor growth in both trastuzumab-sensitive and trastuzumab-resistant breast cancer models," AACR-NCI-EORTC International Conference on Molecular Targets and Cancer Therapeutics, Abstract A112, Presentation Time Sunday Oct. 20, 2013, 12:30 PM-3:00 PM. Abstract.
Steiner et al., 2013, "Combined targeting of HER2 and HER3 inhibits tumor growth in both trastuzumab-sensitive and trastuzumab-resistant breast cancer models," AACR-NCI-EORTC International Conference on Molecular Targets and Cancer Therapeutics, Oct. 19-23, 2013. Poster.
Tanner et al., 2006, "ErbB-3 predicts survival in ovarian cancer," J. Clin. Oncol. 24:4317-4323.

(56) References Cited

OTHER PUBLICATIONS

Turke et al., 2012, "MEK inhibition leads to PI3K/AKT activation by relieving a negative feedback on ERBB receptors," Cancer Res. 72(13):3228-3237.

Van Der Horst et al., 2005, "Anti-HER-3 Mabs Inhibit HER-3-Mediated Signaling in Breast Cancer Cell Lines Resistant to Anti-HER-2 Antibodies," Int. J. Cancer 115:519-527.

Vincent et al., 2011, "Functional characterization of a diverse set of ERBB3 inhibitory antibodies," AACR 102nd Annual Meeting, Abstract No. 628, Presentation Time Sunday Apr. 3, 2011, 1:00 PM-5:00 PM. Poster Section 27, Poster Board No. 2. Abstract.

Xiao et al., 2012, "MEDI3379, an antibody against HER3, is active in HER2-driven human breast tumor models," 35th annual San Antonio Breast Cancer Symposium (SABCS), Dec. 4-8, 2012. Poster.

Xiao et al., 2012, "MEDI3379, an antibody against HER3, is active in HER2-driven human breast tumor models," Cancer Res. 72(24 Suppl.):380s. CTRC-AACR San Antonio Breast Cancer Symposium, P4-07-05. Abstract.

Xue et al., 2006, "ErbB3-dependent motility and intravasation in breast cancer metastasis," Canc. Res. 66:1418-1426.

Yarden et al., 2001, "Untangling the ErbB signalling network," Nat. Rev. Mol. Cell. Biol. 2:127-137.

* cited by examiner

| Kabat # | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 27a | 27b | 28 |
|---|---|---|---|---|---|---|---|---|---|---|---|---|---|---|---|---|---|---|---|---|---|---|---|---|---|---|---|---|---|---|
| CL16 (original) | Q | Y | E | L | T | Q | P | P | S | - | A | S | G | T | P | G | Q | S | V | T | M | S | C | S | G | S | S | S | N | I |
| CL16 (GL) | Q | S | V | L | T | Q | P | P | S | - | A | S | G | T | P | G | Q | R | V | T | I | S | C | S | G | S | S | S | N | I |
| 5H6 | Q | S | V | L | T | Q | P | P | S | - | A | S | G | T | P | G | Q | R | V | T | I | S | C | S | G | S | S | S | N | I |
| 8A3 | Q | S | V | L | T | Q | P | P | S | - | A | S | G | T | P | G | Q | R | V | T | I | S | C | S | G | S | S | S | N | I |
| 4H6 | Q | S | V | L | T | Q | P | P | S | - | A | S | G | T | P | G | Q | R | V | T | I | S | C | R | G | S | S | S | N | I |
| 6E.3 | Q | S | V | L | T | Q | P | P | S | - | A | S | G | T | P | G | Q | R | V | T | I | S | C | S | G | S | L | S | N | I |
| 2B11 | Q | S | V | L | T | Q | P | P | S | - | A | S | G | T | P | G | Q | R | V | T | I | S | C | S | G | S | S | S | N | I |
| 2D1 | Q | S | V | L | T | Q | P | P | S | - | A | S | G | T | P | G | Q | R | V | T | I | S | C | S | G | S | S | S | N | I |
| 3A6 | Q | S | V | L | T | Q | P | P | S | - | A | S | G | T | P | G | Q | R | V | T | I | S | C | S | G | S | S | S | N | I |
| 4C4 | Q | S | V | L | T | Q | P | P | S | - | A | S | G | T | P | G | Q | R | V | T | I | S | C | S | G | S | S | S | N | I |

CDR1 (positions 24-30 underlined)

| Kabat # | 29 | 30 | 31 | 32 | 33 | 34 | 35 | 36 | 37 | 38 | 39 | 40 | 41 | 42 | 43 | 44 | 45 | 46 | 47 | 48 | 49 | 50 | 51 | 52 | 53 | 54 | 55 | 56 | 57 | 58 |
|---|---|---|---|---|---|---|---|---|---|---|---|---|---|---|---|---|---|---|---|---|---|---|---|---|---|---|---|---|---|---|
| CL16 (original) | G | L | N | Y | V | S | W | Y | Q | H | L | P | G | T | A | P | K | L | L | I | S | R | N | N | Q | R | P | S | G | V |
| CL16 (GL) | G | L | N | Y | V | S | W | Y | Q | Q | L | P | G | T | A | P | K | L | L | I | S | R | N | N | Q | R | P | S | G | V |
| 5H6 | G | L | N | Y | V | S | W | Y | Q | Q | L | P | G | T | A | P | K | L | L | I | S | R | N | N | Q | R | P | S | G | V |
| 8A3 | G | L | N | Y | V | S | W | Y | Q | Q | L | P | G | T | A | P | K | L | L | I | S | R | N | N | Q | R | P | S | G | V |
| 4H6 | G | L | N | Y | V | S | W | Y | Q | Q | L | P | G | T | A | P | K | L | L | I | S | R | N | N | Q | R | P | S | G | V |
| 6E.3 | G | L | N | Y | V | S | W | Y | Q | Q | L | P | G | T | A | P | K | L | L | I | S | R | N | N | Q | R | P | S | G | V |
| 2B11 | G | L | N | Y | V | S | W | Y | Q | Q | L | P | G | T | A | P | K | L | L | I | S | R | N | N | Q | R | P | S | G | V |
| 2D1 | G | L | N | Y | V | S | W | Y | Q | Q | L | P | G | T | A | P | K | L | L | I | S | R | N | N | Q | R | P | S | G | V |
| 3A6 | G | L | N | Y | V | S | W | Y | Q | Q | L | P | G | T | A | P | K | L | L | I | S | R | N | N | Q | R | P | S | G | V |
| 4C4 | G | L | N | Y | V | S | W | Y | Q | Q | L | P | G | T | A | P | K | L | L | I | S | R | N | N | Q | R | P | S | G | V |

CDR2 (positions 50-56 underlined)

Fig. 2A part I

| Kabat # | 59 | 60 | 61 | 62 | 63 | 64 | 65 | 66 | 67 | 68 | 69 | 70 | 71 | 72 | 73 | 74 | 75 | 76 | 77 | 78 | 79 | 80 | 81 | 82 | 83 | 84 | 85 | 86 | 87 | 88 |
|---|---|---|---|---|---|---|---|---|---|---|---|---|---|---|---|---|---|---|---|---|---|---|---|---|---|---|---|---|---|---|
| CL16 (original) | P | D | R | F | S | G | S | K | S | G | T | S | A | S | L | A | I | S | G | L | R | S | E | D | E | A | D | Y | Y | C |
| CL16 (GL) | P | D | R | F | S | G | S | K | S | G | T | S | A | S | L | A | I | S | G | L | R | S | E | D | E | A | D | Y | Y | C |
| 5H6 | P | D | R | F | S | G | S | K | S | G | T | S | A | S | L | A | I | S | G | L | R | S | E | D | E | A | D | Y | Y | C |
| 8A3 | P | D | R | F | S | G | S | K | S | G | T | S | A | S | L | A | I | S | G | L | R | S | E | D | E | A | D | Y | Y | C |
| 4H6 | P | D | R | F | S | G | S | K | S | G | T | S | A | S | L | A | I | S | G | L | R | S | E | D | E | A | D | Y | Y | C |
| 6E.3 | P | D | R | F | S | G | S | K | S | G | T | S | A | S | L | A | I | S | G | L | R | S | E | D | E | A | D | Y | Y | C |
| 2B11 | P | D | R | F | S | G | S | K | S | G | T | S | A | S | L | A | I | S | G | L | R | S | E | D | E | A | D | Y | Y | C |
| 2D1 | P | D | R | F | S | G | S | K | S | G | T | S | A | S | L | A | I | S | G | L | R | S | E | D | E | A | D | Y | Y | C |
| 3A6 | P | D | R | F | S | G | S | K | S | G | T | S | A | S | L | A | I | S | G | L | R | S | E | D | E | A | D | Y | Y | C |
| 4C4 | P | D | R | F | S | G | S | K | S | G | T | S | A | S | L | A | I | S | G | L | R | S | E | D | E | A | D | Y | Y | C |

| Kabat # | 89 | 90 | 91 | 92 | 93 | 94 | 95 | 95a | 95b | 96 | 97 | 98 | 99 | 100 | 101 | 102 | 103 | 104 | 105 | 106 | 107 |
|---|---|---|---|---|---|---|---|---|---|---|---|---|---|---|---|---|---|---|---|---|---|
| CL16 (original) | A | A | W | D | D | S | L | S | G | E | V | F | G | G | G | T | K | L | T | V | L |
| CL16 (GL) | A | A | W | D | D | S | L | S | G | E | V | F | G | G | G | T | K | L | T | V | L |
| 5H6 | A | A | W | D | D | G | L | P | G | E | V | F | G | G | G | T | K | L | T | V | L |
| 8A3 | A | A | W | D | D | S | L | I | G | E | V | F | G | G | G | T | K | L | T | V | L |
| 4H6 | A | A | W | D | D | S | L | S | G | E | V | F | G | G | G | T | K | L | T | V | L |
| 6E.3 | A | A | W | D | D | S | L | S | G | E | V | F | G | G | G | T | K | L | T | V | L |
| 2B11 | A | A | W | D | D | S | L | P | G | E | V | F | G | G | G | T | K | L | T | V | L |
| 2D1 | A | A | W | D | D | S | L | S | G | E | A | F | G | G | G | T | K | L | T | V | L |
| 3A6 | A | A | W | D | D | S | P | S | G | E | V | F | G | G | G | T | K | L | T | V | L |
| 4C4 | A | A | W | D | D | S | L | R | G | E | V | F | G | G | G | T | K | L | T | V | L |

CDR3

Fig. 2A part II

| Kabat # | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 |
|---|---|---|---|---|---|---|---|---|---|---|---|---|---|---|---|---|---|---|---|---|---|---|---|---|---|---|---|---|---|---|
| CL16 VH | E | V | Q | L | L | E | S | G | G | G | L | V | Q | P | G | G | S | L | R | L | S | C | A | A | S | G | F | T | F | S |
| 15D12.1 VH | E | V | Q | L | L | E | S | G | G | G | L | V | Q | P | G | G | S | L | R | L | S | C | A | A | S | G | F | T | F | S |
| 15D12.2 VH | E | V | Q | L | L | E | S | G | G | G | L | V | Q | P | G | G | S | L | R | L | S | C | A | A | S | G | F | T | F | S |

| Kabat # | 31 | 32 | 33 | 34 | 35 | 36 | 37 | 38 | 39 | 40 | 41 | 42 | 43 | 44 | 45 | 46 | 47 | 48 | 49 | 50 | 51 | 52 | 52a | 53 | 54 | 55 | 56 | 57 | 58 | 59 |
|---|---|---|---|---|---|---|---|---|---|---|---|---|---|---|---|---|---|---|---|---|---|---|---|---|---|---|---|---|---|---|
| CL16 VH | Y | Y | Y | M | Q | W | V | R | Q | A | P | G | K | G | L | E | W | V | S | Y | I | G | S | S | G | G | V | T | N | Y |
| 15D12.1 VH | Y | Y | Y | M | Q | W | V | R | Q | A | P | G | K | G | L | E | W | V | S | I | I | G | S | S | G | G | V | T | N | Y |
| 15D12.2 VH | Y | Y | Y | M | Q | W | V | R | Q | A | P | G | K | G | L | E | W | V | S | V | I | G | S | S | G | G | V | T | N | Y |

CDR1 (positions 31-35), CDR2 (positions 50-59)

Fig. 2B part I

| Kabat # | 59 60 61 62 63 64 65 66 67 68 69 70 71 72 73 74 75 76 77 78 79 80 81 82 82a 82b 82c 83 84 85 |
|---|---|
| CL16 VH | Y A D S V K G R F T I S R D N S K N T L Y L Q M N S L R A E |
| 15D12.1 VH | Y A D S V K G R F T I S R D N S K N T L Y L Q M N S L R A E |
| 15D12.2 VH | Y A D S V K G R F T I S R D N S K N T L Y L Q M N S L R A E |

| Kabat # | 86 87 88 89 90 91 92 93 94 95 96 97 98 99 100 100a 101 102 103 104 105 106 107 108 109 110 111 112 113 |
|---|---|
| CL16 VH | D T A V Y Y C A R V G L G D A F D I W G Q G T M V T V S S |
| 15D12.1 VH | D T A V Y Y C A R V G L G D A F D I W G Q G T M V T V S S |
| 15D12.2 VH | D T A V Y Y C A R V G L G D A F D I W G Q G T M V T V S S |

CDR3

Fig. 2B part II

| Kabat # | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 27a | 27b |
|---|---|---|---|---|---|---|---|---|---|---|---|---|---|---|---|---|---|---|---|---|---|---|---|---|---|---|---|---|---|
| CL16 (original) | Q | T | E | L | T | Q | P | P | S | - | A | S | G | T | P | G | Q | S | V | T | M | S | C | S | G | S | S | S | N |
| CL16 (GL) | Q | S | V | L | T | Q | P | P | S | - | A | S | G | T | P | G | Q | R | V | T | I | S | C | S | G | S | S | S | N |
| 1A4 | Q | S | V | L | T | Q | P | P | S | - | A | S | G | T | P | G | Q | R | V | T | I | S | C | S | G | S | S | S | N |
| 2C2 | Q | S | V | L | T | Q | P | P | S | - | A | S | G | T | P | G | Q | R | V | T | I | S | C | S | G | S | L | S | N |
| 3E.1 | Q | S | V | L | T | Q | P | P | S | - | A | S | G | T | P | G | Q | R | V | T | I | S | C | R | G | S | S | S | N |
| 2F10 | Q | S | V | L | T | Q | P | P | S | - | A | S | G | T | P | G | Q | R | V | T | I | S | C | S | G | S | S | S | N |
| 2B11 | Q | S | V | L | T | Q | P | P | S | - | A | S | G | T | P | G | Q | R | V | T | I | S | C | S | G | S | S | S | N |

CDR1 (positions 24-27b underlined)

| Kabat # | 28 | 29 | 30 | 31 | 32 | 33 | 34 | 35 | 36 | 37 | 38 | 39 | 40 | 41 | 42 | 43 | 44 | 45 | 46 | 47 | 48 | 49 | 50 | 51 | 52 | 53 | 54 | 55 | 56 |
|---|---|---|---|---|---|---|---|---|---|---|---|---|---|---|---|---|---|---|---|---|---|---|---|---|---|---|---|---|---|
| CL16 (original) | I | G | L | N | Y | V | S | W | Y | Q | H | L | P | G | T | A | P | K | L | L | I | S | R | N | N | Q | R | P | S |
| CL16 (GL) | I | G | L | N | Y | V | S | W | Y | Q | Q | L | P | G | T | A | P | K | L | L | I | S | R | N | N | Q | R | P | S |
| 1A4 | I | G | L | N | Y | V | S | W | Y | Q | Q | L | P | G | T | A | P | K | L | L | I | S | R | N | N | Q | R | P | S |
| 2C2 | I | G | L | N | Y | V | S | W | Y | Q | Q | L | P | G | T | A | P | K | L | L | I | S | R | N | N | Q | R | P | S |
| 3E.1 | I | G | L | N | Y | V | S | W | Y | Q | Q | L | P | G | T | A | P | K | L | L | I | S | R | N | N | Q | R | P | S |
| 2F10 | I | G | L | N | Y | V | S | W | Y | Q | Q | L | P | G | T | A | P | K | L | L | I | S | R | N | N | Q | R | P | S |
| 2B11 | I | G | L | N | Y | V | S | W | Y | Q | Q | L | P | G | T | A | P | K | L | L | I | S | R | N | N | Q | R | P | S |

CDR2 (positions 50-56 underlined)

Fig. 2C part I

| Kabat # | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 | 81 | 82 | 83 | 84 | 85 |
|---|---|---|---|---|---|---|---|---|---|---|---|---|---|---|---|---|---|---|---|---|---|---|---|---|---|---|---|---|---|
| CL16 (original) | G | V | P | D | R | F | S | G | S | K | S | G | T | S | A | S | L | A | I | S | G | L | R | S | E | D | E | A | D |
| CL16 (GL) | G | V | P | D | R | F | S | G | S | K | S | G | T | S | A | S | L | A | I | S | G | L | R | S | E | D | E | A | D |
| 1A4 | G | V | P | D | R | F | S | G | S | K | S | G | T | S | A | S | L | A | I | S | G | L | R | S | E | D | E | A | D |
| 2C2 | G | V | P | D | R | F | S | G | S | K | S | G | T | S | A | S | L | A | I | S | G | L | R | S | E | D | E | A | D |
| 3E.1 | G | V | P | D | R | F | S | G | S | K | S | G | T | S | A | S | L | A | I | S | G | L | R | S | E | D | E | A | D |
| 2F10 | G | V | P | D | R | F | S | G | S | K | S | G | T | S | A | S | L | A | I | S | G | L | R | S | E | D | E | A | D |
| 2B11 | G | V | P | D | R | F | S | G | S | K | S | G | T | S | A | S | L | A | I | S | G | L | R | S | E | D | E | A | D |

| Kabat # | 86 | 87 | 88 | 89 | 90 | 91 | 92 | 93 | 94 | 95 | 95a | 95b | 96 | 97 | 98 | 99 | 100 | 101 | 102 | 103 | 104 | 105 | 106 | 107 |
|---|---|---|---|---|---|---|---|---|---|---|---|---|---|---|---|---|---|---|---|---|---|---|---|---|
| CL16 (original) | Y | Y | C | A | A | W | D | D | S | L | S | G | E | V | F | G | G | G | T | K | L | T | V | L |
| CL16 (GL) | Y | Y | C | A | A | W | D | D | S | L | S | G | E | V | F | G | G | G | T | K | L | T | V | L |
| 1A4 | Y | Y | C | A | A | W | D | D | S | P | P | G | E | A | F | G | G | G | T | K | L | T | V | L |
| 2C2 | Y | Y | C | A | A | W | D | D | S | P | P | G | E | A | F | G | G | G | T | K | L | T | V | L |
| 3E.1 | Y | Y | C | A | A | W | D | D | S | P | P | G | E | A | F | G | G | G | T | K | L | T | V | L |
| 2F10 | Y | Y | C | A | A | W | D | D | S | P | S | G | E | A | F | G | G | G | T | K | L | T | V | L |
| 2B11 | Y | Y | C | A | A | W | D | D | S | L | P | G | E | V | F | G | G | G | T | K | L | T | V | L |

CDR3

Fig. 2C part II

|  | 2C2 | AMG | MM |
|---|---|---|---|
| Maximum inhibition % | 72 | 39 | 49 |
| IC50 (ug/ml) | 0.14 | 0.99 | 0.95 |

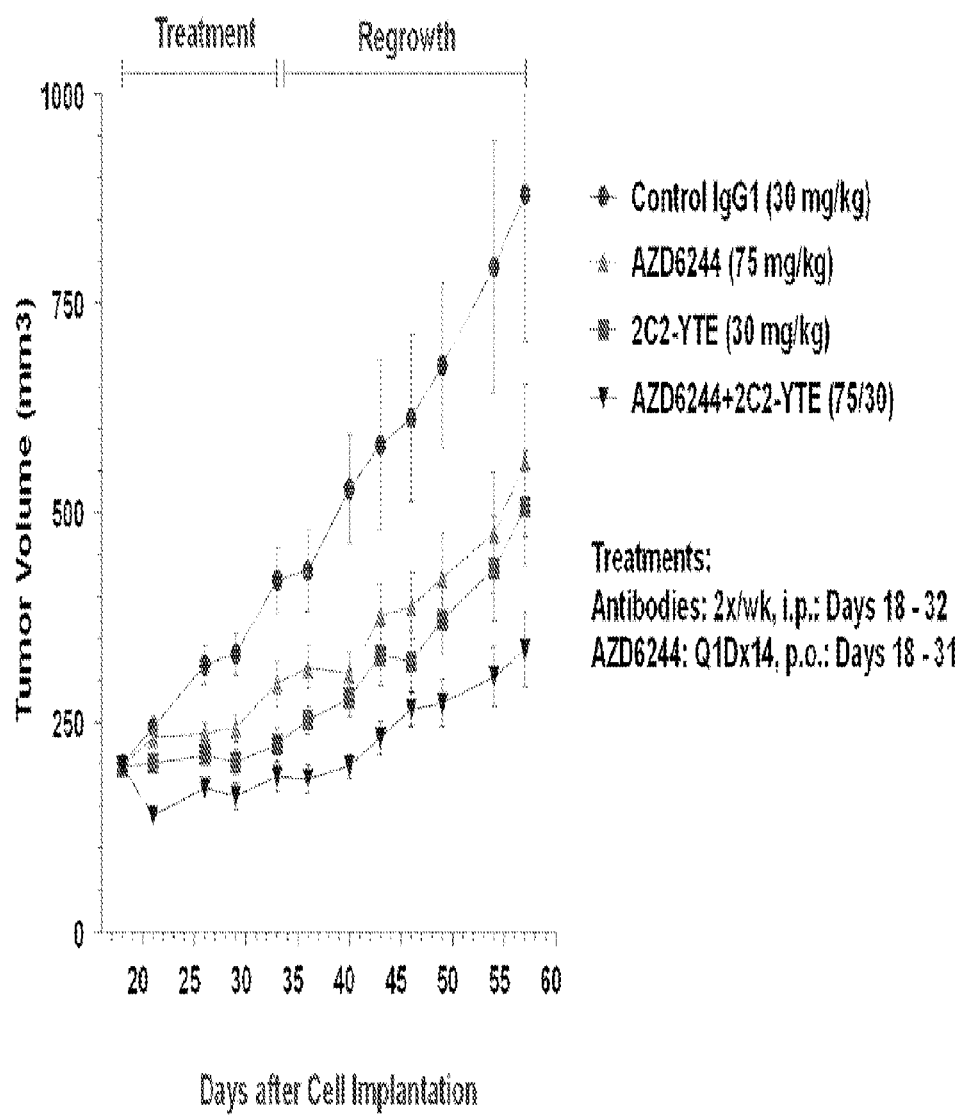
Fig. 37A part I

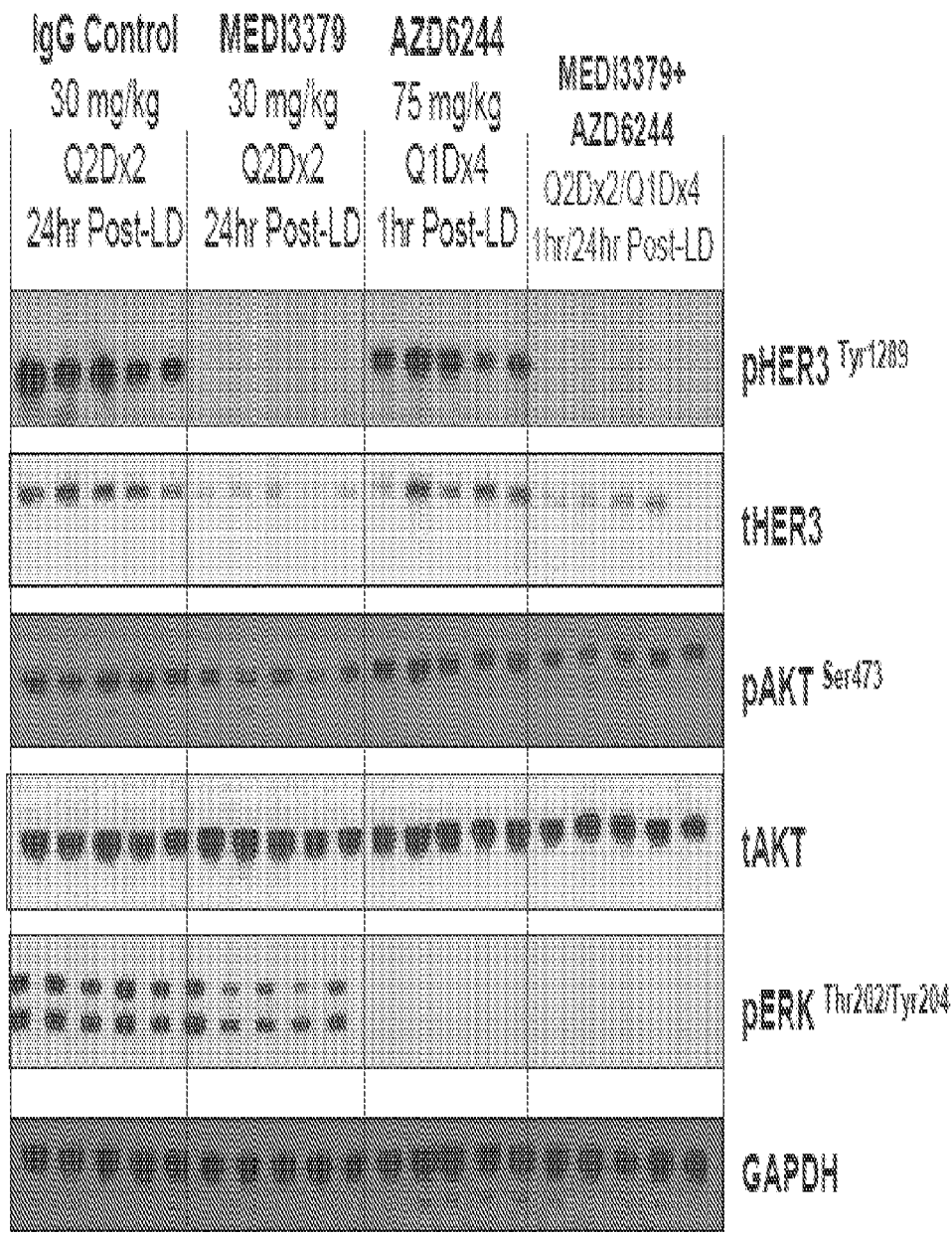
Fig. 37A part II

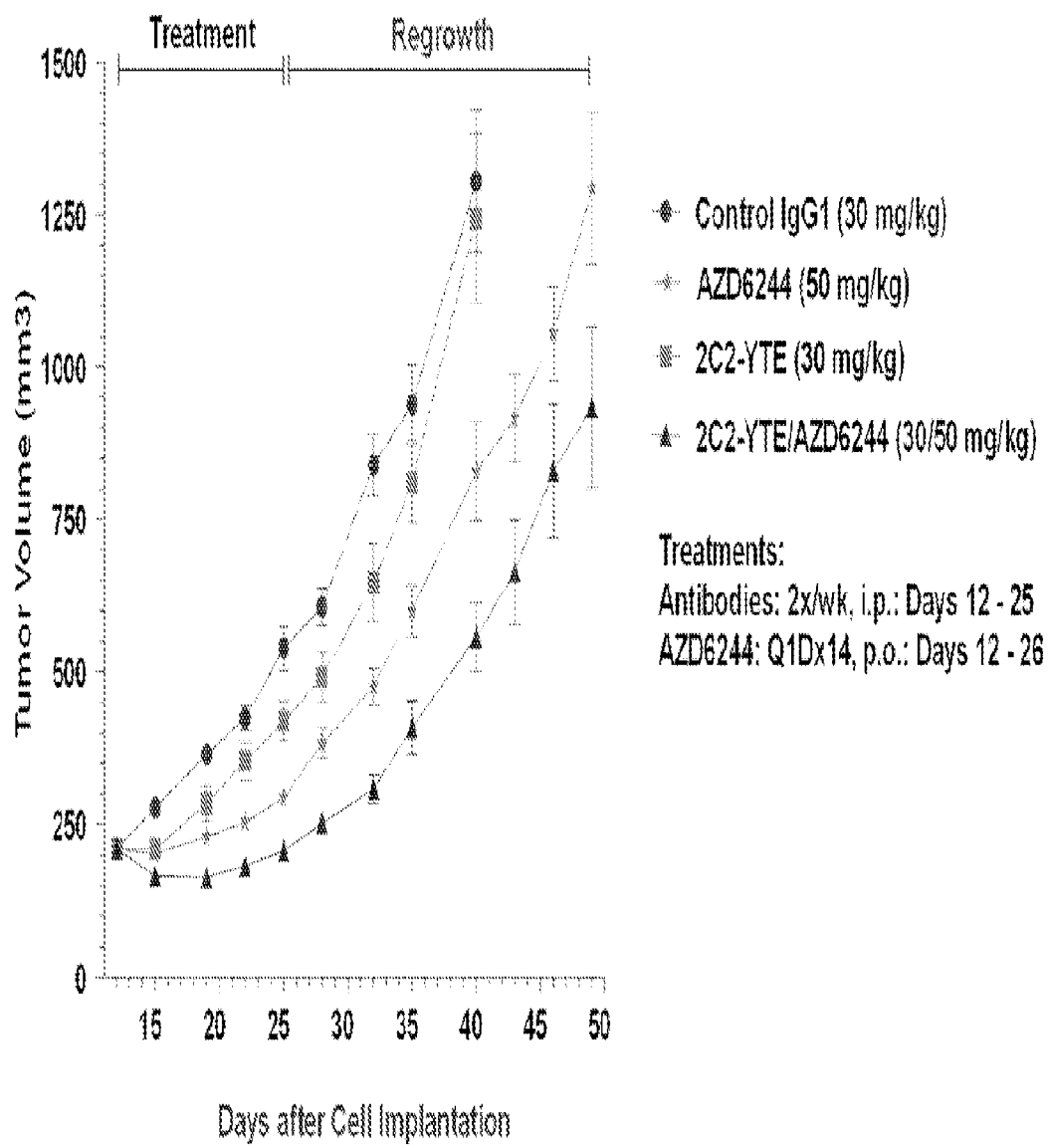
Fig. 37B part I

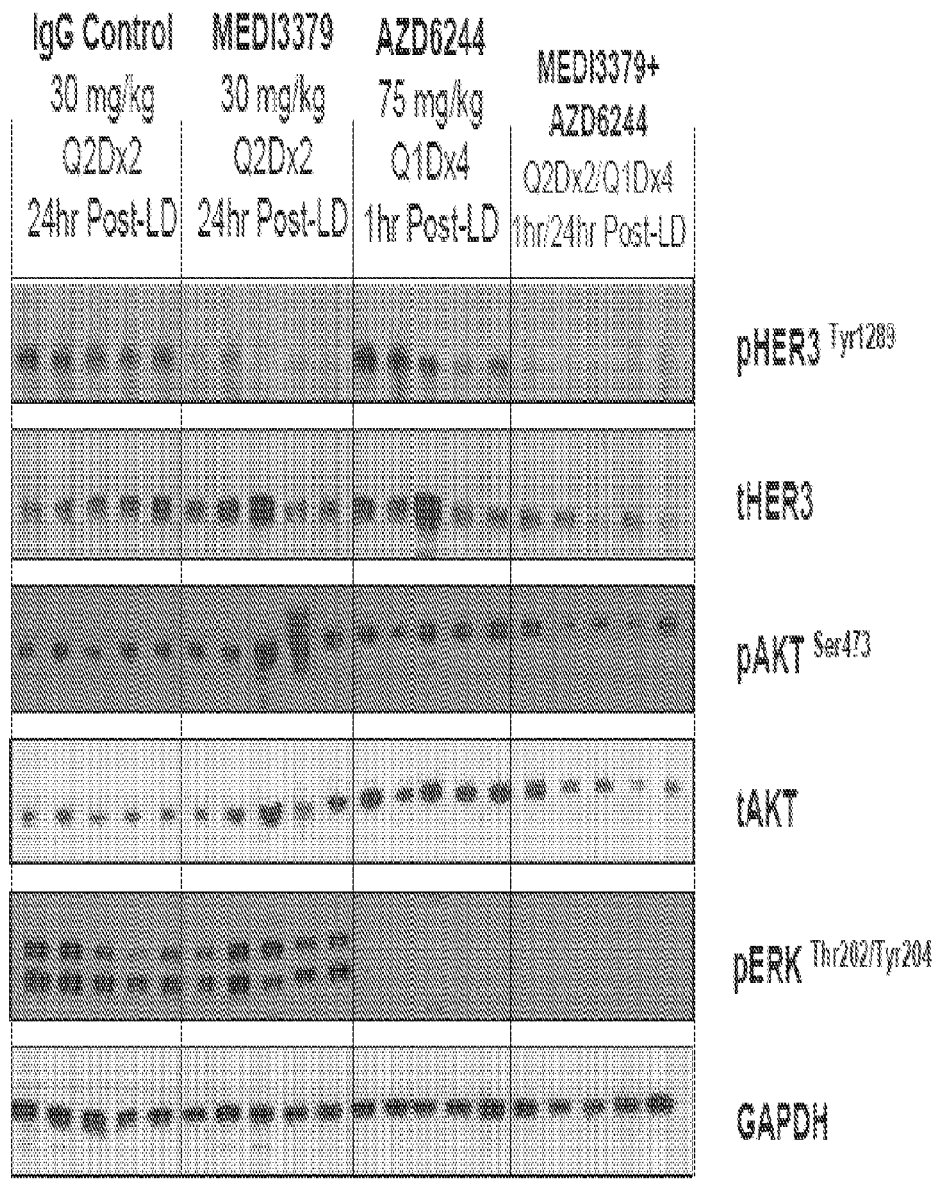
Fig. 37B part II

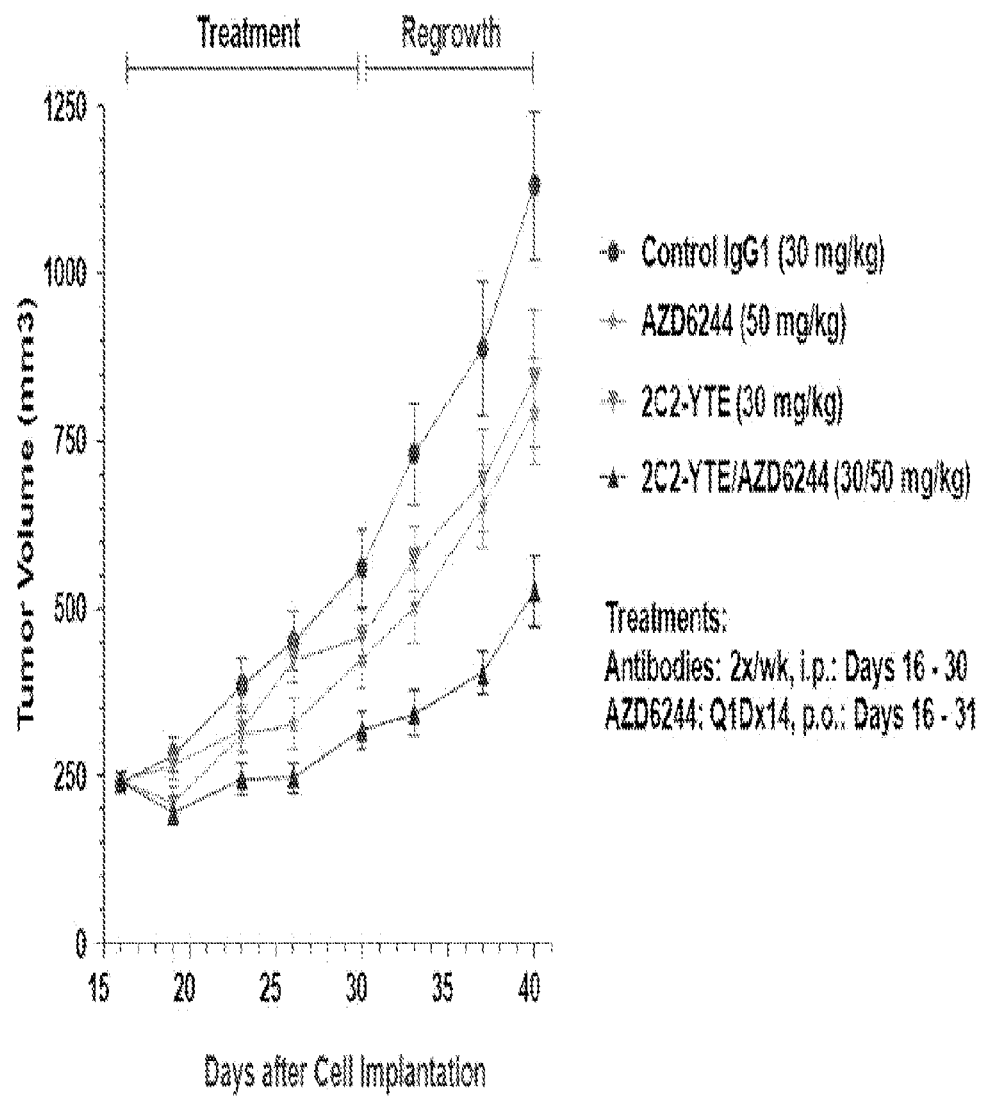
Fig. 37C part I

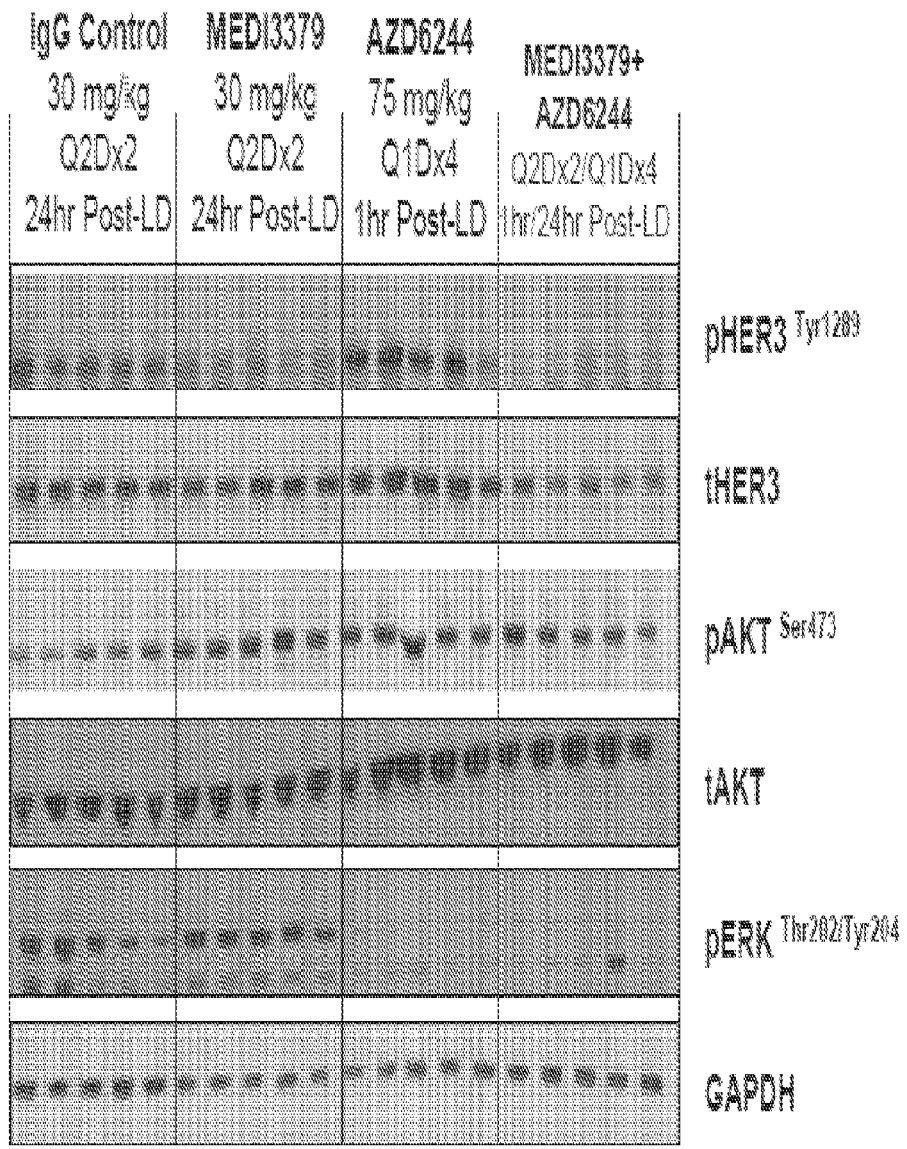
Fig. 37C part II

BINDING MOLECULES SPECIFIC FOR HER3 AND USES THEREOF

REFERENCE TO SEQUENCE LISTING SUBMITTED ELECTRONICALLY

This application incorporates by reference a Sequence Listing submitted with this application as text file entitled "Her3-100WO1_SL" created on Nov. 12, 2012 and having a size of 31.3 kilobytes.

FIELD OF THE INVENTION

The present invention provides compositions that specifically bind to HER3 and methods for the use of such compositions for the treatment of cancer.

BACKGROUND ART

The human epidermal growth factor receptor 3 (HER3, also known as Erbb3) is a receptor protein tyrosine and belongs to the epidermal growth factor receptor (EGFR) EGFR/HER subfamily of receptor protein tyrosine kinases (RTK), consisting of EGFR (HER1/Erbb1), HER2/Erbb2, HER3/Erbb3 and HER4/Erbb4. EGFR and HER2 are among the most well-established oncogenic RTKs driving the tumorigenesis of multiple types of solid tumors, including major categories such as breast, colorectal, and lung cancers. The tyrosine kinase activities of EGFR and HER2 have been shown to be essential for their oncogenic activities.

Like the prototypical EGFR, the transmembrane receptor HER3 consists of an extracellular ligand-binding domain (ECD), a dimerization domain within the ECD, an transmembrane domain, and intracellular protein tyrosine kinase domain (TKD) and a C-terminal phosphorylation domain (see, e.g., Kim et al. (1998), Biochem. J. 334, 189-195; Roepstorff et al. (2008) Histochem. Cell Biol. 129, 563-578).

The ligand Heregulin (HRG) binds to the extracellular domain of HER3 and activates the receptor-mediated signaling pathway by promoting dimerization with other EGFR family members (e.g., other HER receptors) and transphosphorylation of its intracellular domain. HER3 has been shown to lack detectable tyrosine kinase activity, likely due to a non-conservative replacement of certain key residues in the tyrosine kinase domain. Therefore, a consequence of this kinase-deficiency, HER3 needs to form hetero-dimers with other RTKs, especially EGFR and HER2, to undergo phosphorylation and be functionally active.

The central role for HER3 in oncogenesis is acting as a scaffolding protein to enable the maximum induction of the PI3K/AKT pathway. HER3 has been shown to contain a cluster of six C-terminal tyrosine-containing motifs that when phosphorylated, mimics the consensus PI3K/p85 binding site. Hence by forming heterodimers with HER3, the upstream onco-drivers, EGFR, HER2, cMET and FGFR2, can couple most efficiently to the PI3K/AKT pathway. Therefore, it is reasonable to expect that a loss of HER3 activity can block cancer progression in diverse systems driven by divergent RTKs. Studies have shown that HER3 siRNA knockdown in HER2-amplified breast cancer cells led to similar anti-proliferation effects as HER2 siRNA knockdown, further demonstrating the cancer's critical need for HER3.

Besides promoting tumor growth in unstressed conditions, HER3 has been found to be highly involved in conferring therapeutic resistances to many targeted drugs, including EGFR tyrosine kinase inhibitors, HER2 monoclonal antibodies such as trastuzumab, as well as small molecule inhibitors of PI3K or AKT or MEK. This adds another layer of attraction to HER3 as a promising cancer target for both primary tumor debulking as well as combating cancer resistance issues that invariably come up despite initial clinical responses.

HER3 has two different ways to dimerize with its partner RTKs: ligand-dependent (in the presence of HRG) or ligand-independent. In terms of HER2-HER3 dimers, it is known that in cells with low to medium HER2 expression, HER3 can only complex with HER2 after ligand-binding; in contrast, in cells with amplified HER2 (HER2 IHC 3+), they form spontaneous dimers without HRG (Junttila et al. (2009) Cancer Cell. 15(5):429-40). The dimers formed in the presence or absence of the ligand are structurally distinct as was demonstrated by an earlier study showing that trastuzumab/Herceptin® (Genentech/Roche HER2 monoclonal antibody approved for HER2 3+ breast cancers) can only disrupt the ligand-independent dimer but not the ligand-dependent dimer, whereas pertuzumab\Omnitarg® (rhuMAb 2C4, Genentech/Roche HER2 monoclonal antibody in phase 3 trials) can only disrupt the ligand-dependent dimers.

Dimer formation between HER family members expands the signaling potential of HER3 and is a means not only for signal diversification but also for signal amplification. HER3 has been shown to be phosphorylated in a variety of cellular contexts. For example, HER3 is constitutively phosphorylated on tyrosine residues in a subset of human breast cancer cells overexpressing HER3 (see, e.g., Kraus et al. (1993) Proc. Natl. Acad. Sci. USA 90, 2900-2904; Kim et al. (1998), Biochem. J. 334, 189-195; Schaefer et al. (2004) Cancer Res. 64, 3395-3405; Schaefer et al. (2006) Neoplasia 8, 612-622). Accordingly, therapies that effectively interfere with HER3 phosphorylation are desirable.

In addition, HER3 has been found to be overexpressed and/or overactivated in several types of cancers such as breast cancer, ovarian cancer, prostate cancer, liver cancer, kidney and urinary bladder cancers, pancreatic cancers, brain cancers, hematopoietic neoplasms, retinoblastomas, melanomas, colorectal cancers, gastric cancers, head and neck cancers, lung cancer, etc. (see, e.g., Sithanandam & Anderson (2008) Cancer Gene Ther. 15, 413-448). In general, HER3 is frequently activated in EGFR, HER2, C-Met, and FGFRII-expressing cancers.

A correlation between the expression of HER2/HER3 and the progression from a non-invasive to an invasive stage has been shown (Alimandi et al., Oncogene 10, 1813-1821; DeFazio et al., Cancer 87, 487-498; Naidu et al., Br. J. Cancer 78, 1385-1390). Thus, HER3 can be used as a diagnostic marker for increased tumor aggressiveness and poor survival. Sustained HER3 activation of PI3K/AKT has been repetitively shown to account for tumor resistance to EGFR/HER2 inhibitors.

Although the role of HER3 in the development and progression of cancer has been explored (see, e.g., Horst et al. (2005) Int. J. Cancer 115, 519-527; Xue et al. (2006) Cancer Res. 66, 1418-1426), HER3 remains largely unappreciated as a target for clinical intervention. Most current immunotherapies primarily focus on inhibiting the action of HER2 and, in particular, heterodimerization of HER2/HER3 complexes (see, e.g., Sliwkowski et al. (1994) J. Biol. Chem. 269, 14661-14665). Thus, it is an object of the present invention to provide improved immunotherapeutic agents that effectively inhibit HER3-mediated cell signaling that can be used for diagnosis, prognosis prediction, and treatment of a variety of cancers.

BRIEF SUMMARY OF THE INVENTION

The disclosure provides anti-HER3 binding molecules, e.g., antibodies or antigen-binding fragments thereof, e.g., monoclonal antibodies capable of suppressing HER3 activity in both ligand-dependent and independent settings. In contrast, other anti-HER3 monoclonal antibodies in the art (e.g., Ab #6 (International Patent Publication WO 2008/100624) and U1-59 (International Patent Publication WO 2007077028; also referred to herein as AMG), can only suppress ligand-dependent HER3 activity. Also disclosed are affinity matured anti-HER3-binding molecules with increased potency and extended half-life, which consequently can be administered less frequently, at an increased inter-dose interval, and in smaller dose volumes. The disclosure also provides methods of treating diseases such as cancer in a human subject comprising administration of an anti-HER3 binding molecule. In some specific aspects a 2C2-derived YTE mutant human antibody is used.

The disclosure provides an isolated binding molecule or antigen-binding fragment thereof which specifically binds to an epitope within the extracellular domain of HER3, wherein the binding molecule specifically binds to the same HER3 epitope as an antibody or antigen-binding fragment thereof comprising the heavy chain variable region (VH) and light chain variable region (VL) of CL16 or 2C2. Also provided is an isolated binding molecule or antigen-binding fragment thereof which specifically binds to HER3, and competitively inhibits HER3 binding by an antibody or antigen-binding fragment thereof comprising the VH and VL of CL16 or 2C2.

The disclosure also provides an isolated binding molecule or antigen binding fragment thereof which specifically binds to HER3 comprising an antibody VL, wherein the VL comprises the amino acid sequence:

[FW$_1$]X$_1$GSX$_2$SNIGLNYVS (SEQ ID NO: 49)

[FW$_2$]RNNQRPS (SEQ ID NO: 21)

[FW$_3$]AAWDDX$_3$X$_4$X$_5$GEX$_6$ (SEQ ID NO: 50)

[FW$_4$]

wherein [FW$_1$], [FW$_2$], [FW$_3$] and [FW$_4$] represent VL framework regions, and wherein
(a) X$_1$ represents amino acid residues Arginine (R) or Serine (S),
(b) X$_2$ represents amino acid residues Serine (S) or Leucine (L),
(c) X$_3$ represents amino acid residues Serine (S) or Glycine (G),
(d) X$_4$ represents amino acid residues Leucine (L) or Proline (P),
(e) X$_5$ represents amino acid residues Arginine (R), Isoleucine (I), Proline (P) or Serine (S), and
(f) X$_6$ represents amino acid residues Valine (V) or Alanine (A).

Furthermore, the disclosure provides an isolated binding molecule or antigen binding fragment thereof which specifically binds to HER3 comprising an antibody VH, wherein the VH comprises the amino acid sequence:

[FW$_5$]YYYMQ (SEQ ID NO: 31)

[FW$_6$]X$_7$IGSSGGVTNYADSVKG (SEQ ID NO: 51)

[FW$_7$]VGLGDAFDI (SEQ ID NO: 35)

[FW$_8$]

wherein [FW$_5$], [FW$_6$], [FW$_7$] and [FW$_8$] represent VH framework regions, and wherein X$_7$ represents amino acid residues Tyrosine (Y), Isoleucine (I) or Valine (V).

The disclosure provides an isolated binding molecule or antigen binding fragment thereof which specifically binds to HER3 comprising an antibody VL and an antibody VH, wherein the VL comprises the amino acid sequence:

[FW$_1$]X$_1$GSX$_2$SNIGLNYVS (SEQ ID NO: 49)

[FW$_2$]RNNQRPS (SEQ ID NO: 21)

[FW$_3$]AAWDDX$_3$X$_4$X$_5$GEX$_6$ (SEQ ID NO: 50)

[FW$_4$]

wherein [FW$_1$], [FW$_2$], [FW$_3$] and [FW$_4$] represent VL framework regions, and wherein
(a) X$_1$ represents amino acid residues Arginine (R) or Serine (S),
(b) X$_2$ represents amino acid residues Serine (S) or Leucine (L),
(c) X$_3$ represents amino acid residues Serine (S) or Glycine (G),
(d) X$_4$ represents amino acid residues Leucine (L) or Proline (P),
(e) X$_5$ represents amino acid residues Arginine (R), Isoleucine (I), Proline (P) or Serine (S), and
(f) X$_6$ represents amino acid residues Valine (V) or Alanine (A), and
wherein the VH comprises the amino acid sequence:

[FW$_5$]YYYMQ (SEQ ID NO: 31)

[FW$_6$]X$_7$IGSSGGVTNYADSVKG (SEQ ID NO: 51)

[FW$_7$]VGLGDAFDI (SEQ ID NO: 35)

[FW$_8$]

wherein [FW$_5$], [FW$_6$], [FW$_7$] and [FW$_8$] represent VH framework regions, and wherein X$_7$ represents amino acid residues Tyrosine (Y), Isoleucine (I) or Valine (V).

The disclosure also provides an isolated binding molecule or antigen binding fragment thereof which specifically binds to HER3 comprising an antibody VL, wherein the VL comprises a VL complementarity determining region-1 (VL-CDR1) amino acid sequence identical to, or identical except for four, three, two or one amino acid substitutions to: SEQ ID NO: 18, SEQ ID NO: 19, or SEQ ID NO: 20. Also, the disclosure provides an isolated binding molecule or antigen binding fragment thereof which specifically binds to HER3 comprising an antibody VL, wherein the VL comprises a VL complementarity determining region-2 (VL-CDR2) amino acid sequence identical to, or identical except for four, three, two or one amino acid substitutions to SEQ ID NO: 21.

In addition, the disclosure provides an isolated binding molecule or antigen binding fragment thereof which specifically binds to HER3 comprising an antibody VL, wherein the VL comprises a complementarity determining region-3 (VL-CDR3) amino acid sequence identical to, or identical except for four, three, two, or one amino acid substitutions to: SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, or SEQ ID NO: 30. Also, the disclosure provides an isolated binding molecule or antigen binding fragment thereof which specifically binds to HER3 comprising an antibody VH, wherein the VH comprises a complementarity determining region-1 (VH-CDR1) amino acid sequence identical to, or identical except for four, three, two, or one amino acid substitutions to SEQ ID NO: 31.

Furthermore, the disclosure provides an isolated binding molecule or antigen binding fragment thereof which specifically binds to HER3 comprising an antibody VH, wherein the VH comprises a complementarity determining region-2 (VH-CDR2) amino acid sequence identical to, or identical except for four, three, two, or one amino acid substitutions to: SEQ ID NO: 32, SEQ ID NO: 33, or SEQ ID NO: 34. Also provided is an isolated binding molecule or antigen binding fragment thereof which specifically binds to HER3 comprising an antibody VH, wherein the VH comprises a complementarity determining region-3 (VH-CDR3) amino acid sequence identical to, or identical except for four, three, two, or one amino acid substitutions to SEQ ID NO: 35.

The disclosure provides an isolated binding molecule or antigen binding fragment thereof which specifically binds to HER3 comprising an antibody VL, wherein the VL comprises VL-CDR1, VL-CDR2, and VL-CDR3 amino acid sequences identical to, or identical except for four, three, two, or one amino acid substitutions in one or more of the VL-CDRS to: SEQ ID NOs: 18, 21 and 22, SEQ ID NOs: 18, 21, and 26, SEQ ID NOs: 18, 21, and 27, SEQ ID NOs: 20, 21, and 22, SEQ ID NOs: 19, 21, and 22, SEQ ID NOs: 18, 21, and 25, SEQ ID NOs: 18, 21, and 28, SEQ ID NOs: 18, 21, and 29, SEQ ID NOs: 18, 21, and 30, SEQ ID NOs: 18, 21, and 23, SEQ ID NOs: 19, 21, and 23, SEQ ID NOs: 20, 21, and 23, SEQ ID NOs: 18, 21, and 24, or SEQ ID NOs: 18, 21, and 25, respectively. The disclosure also provides an isolated binding molecule or antigen binding fragment thereof which specifically binds to HER3 comprising an antibody VH, wherein the VH comprises VH-CDR1, VH-CDR2, and VH-CDR3 amino acid sequences identical to, or identical except for four, three, two, or one amino acid substitutions in one or more of the VH-CDRS to: SEQ ID NOs: 31, 32 and 35, SEQ ID NOs: 31, 33, and 35, or SEQ ID NOs: 31, 34, and 35, respectively.

In addition, the disclosure provides an isolated antibody or antigen-binding fragment thereof which specifically binds to HER3 comprising a VL and a VH comprising VL-CDR1, VL-CRD2, VL-CDR3, VH-CDR1, VH-CDR2, and VH-CDR3 amino acid sequences identical or identical except for four, three, two, or one amino acid substitutions in one or more CDRs to: SEQ ID NOs: 18, 21, 22, 31, 32, and 35, SEQ ID NOs: 18, 21, 26, 31, 32 and 35, SEQ ID NOs: 18, 21, 27, 31, 32 and 35, SEQ ID NOs: 20, 21, 22, 31, 32 and 35, SEQ ID NOs: 19, 21, 22, 31, 32 and 35, SEQ ID NOs: 18, 21, 25, 31, 32 and 35, SEQ ID NOs: 18, 21, 28, 31, 32 and 35, SEQ ID NOs: 18, 21, 29, 31, 32 and 35, SEQ ID NOs: 18, 21, 30, 31, 32 and 35, SEQ ID NOs: 18, 21, 23, 31, 32 and 35, SEQ ID NOs: 19, 21, 23, 31, 32 and 35, SEQ ID NOs: 20, 21, 23, 31, 32 and 35, SEQ ID NOs: 18, 21, 24, 31, 32 and 35, or SEQ ID NOs: 18, 21, 25, 31, 32 and 35, respectively. Also provided is an isolated binding molecule or antigen binding fragment thereof which specifically binds to HER3 comprising an antibody VL and an antibody VH, wherein the VL comprises an amino acid sequence at least about 90% to about 100% identical to a reference amino acid sequence selected from the group consisting of SEQ ID NO: 1, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 14, SEQ ID NO: 15, SEQ ID NO: 16, and SEQ ID NO: 17. The disclosure also provides an isolated binding molecule or antigen binding fragment thereof which specifically binds to HER3 comprising an antibody VL and an antibody VH, wherein the VH comprises an amino acid sequence at least about 90% to about 100% identical to a reference amino acid sequence selected from the group consisting of SEQ ID NO: 2, SEQ ID NO: 12 and SEQ ID NO: 13. Furthermore, the disclosure provides an isolated antibody or antigen binding fragment thereof which specifically binds to HER3, wherein the antibody or antigen binding fragment comprises a VL comprising a sequence at least about 90% to about 100% identical to a reference amino acid sequence selected from the group consisting of SEQ ID NO: 1, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 14, SEQ ID NO: 15, SEQ ID NO: 16, and SEQ ID NO: 17, and wherein the antibody or antigen binding fragment comprises a VH comprising a sequence at least about 90% to about 100% identical to a reference amino acid sequence selected from the group consisting of SEQ ID NO: 2, SEQ ID NO: 12 and SEQ ID NO: 13.

The disclosure also provides an isolated antibody or antigen binding fragment thereof, which comprises a VL comprising SEQ ID NO: 49 and a VH comprising SEQ ID NO: 50. In addition, the disclosure provides an isolated antibody or antigen binding fragment thereof, which comprises a VL comprising SEQ ID NO: 3 and a VH comprising SEQ ID NO: 2. Further, the disclosure provides an isolated binding molecule or antigen-binding fragment thereof which specifically binds to an epitope within the extracellular domain of HER3, comprising an antibody VL of SEQ ID NO:3, an antibody VH of SEQ ID NO: 2, and an IgG1 constant region of SEQ ID 46. Also provided is an isolated binding molecule or antigen-binding fragment thereof which specifically binds to an epitope within the extracellular domain of HER3, consisting of an antibody VL of SEQ ID NO: 3, an antibody VH of SEQ ID NO: 2, and an IgG1 constant region of SEQ ID 46.

BRIEF DESCRIPTION OF THE DRAWINGS/FIGURES

FIG. 1 shows the internalization of Clone 16 anti-HER3 monoclonal antibodies in KPL4 cells shown as depletion of surface fluorescent staining. The top panel shows internalization at time=0. The bottom panels show internalization after 2.5 hours.

FIG. 2A shows a multiple sequence alignment corresponding to the VL sequences of anti-HER3 monoclonal antibodies Clone 16 (CL16; original, parent clone; SEQ ID NO:17), Clone 16 (GL; germlined clone; SEQ ID NO:1), 5H6 (SEQ ID NO:4), 8A3 (SEQ ID NO:5), 4H6 (SEQ ID NO:6), 6E.3 (SEQ ID NO:7), 2B11 (SEQ ID NO:8), 2D1 (SEQ ID NO:9), 3A6 (SEQ ID NO:10) and 4C4 (SEQ ID NO:11). The location of CDR1, CDR2, and CDR3 is indicated. Amino acid residues which differ with respect to the CL16 (GL) antibody are highlighted.

FIG. 2B shows a multiple sequence alignment corresponding to the VH sequences of anti-HER3 monoclonal antibodies Clone 16 (CL16; parent clone; SEQ ID NO: 2), and clones 15D12.1 (also referred to as 15D12.I; SEQ ID NO 12) and 15D12.2 (also referred to as 15D12.V; SEQ ID NO 13). The locations of CDR1, CDR2, and CDR3 are indicated. Amino acid residues which differ with respect to the CL16 parent antibody are highlighted.

FIG. 2C shows a multiple sequence alignment corresponding to the VL sequences of anti-HER3 monoclonal antibodies CL16 (original, parent clone; SEQ ID NO: 17), CL16 (GL; germlined clone; SEQ ID NO: 1), 1A4 (SEQ ID NO: 14), 2C2 (SEQ ID NO: 3), 3E.1 (SEQ ID NO: 15), 2F10 (SEQ ID NO: 16), and 2B11 (SEQ ID NO: 8). The location of CDR1, CDR2, and CDR3 is indicated. Amino acid residues which differ with respect to the CL16 (GL) antibody are highlighted.

FIG. 3 shows suppression of HER3 phosphorylation (pHER3) in ligand-driven MCF-7 cells, where HER3 is only activated by exogenous HRG (ligand). The 2C2 anti-HER3 monoclonal, published anti-HER3 monoclonal antibodies AMG and MM, and R347 control antibody were assayed. Maximum percentages of pHER3 inhibition and $IC_{50}$'s are presented.

FIG. 4 shows growth suppression in MDA-MB-175 cells, an established HRG-autocrine loop driven model wherein endogenous HRG drives HER3 activity and cell growth. The 2C2 anti-HER3 monoclonal, published anti-HER3 monoclonal antibodies AMG and MM, and R347 control antibody were assayed. Maximum percentages of growth inhibition and $IC_{50}$'s are presented.

FIG. 8 shows suppression of HER3 phosphorylation (pHER3) in cell models for Lung Gastric and Breast cancer. Panel A shows suppression of pHER3 in the HCC827 cell line, a mutant EGFR-driven NSCLC model with EGFR/HER3 cross-talk. Panel B shows suppression of pHER3 in an EGFR-TKI-resistant HCC827 NSCLC model obtained through long-term treatment with EGFR TKI. Panel C shows suppression of pHER3 in the MKN45 cell line, a cMET-amplified gastric cancer model with cMET-HER3 cross-talk. Panel D shows suppression of pHER3 in the Kato III cell line, an FGFR2-amplified gastric cancer model with FGFR2-HER3 cross-talk. Panel E shows suppression of pHER3 in the BT-474 cell line, a HER2-amplified breast cancer ligand-independent model (i.e., cells lack HRG expression). The 2C2 anti-HER3 monoclonal, published anti-HER3 monoclonal antibodies AMG and MM, and R347 control antibody were assayed. Maximum percentages of pHER3 inhibition and $IC_{50}$'s are presented.

FIG. 9 shows suppression of AKT phosphorylation (pAKT) in cell models for gastric and breast cancer. Panel A shows suppression of pAKT in the MKN45 cell line. Panel B shows suppression of pAKT in the Kato III cell line. Panel C shows suppression of pAKT in the BT-474 cell line, a HER2-amplified breast cancer ligand-independent model (i.e., cells lack HRG expression). The 2C2 anti-HER3 monoclonal, published anti-HER3 monoclonal antibodies AMG and MM, and R347 control antibody were assayed. Maximum percentages of pAKT inhibition and $IC_{50}$'s are presented.

Figure 10A:
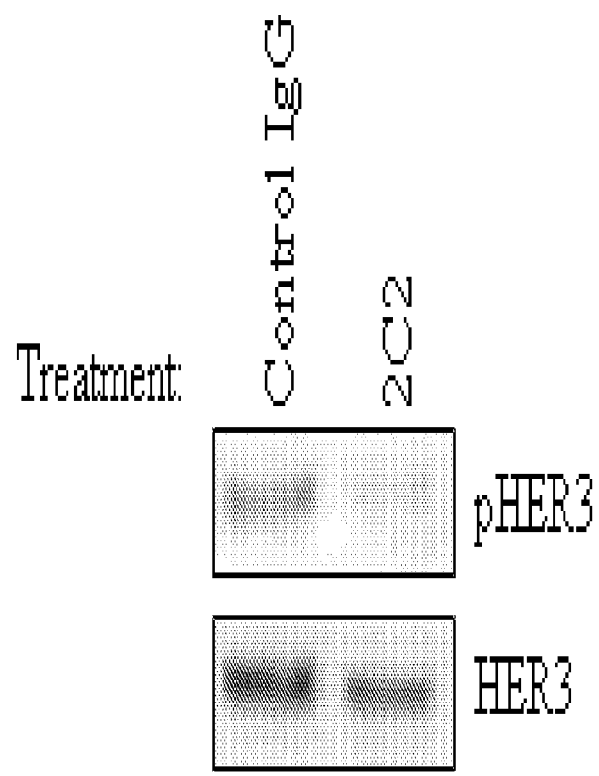
Figure 10B:
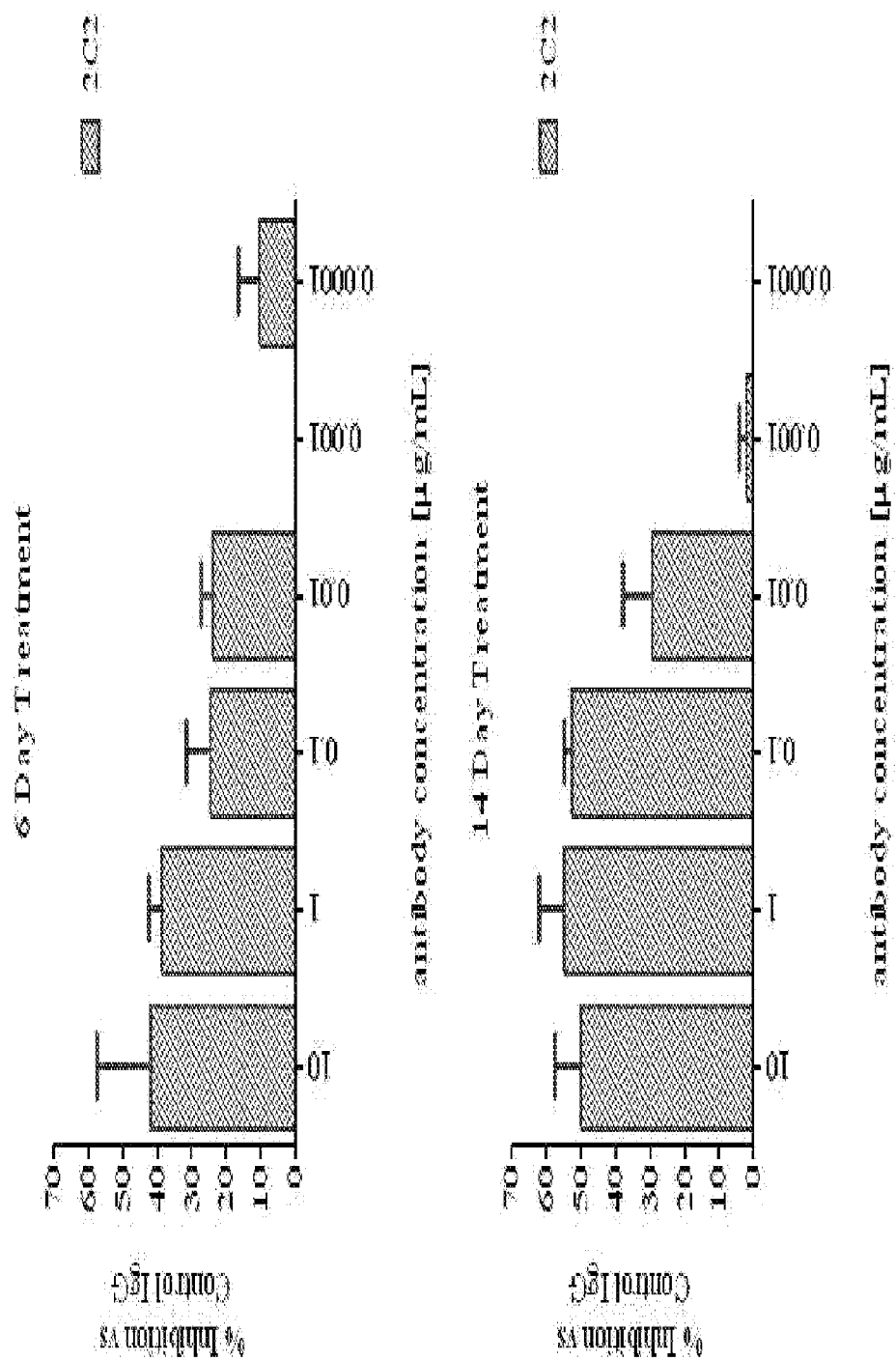

FIG. 10 shows 2C2 suppresses cell signaling and proliferation in MDA-MB-361 cells. Panel A shows that 2C2 suppressed HER3 phosphorylation (pHER3) in HER2-amplified MDA-MB-361 cells. Panel B shows that 2C2 suppressed cell growth in a dose dependent manner. The percent inhibition is shown for 6 and 14 day treatments (top and bottom panels, respectively).

Figure 11:
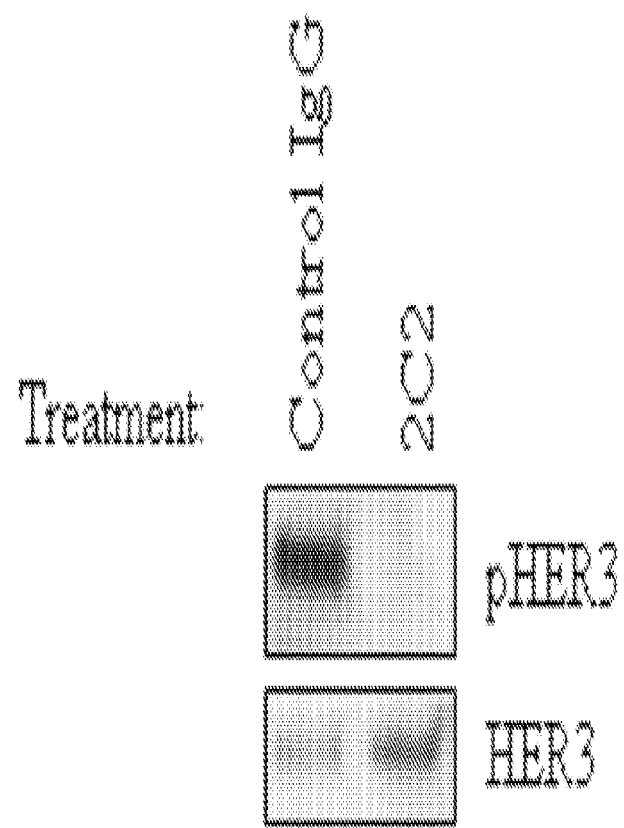

FIG. 11 shows that 2C2 suppressed HER3 phosphorylation (pHER3) in HARA-B cells expressing high levels of HRG.

Figure 12A:
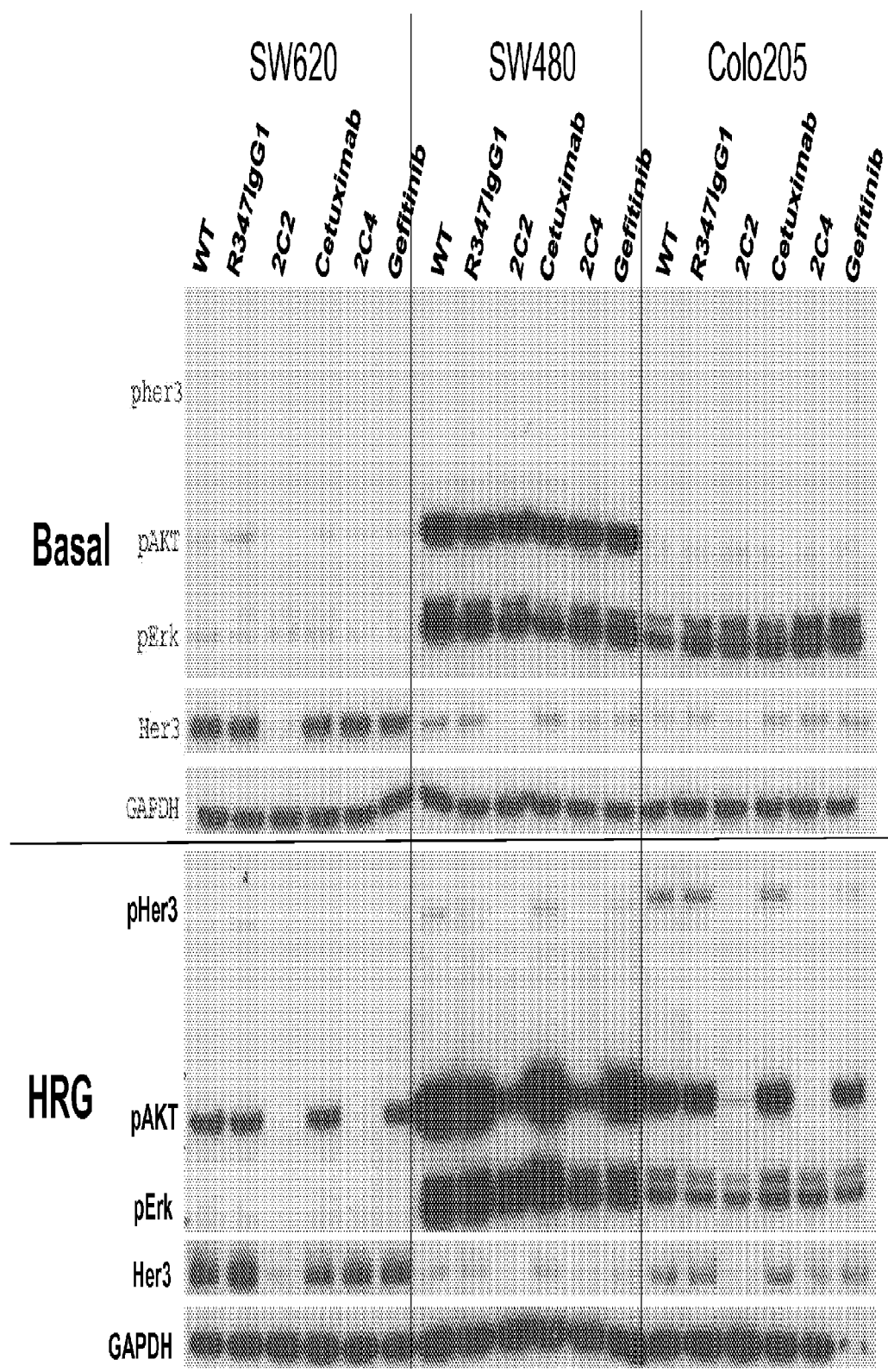
Figure 12B:
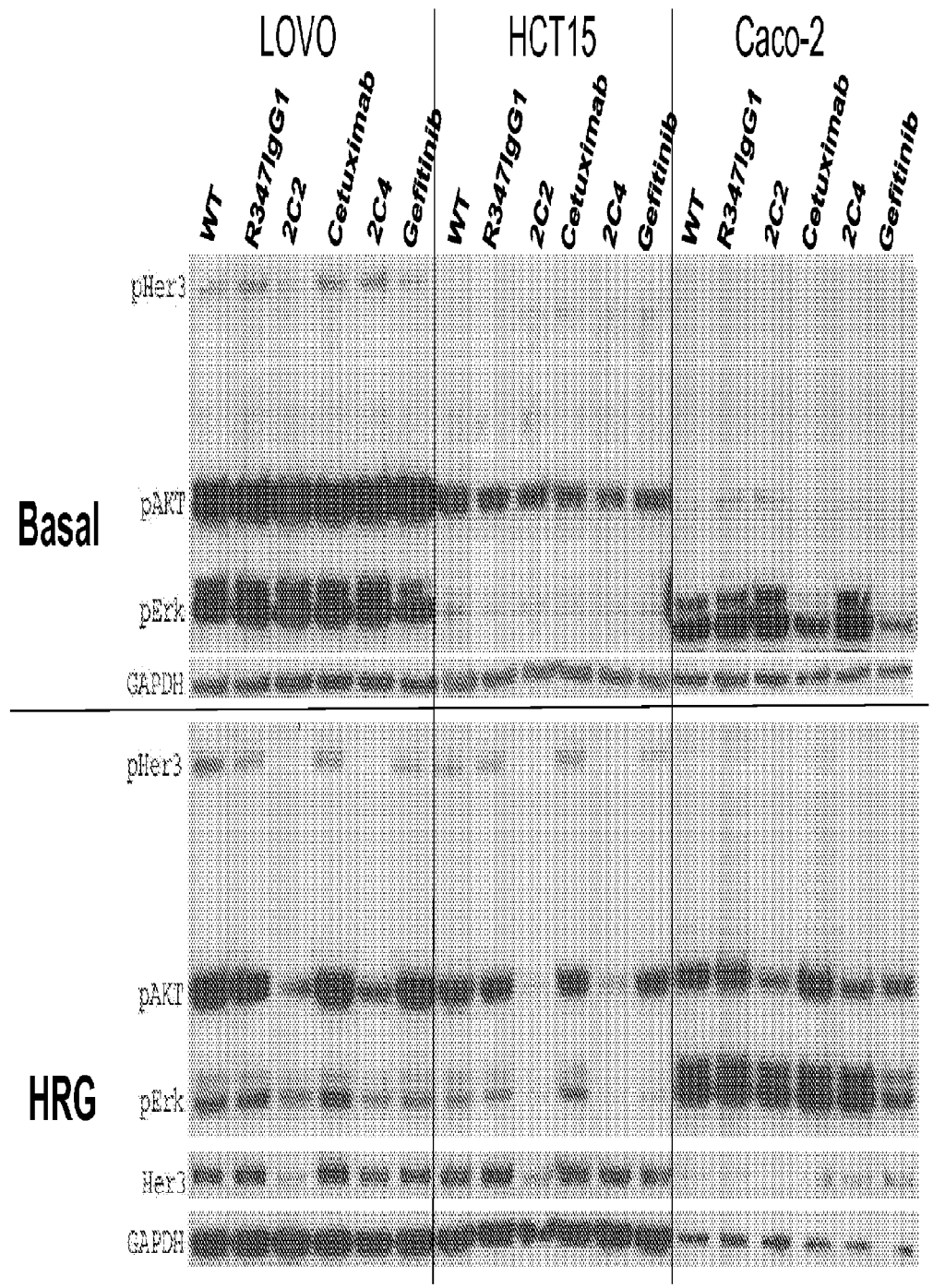

FIG. 12 shows that 2C2 and rhuMab 2C4, but not the EGFR antagonists cetuximab or gefitinib, inhibit HRG ligand-dependent signaling (bottom of Panels A and B). The top portion of Panels A and B are basal cells, SW620 (Panel A, left), SW480 (Panel A, middle), Colo205 (Panel A, right), LOVO (Panel B, left), HCT15 (Panel B, middle) and Caco-2 (Panel B, right).

Figure 13:
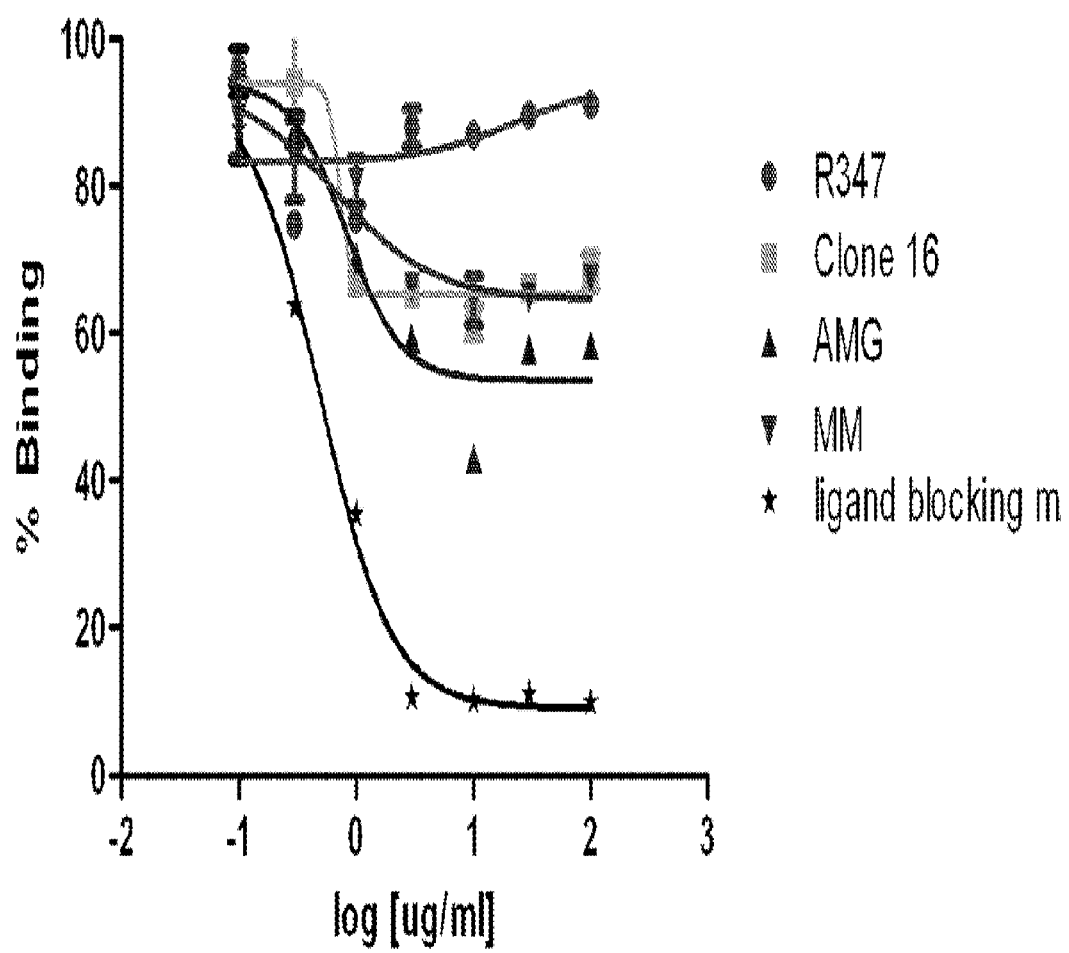

FIG. 13 shows an HRG-HER3 ELISA binding assay measuring the direct blocking of HRG binding to HER3 by the Clone 16, published AMG and MM anti-HER3 monoclonal antibodies, a positive control ligand-blocking anti-HER3 monoclonal antibody, and the R347 control antibody.

FIG. 14 shows 2C2 blocks HER2-HER3 dimerization. Panel A shows a HRG-inducible HER2-HER3 dimerization assay that assesses the extent of HER2-HER3 complex formation in T-47D cells, a ligand-dependent model showing clear HRG-induced HER2-HER3 association, pre-treated with 2C2, CL16, AMG and MM anti-HER3 monoclonal antibodies. All anti-HER3 antibodies blocked this ligand-induced HER2-HER3 dimerization. Panel B shows a ligand-independent HER2-HER3 dimerization assay that assesses the extent of HER2-HER3 complex formation in BT-474 cells, pre-treated with 2C2 or CL16 blocked this ligand-independent HER2-HER3 dimerization.

FIG. 15 shows HER3 internalization and degradation induced by 2C2. Panel A shows a FACS-based internalization assay that quantifies time course and extent of target internalization in response to two different 2C2 monoclonal antibody concentrations. Panel B shows HER3 degradation in model colorectal cancer cells Lovo, HCT15, and SW620 pretreated with anti-HER3 2C2 monoclonal antibody, or the R347 control antibody.

Figure 16:
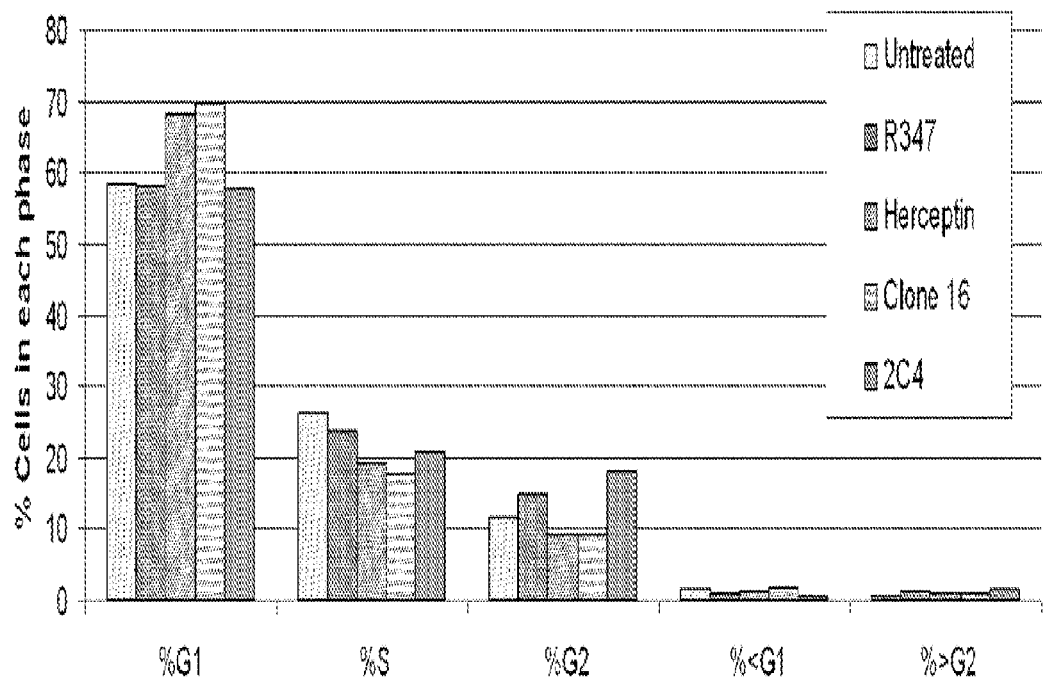

FIG. 16 shows a FACS-based cell-cycle analysis demonstrating that in SkBR3 cells, a HER2-amplified breast cancer cell-line similar to BT-474, both Herceptin® (trastuzumab) and CL16 monoclonal antibody (parental lead for the 2C2 monoclonal antibody) caused cell-cycle arrest at the G1-phase. Results corresponding to cells treated with the R347 control antibody and with the rhuMAb 2C4 anti-HER2 monoclonal antibody (pertuzumab/Omnitarg®) are also shown.

Figure 17A:
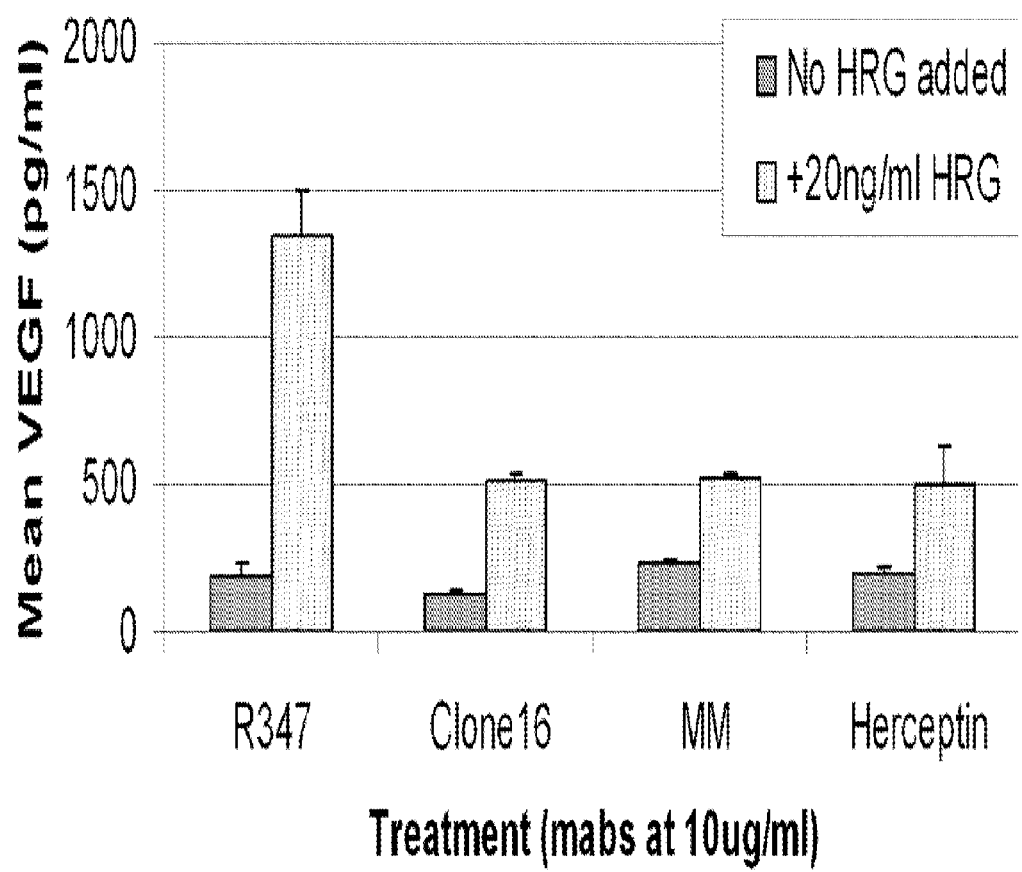
Figure 17B:
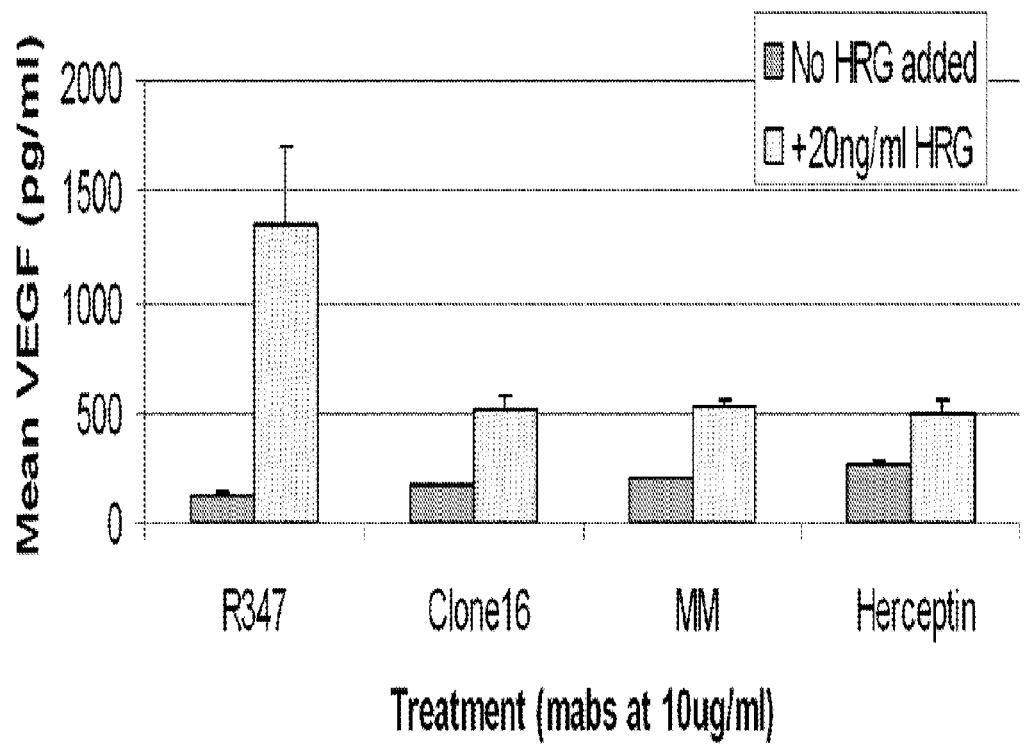

FIG. 17 shows inhibition of HRG induced VEGF secretion by anti-HER3 antibodies. Panel A shows changes in VEGF secretion in BT-474 breast cancer cells pretreated with anti-HER3 monoclonal antibodies CL16 and Merrimack MM, anti-HER2 monoclonal antibody Herceptin® (trastuzumab), or the R347 control antibody. Panel B shows changes in VEGF secretion in MCF-7 model breast cancer cells pretreated with anti-HER3 monoclonal antibodies CL16 and Merrimack MM, anti-HER2 monoclonal antibody Herceptin® (trastuzumab), or the R347 control antibody.

FIG. 18 shows that the anti-HER3 monoclonal antibody 2C2 binds to cell-surface based cyno HER3 ectopically expressed in Ad293 cells and modulates its activity. Panel A shows a Western blot analysis of Ad293 cells transfected with a control vector (left side) or a vector expressing cyno HER3 (right side). The cells were treated with 2C2 or a control antibody (R347) with or without co-stimulation with HRG and probed with anti-HER3 (middle blot), anti-pHER3 (top blot), and anti-GAPDH (bottom blot) antibodies. Panel B represents the densitometry-based quantification of pHER3 in the upper four lanes of Panel A.

FIG. 19 shows a dose-dependent reduction in tumor volume after administration of the 2C2 monoclonal antibody using the human FADU head and neck xenograft model. Panel A shows that 7 mg/kg of 2C2 administered twice per week was maximally efficacious at 99% dTGI (tumor growth inhibition) in this model. Panel B shows strong reduction in tumor volume after the combined administration of the 2C2 monoclonal antibody with the anti-EGFR monoclonal antibody cetuximab using the human FADU head and neck xenograft model. The combination treatment produced 7 out of 10 partial regressions and 2/10 complete regressions.

Figure 20:
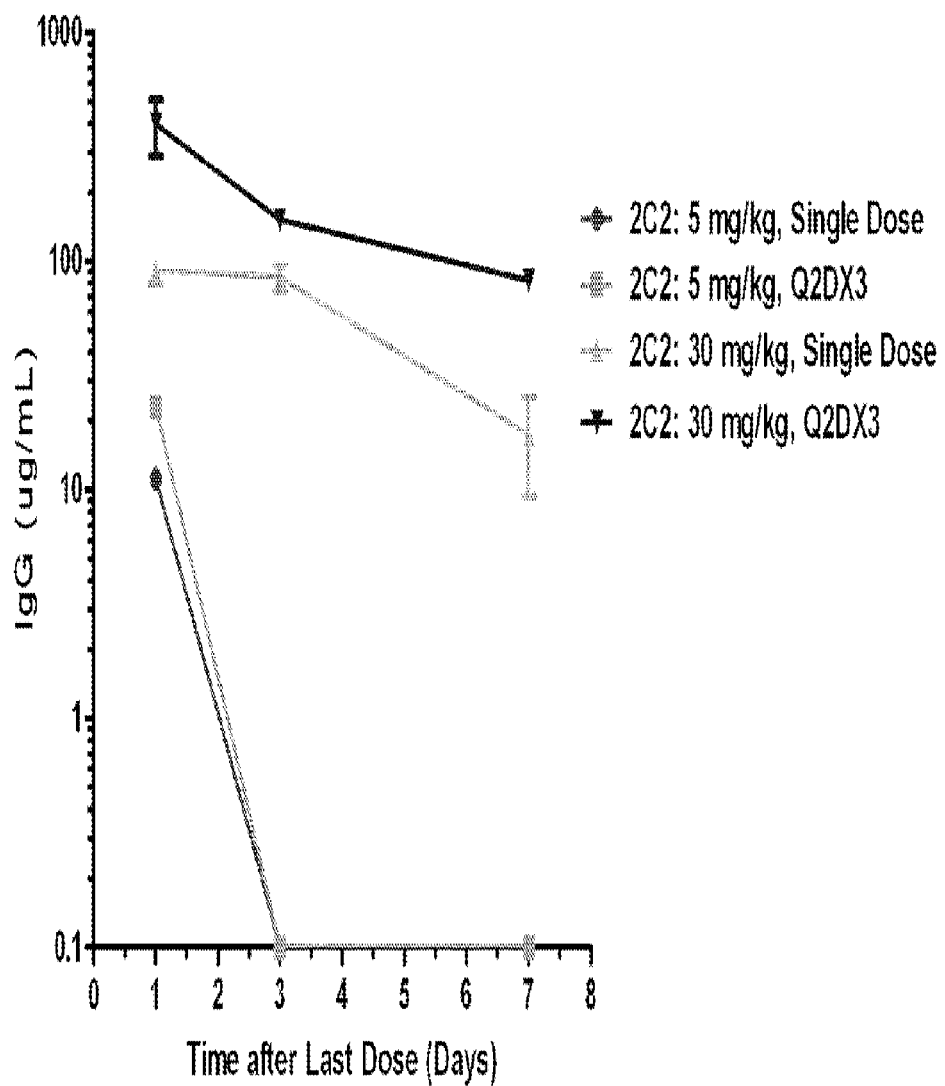

FIG. 20 shows non-linear pharmacokinetics for 2C2 after single dose and repeat-dose administration of 5 mg/kg or 30 mg/kg to tumor-bearing mice. Data suggest that mouse HER3 serves as a sink to bind 2C2 administered to the mice and that 30 mg/kg as a single dose is sufficient to saturate the sink.

Figure 21:
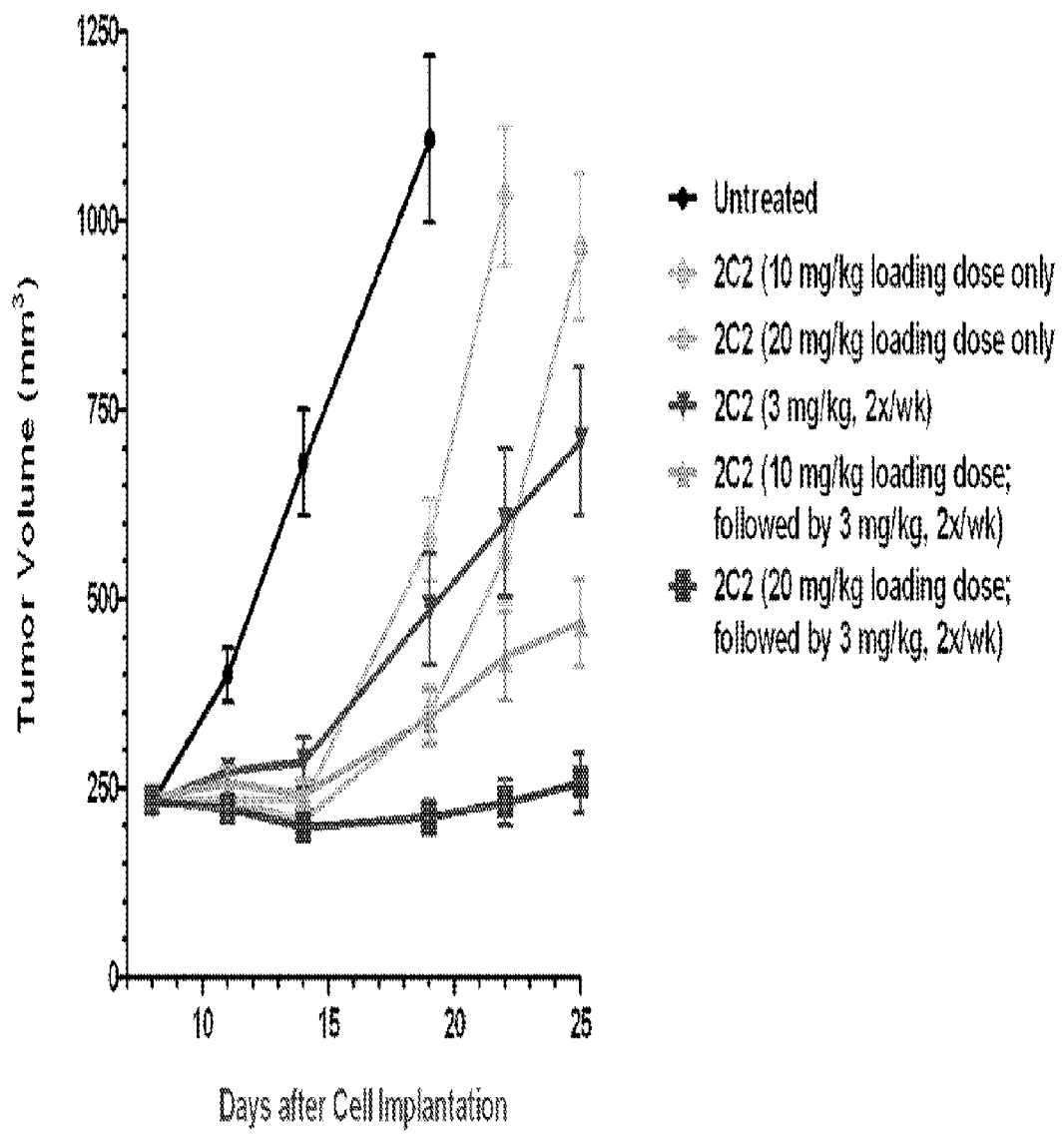

FIG. 21 shows the anti-tumor benefit of a 10 mg/kg loading dose of the monoclonal antibody 2C2 using the human FADU head and neck xenograft model. Administration of a loading dose of 2C2 to saturate the mouse HER3 sink enabled 2C2 at 3 mg/kg to demonstrate strong anti-tumor activity while 3 mg/kg of 2C2 without a loading dose has only modest activity.

Figure 22:
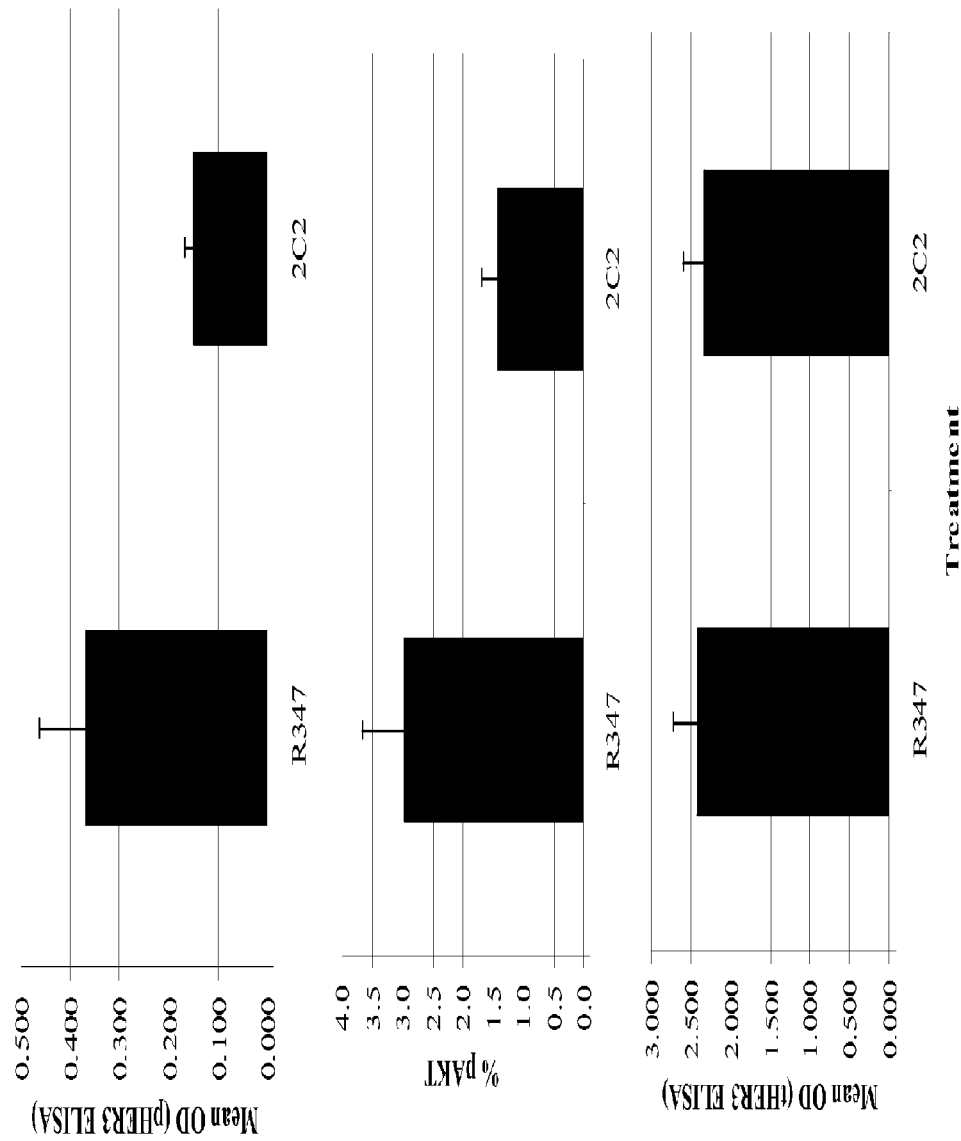

FIG. 22 shows that treatment with 2C2-YTE reduces the levels of pHER3 and pAKT in FADU xenograft tumor extracts. In this experiment the levels of pHER3 and pAKT were reduced by 59.5% and 51.7%, respectively. No change was seen in total HER3 levels in this experiment.

FIG. 23 shows a dose-dependent reduction in tumor volume after administration of the 2C2 monoclonal antibody using the human Detroit562 head and neck xenograft model. Panel A shows that 10 mg/kg of 2C2 administered twice per week was maximally efficacious at 72% dTGI. Panel B shows a reduction in tumor volume after the combined administration of the 2C2 monoclonal antibody with the anti-EGFR monoclonal antibody cetuximab using the human Detroit562 head and neck xenograft model. The combination treatment produced 9 out of 10 partial regressions while cetuximab alone produced 5/10 partial regressions. The Detroit562 xenograft model contains a PIK3CA mutation.

Figure 24:
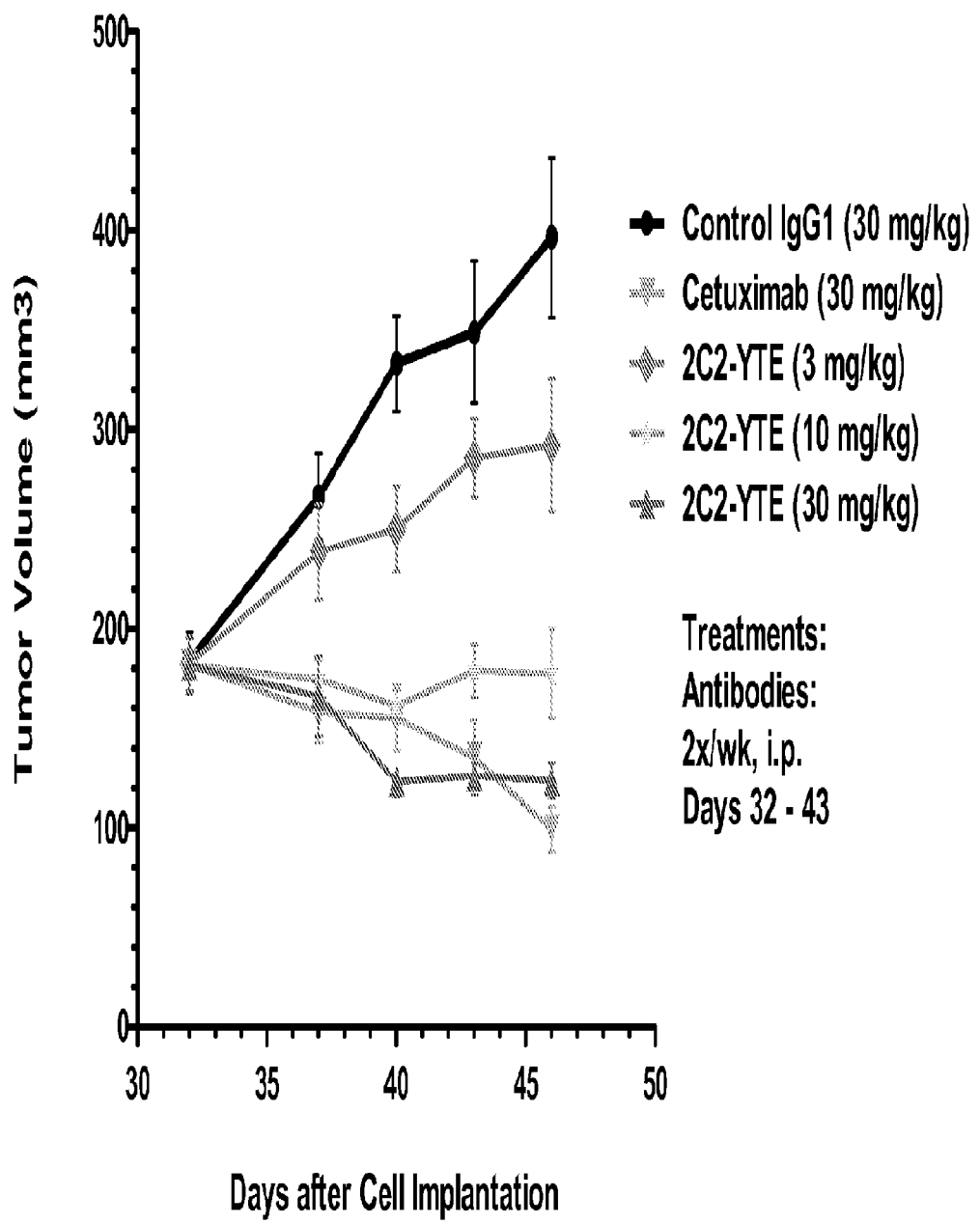

FIG. 24 shows a dose dependent reduction in tumor volume after the administration of the 2C2-YTE monoclonal antibody using the human CAL27 head and neck xenograft model.

Figure 25A:
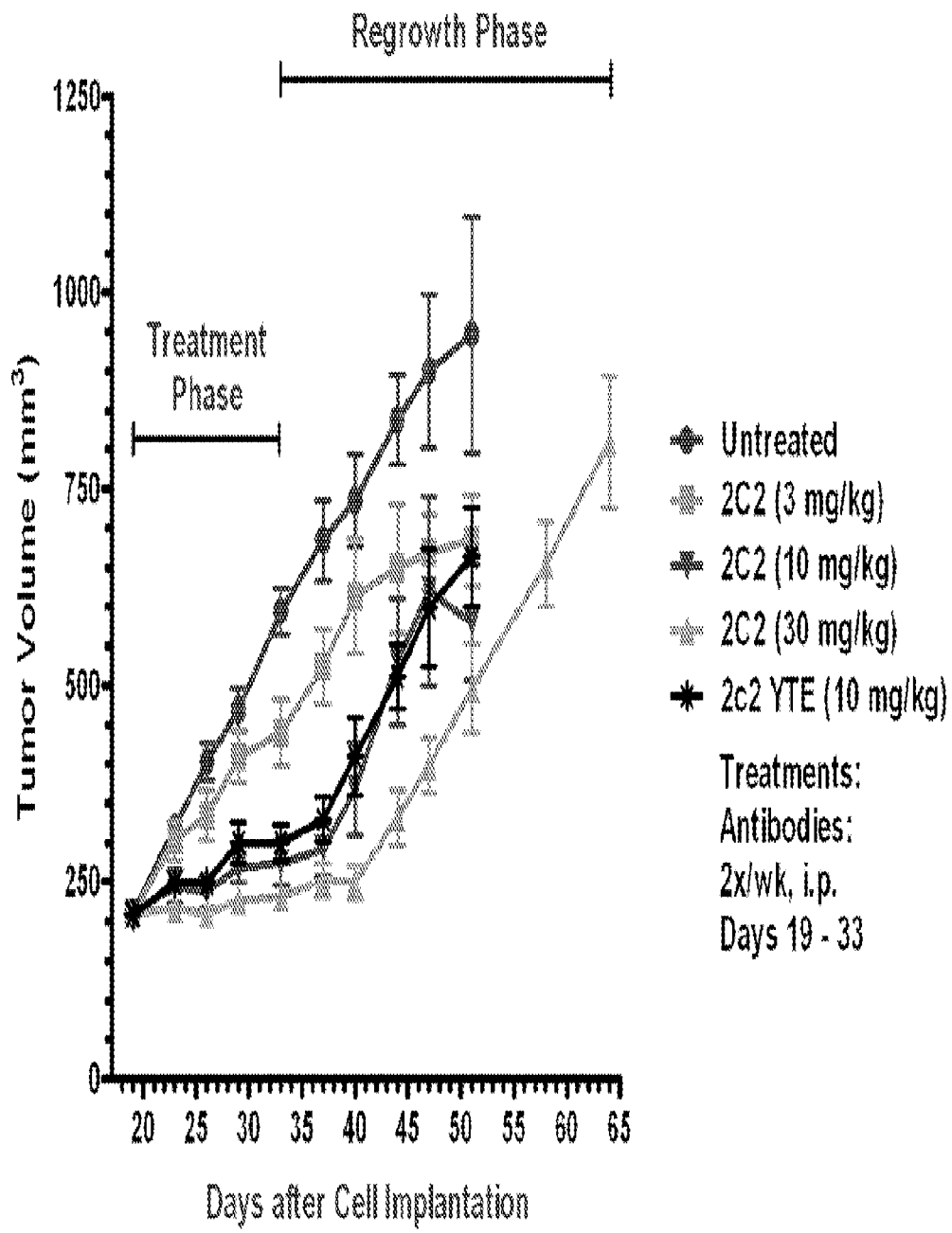

FIG. 25 shows a dose-dependent reduction in tumor volume after administration of the 2C2 monoclonal antibody using the human A549 NSCLC xenograft model. Panel A shows that 30 mg/kg of 2C2 administered twice per week was maximally efficacious at 91% dTGI up to the last day of the treatment phase (day 33; regrowth afterwards). 2C2-YTE and 2C2 both at 10 mg/kg have comparable activity. Panel B shows a reduction in tumor volume after the combined administration of the 2C2 monoclonal antibody with the anti-EGFR monoclonal antibody cetuximab using the human A549 NSCLC xenograft model. The addition of cetuximab to 2C2 increased the activity of 2C2 during the treatment phase and delayed tumor regrowth during the tumor regrowth phase. The A549 xenograft model contains a KRAS mutation and a LKB-1 deletion.

Figure 26:
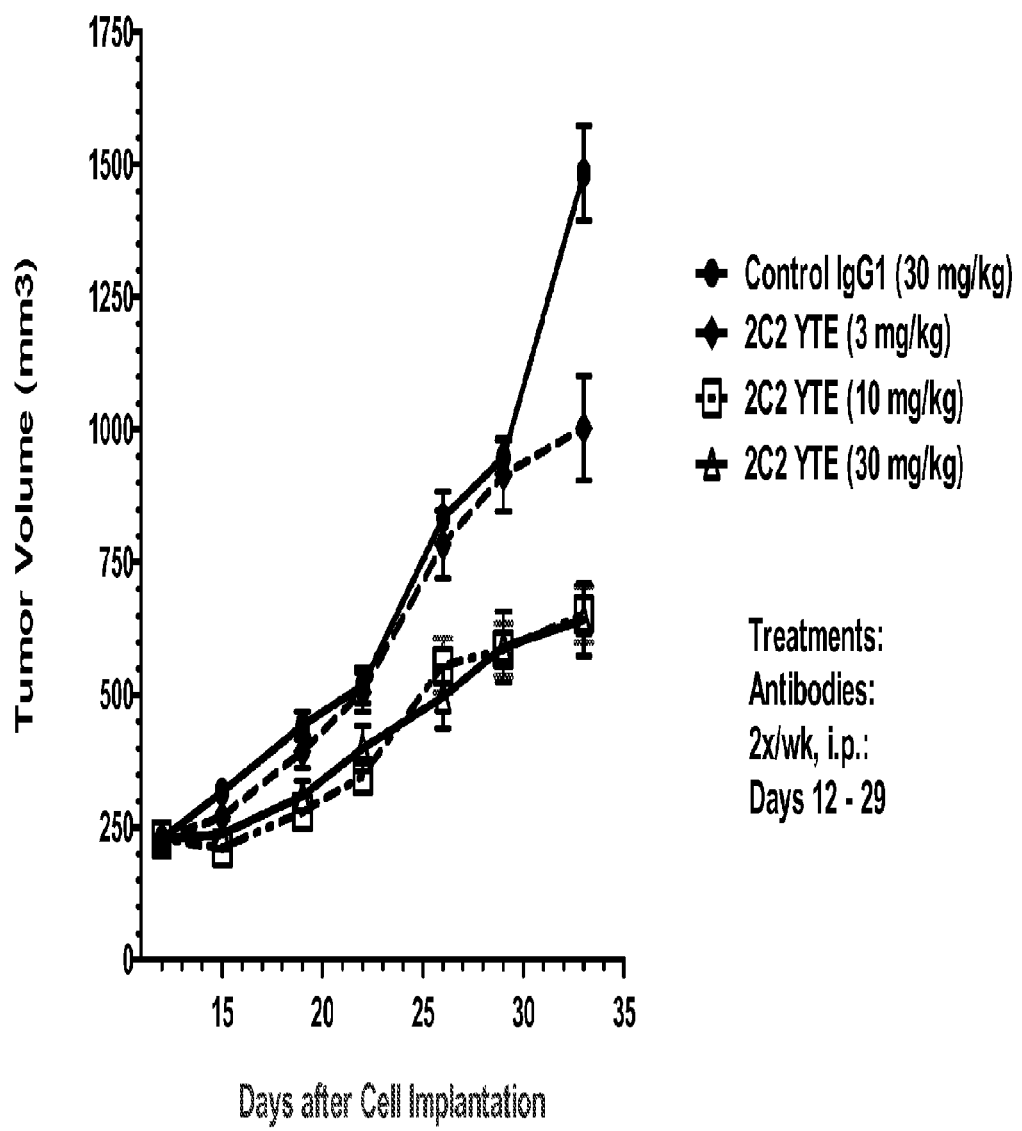

FIG. 26 shows a reduction in tumor volume after administration of the 2C2-YTE monoclonal antibody using the human HARA-B squamous cell carcinoma xenograft model. 30 mg/kg of 2C2-YTE administered twice per week was maximally efficacious at 64.6% dTGI. 2C2-YTE at 10 mg/kg had comparable activity while 2C2-YTE at 3 mg/kg was not active.

Figure 27:
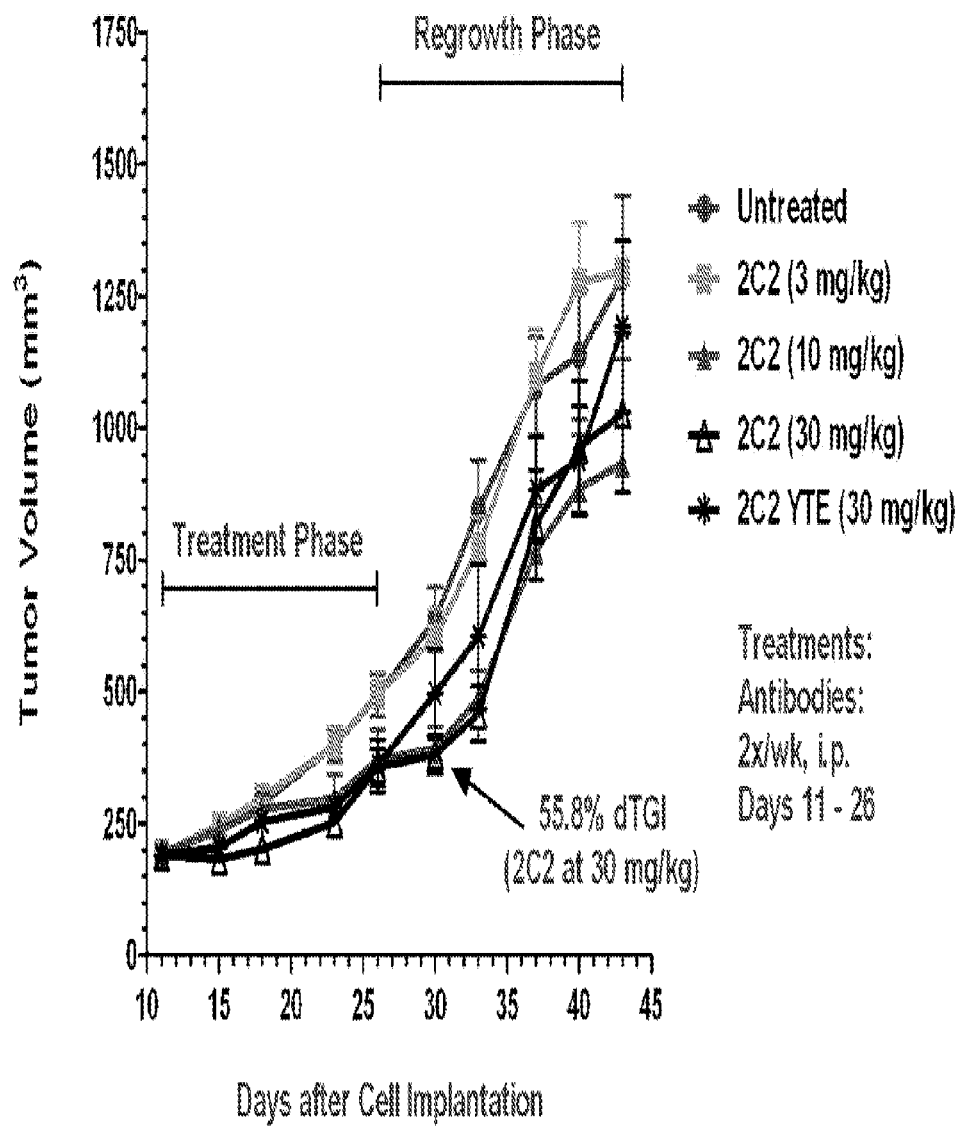

FIG. 27 shows a dose-dependent reduction in tumor volume after administration of the 2C2 monoclonal antibody using the human HT-29 colorectal xenograft model. 30 mg/kg of 2C2 administered twice per week was maximally efficacious at 56% dTGI up to the last day of the treatment phase (day 26; regrowth afterwards). 2C2-YTE and 2C2 both at 30 mg/kg have comparable activity. The HT-29 xenograft model contains a BRAF mutation.

Figure 28:
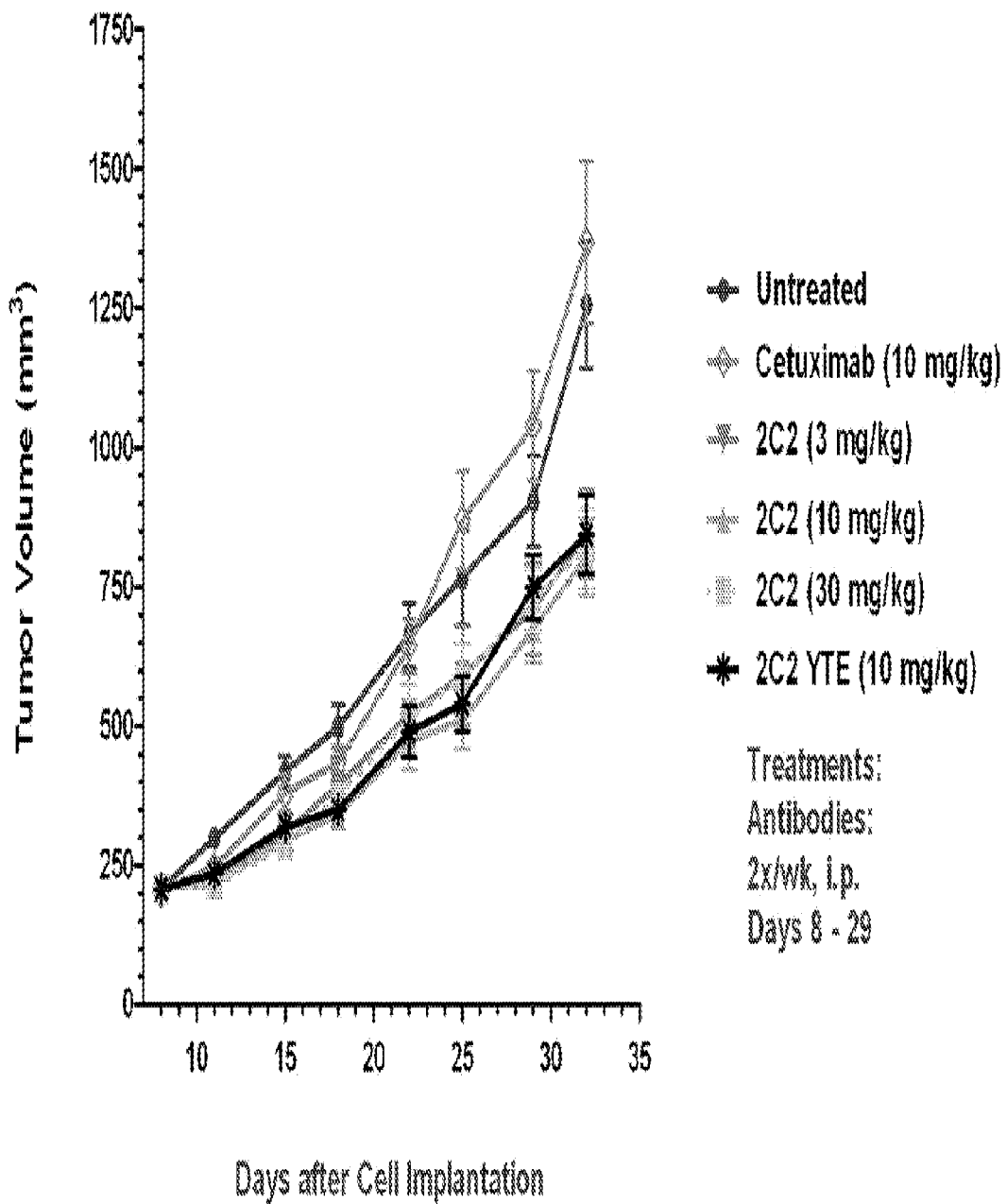

FIG. 28 shows a reduction in tumor volume after administration of the 2C2 monoclonal antibody using the human HCT-116 colorectal xenograft model. 30 mg/kg of 2C2 administered twice per week was maximally efficacious at 43% dTGI. 2C2-YTE and 2C2 both at 10 mg/kg have comparable activity. The HCT-116 xenograft model contains a KRAS mutation.

Figure 29:
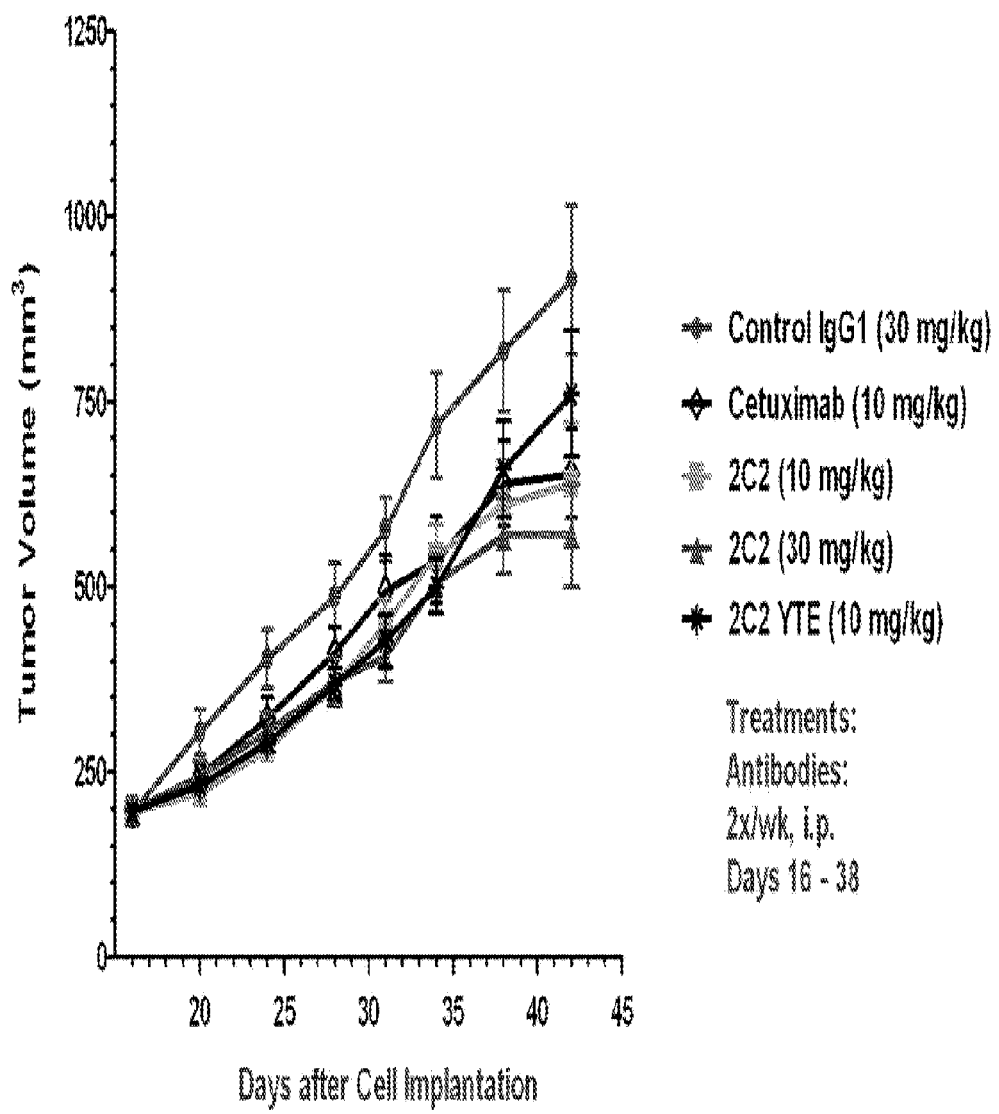

FIG. 29 shows a reduction in tumor volume after administration of the 2C2 monoclonal antibody using the human LOVO colorectal xenograft model. 30 mg/kg of 2C2 administered twice per week was maximally efficacious at 48% dTGI. 2C2-YTE and 2C2 both at 10 mg/kg have comparable activity. The LOVO xenograft model contains a KRAS mutation.

Figure 30:
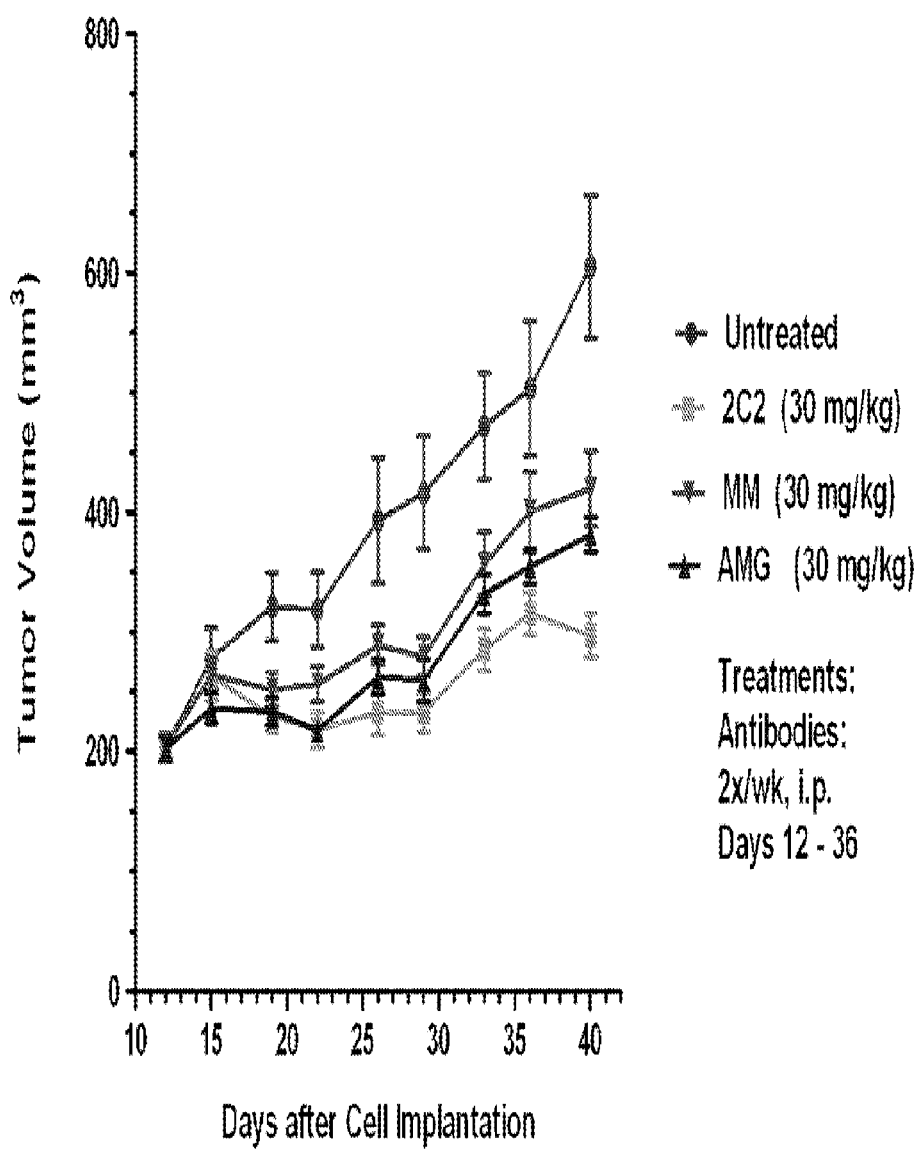

FIG. 30 shows a reduction in tumor volume after administration of the 2C2 monoclonal antibody using the human DU145 prostate xenograft model. 30 mg/kg of 2C2 administered twice per week was maximally efficacious at 77% dTGI. The DU145 xenograft model contains a LKB-1 deletion.

FIG. 31 shows a reduction in tumor volume after administration of the 2C2 monoclonal antibody using the human BT-474 breast cancer orthotopic xenograft model. Panel A shows 30 mg/kg of 2C2 administered twice per week was maximally efficacious at 55% dTGI. Panel B shows a reduction in tumor volume after the combined administration of the 2C2 monoclonal antibody with the small molecule drug lapatinib using the human BT-474 breast cancer orthotopic xenograft model. The addition of 2C2 to lapatinib increased the activity of lapatinib during the treatment phase and modestly delayed tumor regrowth during the tumor regrowth phase. 2C2-YTE and 2C2 both at 30 mg/kg have comparable activity during the treatment phase as monoefficacy treatments. Panel C shows a reduction in tumor volume after the administration of the 2C2 monoclonal antibody using the human BT-474 breast cancer orthotopic xenograft model. Trastuzumab alone was very active in this model and little enhancement was seen by the addition of 2C2 in this model. The BT-474 xenograft model contains amplified HER2 (3+ by HercepTest).

Figure 32:
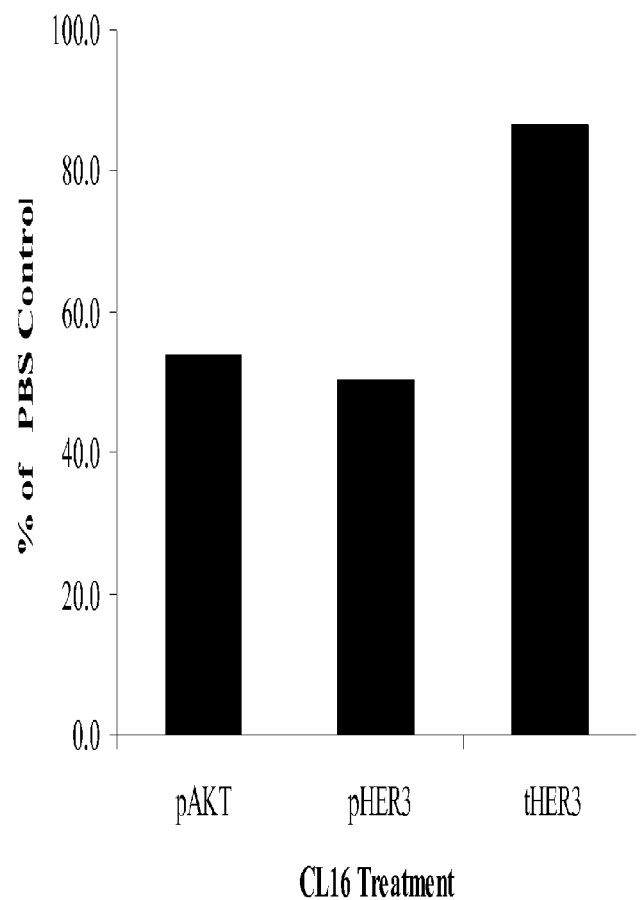

FIG. 32 shows that treatment with Clone 16 (2C2 precursor) reduces the levels of pHER3 and pAKT in BT-474 xenograft tumor extracts. In this experiment the levels were of pHER3 and pAKT were reduced by 50% and 46.1%, respectively. No change was seen in total HER3 levels in this experiment.

FIG. 33 shows a reduction in tumor volume after administration of the 2C2 monoclonal antibody using the human MCF-7 breast cancer orthotopic xenograft model. Panel A shows 10 mg/kg of 2C2 administered twice per week was maximally efficacious at 34% dTGI. 2C2-YTE and 2C2 both at 10 mg/kg have comparable activity. Panel B shows a reduction in tumor volume after the combined administration of the 2C2 monoclonal antibody with the small molecule drug paclitaxel using the human MCF-7 breast cancer orthotopic xenograft model. The addition of 2C2 to paclitaxel increased the activity of paclitaxel during the treatment phase. The MCF-7 xenograft model contains low levels of HER2 (1+ by HercepTest).

FIG. 34 shows a reduction in tumor volume after administration of 2C2-YTE using the human MDA-MB-361 breast cancer orthotopic xenograft model (Panels A-C). The addition of 2C2-YTE to the monoclonal antibody trastuzumab increased the activity of trastuzumab during the treatment phase and delayed tumor regrowth during the tumor regrowth phase (Panel A). The addition of 2C2-YTE to the monoclonal antibody rhuMAb 2C4 modestly increased the activity of rhuMAb 2C4 but did not delay the regrowth of the tumors (Panel B). Addition of 2C2-YTE to the small molecule drug lapatinib increased the activity of lapatinib but did not delay the regrowth of the tumors (Panel C).

Figure 35:
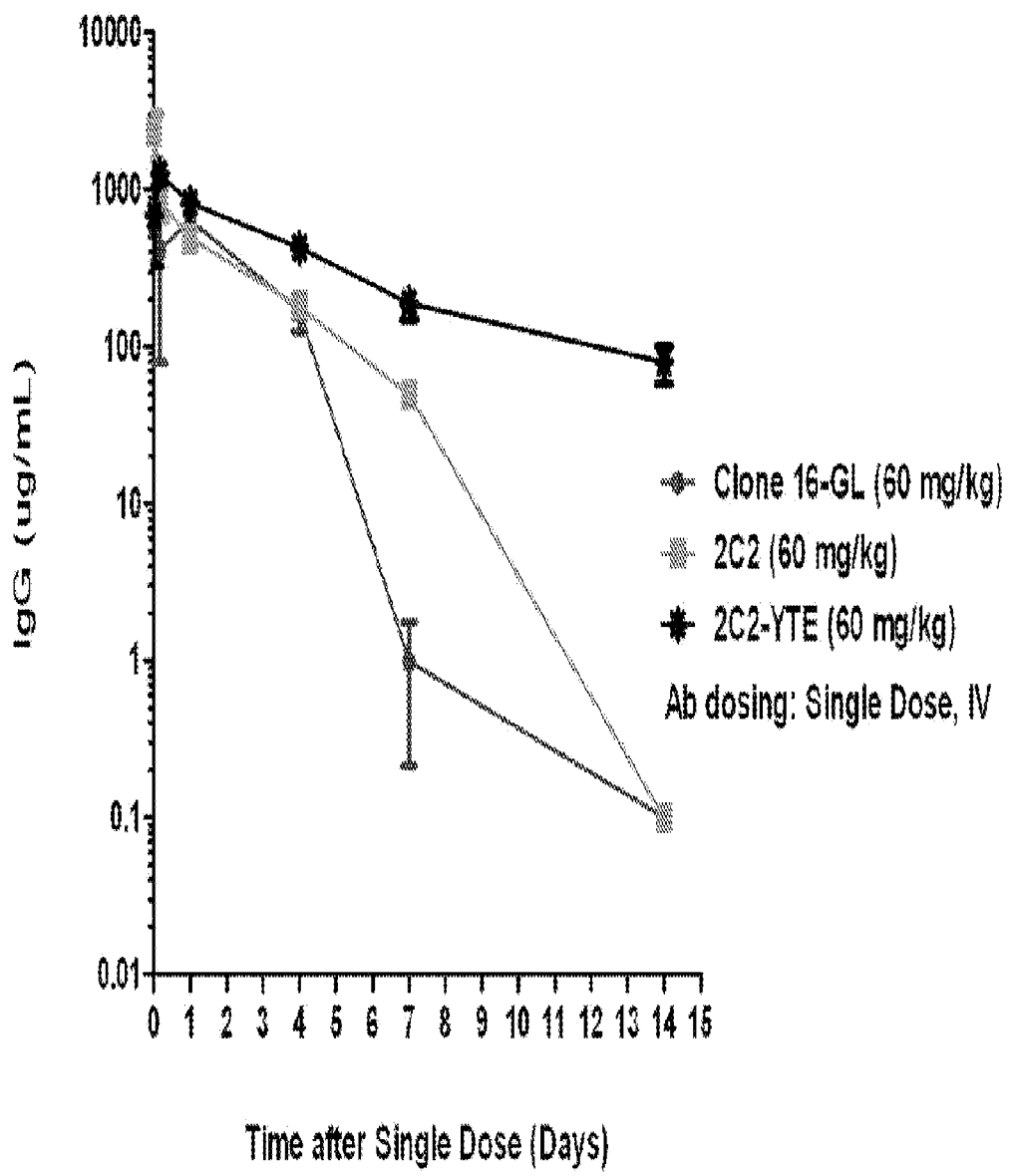

FIG. 35 shows prolonged exposure levels of the monoclonal antibody 2C2-YTE in serum of naïve human FcRn SCID transgenic mice compared to 2C2 and Clone 16-GL after a single dose of these antibodies at 60 mg/kg.

Figure 36:
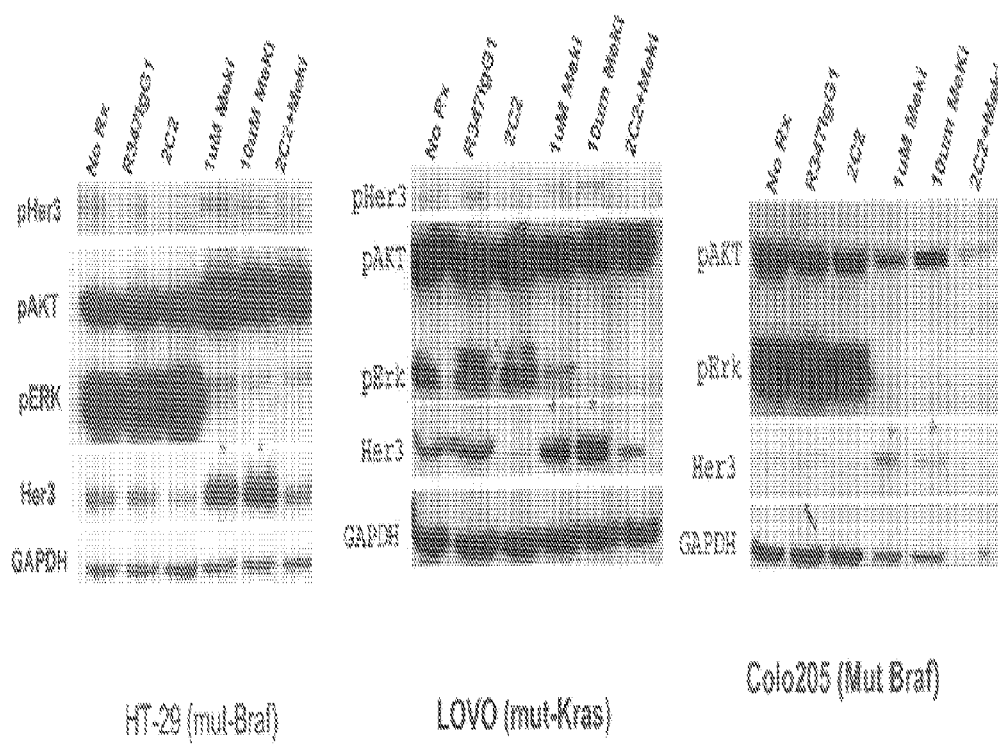

FIG. 36 shows HER3 protein levels increase in response to treatment with the MEK inhibitor (MEKi) selumetinib (indicated by a star). Treatment with the MEKi in combination with 2C2 reduces the HER3 levels back to normal in HT-29 cells (left), LOVO (middle) and Colo205 (right) cancer models. The levels of pHER3 were also examined in the HT-29 and LOVO models and shown to respond similarly.

FIG. 37 shows that the combination of 2C2-YTE and selumetinib increases the anti-tumor efficacy of either agent alone in subcutaneous cancer xenograft models and A549 (Panel A, top), HT-29 (Panel B, top), LOVO (Panel C, top). Western blot analysis from tumor lysates (A549, HT-29 and LOVO xenograph models) of mice treated with the combination showed that phospho-HER3 and phospho-ERK were completely inhibited (Panels A-C, bottom).

DETAILED DESCRIPTION OF THE INVENTION

The present invention provides molecules and antigen-binding fragments thereof that bind to HER3. In some aspects, such molecules are antibodies and antigen-binding fragments thereof that specifically bind to HER3. Related polynucleotides, compositions comprising the anti-HER3 antibodies or antigen-binding fragments thereof, and methods of making the anti-HER3 antibodies and antigen-binding fragments are also provided. Methods of using the novel anti-HER3 antibodies, such as methods of treating cancer in a subject and diagnostic uses, are further provided.

In order that the present invention can be more readily understood, certain terms are first defined. Additional definitions are set forth throughout the detailed description.

I. Definitions

Before describing the present invention in detail, it is to be understood that this invention is not limited to specific compositions or process steps, as such can vary. As used in this specification and the appended claims, the singular forms "a", "an" and "the" include plural referents unless the context clearly dictates otherwise. The terms "a" (or "an"), as well as the terms "one or more," and "at least one" can be used interchangeably herein.

Furthermore, "and/or" where used herein is to be taken as specific disclosure of each of the two specified features or components with or without the other. Thus, the term and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this invention.

Units, prefixes, and symbols are denoted in their Système International de Unites (SI) accepted form. Numeric ranges are inclusive of the numbers defining the range. Unless otherwise indicated, amino acid sequences are written left to right in amino to carboxy orientation. The headings provided herein are not limitations of the various aspects, which can be had by reference to the specification as a whole. Accordingly, the terms defined immediately below are more fully defined by reference to the specification in its entirety.

It is understood that wherever aspects are described herein with the language "comprising," otherwise analogous aspects described in terms of "consisting of" and/or "consisting essentially of" are also provided.

Amino acids are referred to herein by either their commonly known three letter symbols or by the one-letter symbols recommended by the IUPAC-IUB Biochemical Nomenclature Commission. Nucleotides, likewise, are referred to by their commonly accepted single-letter codes.

The terms "HER3" and "HER3 receptor" are used interchangeably herein, and refer to the ErbB3 protein (also referred to as HER3, ErbB3 receptor in the literature) as described in U.S. Pat. No. 5,480,968 and in Plowman et al. (1990) Proc. Natl. Acad. Sci. USA 87, 4905-4909; see also, Kani et al. (2005) Biochemistry 44, 15842-15857, and Cho & Leahy (2002) Science 297, 1330-1333. The full-length, mature HER3 protein sequence (without leader sequence) corresponds to the sequence shown in FIG. 4 and SEQ ID NO: 4 of U.S. Pat. No. 5,480,968 minus the 19 amino acid leader sequence that is cleaved from the mature protein.

The terms "inhibition" and "suppression" are used interchangeably herein and refer to any statistically significant decrease in biological activity, including full blocking of the activity. For example, "inhibition" can refer to a decrease of about 10%, 20%, 30%, 40%, 50%, 60%, 70%, 80%, 90% or 100% in biological activity. Accordingly, when the terms "inhibition" or "suppression" are applied to describe, e.g., an effect on ligand-mediated HER3 phosphorylation, the term refers to the ability of an antibody or antigen binding fragment thereof to statistically significantly decrease the phosphorylation of HER3 induced by an EGF-like ligand, relative to the phosphorylation in an untreated (control) cell. The cell which expresses HER3 can be a naturally occurring cell or cell line (e.g., a cancer cell) or can be recombinantly produced by introducing a nucleic acid encoding HER3 into a host cell. In one aspect, the anti-HER3 binding molecule, e.g., an antibody or antigen binding fragment thereof inhibits ligand mediated phosphorylation of HER3 by at least 10%, or at least 20%, or at least 30%, or at least 40%, or at least 50%, or at least 60%, or at least 70%, or at least 80%, or at least 905, or about 100%, as determined, for example, by Western blotting followed by probing with an anti-phosphotyrosine antibody or by ELISA, as described in the Examples infra.

The term "growth suppression" of a cell expressing HER3, as used herein, refer to the ability of anti-HER3 binding molecule, e.g., an antibody or antigen-binding fragment thereof to statistically significantly decrease proliferation of a cell expressing HER3 relative to the proliferation in the absence of the anti-HER3 binding molecule, e.g., an antibody or antigen-binding fragment thereof. In one aspect, the proliferation of a cell expressing HER3 (e.g., a cancer cell) can be decreased by at least 10%, or at least 20%, or at least 30%, or at least 40%, or at least 50%, or at least 60%, or at least 70%, or at least 80%, or at least 90%, or about 100% when cells are contacted with an anti-HER3 binding molecule, e.g., an antibody or antigen-binding fragment thereof of the present invention, relative to the proliferation measured in the absence of the anti-HER3 binding molecule, e.g., an antibody or antigen-binding fragment thereof (control conditions). Cellular proliferation can be assayed using art recognized techniques with measure rate of cell division, the fraction of cells within a cell population undergoing cell division, and/or rate of cell loss from a cell population due to terminal differentiation or cell death (e.g., thymidine incorporation).

The terms "antibody" or "immunoglobulin," as used interchangeably herein, include whole antibodies and any antigen binding fragment or single chains thereof.

A typical antibody comprises at least two heavy (H) chains and two light (L) chains interconnected by disulfide bonds. Each heavy chain is comprised of a heavy chain variable region (abbreviated herein as VH) and a heavy chain constant region. The heavy chain constant region is comprised of three domains, CH1, CH2, and CH3. Each light chain is comprised of a light chain variable region (abbreviated herein as VL) and a light chain constant region. The light chain constant region is comprised of one domain, CL. The VH and VL regions can be further subdivided into regions of hypervariability, termed Complementarity Determining Regions (CDR), interspersed with regions that are more conserved, termed framework regions (FW). Each VH and VL is composed of three CDRs and four FWs, arranged from amino-terminus to carboxy-terminus in the following order: FW1, CDR1, FW2, CDR2, FW3, CDR3, FW4. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (C1q) of the classical complement system. Exemplary antibodies of the present disclosure include the Clone 16 (CL16) anti-HER3 antibodies (original and germlined), affinity optimized clones including for example, the anti-HER3 2C2 antibody, and serum half-life-optimized anti-HER3 antibodies including for example the anti-HER3 2C2-YTE antibody.

The term "germlining" means that amino acids at specific positions in an antibody are mutated back to those in the germ line. E.g., the CL16 "germlined" antibody is generated from the original CL16 antibody by introducing three point mutations, Y2S, E3V and M20I, into FW1 of the VL regions.

The term "antibody" means an immunoglobulin molecule that recognizes and specifically binds to a target, such as a protein, polypeptide, peptide, carbohydrate, polynucleotide, lipid, or combinations of the foregoing through at least one antigen recognition site within the variable region of the immunoglobulin molecule. As used herein, the term "antibody" encompasses intact polyclonal antibodies, intact monoclonal antibodies, antibody fragments (such as Fab, Fab', F(ab')2, and Fv fragments), single chain Fv (scFv) mutants, multispecific antibodies such as bispecific antibodies generated from at least two intact antibodies, chimeric antibodies, humanized antibodies, human antibodies, fusion proteins comprising an antigen determination portion of an antibody, and any other modified immunoglobulin molecule comprising an antigen recognition site so long as the antibodies exhibit the desired biological activity. An antibody can be of any the five major classes of immunoglobulins: IgA, IgD, IgE, IgG, and IgM, or subclasses (isotypes) thereof (e.g. IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well known subunit structures and three-dimensional configurations. Antibodies can be naked or conjugated to other molecules such as toxins, radioisotopes, etc.

A "blocking" antibody or an "antagonist" antibody is one which inhibits or reduces biological activity of the antigen it binds, such as HER3. In a certain aspect blocking antibodies or antagonist antibodies substantially or completely inhibit the biological activity of the antigen. Desirably, the biological activity is reduced by 10%, 20%, 30%, 50%, 70%, 80%, 90%, 95%, or even 100%.

The term "HER3 antibody" or "an antibody that binds to HER3" or "anti-HER3" refers to an antibody that is capable of binding HER3 with sufficient affinity such that the antibody is useful as a therapeutic agent or diagnostic reagent in targeting HER3. The extent of binding of an anti-HER3 antibody to an unrelated, non-HER3 protein is less than about 10% of the binding of the antibody to HER3 as measured, e.g., by a radioimmunoassay (RIA), BIACORE™ (using recombinant HER3 as the analyte and antibody as the ligand, or vice versa), or other binding assays known in the art. In certain aspects, an antibody that binds to HER3 has a dissociation constant ($K_D$) of ≤1 µM, ≤100 nM, ≤10 nM, ≤1 nM, ≤0.1 nM, ≤10 pM, ≤1 pM, or ≤0.1 pM.

The terms "antigen binding fragment" refers to a portion of an intact antibody and refers to the antigenic determining variable regions of an intact antibody. It is known in the art that the antigen binding function of an antibody can be performed by fragments of a full-length antibody. Examples of antibody fragments include, but are not limited to Fab, Fab', F(ab')2, and Fv fragments, linear antibodies, single chain antibodies, and multispecific antibodies formed from antibody fragments.

A "monoclonal antibody" refers to a homogeneous antibody population involved in the highly specific recognition and binding of a single antigenic determinant, or epitope. This is in contrast to polyclonal antibodies that typically include different antibodies directed against different antigenic determinants. The term "monoclonal antibody" encompasses both intact and full-length monoclonal antibodies as well as antibody fragments (such as Fab, Fab', F(ab')2, Fv), single chain (scFv) mutants, fusion proteins comprising an antibody portion, and any other modified immunoglobulin molecule comprising an antigen recognition site. Furthermore, "monoclonal antibody" refers to such antibodies made in any number of ways including, but not limited to, by hybridoma, phage selection, recombinant expression, and transgenic animals.

The term "humanized antibody" refers to an antibody derived from a non-human (e.g., murine) immunoglobulin, which has been engineered to contain minimal non-human (e.g., murine) sequences. Typically, humanized antibodies are human immunoglobulins in which residues from the complementary determining region (CDR) are replaced by residues from the CDR of a non-human species (e.g., mouse, rat, rabbit, or hamster) that have the desired specificity, affinity, and capability (Jones et al., 1986, *Nature,* 321:522-525; Riechmann et al., 1988, *Nature,* 332:323-327; Verhoeyen et al., 1988, *Science,* 239:1534-1536). In some instances, the Fv framework region (FW) residues of a human immunoglobulin are replaced with the corresponding residues in an antibody from a non-human species that has the desired specificity, affinity, and capability.

The humanized antibody can be further modified by the substitution of additional residues either in the Fv framework region and/or within the replaced non-human residues to refine and optimize antibody specificity, affinity, and/or capability. In general, the humanized antibody will comprise substantially all of at least one, and typically two or three, variable domains containing all or substantially all of the CDR regions that correspond to the non-human immunoglobulin whereas all or substantially all of the FR regions are those of a human immunoglobulin consensus sequence. The humanized antibody can also comprise at least a portion of an immunoglobulin constant region or domain (Fc), typically that of a human immunoglobulin. Examples of methods used to generate humanized antibodies are described in U.S. Pat. No. 5,225,539 or U.S. Pat. No. 5,639,641.

A "variable region" of an antibody refers to the variable region of the antibody light chain or the variable region of the antibody heavy chain, either alone or in combination. The variable regions of the heavy and light chain each consist of four framework regions (FW) connected by three complementarity determining regions (CDRs) also known as hypervariable regions. The CDRs in each chain are held together in close proximity by the FW regions and, with the CDRs from the other chain, contribute to the formation of the antigen-binding site of antibodies. There are at least two techniques for determining CDRs: (1) an approach based on cross-species sequence variability (i.e., Kabat et al. Sequences of Proteins of Immunological Interest, (5th ed., 1991, National Institutes of Health, Bethesda Md.)); and (2) an approach based on crystallographic studies of antigen-antibody complexes (Al-lazikani et al. (1997) *J. Molec. Biol.* 273:927-948)). In addition, combinations of these two approaches are sometimes used in the art to determine CDRs.

The Kabat numbering system is generally used when referring to a residue in the variable domain (approximately residues 1-107 of the light chain and residues 1-113 of the heavy chain) (e.g., Kabat et al., Sequences of Immunological Interest, 5th Ed. Public Health Service, National Institutes of Health, Bethesda, Md. (1991)).

The amino acid position numbering as in Kabat, refers to the numbering system used for heavy chain variable domains or light chain variable domains of the compilation of antibodies in Kabat et al., Sequences of Proteins of Immunological Interest, 5th Ed. Public Health Service, National Institutes of Health, Bethesda, Md. (1991). Using this numbering system, the actual linear amino acid sequence can contain fewer or additional amino acids corresponding to a shortening of, or insertion into, a FW or CDR of the variable domain. For example, a heavy chain variable domain can include a single amino acid insert (residue 52a according to Kabat) after residue 52 of H2 and inserted residues (e.g., residues 82a, 82b, and 82c, etc. according to Kabat) after heavy chain FW residue 82.

TABLE 1

| Loop | Kabat | AbM | Chothia |
|---|---|---|---|
| L1 | L24-L34 | L24-L34 | L24-L34 |
| L2 | L50-L56 | L50-L56 | L50-L56 |
| L3 | L89-L97 | L89-L97 | L89-L97 |
| H1 | H31-H35B | H26-H35B | H26-H32 . . . 34 |
| | | (Kabat Numbering) | |
| H1 | H31-H35 | H26-H35 | H26-H32 |
| | | (Chothia Numbering) | |
| H2 | H50-H65 | H50-H58 | H52-H56 |
| H3 | H95-H102 | H95-H102 | H95-H102 |

The Kabat numbering of residues can be determined for a given antibody by alignment at regions of homology of the sequence of the antibody with a "standard" Kabat numbered sequence. Chothia refers instead to the location of the structural loops (Chothia and Lesk, J. Mol. Biol. 196:901-917 (1987)). The end of the Chothia CDR-H1 loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34). The AbM hypervariable regions represent a compromise between the Kabat CDRs and Chothia structural loops, and are used by Oxford Molecular's AbM antibody modeling software.

IMGT (ImMunoGeneTics) also provides a numbering system for the immunoglobulin variable regions, including the CDRs. See e.g., Lefranc, M. P. et al., Dev. Comp. Immunol. 27: 55-77(2003), which is herein incorporated by reference. The IMGT numbering system was based on an alignment of more than 5,000 sequences, structural data, and characterization of hypervariable loops and allows for easy comparison of the variable and CDR regions for all species. According to the IMGT numbering schema VH-CDR1 is at positions 26 to 35, VH-CDR2 is at positions 51 to 57, VH-CDR3 is at positions 93 to 102, VL-CDR1 is at positions 27 to 32, VL-CDR2 is at positions 50 to 52, and VL-CDR3 is at positions 89 to 97.

As used throughout the specification the VH CDRs sequences described correspond to the classical Kabat numbering locations, namely Kabat VH-CDR1 is at positions 31-35, VH-CDR2 is a positions 50-65, and VH-CDR3 is at positions 95-102. VL-CDR2 and VL-CDR3 also correspond to classical Kabat numbering locations, namely positions 50-56 and 89-97, respectively. As used herein, the terms "VL-CDR1" or "light chain CDR1" correspond to sequences located at Kabat positions 23-34 in the VL (in contrast, the classical VL-CDR1 location according to the Kabat numbering schema corresponds to positions 24-34).

As used herein the Fc region includes the polypeptides comprising the constant region of an antibody excluding the first constant region immunoglobulin domain. Thus Fc refers to the last two constant region immunoglobulin domains of IgA, IgD, and IgG, and the last three constant region immunoglobulin domains of IgE and IgM, and the flexible hinge N-terminal to these domains. For IgA and IgM Fc may include the J chain. For IgG, Fc comprises immunoglobulin domains Cgamma2 and Cgamma3 (Cγ2 and Cγ3) and the hinge between Cgamma1 (Cγ1) and Cgamma2 (Cγ2). Although the boundaries of the Fc region may vary, the human IgG heavy chain Fc region is usually defined to comprise residues C226 or P230 to its carboxyl-terminus, wherein the numbering is according to the EU index as set forth in Kabat (Kabat et al., Sequences of Proteins of Immunological Interest, 5th Ed. Public Health Service, National Institutes of Health, Bethesda, Md. (1991)). Fc may refer to this region in isolation, or this region in the context of an antibody, antibody fragment, or Fc fusion protein. Polymorphisms have been observed at a number of different Fc positions, including but not limited to positions 270, 272, 312, 315, 356, and 358 as numbered by the EU index, and thus slight differences between the presented sequence and sequences in the prior art may exist.

The term "human antibody" means an antibody produced by a human or an antibody having an amino acid sequence corresponding to an antibody produced by a human made using any technique known in the art. This definition of a human antibody includes intact or full-length antibodies, fragments thereof, and/or antibodies comprising at least one human heavy and/or light chain polypeptide such as, for example, an antibody comprising murine light chain and human heavy chain polypeptides.

The term "chimeric antibodies" refers to antibodies wherein the amino acid sequence of the immunoglobulin molecule is derived from two or more species. Typically, the variable region of both light and heavy chains corresponds to the variable region of antibodies derived from one species of mammals (e.g., mouse, rat, rabbit, etc) with the desired specificity, affinity, and capability while the constant regions are homologous to the sequences in antibodies derived from another (usually human) to avoid eliciting an immune response in that species.

The terms "YTE" or "YTE mutant" refer to a mutation in IgG1 Fc that results in an increase in the binding to human FcRn and improves the serum half-life of the antibody having the mutation. A YTE mutant comprises a combination of three mutations, M252Y/S254T/T256E (EU numbering Kabat et al. (1991) Sequences of Proteins of Immunological Interest, U.S. Public Health Service, National Institutes of Health, Washington, D.C.), introduced into the heavy chain of an IgG1. See U.S. Pat. No. 7,658,921, which is incorporated by reference herein. The YTE mutant has been shown to increase the serum half-life of antibodies approximately four-times as compared to wild-type versions of the same antibody (Dall'Acqua et al., J. Biol. Chem. 281:23514-24 (2006)). See also U.S. Pat. No. 7,083,784, which is hereby incorporated by reference in its entirety.

"Binding affinity" generally refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant ($K_D$). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention.

"Potency" is normally expressed as an $IC_{50}$ value, in nM unless otherwise stated. $IC_{50}$ is the median inhibitory concentration of an antibody molecule. In functional assays, $IC_{50}$ is the concentration that reduces a biological response by 50% of its maximum. In ligand-binding studies, $IC_{50}$ is the concentration that reduces receptor binding by 50% of maximal specific binding level. $IC_{50}$ can be calculated by any number of means known in the art. Improvement in potency can be determined by measuring, e.g., against the parent CL16 (Clone 16) monoclonal antibody.

The fold improvement in potency for the antibodies or polypeptides of the invention as compared to a Clone 16 antibody can be at least about 2-fold, at least about 4-fold, at least about 6-fold, at least about 8-fold, at least about 10-fold, at least about 20-fold, at least about 30-fold, at least about 40-fold, at least about 50-fold, at least about 60-fold, at least about 70-fold, at least about 80-fold, at least about 90-fold, at least about 100-fold, at least about 110-fold, at least about 120-fold, at least about 130-fold, at least about 140-fold, at least about 150-fold, at least about 160-fold, at least about 170-fold, or at least about 180-fold or more.

"Antibody-dependent cell-mediated cytotoxicity" or "ADCC" refers to a form of cytotoxicity in which secreted Ig bound onto Fc receptors (FcRs) present on certain cytotoxic cells (e.g., Natural Killer (NK) cells, neutrophils, and macrophages) enables these cytotoxic effector cells to bind specifically to an antigen-bearing target cell and subsequently kill the target cell with cytotoxins. Specific high-affinity IgG antibodies directed to the surface of target cells "arm" the cytotoxic cells and are absolutely required for such killing. Lysis of the target cell is extracellular, requires direct cell-to-cell contact, and does not involve complement. It is contemplated that, in addition to antibodies, other proteins comprising Fc regions, specifically Fc fusion proteins, having the capacity to bind specifically to an antigen-bearing target cell will be able to effect cell-mediated cytotoxicity. For simplicity, the cell-mediated cytotoxicity resulting from the activity of an Fc fusion protein is also referred to herein as ADCC activity.

A polypeptide, antibody, polynucleotide, vector, cell, or composition which is "isolated" is a polypeptide, antibody, polynucleotide, vector, cell, or composition which is in a form not found in nature. Isolated polypeptides, antibodies, polynucleotides, vectors, cells or compositions include those which have been purified to a degree that they are no longer in a form in which they are found in nature. In some aspects, an antibody, polynucleotide, vector, cell, or composition which is isolated is substantially pure.

The term "subject" refers to any animal (e.g., a mammal), including, but not limited to, humans, non-human primates, rodents, and the like, which is to be the recipient of a particular treatment. Typically, the terms "subject" and "patient" are used interchangeably herein in reference to a human subject.

The term "pharmaceutical composition" refers to a preparation which is in such form as to permit the biological activity of the active ingredient to be effective, and which contains no additional components which are unacceptably toxic to a subject to which the composition would be administered. Such composition can be sterile.

An "effective amount" of an antibody as disclosed herein is an amount sufficient to carry out a specifically stated purpose. An "effective amount" can be determined empirically and in a routine manner, in relation to the stated purpose.

The term "therapeutically effective amount" refers to an amount of an antibody or other drug effective to "treat" a disease or disorder in a subject or mammal.

The word "label" when used herein refers to a detectable compound or composition which is conjugated directly or indirectly to the antibody so as to generate a "labeled" antibody. The label can be detectable by itself (e.g., radioisotope labels or fluorescent labels) or, in the case of an enzymatic label, can catalyze chemical alteration of a substrate compound or composition which is detectable.

Terms such as "treating" or "treatment" or "to treat" or "alleviating" or "to alleviate" refer to both (1) therapeutic measures that cure, slow down, lessen symptoms of, and/or halt progression of a diagnosed pathologic condition or disorder and (2) prophylactic or preventative measures that prevent and/or slow the development of a targeted pathologic condition or disorder. Thus, those in need of treatment include those already with the disorder; those prone to have the disorder; and those in whom the disorder is to be prevented. In certain aspects, a subject is successfully "treated" for cancer according to the methods of the present invention if the patient shows, e.g., total, partial, or transient remission of a certain type of cancer.

The terms "cancer", "tumor", "cancerous", and "malignant" refer to or describe the physiological condition in mammals that is typically characterized by unregulated cell growth. Examples of cancers include but are not limited to, carcinoma including adenocarcinomas, lymphomas, blastomas, melanomas, sarcomas, and leukemias. More particular examples of such cancers include squamous cell cancer, small-cell lung cancer, non-small cell lung cancer, gastrointestinal cancer, Hodgkin's and non-Hodgkin's lymphoma, pancreatic cancer, glioblastoma, glioma, cervical cancer, ovarian cancer, liver cancer such as hepatic carcinoma and hepatoma, bladder cancer, breast cancer (including hormonally mediated breast cancer, see, e.g., Innes et al. (2006) Br. J. Cancer 94:1057-1065), colon cancer, colorectal cancer, endometrial carcinoma, myeloma (such as multiple myeloma), salivary gland carcinoma, kidney cancer such as renal cell carcinoma and Wilms' tumors, basal cell carcinoma, melanoma, prostate cancer, vulval cancer, thyroid cancer, testicular cancer, esophageal cancer, various types of head and neck cancer and cancers of mucinous origins, such as, mucinous ovarian cancer, cholangiocarcinoma (liver) and renal papillary carcinoma.

As used herein, the term "carcinomas" refers to cancers of epithelial cells, which are cells that cover the surface of the body, produce hormones, and make up glands. Examples of carcinomas are cancers of the skin, lung, colon, stomach, breast, prostate and thyroid gland.

The term "KRAS mutation," as used herein, refers to mutations found in certain cancers in a human homolog of the v-Ki-ras2 Kirsten rat sarcoma viral oncogene. Non-limiting examples of human KRAS gene mRNA sequences include Genbank Accession Nos. NM004985 and NM033360. It has been reported that KRAS mutations are found in 73% of pancreatic tumors, 35% of colorectal tumors, 16% of ovarian tumors and 17% of lung tumors. KRAS mutation generally occur in codons 12 or 143 of the human KRAS gene.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase. A polynucleotide can comprise modified nucleotides, such as methylated nucleotides and their analogs. The preceding description applies to all polynucleotides referred to herein, including RNA and DNA.

The term "vector" means a construct, which is capable of delivering, and in some aspects, expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

The terms "polypeptide," "peptide," and "protein" are used interchangeably herein to refer to polymers of amino acids of any length. The polymer can be linear or branched, it can comprise modified amino acids, and it can be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that, because the polypeptides of this invention are based upon antibodies, in certain aspects, the polypeptides can occur as single chains or associated chains.

The terms "identical" or percent "identity" in the context of two or more nucleic acids or polypeptides, refer to two or more sequences or subsequences that are the same or have a specified percentage of nucleotides or amino acid residues that are the same, when compared and aligned (introducing gaps, if necessary) for maximum correspondence, not considering any conservative amino acid substitutions as part of the sequence identity. The percent identity can be measured using sequence comparison software or algorithms or by visual inspection. Various algorithms and software are known in the art that can be used to obtain alignments of amino acid or nucleotide sequences.

One such non-limiting example of a sequence alignment algorithm is the algorithm described in Karlin et al., 1990, *Proc. Natl. Acad. Sci.*, 87:2264-2268, as modified in Karlin et al., 1993, *Proc. Natl. Acad. Sci.*, 90:5873-5877, and incorporated into the NBLAST and XBLAST programs (Altschul et al., 1991, *Nucleic Acids Res.*, 25:3389-3402). In certain aspects, Gapped BLAST can be used as described in Altschul et al., 1997, *Nucleic Acids Res.* 25:3389-3402. BLAST-2, WU-BLAST-2 (Altschul et al., 1996, *Methods in Enzymology*, 266:460-480), ALIGN, ALIGN-2 (Genentech, South San Francisco, Calif.) or Megalign (DNASTAR) are additional publicly available software programs that can be used to align sequences. In certain aspects, the percent identity between two nucleotide sequences is determined using the GAP program in the GCG software package (e.g., using a NWSgapdna.CMP matrix and a gap weight of 40, 50, 60, 70, or 90 and a length weight of 1, 2, 3, 4, 5, or 6). In certain alternative aspects, the GAP program in the GCG software package, which incorporates the algorithm of Needleman and Wunsch (*J. Mol. Biol.* (48):444-453 (1970)) can be used to determine the percent identity between two amino acid sequences (e.g., using either a BLOSUM 62 matrix or a PAM250 matrix, and a gap weight of 16, 14, 12, 10, 8, 6, or 4 and a length weight of 1, 2, 3, 4, 5). Alternatively, in certain aspects, the percent identity between nucleotide or amino acid sequences is determined using the algorithm of Myers and Miller (CABIOS, 4:11-17 (1989)). For example, the percent identity can be determined using the ALIGN program (version 2.0) and using a PAM120 with residue table, a gap length penalty of 12 and a gap penalty of 4. Appropriate parameters for maximal alignment by particular alignment software can be determined by one skilled in the art. In certain aspects, the default parameters of the alignment software are used.

In certain aspects, the percentage identity "X" of a first amino acid sequence to a second sequence amino acid is calculated as 100× (Y/Z), where Y is the number of amino acid residues scored as identical matches in the alignment of the first and second sequences (as aligned by visual inspection or a particular sequence alignment program) and Z is the total number of residues in the second sequence. If the length of a first sequence is longer than the second sequence, the percent identity of the first sequence to the second sequence will be higher than the percent identity of the second sequence to the first sequence.

A "conservative amino acid substitution" is one in which one amino acid residue is replaced with another amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., asparagine, glutamine, serine, threonine, tyrosine, cysteine), nonpolar side chains (e.g., glycine, alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). For example, substitution of a phenylalanine for a tyrosine is a conservative substitution. In certain aspects, conservative substitutions in the sequences of the polypeptides and antibodies of the invention do not abrogate the binding of the polypeptide or antibody containing the amino acid sequence, to the antigen(s), i.e., the HER3 to which the polypeptide or antibody binds. Methods of identifying nucleotide and amino acid conservative substitutions which do not eliminate antigen binding are well-known in the art (see, e.g., Brummell et al., *Biochem.* 32: 1180-1 187 (1993); Kobayashi et al., *Protein Eng.* 12(10):879-884 (1999); and Burks et al., *Proc. Natl. Acad. Sci. USA* 94:412-417 (1997)).

The term "consensus sequence," as used herein with respect to light chain (VL) and heavy chain (VH) variable regions, refers to a composite or genericized VL or VH sequence defined based on information as to which amino acid residues within the VL or VH chain are amenable to modification without detriment to antigen binding. Thus, in a "consensus sequence" for a VL or VH chain, certain amino acid positions are occupied by one of multiple possible amino acid residues at that position. For example, if an arginine (R) or a serine (S) occur at a particular position, then that particular position within the consensus sequence can be either arginine or serine (R or S). Consensus sequences for VH and VL chain can be defined, for example, by in vitro affinity maturation (e.g., randomizing every amino acid position in a certain CDR using degenerate coding primers), by scanning mutagenesis (e.g., alanine scanning mutagenesis) of amino acid residues within the antibody CDRs, or any other methods known in the art, followed by evaluation of the binding of the mutants to the antigen to determine whether the mutated amino acid position affects antigen binding. In some aspects, mutations are introduced in the CDR regions. In other aspects, mutations are introduced in framework regions. In some other aspects, mutations are introduced in CDR and framework regions.

II. Anti-HER3-Binding Molecules

The present invention provides HER3 binding molecules, e.g., antibodies and antigen-binding fragments thereof that specifically bind HER3. The full-length amino acid (aa) and nucleotide (nt) sequences for HER3 are known in the art (see, e.g., UniProt Acc. No. P2186 for human HER3, or UniProt Acc. No. O88458 for mouse HER3). In some aspects, the anti-HER3 binding molecules are human antibodies. In certain aspects, the HER3 binding molecules are antibodies or antigen-binding fragments thereof. In some aspects, HER3 binding molecules, e.g., antibodies or antigen-binding fragments thereof comprise a Fab, a Fab', a F(ab')$_2$, a Fd, a single chain Fv or scFv, a disulfide linked Fv, a V-NAR domain, an IgNar, an intrabody, an IgGΔCH2, a minibody, a F(ab')$_3$, a tetrabody, a triabody, a diabody, a single-domain antibody, DVD-Ig, Fcab, mAb$^2$, a (scFv)$_2$, or a scFv-Fc. In some aspects, the antibody is of the IgG1 subtype and comprises the triple mutant YTE, as disclosed supra in the Definitions section.

In certain aspects, anti-HER3 antibodies or antigen-binding fragments thereof of the invention are modified compared to the parent Clone 16 (CL16) antibody. The modifications can include mutations in the CDR regions and/or in the FW regions as compared to CL16. In certain aspects, an anti-HER3 antibody of the invention comprises modifications to CDR1 and/or CDR3 of the light chain of CL16, including, but not limited to:

1) a light chain CDR1 comprising the consensus sequence X$_1$GSX$_2$SNIGLNYVS(SEQ ID NO:49), wherein X$_1$ is selected from R or S, and X$_2$ is selected from S or L; and 2) a light chain CDR3 comprising the consensus sequence AAWDDX$_3$X$_4$X$_5$GEX$_6$(SEQ ID NO:50), wherein X$_3$ is selected from S or G, X$_4$ is selected from L or P, X$_5$ is selected from R, I, P or S, and X$_6$ is selected from V or A.

In certain aspects, an anti-HER3 antibody or antigen-binding fragment thereof of the invention comprises modifications to CDR2 of the heavy chain of CL16, including, but not limited to a heavy chain CDR1 comprising the consensus sequence X$_7$IGSSGGVTNYADSVKG(SEQ ID NO:51), wherein X$_7$ is selected from Y, I or V.

In one aspect, an anti-HER3 antibody or antigen binding fragment thereof comprises a VL region comprising the consensus amino acid sequence:

```
[FW1]X1GSX2SNIGLNYVS (SEQ ID NO: 49)

[FW2]RNNQRPS (SEQ ID NO: 21)

[FW3]AAWDDX3X4X5GEX6 (SEQ ID NO: 50)

[FW4]
``` wherein [FW$_1$], [FW$_2$], [FW$_3$] and [FW$_4$] represent the amino acid residues of VL framework region 1 (SEQ ID NO: 40 or 44), VL framework region 2 (SEQ ID NO: 41), VL framework region 3 (SEQ ID NO: 42) and VL framework region 4 (SEQ ID NO: 43), and wherein X$_1$ represents amino acid residues arginine (R) or serine (S), X$_2$ represents amino acid residues serine (S) or leucine (L), X$_3$ represents amino acid residues serine (S) or glutamic acid (E), X$_4$ represents amino acid residues leucine (L) or proline (P), X$_5$ represents amino acid residues arginine (R), isoleucine (I), proline (P) or serine (S), and X$_6$ represents amino acid residues valine (V) or arginine (R).

In one aspect, an anti-HER3 antibody or antigen binding fragment thereof comprises a VH region comprises the consensus amino acid sequence:

```
[FW5]YYYMQ (SEQ ID NO: 31)

[FW6]X7IGSSGGVTNYADSVKG (SEQ ID NO: 51)

[FW7]VGLGDAFDI (SEQ ID NO: 35)

[FW8]
``` wherein [FW$_5$], [FW$_6$], [FW$_7$] and [FW$_8$] represent the amino acid residues of VH framework region 1 (SEQ ID NO: 36), VH framework region 2 (SEQ ID NO: 37), VH framework region 3 (SEQ ID NO: 38) and VH framework region 4 (SEQ ID NO: 39), and wherein X$_7$ represents amino acid residues tyrosine (Y), isoleucine (I) or valine (V).

In one aspect, an anti-HER3 antibody or antigen binding fragment thereof comprises a VL region comprising the consensus amino acid sequence:

```
[FW1]X1GSX2SNIGLNYVS (SEQ ID NO: 49)

[FW2]RNNQRPS (SEQ ID NO: 21)

[FW3]AAWDDX3X4X5GEX6 (SEQ ID NO: 50)

[FW4]
``` wherein [FW$_1$], [FW$_2$], [FW$_3$] and [FW$_4$] represent the amino acid residues of VL framework region 1 (SEQ ID NO: 40 or 44), VL framework region 2 (SEQ ID NO:

41), VL framework region 3 (SEQ ID NO: 42) and VL framework region 4 (SEQ ID NO: 43), and wherein $X_1$ represents amino acid residues arginine (R) or serine (S), $X_2$ represents amino acid residues serine (S) or leucine (L), $X_3$ represents amino acid residues serine (S) or glutamic acid (E), $X_4$ represents amino acid residues leucine (L) or proline (P), $X_5$ represents amino acid residues arginine (R), isoleucine (I), proline (P) or serine (S), and $X_6$ represents amino acid residues valine (V) or arginine (R); and wherein said anti-HER3 antibody or antigen binding fragment thereof further comprises a VH region which comprises the consensus amino acid sequence:

[FW$_5$]YYYMQ (SEQ ID NO: 31)

[FW$_6$]X$_7$IGSSGGVTNYADSVKG (SEQ ID NO: 51)

[FW$_7$]VGLGDAFDI (SEQ ID NO: 35)

[FW$_8$]

wherein [FW$_5$], [FW$_6$], [FW$_D$] and [FW$_8$] represent the amino acid residues of VH framework region 1 (SEQ ID NO: 36), VH framework region 2 (SEQ ID NO: 37), VH framework region 3 (SEQ ID NO: 38) and VH framework region 4 (SEQ ID NO: 39), and wherein $X_7$ represents amino acid residues tyrosine (Y), isoleucine (I) or valine (V).

In some aspects, an anti-HER3 antibody or antigen-binding fragment thereof of the invention comprises a VL-CDR1 consisting of sequence selected from the group consisting of SEQ ID NOs: 18, 19 and 20. In some aspects, an anti-HER3 antibody or antigen-binding fragment thereof of the invention comprises a VL-CDR1 comprising a sequence selected from the group consisting of SEQ ID NOs: 18, 19 and 20. In some aspects, an anti-HER3 antibody or antigen-binding fragment thereof of the invention comprises a VL-CDR2 consisting of SEQ ID NO: 21. In some aspects, an anti-HER3 antibody or antigen-binding fragment thereof of the invention comprises a VL-CDR2 comprising SEQ ID NO: 21. In some aspects, an anti-HER3 antibody or antigen-binding fragment thereof of the invention comprises a VL-CDR3 consisting of a sequence selected from the group consisting of SEQ ID NOs: 22, 23, 24, 25, 26, 27, 28, 29, and 30. In some aspects, an anti-HER3 antibody or antigen-binding fragment thereof of the invention comprises a VL-CDR3 comprising a sequence selected from the group consisting of SEQ ID NOs: 22, 23, 24, 25, 26, 27, 28, 29, and 30.

In some aspects, an anti-HER3 antibody or antigen-binding fragment thereof of the invention comprises a VH-CDR1 consisting of SEQ ID NO: 31. In some aspects, an anti-HER3 antibody or antigen-binding fragment thereof of the invention comprises a VH-CDR1 comprising SEQ ID NO: 31. In some aspects, an anti-HER3 antibody or antigen-binding fragment thereof of the invention comprises a VH-CDR2 consisting of a sequence selected from the group consisting of SEQ ID NOs: 32, 33 and 34. In some aspects, an anti-HER3 antibody or antigen-binding fragment thereof of the invention comprises a VH-CDR2 comprising a sequence selected from the group consisting of SEQ ID NOs: 32, 33 and 34. In some aspects, an anti-HER3 antibody or antigen-binding fragment thereof of the invention comprises a VH-CDR3 consisting of SEQ ID NO: 35. In some aspects, an anti-HER3 antibody or antigen-binding fragment thereof of the invention comprises a VH-CDR3 comprising SEQ ID NO: 35.

In some aspects, an anti-HER3 antibody or antigen-binding fragment thereof of the invention comprises a VL-CDR1 consisting of a sequence selected from the group consisting of SEQ ID NOs: 18, 19 and 20, except for one, two, three or four amino acid substitutions. In some aspects, an anti-HER3 antibody or antigen-binding fragment thereof of the invention comprises a VL-CDR1 comprising a sequence selected from the group consisting of SEQ ID NOs: 18, 19 and 20, except for one, two, three or four amino acid substitutions. In some aspects, an anti-HER3 antibody or antigen-binding fragment thereof of the invention comprises a VL-CDR2 consisting of SEQ ID NO: 21, except for one, two, three or four amino acid substitutions. In some aspects, an anti-HER3 antibody or antigen-binding fragment thereof of the invention comprises a VL-CDR2 comprising SEQ ID NO: 21, except for one, two, three or four amino acid substitutions. In some aspects, an anti-HER3 antibody or antigen-binding fragment thereof of the invention comprises a VL-CDR3 consisting of a sequence selected from the group consisting of SEQ ID NOs: 22, 23, 24, 25, 26, 27, 28, 29, and 30, except for one, two, three or four amino acid substitutions. In some aspects, an anti-HER3 antibody or antigen-binding fragment thereof of the invention comprises a VL-CDR3 comprising a sequence selected from the group consisting of SEQ ID NOs: 22, 23, 24, 25, 26, 27, 28, 29, and 30, except for one, two, three or four amino acid substitutions.

In some aspects, an anti-HER3 antibody or antigen-binding fragment thereof of the invention comprises a VH-CDR1 consisting of SEQ ID NO: 31, except for one, two, three or four amino acid substitutions. In some aspects, an anti-HER3 antibody or antigen-binding fragment thereof of the invention comprises a VH-CDR1 comprising SEQ ID NO: 31, except for one, two, three or four amino acid substitutions. In some aspects, an anti-HER3 antibody or antigen-binding fragment thereof of the invention comprises a VH-CDR2 consisting of a sequence selected from the group consisting of SEQ ID NOs: 32, 33 and 34, except for one, two, three or four amino acid substitutions. In some aspects, an anti-HER3 antibody or antigen-binding fragment thereof of the invention comprises a VH-CDR2 comprising a sequence selected from the group consisting of SEQ ID NOs: 32, 33 and 34, except for one, two, three or four amino acid substitutions. In some aspects, an anti-HER3 antibody or antigen-binding fragment thereof of the invention comprises a VH-CDR3 consisting of SEQ ID NO: 35, except for one, two, three or four amino acid substitutions. In some aspects, an anti-HER3 antibody or antigen-binding fragment thereof of the invention comprises a VH-CDR3 comprising SEQ ID NO: 35, except for one, two, three or four amino acid substitutions.

In some aspects, an anti-HER3 antibody or antigen-binding fragment thereof of the invention comprises a VL-CDR1 consisting of a sequence selected from the group consisting of SEQ ID NOs: 18, 19 and 20; a VL-CDR2 consisting of SEQ ID NO: 21; and a VL-CDR3 consisting of a sequence selected from the group consisting of SEQ ID NOs: 22, 23, 24, 25, 26, 27, 28, 29, and 30. In some aspects, an anti-HER3 antibody or antigen-binding fragment thereof of the invention comprises a VL-CDR1 comprising a sequence selected from the group consisting of SEQ ID NOs: 18, 19 and 20; a VL-CDR2 comprising SEQ ID NO: 21; and a VL-CDR3 comprising a sequence selected from the group consisting of SEQ ID NOs: 22, 23, 24, 25, 26, 27, 28, 29, and 30.

In some aspects, an anti-HER3 antibody or antigen-binding fragment thereof of the invention comprises a VH-CDR1 consisting of SEQ ID NO: 31; a VH-CDR2 consisting of a sequence selected from the group consisting of SEQ ID NOs: 32, 33 and 34; and a VH-CDR3 consisting of SEQ ID NO: 35.

In some aspects, an anti-HER3 antibody or antigen-binding fragment thereof of the invention comprises a VH-CDR1 comprising SEQ ID NO: 31; a VH-CDR2 comprising a sequence selected from the group consisting of SEQ ID NOs: 32, 33 and 34; a VH-CDR3 comprising SEQ ID NO: 35.

In some aspects, an anti-HER3 antibody or antigen-binding fragment thereof of the invention comprises a VL-CDR1 consisting of a sequence selected from the group consisting of SEQ ID NOs: 18, 19 and 20, except for one, two, three or four amino acid substitutions; a VL-CDR2 consisting of SEQ ID NO: 21, except for one, two, three or four amino acid substitutions; and a VL-CDR3 consisting of a sequence selected from the group consisting of SEQ ID NOs: 22, 23, 24, 25, 26, 27, 28, 29, and 30, except for one, two, three or four amino acid substitutions. In some aspects, an anti-HER3 antibody or antigen-binding fragment thereof of the invention comprises a VL-CDR1 comprising a sequence selected from the group consisting of SEQ ID NOs: 18, 19 and 20, except for one, two, three or four amino acid substitutions; a VL-CDR2 comprising SEQ ID NO: 21, except for one, two, three or four amino acid substitutions; and a VL-CDR3 comprising a sequence selected from the group consisting of SEQ ID NOs: 22, 23, 24, 25, 26, 27, 28, 29, and 30, except for one, two, three or four amino acid substitutions.

In some aspects, an anti-HER3 antibody or antigen-binding fragment thereof of the invention comprises a VH-CDR1 consisting of SEQ ID NO: 31, except for one, two, three or four amino acid substitutions; a VH-CDR2 consisting of a sequence selected from the group consisting of SEQ ID NOs: 32, 33 and 34, except for one, two, three or four amino acid substitutions; and a VH-CDR3 consisting of SEQ ID NO: 35, except for one, two, three or four amino acid substitutions. In some aspects, an anti-HER3 antibody or antigen-binding fragment thereof antibody of the invention comprises a VH-CDR1 comprising SEQ ID NO: 31, except for one, two, three or four amino acid substitutions; a VH-CDR2 comprising a sequence selected from the group consisting of SEQ ID NOs: 32, 33 and 34, except for one, two, three or four amino acid substitutions; and VH-CDR3 comprising SEQ ID NO: 35, except for one, two, three or four amino acid substitutions.

In certain aspects, an anti-HER3 antibody or antigen-binding fragment thereof of the invention comprises modifications to CDR1, CDR2, and/or CDR3 of the heavy and/or light chain, and further comprises modifications to FW1, FW2, FW3, and/or FW4 of the heavy and/or light chain. In some aspects, $FW_1$ comprises SEQ ID NO: 40 or 44, $FW_2$ comprises SEQ ID NO: 41, $FW_3$ comprises SEQ ID NO: 42, $FW_4$ comprises SEQ ID NO: 43, $FW_5$ comprises SEQ ID NO: 36, $FW_6$ comprises SEQ ID NO: 37, $FW_7$ comprises SEQ ID NO: 38, and $FW_8$ comprises SEQ ID NO: 39.

In some aspects, $FW_1$ comprises SEQ ID NO: 40 or 44, except for one, two, three or four amino acid substitutions; $FW_2$ comprises SEQ ID NO: 41, except for one, two, three or four amino acid substitutions; $FW_3$ comprises SEQ ID NO: 42, except for one, two, three or four amino acid substitutions; $FW_4$ comprises SEQ ID NO: 43, except for one, two, three or four amino acid substitutions; $FW_5$ comprises SEQ ID NO: 36, except for one, two, three or four amino acid substitutions; $FW_6$ comprises SEQ ID NO: 37, except for one, two, three or four amino acid substitutions; $FW_7$ comprises SEQ ID NO: 38, except for one, two, three or four amino acid substitutions; and $FW_8$ comprises SEQ ID NO: 39, except for one, two, three or four amino acid substitutions.

In certain aspects, an anti-HER3 antibody or antigen-binding fragment thereof of the invention comprises a VL and a VH comprising VL-CDR1, VL-CRD2, VL-CDR3, VH-CDR1, VH-CDR2, and VH-CDR3 amino acid sequences identical or identical except for four, three, two, or one amino acid substitutions in one or more CDRs to: SEQ ID NOs: 18, 21, 22, 31, 32, and 35, SEQ ID NOs: 18, 21, 26, 31, 32 and 35, SEQ ID NOs: 18, 21, 27, 31, 32 and 35, SEQ ID NOs: 20, 21, 22, 31, 32 and 35, SEQ ID NOs: 19, 21, 22, 31, 32 and 35, SEQ ID NOs: 18, 21, 25, 31, 32 and 35, SEQ ID NOs: 18, 21, 28, 31, 32 and 35, SEQ ID NOs: 18, 21, 29, 31, 32 and 35, SEQ ID NOs: 18, 21, 30, 31, 32 and 35, SEQ ID NOs: 18, 21, 23, 31, 32 and 35, SEQ ID NOs: 19, 21, 23, 31, 32 and 35, SEQ ID NOs: 20, 21, 23, 31, 32 and 35, SEQ ID NOs: 18, 21, 24, 31, 32 and 35, or SEQ ID NOs: 18, 21, 25, 31, 32 and 35, respectively.

Heavy and light chain variable domains of the anti-HER3 antibody or antigen-binding fragment thereof of the invention include the sequences listed in TABLE 2.

TABLE 2

| SEQ ID NO. | Description | Sequence |
|---|---|---|
| 1 | CL16VL (Germlined) | QSVLTQPPSASGTPGQRVTISCSGSSSNIGLNYVSWYQQLPGTAPKLLISRNNQRP SGVPDRFSGSKSGTSASLAISGLRSEDEADYYCAAWDDSLSGEVFGGGTKLTVL |
| 17 | CL16VL (original) | QYELTQPPSASGTPGQRVTMSCSGSSSNIGLNYVSWYQQLPGTAPKLLISRNNQR PSGVPDRFSGSKSGTSASLAISGLRSEDEADYYCAAWDDSLSGEVFGGGTKLTVL |
| 2 | CL16 VH | EVQLLESGGGLVQPGGSLRLSCAASGFTFSYYYMQWVRQAPGKGLEWVSYIGS SGGVTNYADSVKGRFTISRDNSKNTLYLQMNSLRAEDTAVYYCARVGLGDAFD IWGQGTMVTVSS |
| 4 | 5H6 VL | QSVLTQPPSASGTPGQRVTISCSGSSSNIGLNYVSWYQQLPGTAPKLLISRNNQRP SGVPDRFSGSKSGTSASLAISGLRSEDEADYYCAAWDDGLPGEVFGGGTKLTVL |
| 5 | 8A3 VL | QSVLTQPPSASGTPGQRVTISCSGSSSNIGLNYVSWYQQLPGTAPKLLISRNNQRP SGVPDRFSGSKSGTSASLAISGLRSEDEADYYCAAWDDSLIGEVFGGGTKLTVL |
| 6 | 4H6 VL | QSVLTQPPSASGTPGQRVTISCRGSSSNIGLNYVSWYQQLPGTAPKLLISRNNQRP SGVPDRFSGSKSGTSASLAISGLRSEDEADYYCAAWDDSLSGEVFGGGTKLTVL |
| 7 | 6E.3 VL | QSVLTQPPSASGTPGQRVTISCSGSLSNIGLNYVSWYQQLPGTAPKLLISRNNQRP SGVPDRFSGSKSGTSASLAISGLRSEDEADYYCAAWDDSLSGEVFGGGTKLTVL |
| 8 | 2B11 VL | QSVLTQPPSASGTPGQRVTISCSGSSSNIGLNYVSWYQQLPGTAPKLLISRNNQRP SGVPDRFSGSKSGTSASLAISGLRSEDEADYYCAAWDDSLPGEVFGGGTKLTVL |

TABLE 2 -continued

| SEQ ID NO. | Description | Sequence |
|---|---|---|
| 9 | 2D1 VL | QSVLTQPPSASGTPGQRVTISCSGSSSNIGLNYVSWYQQLPGTAPKLLISRNNQRPSGVPDRFSGSKSGTSASLAISGLRSEDEADYYCAAWDDSLSGEAFGGGTKLTVL |
| 10 | 3A6 VL | QSVLTQPPSASGTPGQRVTISCSGSSSNIGLNYVSWYQQLPGTAPKLLISRNNQRPSGVPDRFSGSKSGTSASLAISGLRSEDEADYYCAAWDDSPSGEVFGGGTKLTVL |
| 11 | 4C4 VL | QSVLTQPPSASGTPGQRVTISCSGSSSNIGLNYVSWYQQLPGTAPKLLISRNNQRPSGVPDRFSGSKSGTSASLAISGLRSEDEADYYCAAWDDSLRGEVFGGGTKLTVL |
| 12 | 15D12.1 (15D12.I) VH | EVQLLESGGGLVQPGGSLRLSCAASGFTFSYYYMQWVRQAPGKGLEWVSIIGSSGGVTNYADSVKGRFTISRDNSKNTLYLQMNSLRAEDTAVYYCARVGLGDAFDIWGQGTMVTVSS |
| 13 | 15D12.2 (15D12.V) VH | EVQLLESGGGLVQPGGSLRLSCAASGFTFSYYYMQWVRQAPGKGLEWVSVIGSSGGVTNYADSVKGRFTISRDNSKNTLYLQMNSLRAEDTAVYYCARVGLGDAFDIWGQGTMVTVSS |
| 14 | 1A4 VL | QSVLTQPPSASGTPGQRVTISCSGSSSNIGLNYVSWYQQLPGTAPKLLISRNNQRPSGVPDRFSGSKSGTSASLAISGLRSEDEADYYCAAWDDSPPGEAFGGGTKLTVL |
| 3 | 2C2 VL | QSVLTQPPSASGTPGQRVTISCSGSLSNIGLNYVSWYQQLPGTAPKLLISRNNQRPSGVPDRFSGSKSGTSASLAISGLRSEDEADYYCAAWDDSPPGEAFGGGTKLTVL |
| 15 | 3E.1 VL | QSVLTQPPSASGTPGQRVTISCRGSSSNIGLNYVSWYQQLPGTAPKLLISRNNQRPSGVPDRFSGSKSGTSASLAISGLRSEDEADYYCAAWDDSPPGEAFGGGTKLTVL |
| 16 | 2F10 | QSVLTQPPSASGTPGQRVTISCSGSSSNIGLNYVSWYQQLPGTAPKLLISRNNQRPSGVPDRFSGSKSGTSASLAISGLRSEDEADYYCAAWDDSPSGEAFGGGTKLTVL |

In certain aspects, an anti-HER3 antibody or antigen-binding fragment thereof of the invention comprises an antibody VL and an antibody VH, wherein the VL comprises an amino acid sequence at least about 80%, about 85%, about 90%, about 95%, about 96%, about 97%, about 98%, about 99%, or about 100% identical to a reference amino acid sequence selected from the group consisting of SEQ ID NO: 1, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 14, SEQ ID NO: 15, SEQ ID NO: 16, and SEQ ID NO: 17.

In other aspects, an anti-HER3 antibody or antigen-binding fragment thereof of the invention comprises an antibody VL and an antibody VH, wherein the VH comprises an amino acid sequence at least about 80%, about 85%, about 90%, about 95%, about 96%, about 97%, about 98%, about 99%, or about 100% identical to a reference amino acid sequence selected from the group consisting of SEQ ID NO: 2, SEQ ID NO: 12 and SEQ ID NO: 13.

In other aspects, an anti-HER3 antibody or antigen-binding fragment thereof of the invention comprises a VL comprising a sequence at least about 80%, about 85%, about 90%, about 95%, about 96%, about 97%, about 98%, about 99%, or about 100% identical to a reference amino acid sequence selected from the group consisting of SEQ ID NO: 1, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 14, SEQ ID NO: 15, SEQ ID NO: 16, and SEQ ID NO: 17, and further comprises a VH comprising a sequence at least about 80%, about 85%, about 90%, about 95%, about 96%, about 97%, about 98%, about 99%, or about 100% identical to a reference amino acid sequence selected from the group consisting of SEQ ID NO: 2, SEQ ID NO: 12 and SEQ ID NO: 13.

In some aspects, an anti-HER3 antibody or antigen-binding fragment thereof comprises a VH of TABLE 2 and a VL of TABLE 2. Antibodies are designated throughout the specification according to their VL chains. The heavy chains of the specific antibodies disclosed in the present specification correspond to the CL16 original heavy chain (SEQ ID NO: 2). Thus, the "CL16 antibody" is an IgG1 comprising two original CL16 light chains (SEQ ID NO: 17) and two CL16 original heavy chains (SEQ ID NO: 2), whereas the "2C2 antibody" is an IgG1 comprising two 2C2 light chains (2C2 VL (SEQ ID NO: 3) and two CL16 original heavy chains (SEQ ID NO: 2).

In some aspects, the anti-HER3 antibody or antigen-binding fragment thereof comprises a heavy chain constant region or fragment thereof. In some specific aspects, the heavy chain constant region is an IgG constant region. The IgG constant region can comprise a light chain constant region selected from the group consisting of a kappa constant region and a lambda constant region.

In certain aspects, an anti-HER3 antibody or antigen-binding fragment thereof of the invention binds HER3 with substantially the same or better affinity as the CL16 antibody, comprising the CL16 original heavy chain (SEQ ID NO: 2) and the original CL16 light chain (SEQ ID NO: 17). In certain aspects, an anti-HER3 antibody or antigen-binding fragment thereof of the invention binds HER3 with substantially the same or better affinity as the 2C2 antibody, comprising the 2C2 light chain (2C2 VL (SEQ ID NO: 3) and the CL16 original heavy chain (SEQ ID NO: 2).

In one aspect of the present invention, an anti-HER3 antibody or antigen-binding fragment thereof specifically binds HER3 and antigenic fragments thereof with a dissociation constant of $k_d$ ($k_{off}/k_{on}$) of less than $10^{-6}$ M, or of less than $10^{-7}$ M, or of less than $10^{-8}$ M, or of less than $10^{-9}$ M, or of less than $10^{-10}$ M, or of less than $10^{-11}$ M, or of less than $10^{-12}$ M, or of less than $10^{-13}$ M. In a particular aspect of the present invention, an anti-HER3 antibody or antigen-binding fragment thereof specifically binds HER3 and antigenic fragments thereof with a dissociation constant between $2 \times 10^{-10}$ M and $6 \times 10^{-10}$ M.

In another aspect, an anti-HER3 antibody or antigen-binding fragment thereof of the invention binds to HER3 and/or antigenic fragments thereof with a $K_{off}$ of less than $1 \times 10^{-3}$ s$^{-1}$, or less than $2 \times 10^{-3}$ s$^{-1}$. In other aspects, an anti-HER3 antibody or antigen-binding fragment thereof binds to HER3 and antigenic fragments thereof with a $K_{off}$ of less than $10^{-3}$ s$^{-1}$, less than $5 \times 10^{-3}$ s$^{-1}$, less than $10^{-4}$ s$^{-1}$, less than $5 \times 10^{-4}$ s$^{-1}$, less than $10^{-5}$ s$^{-1}$, less than $5 \times 10^{-5}$ s$^{-1}$, less than $10^{-6}$ s$^{-1}$, less than $5 \times 10^{-6}$ s$^{-1}$, less than less than $5 \times 10^{-7}$ s$^{-1}$, less than $10^{-8}$ s$^{-1}$, less than $5 \times 10^{-8}$ s$^{-1}$, less than $10^{-9}$ s$^{-1}$, less than $5 \times 10^{-9}$ s$^{-1}$, or less than $10^{-10}$ s$^{-1}$. In a particular aspect, an anti-HER3 antibody or antigen-binding fragment thereof of the invention binds to HER3 and/or antigenic fragments thereof with a $K_{off}$ of between $0.5 \times 10^{-4}$ s$^{-1}$ and $2.0 \times 10^{-4}$ s$^{-1}$.

In another aspect, an anti-HER3 antibody or antigen-binding fragment thereof of the invention binds to HER3 and/or antigenic fragments thereof with an association rate constant or $k_{on}$ rate of at least $10^5$ M$^{-1}$ s$^{-1}$, at least $5 \times 10^5$ M$^{-1}$ s$^{-1}$, at least $10^6$ M$^{-1}$ s$^{-1}$, at least $5 \times 10^6$ M$^{-1}$ s$^{-1}$, at least $10^{-7}$ M$^{-1}$ s$^{-1}$, at least $5 \times 10^{-7}$ M$^{-1}$ s$^{-1}$ or at least $10^8$ M$^{-1}$ s$^{-1}$, or at least $10^9$ M$^{-1}$ s$^{-1}$. In another aspect, an anti-HER3 antibody or antigen-binding fragment thereof of the invention binds to HER3 and/or antigenic fragments thereof with an association rate constant or $k_{on}$ rate of between $1 \times 10^5$ M$^{-1}$ s$^{-1}$ and $6 \times 10^5$ M$^{-1}$ s$^{-1}$.

The VH and VL sequences disclosed in TABLE 1 can be "mixed and matched" to create other anti-HER3 binding molecules of the invention. In certain aspects, the VH sequences of 15D12.I and 15D12.V are mixed and matched. Additionally or alternatively, the VL sequences of 5H6, 8A3, 4H6, 6E.3, 2B11, 2D1, 3A6, 4C4, 1A4, 2C2, 3E.1 can be mixed and matched.

In certain aspects, an anti-HER3 antibody or antigen-binding fragment thereof of the invention comprises mutations that improve the binding to human FcRn and improve the half-life of the anti-HER3 antibody or antigen-binding fragment thereof. In some aspects, such mutations are a methionine (M) to tyrosine (Y) mutation in position 252, a serine (S) to threonine (T) mutation in position 254, and a threonine (T) to glutamic acid (E) mutation in position 256, numbered according to the EU index as in Kabat (Kabat, et al. (1991) Sequences of Proteins of Immunological Interest, U.S. Public Health Service, National Institutes of Health, Washington, D.C.), introduced into the constant domain of an IgG1. See U.S. Pat. No. 7,658,921, which is incorporated by reference herein. This type of mutant IgG, referred to as a "YTE mutant" has been shown display approximately four-times increased half-life as compared to wild-type versions of the same antibody (Dall'Acqua et al., J. Biol. Chem. 281:23514-24 (2006)). In some aspects, an anti-HER3 antibody or antigen-binding fragment thereof comprising an IgG constant domain comprises one or more amino acid substitutions of amino acid residues at positions 251-257, 285-290, 308-314, 385-389, and 428-436, numbered according to the EU index as in Kabat, wherein such mutations increase the serum half-life of the anti-HER3 antibody or antigen-binding fragment thereof.

In some aspects, a YTE mutant further comprises a substitution at position 434 of the IgG constant domain, numbered according to the EU index as in Kabat, with an amino acid selected from the group consisting of tryptophan (W), methionine (M), tyrosine (Y), and serine (S). In other aspects, a YTE mutant further comprises a substitution at position 434 of the IgG constant domain, numbered according to the EU index as in Kabat, with an amino acid selected from the group consisting of tryptophan (W), methionine (M), tyrosine (Y), and serine (S), and substitution at position 428 of the IgG constant domain, numbered according to the EU index as in Kabat, with an amino acid selected from the group consisting of threonine (T), leucine (L), phenylalanine (F), and serine (S).

In yet other aspect, a YTE mutant further comprises a substitution at position 434 of the IgG constant domain, numbered according to the EU index as in Kabat, with tyrosine (Y), and a substitution at position 257 of the IgG constant domain, numbered according to the EU index as in Kabat, with leucine (L). In some aspects, a YTE mutant further comprises a substitution at position 434 of the IgG constant domain, numbered according to the EU index as in Kabat, with serine (S), and a substitution at position 428 of the IgG constant domain, numbered according to the EU index as in Kabat, with leucine (L).

In a specific aspect, an anti-HER3 antibody or antigen-binding fragment thereof comprises a 2C2 light chain variable region (2C2 VL; SEQ ID NO: 3), an original CL16 heavy chain variable region (SEQ ID NO: 2), and an IgG1 constant domain comprising a methionine (M) to tyrosine (Y) mutation in position 252, a serine (S) to threonine (T) mutation in position 254, and a threonine (T) to glutamic acid (E) mutation in position 256 of the IgG1 constant domain, numbered according to the EU index as in Kabat.

In certain aspects, an anti-HER3 antibody or antigen-binding fragment thereof of the invention comprise at least one IgG constant domain amino acid substitution selected from the group consisting of:

(a) substitution of the amino acid at position 252 with tyrosine (Y), phenylalanine (F), tryptophan (W), or threonine (T), (b) substitution of the amino acid at position 254 with threonine (T), (c) substitution of the amino acid at position 256 with serine (S), arginine (R), glutamine (Q), glutamic acid (E), aspartic acid (D), or threonine (T), (d) substitution of the amino acid at position 257 with leucine (L), (e) substitution of the amino acid at position 309 with proline (P), (f) substitution of the amino acid at position 311 with serine (S), (g) substitution of the amino acid at position 428 with threonine (T), leucine (L), phenylalanine (F), or serine (S), (h) substitution of the amino acid at position 433 with arginine (R), serine (S), isoleucine (I), proline (P), or glutamine (Q), (i) substitution of the amino acid at position 434 with tryptophan (W), methionine (M), serine (S), histidine (H), phenylalanine (F), or tyrosine, and (j) a combination of two or more of said substitutions, wherein the positions are numbered according to the EU index as in Kabat, and wherein the modified IgG has an increased serum half-life compared to the serum half-life of an IgG having the wild-type IgG constant domain.

In other aspects, the VH and/or VL amino acid sequences can be 85%, 90%, 95%, 96%, 97%, 98% or 99% similar to the sequences set forth above, and comprise 1, 2, 3, 4, 5 or more conservative substitutions. A HER3 antibody having VH and VL regions having high (i.e., 80% or greater) similarity to the VH regions of SEQ ID NOs: 2, 12 or 13 and/or VL regions of SEQ ID NOs: 1, 3, 4, 5, 6, 7, 8, 9, 10, 11, 14, 15, 16, or 17, respectively, can be obtained by mutagenesis (e.g., site-directed or PCR-mediated mutagenesis) of nucleic acid molecules encoding SEQ ID NOs: 1-17, followed by testing of the encoded altered antibody for retained function using the functional assays described herein.

The affinity or avidity of an antibody for an antigen can be determined experimentally using any suitable method well known in the art, e.g., flow cytometry, enzyme-linked immunosorbent assay (ELISA), or radioimmunoassay (RIA), or kinetics (e.g., BIACORE™ analysis). Direct binding assays as well as competitive binding assay formats can be readily employed. (See, for example, Berzofsky et al., "Antibody-Antigen Interactions," In Fundamental Immunology, Paul, W. E., Ed., Raven Press: New York, N.Y. (1984); Kuby, Immunology, W. H. Freeman and Company: New York, N.Y. (1992); and methods described herein. The measured affinity of a particular antibody-antigen interaction can vary if measured under different conditions (e.g., salt concentration, pH, temperature). Thus, measurements of affinity and other antigen-binding parameters (e.g., $K_D$ or Kd, $K_{on}$, $K_{off}$) are made with standardized solutions of antibody and antigen, and a standardized buffer, as known in the art and such as the buffer described herein.

It also known in the art that affinities measured using BIACORE™ analysis can vary depending on which one of the reactants is bound to the chip. In this respect, affinity can be measured using a format in which the targeting antibody (e.g., the 2C2 monoclonal antibody) is immobilized onto the chip (referred to as an "IgG down" format) or using a format in which the target protein (e.g., HER3) is immobilized onto the chip (referred to as, e.g., a "HER3 down" format).

III. Binding Molecules that Bind to the Same Epitope as Anti-HER3 Antibodies and Antigen-Binding Fragments Thereof of the Invention In another aspect, the invention comprises HER3-binding molecules that bind to the same epitope as do the various anti-HER3 antibodies described herein. The term "epitope" as used herein refers to a protein determinant capable of binding to an antibody of the invention. Epitopes usually consist of chemically active surface groupings of molecules such as amino acids or sugar side chains and usually have specific three dimensional structural characteristics, as well as specific charge characteristics. Conformational and nonconformational epitopes are distinguished in that the binding to the former but not the latter is lost in the presence of denaturing solvents. Such antibodies can be identified based on their ability to cross-compete (e.g., to competitively inhibit the binding of, in a statistically significant manner) with antibodies such as the CL16 antibody, the 2C2 antibody, or the 2C2-YTE mutant, in standard HER3 binding assays. Accordingly, in one aspect, the invention provides anti-HER3 antibodies and antigen-binding fragments thereof, e.g., human monoclonal antibodies, that compete for binding to HER3 with another anti-HER3 antibody or antigen-binding fragment thereof of the invention, such as the CL16 antibody or the 2C2 antibody. The ability of a test antibody to inhibit the binding of, e.g., the CL16 antibody or the 2C2 antibody demonstrates that the test antibody can compete with that antibody for binding to HER3; such an antibody can, according to non-limiting theory, bind to the same or a related (e.g., a structurally similar or spatially proximal) epitope on HER3 as the anti-HER3 antibody or antigen-binding fragment thereof with which it competes. In one aspect, the anti-HER3 antibody or antigen-binding fragment thereof that binds to the same epitope on HER3 as, e.g., the CL16 antibody or the 2C2 antibody, is a human monoclonal antibody.

IV. Mechanism of Action

In some aspects, a HER3-binding molecule, e.g., an anti-HER3 antibody or antigen-binding fragment thereof can suppress HER3 phosphorylation. In other aspects, a HER3-binding molecule, e.g., an anti-HER3 antibody or antigen-binding fragment thereof can suppress AKT phosphorylation. In still other aspects, a HER3-binding molecule, e.g., an anti-HER3 antibody or antigen-binding fragment thereof can suppress HER2-HER3 dimer formation. In some aspects, a HER3-binding molecule, e.g., an anti-HER3 antibody or antigen-binding fragment thereof can suppress cell growth. In some aspects, a HER3-binding molecule, e.g., an anti-HER3 antibody or antigen-binding fragment thereof lacks ADCC effect. In specific aspects, a HER3-binding molecule, e.g., an anti-HER3 antibody or antigen-binding fragment thereof can suppress HER3 phosphorylation, AKT phosphorylation, and/or tumor colony formation via a ligand-independent mechanism of action.

In some aspects, a HER3-binding molecule, e.g., an anti-HER3 antibody or antigen-binding fragment thereof can suppress HER3 phosphorylation in HRG-driven breast cancer MCF-7 cells as measured by ELISA, with an $IC_{50}$ lower than about 30 ng/mL, lower than about 25 ng/mL, lower than about 20 ng/mL, lower than about 15 ng/mL, or lower than about 10 ng/mL. In a specific aspect, a HER3-binding molecule, e.g., an anti-HER3 antibody or antigen-binding fragment thereof can suppress HER3 phosphorylation in HRG-driven breast cancer MCF-7 cells as measured by ELISA, with an $IC_{50}$ lower than about 20 ng/mL. In a specific aspect, a HER3-binding molecule, e.g., an anti-HER3 antibody or antigen-binding fragment thereof can suppress HER3 phosphorylation in HRG-driven breast cancer MCF-7 cells as measured by ELISA, with an $IC_{50}$ lower than about 15 ng/mL. In another specific aspect, a HER3-binding molecule, e.g., an anti-HER3 antibody or antigen-binding fragment thereof can suppress HER3 phosphorylation in HRG-driven breast cancer MCF-7 cells as measured by ELISA, with an $IC_{50}$ lower than about 10 ng/mL.

In some aspects, a HER3-binding molecule, e.g., an anti-HER3 antibody or antigen-binding fragment thereof can suppress cell growth in MDA-MB-175 breast cancer cells with an $IC_{50}$ lower than about 0.90 µg/mL, lower than about 0.80 µg/mL, lower than about 0.70 µg/mL, lower than about 0.60 µg/mL, lower than about 0.50 µg/mL, lower than about 0.40 µg/mL, lower than about 0.30 µg/mL, or lower than about 0.20 µg/mL. In a specific aspect, a HER3-binding molecule, e.g., an anti-HER3 antibody or antigen-binding fragment thereof can suppress cell growth in MDA-MB-175 breast cancer cells, with an $IC_{50}$ lower than about 0.50 µg/mL. In a specific aspect, a HER3-binding molecule, e.g., an anti-HER3 antibody or antigen-binding fragment thereof can suppress cell growth in MDA-MB-175 breast cancer cells, with an $IC_{50}$ lower than about 0.40 µg/mL. In another specific aspect, a HER3-binding molecule, e.g., an anti-HER3 antibody or antigen-binding fragment thereof can suppress cell growth in MDA-MB-175 breast cancer cells, with an $IC_{50}$ lower than about 0.30 µg/mL. In another specific aspect, a HER3-binding molecule, e.g., an anti-HER3 antibody or antigen-binding fragment thereof can suppress cell growth in MDA-MB-175 breast cancer cells, with an $IC_{50}$ lower than about 0.20 µg/mL.

In some aspects, a HER3-binding molecule, e.g., an anti-HER3 antibody or antigen-binding fragment thereof can suppress cell growth in HMCB melanoma cells with an $IC_{50}$ lower than about 0.20 μg/mL, lower than about 0.15 μg/mL, lower than about 0.10 μg/mL, lower than about 0.05 μg/mL, lower than about 0.04 μg/mL, or lower than about 0.03 μg/mL. In a specific aspect, a HER3-binding molecule, e.g., an anti-HER3 antibody or antigen-binding fragment thereof can suppress cell growth in HMCB melanoma cells, with an $IC_{50}$ lower than about 0.10 μg/mL. In a specific aspect, a HER3-binding molecule, e.g., an anti-HER3 antibody or antigen-binding fragment thereof can suppress cell growth in HMCB melanoma cells, with an $IC_{50}$ lower than about 0.05 μg/mL. In a specific aspect, a HER3-binding molecule, e.g., an anti-HER3 antibody or antigen-binding fragment thereof can suppress cell growth in HMCB melanoma cells, with an $IC_{50}$ lower than about 0.04 μg/mL. In a specific aspect, a HER3-binding molecule, e.g., an anti-HER3 antibody or antigen-binding fragment thereof can suppress cell growth in HMCB melanoma cells, with an $IC_{50}$ lower than about 0.03 μg/mL.

In some aspects, a HER3-binding molecule, e.g., an anti-HER3 antibody or antigen-binding fragment thereof can suppress HER3 phosphorylation in EGFR-driven HCC827 lung cancer cells with an $IC_{50}$ lower than about 20 ng/mL, lower than about 15 ng/mL, lower than about 10 ng/mL, lower than about 8 ng/mL, lower than about 6 ng/mL, lower than about 4 ng/mL, or lower than about 2 ng/mL. In a specific aspect, a HER3-binding molecule, e.g., an anti-HER3 antibody or antigen-binding fragment thereof can suppress HER3 phosphorylation in EGFR-driven HCC827 lung cancer cells, with an $IC_{50}$ lower than about 10 ng/mL. In a specific aspect, a HER3-binding molecule, e.g., an anti-HER3 antibody or antigen-binding fragment thereof can suppress HER3 phosphorylation in EGFR-driven HCC827 lung cancer cells, with an $IC_{50}$ lower than about 8 ng/mL. In a specific aspect, a HER3-binding molecule, e.g., an anti-HER3 antibody or antigen-binding fragment thereof can suppress HER3 phosphorylation in EGFR-driven HCC827 lung cancer cells, with an $IC_{50}$ lower than about 6 ng/mL. In a specific aspect, a HER3-binding molecule, e.g., an anti-HER3 antibody or antigen-binding fragment thereof can suppress HER3 phosphorylation in EGFR-driven HCC827 lung cancer cells, with an $IC_{50}$ lower than about 4 ng/mL. In a specific aspect, a HER3-binding molecule, e.g., an anti-HER3 antibody or antigen-binding fragment thereof can suppress HER3 phosphorylation in EGFR-driven HCC827 lung cancer cells, with an $IC_{50}$ lower than about 2 ng/mL.

In some aspects, a HER3-binding molecule, e.g., an anti-HER3 antibody or antigen-binding fragment thereof can suppress HER3 phosphorylation in EGFR-driven HCC827 lung cancer cells resistant to TKI with an $IC_{50}$ lower than about 30 ng/mL, lower than about 25 ng/mL, lower than about 20 ng/mL, lower than about 15 ng/mL, lower than about 10 ng/mL, or lower than about 5 ng/mL. In a specific aspect, a HER3-binding molecule, e.g., an anti-HER3 antibody or antigen-binding fragment thereof can suppress HER3 phosphorylation in EGFR-driven HCC827 lung cancer cells resistant to TKI, with an $IC_{50}$ lower than about 20 ng/mL. In a specific aspect, a HER3-binding molecule, e.g., an anti-HER3 antibody or antigen-binding fragment thereof can suppress HER3 phosphorylation in EGFR-driven HCC827 lung cancer cells resistant to TKI, with an $IC_{50}$ lower than about 15 ng/mL. In a specific aspect, a HER3-binding molecule, e.g., an anti-HER3 antibody or antigen-binding fragment thereof can suppress HER3 phosphorylation in EGFR-driven HCC827 lung cancer cells resistant to TKI, with an $IC_{50}$ lower than about 10 ng/mL. In a specific aspect, a HER3-binding molecule, e.g., an anti-HER3 antibody or antigen-binding fragment thereof can suppress HER3 phosphorylation in EGFR-driven HCC827 lung cancer cells resistant to TKI, with an $IC_{50}$ lower than about 5 ng/mL.

In some specific aspects, a HER3-binding molecule, e.g., an anti-HER3 antibody or antigen-binding fragment thereof can be used to treat TKI resistant cancers.

In some aspects, a HER3-binding molecule, e.g., an anti-HER3 antibody or antigen-binding fragment thereof can suppress HER3 phosphorylation in cMET-driven MKN45 human gastric adenocarcinoma cells with an $IC_{50}$ is lower than about 15 ng/mL, lower than about 10 ng/mL, lower than about 9 ng/mL, lower than about 8 ng/mL, lower than about 7 ng/mL, lower than about 6 ng/mL, lower than about 5 ng/mL, or lower than about 4 ng/mL. In a specific aspect, a HER3-binding molecule, e.g., an anti-HER3 antibody or antigen-binding fragment thereof can suppress HER3 phosphorylation in cMET-driven MKN45 human gastric adenocarcinoma cells with an $IC_{50}$ lower than about 10 ng/mL. In a specific aspect, a HER3-binding molecule, e.g., an anti-HER3 antibody or antigen-binding fragment thereof can suppress HER3 phosphorylation in cMET-driven MKN45 human gastric adenocarcinoma cells with an $IC_{50}$ lower than about 8 ng/mL. In a specific aspect, a HER3-binding molecule, e.g., an anti-HER3 antibody or antigen-binding fragment thereof can suppress HER3 phosphorylation in cMET-driven MKN45 human gastric adenocarcinoma cells with an $IC_{50}$ lower than about 6 ng/mL. In a specific aspect, a HER3-binding molecule, e.g., an anti-HER3 antibody or antigen-binding fragment thereof can suppress HER3 phosphorylation in cMET-driven MKN45 human gastric adenocarcinoma cells with an $IC_{50}$ lower than about 4 ng/mL.

In some aspects, a HER3-binding molecule, e.g., an anti-HER3 antibody or antigen-binding fragment thereof of the invention can suppress pAKT in cMET-driven MKN45 cells with an $IC_{50}$ lower than about 15 ng/mL, lower than about 10 ng/mL, lower than about 9 ng/mL, lower than about 8 ng/mL, lower than about 7 ng/mL, lower than about 6 ng/mL, lower than about 5 ng/mL, lower than about 4 ng/mL, or lower than about 3 ng/mL. In a specific aspect, a HER3-binding molecule, e.g., an anti-HER3 antibody or antigen-binding fragment thereof can suppress pAKT in cMET-driven MKN45 cells with an $IC_{50}$ lower than about 8 ng/mL. In a specific aspect, a HER3-binding molecule, e.g., an anti-HER3 antibody or antigen-binding fragment thereof can suppress pAKT in cMET-driven MKN45 cells with an $IC_{50}$ lower than about 6 ng/mL. In a specific aspect, a HER3-binding molecule, e.g., an anti-HER3 antibody or antigen-binding fragment thereof can suppress pAKT in cMET-driven MKN45 cells with an $IC_{50}$ lower than about 4 ng/mL. In a specific aspect, a HER3-binding molecule, e.g., an anti-HER3 antibody or antigen-binding fragment thereof can suppress pAKT in cMET-driven MKN45 cells with an $IC_{50}$ lower than about 3 ng/mL.

In some aspects, a HER3-binding molecule, e.g., an anti-HER3 antibody or antigen-binding fragment thereof of the invention can suppress pHER in FGFR2-driven Kato III human gastric signet ring carcinoma cells with an $IC_{50}$ lower than about 9 ng/mL, lower than about 8 ng/mL, lower than about 7 ng/mL, lower than about 6 ng/mL, lower than about 5 ng/mL, lower than about 4 ng/mL, lower than about 3 ng/mL, lower than about 2 ng/mL, or lower than about 1 ng/mL. In a specific aspect, a HER3-binding molecule, e.g., an anti-HER3 antibody or antigen-binding fragment thereof can suppress pHER in FGFR2-driven Kato III human gastric signet ring carcinoma cells with an $IC_{50}$ lower than about 5 ng/mL. In a specific aspect, a HER3-binding molecule, e.g., an anti-HER3 antibody or antigen-binding fragment thereof can suppress pHER in FGFR2-driven Kato III human gastric signet ring carcinoma cells with an $IC_{50}$ lower than about 4 ng/mL. In a specific aspect, a HER3-binding molecule, e.g., an anti-HER3 antibody or antigen-binding fragment thereof can suppress pHER in FGFR2-driven Kato III human gastric signet ring carcinoma cells with an $IC_{50}$ lower than about 3 ng/mL. In a specific aspect, a HER3-binding molecule, e.g., an anti-HER3 antibody or antigen-binding fragment thereof can suppress pHER in FGFR2-driven Kato III human gastric signet ring carcinoma cells with an $IC_{50}$ lower than about 2 ng/mL. In a specific aspect, a HER3-binding molecule, e.g., an anti-HER3 antibody or antigen-binding fragment thereof can suppress pHER in FGFR2-driven Kato III human gastric signet ring carcinoma cells with an $IC_{50}$ lower than about 1 ng/mL.

In some aspects, a HER3-binding molecule, e.g., an anti-HER3 antibody or antigen-binding fragment thereof can suppress pAKT in FGFR-2 driven Kato III cells with an $IC_{50}$ lower than about 6 ng/mL, lower than about 5 ng/mL, lower than about 4 ng/mL, lower than about 3 ng/mL, lower than about 2 ng/mL, or lower than about 1 ng/mL. In a specific aspect, a HER3-binding molecule, e.g., an anti-HER3 antibody or antigen-binding fragment thereof can suppress pAKT in FGFR-2 driven Kato III cells with an $IC_{50}$ lower than about 4 ng/mL. In a specific aspect, a HER3-binding molecule, e.g., an anti-HER3 antibody or antigen-binding fragment thereof can suppress pAKT in FGFR-2 driven Kato III cells with an $IC_{50}$ lower than about 3 ng/mL. In a specific aspect, a HER3-binding molecule, e.g., an anti-HER3 antibody or antigen-binding fragment thereof can suppress pAKT in FGFR-2 driven Kato III cells with an $IC_{50}$ lower than about 2 ng/mL. In a specific aspect, a HER3-binding molecule, e.g., an anti-HER3 antibody or antigen-binding fragment thereof can suppress pAKT in FGFR-2 driven Kato III cells with an $IC_{50}$ lower than about 1 ng/mL.

In some aspects, a HER3-binding molecule, e.g., an anti-HER3 antibody or antigen-binding fragment thereof of the invention can suppress pHER in ligand independent BT-474 breast cancer cells with an $IC_{50}$ lower than about 10 ng/mL, lower than about 9 ng/mL, lower than about 8 ng/mL, lower than about 7 ng/mL, lower than about 6 ng/mL, lower than about 5 ng/mL, lower than about 4 ng/mL. In a specific aspect, a HER3-binding molecule, e.g., an anti-HER3 antibody or antigen-binding fragment thereof can suppress pHER in ligand independent BT-474 breast cancer cells with an $IC_{50}$ lower than about 8 ng/mL. In a specific aspect, a HER3-binding molecule, e.g., an anti-HER3 antibody or antigen-binding fragment thereof can suppress pHER in ligand independent BT-474 breast cancer cells with an $IC_{50}$ lower than about 6 ng/mL. In a specific aspect, a HER3-binding molecule, e.g., an anti-HER3 antibody or antigen-binding fragment thereof can suppress pHER in ligand independent BT-474 breast cancer cells with an $IC_{50}$ lower than about 4 ng/mL.

In some aspects, a HER3-binding molecule, e.g., an anti-HER3 antibody or antigen-binding fragment thereof of the invention can suppress pAKT in ligand independent BT-474 breast cancer cells with an $IC_{50}$ lower than about 10 ng/mL, lower than about 9 ng/mL, lower than about 8 ng/mL, lower than about 7 ng/mL, lower than about 6 ng/mL, lower than about 5 ng/mL, lower than about 4 ng/mL. In a specific aspect, a HER3-binding molecule, e.g., an anti-HER3 antibody or antigen-binding fragment thereof can suppress pAKT in ligand independent BT-474 breast cancer cells with an $IC_{50}$ lower than about 8 ng/mL. In a specific aspect, a HER3-binding molecule, e.g., an anti-HER3 antibody or antigen-binding fragment thereof can suppress pAKT in ligand independent BT-474 breast cancer cells with an $IC_{50}$ lower than about 6 ng/mL. In a specific aspect, a HER3-binding molecule, e.g., an anti-HER3 antibody or antigen-binding fragment thereof can suppress pAKT in ligand independent BT-474 breast cancer cells with an $IC_{50}$ lower than about 4 ng/mL. In some aspects, a HER3-binding molecule, e.g., an anti-HER3 antibody or antigen-binding fragment thereof can suppress pHER3, pAKT, and tumor colony formation in BT-474 cells, a ligand independent breast cancer model.

In some aspects, a HER3-binding molecule, e.g., an anti-HER3 antibody or antigen-binding fragment thereof of the invention can suppress HRG induced VEGF secretion. In a specific aspect, a HER3-binding molecule, e.g., an anti-HER3 antibody or antigen-binding fragment thereof of the invention can suppress HRG induced VEGF secretion in ligand independent BT-474 breast cancer cells and/or HRG-driven breast cancer MCF-7 cells.

In some aspects, a HER3-binding molecule, e.g., an anti-HER3 antibody or antigen-binding fragment thereof of the invention can cause cell cycle arrest. In a specific aspect, a HER3-binding molecule, e.g., an anti-HER3 antibody or antigen-binding fragment thereof of the invention can cause cell cycle arrest in breast cancer cells, including but not limited to SKBR3 or BT474 cells.

V. Preparation of Anti-HER3 Antibodies and Antigen-Binding Fragments

Monoclonal anti-HER3 antibodies can be prepared using hybridoma methods, such as those described by Kohler and Milstein (1975) Nature 256:495. Using the hybridoma method, a mouse, hamster, or other appropriate host animal, is immunized as described above to elicit the production by lymphocytes of antibodies that will specifically bind to an immunizing antigen. Lymphocytes can also be immunized in vitro. Following immunization, the lymphocytes are isolated and fused with a suitable myeloma cell line using, for example, polyethylene glycol, to form hybridoma cells that can then be selected away from unfused lymphocytes and myeloma cells. Hybridomas that produce monoclonal antibodies directed specifically against a chosen antigen as determined by immunoprecipitation, immunoblotting, or by an in vitro binding assay (e.g. radioimmunoassay (RIA); enzyme-linked immunosorbent assay (ELISA)) can then be propagated either in in vitro culture using standard methods (Godding, Monoclonal Antibodies: Principles and Practice, Academic Press, 1986) or in vivo as ascites tumors in an animal. The monoclonal antibodies can then be purified from the culture medium or ascites fluid as described for polyclonal antibodies above.

Alternatively anti-HER3 monoclonal antibodies can also be made using recombinant DNA methods as described in U.S. Pat. No. 4,816,567. The polynucleotides encoding a monoclonal antibody are isolated from mature B-cells or hybridoma cell, such as by RT-PCR using oligonucleotide primers that specifically amplify the genes encoding the heavy and light chains of the antibody, and their sequence is determined using conventional procedures. The isolated polynucleotides encoding the heavy and light chains are then cloned into suitable expression vectors, which when transfected into host cells such as *E. coli* cells, simian COS cells, Chinese hamster ovary (CHO) cells, or myeloma cells that do not otherwise produce immunoglobulin protein, monoclonal antibodies are generated by the host cells. Also, recombinant anti-HER3 monoclonal antibodies or antigen-binding fragments thereof of the desired species can be isolated from phage display libraries expressing CDRs of the desired species as described (McCafferty et al., 1990, Nature, 348:552-

554; Clarkson et al., 1991, Nature, 352:624-628; and Marks et al., 1991, J. Mol. Biol., 222:581-597).

The polynucleotide(s) encoding a anti-HER3 antibody or antigen-binding fragments thereof can further be modified in a number of different manners using recombinant DNA technology to generate alternative antibodies. In some aspects, the constant domains of the light and heavy chains of, for example, a mouse monoclonal antibody can be substituted (1) for those regions of, for example, a human antibody to generate a chimeric antibody or (2) for a non-immunoglobulin polypeptide to generate a fusion antibody. In some aspects, the constant regions are truncated or removed to generate the desired antibody fragment of a monoclonal antibody. Site-directed or high-density mutagenesis of the variable region can be used to optimize specificity, affinity, etc. of a monoclonal antibody.

In certain aspects, the anti-HER3 antibody or antigen-binding fragment thereof is a human antibody or antigen-binding fragment thereof. Human antibodies can be directly prepared using various techniques known in the art Immortalized human B lymphocytes immunized in vitro or isolated from an immunized individual that produce an antibody directed against a target antigen can be generated (See, e.g., Cole et al., Monoclonal Antibodies and Cancer Therapy, Alan R. Liss, p. 77 (1985); Boemer et al., 1991, J. Immunol., 147 (1):86-95; and U.S. Pat. No. 5,750,373).

Also, the anti-HER3 human antibody or antigen-binding fragment thereof can be selected from a phage library, where that phage library expresses human antibodies, as described, for example, in Vaughan et al., 1996, Nat. Biotech., 14:309-314, Sheets et al., 1998, Proc. Nat'l. Acad. Sci., 95:6157-6162, Hoogenboom and Winter, 1991, J. Mol. Biol., 227:381, and Marks et al., 1991, J. Mol. Biol., 222:581). Techniques for the generation and use of antibody phage libraries are also described in U.S. Pat. Nos. 5,969,108, 6,172,197, 5,885,793, 6,521,404; 6,544,731; 6,555,313; 6,582,915; 6,593,081; 6,300,064; 6,653,068; 6,706,484; and 7,264,963; and Rothe et al., 2007, J. Mol. Bio., doi:10.1016/j.jmb.2007.12.018 (each of which is incorporated by reference in its entirety).

Affinity maturation strategies and chain shuffling strategies (Marks et al., 1992, Bio/Technology 10:779-783, incorporated by reference in its entirety) are known in the art and can be employed to generate high affinity human antibodies or antigen-binding fragments thereof.

In some aspects, an anti-HER3 monoclonal antibody can be a humanized antibody. Methods for engineering, humanizing or resurfacing non-human or human antibodies can also be used and are well known in the art. A humanized, resurfaced or similarly engineered antibody can have one or more amino acid residues from a source that is non-human, e.g., but not limited to, mouse, rat, rabbit, non-human primate or other mammal. These non-human amino acid residues are replaced by residues that are often referred to as "import" residues, which are typically taken from an "import" variable, constant or other domain of a known human sequence. Such imported sequences can be used to reduce immunogenicity or reduce, enhance or modify binding, affinity, on-rate, off-rate, avidity, specificity, half-life, or any other suitable characteristic, as known in the art. In general, the CDR residues are directly and most substantially involved in influencing HER3 binding. Accordingly, part or all of the non-human or human CDR sequences are maintained while the non-human sequences of the variable and constant regions can be replaced with human or other amino acids.

Antibodies can also optionally be humanized, resurfaced, engineered or human antibodies engineered with retention of high affinity for the antigen HER3 and other favorable biological properties. To achieve this goal, humanized (or human) or engineered anti-HER3 antibodies and resurfaced antibodies can be optionally prepared by a process of analysis of the parental sequences and various conceptual humanized and engineered products using three-dimensional models of the parental, engineered, and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen, such as HER3. In this way, framework (FW) residues can be selected and combined from the consensus and import sequences so that the desired antibody characteristic, such as increased affinity for the target antigen(s), is achieved.

Humanization, resurfacing or engineering of anti-HER3 antibodies or antigen-binding fragments thereof of the present invention can be performed using any known method, such as but not limited to those described in, Jones et al., Nature 321:522 (1986); Riechmann et al., Nature 332:323 (1988); Verhoeyen et al., Science 239:1534 (1988)), Sims et al., J. Immunol. 151: 2296 (1993); Chothia and Lesk, J. Mol. Biol. 196:901 (1987), Carter et al., Proc. Natl. Acad. Sci. U.S.A. 89:4285 (1992); Presta et al., J. Immunol. 151:2623 (1993), U.S. Pat. Nos. 5,639,641, 5,723,323; 5,976,862; 5,824,514; 5,817,483; 5,814,476; 5,763,192; 5,723,323; 5,766,886; 5,714,352; 6,204,023; 6,180,370; 5,693,762; 5,530,101; 5,585,089; 5,225,539; 4,816,567, 7,557,189; 7,538,195; and 7,342,110; International Application Nos. PCT/US98/16280; PCT/US96/18978; PCT/US91/09630; PCT/US91/05939; PCT/US94/01234; PCT/GB89/01334; PCT/GB91/01134; PCT/GB92/01755; International Patent Application Publication Nos. WO90/14443; WO90/14424; WO90/14430; and European Patent Publication No. EP 229246; each of which is entirely incorporated herein by reference, including the references cited therein.

Anti-HER3 humanized antibodies and antigen-binding fragments thereof can also be made in transgenic mice containing human immunoglobulin loci that are capable upon immunization of producing the full repertoire of human antibodies in the absence of endogenous immunoglobulin production. This approach is described in U.S. Pat. Nos. 5,545, 807; 5,545,806; 5,569,825; 5,625,126; 5,633,425; and 5,661, 016.

In certain aspects an anti-HER3 antibody fragment is provided. Various techniques are known for the production of antibody fragments. Traditionally, these fragments are derived via proteolytic digestion of intact antibodies (for example Morimoto et al., 1993, Journal of Biochemical and Biophysical Methods 24:107-117; Brennan et al., 1985, Science, 229:81). In certain aspects, anti-HER3 antibody fragments are produced recombinantly. Fab, Fv, and scFv antibody fragments can all be expressed in and secreted from *E. coli* or other host cells, thus allowing the production of large amounts of these fragments. Such anti-HER3 antibody fragments can also be isolated from the antibody phage libraries discussed above. The anti-HER3 antibody fragments can also be linear antibodies as described in U.S. Pat. No. 5,641,870. Other techniques for the production of antibody fragments will be apparent to the skilled practitioner.

According to the present invention, techniques can be adapted for the production of single-chain antibodies specific to HER3 (see, e.g., U.S. Pat. No. 4,946,778). In addition, methods can be adapted for the construction of Fab expression libraries (see, e.g., Huse et al., Science 246:1275-1281 (1989)) to allow rapid and effective identification of monoclonal Fab fragments with the desired specificity for HER3, or derivatives, fragments, analogs or homologs thereof. Antibody fragments can be produced by techniques in the art including, but not limited to: (a) a F(ab')2 fragment produced by pepsin digestion of an antibody molecule; (b) a Fab fragment generated by reducing the disulfide bridges of an F(ab')2 fragment, (c) a Fab fragment generated by the treatment of the antibody molecule with papain and a reducing agent, and (d) Fv fragments.

It can further be desirable, especially in the case of antibody fragments, to modify an anti-HER3 antibody or antigen-binding fragment thereof in order to increase its serum half-life. This can be achieved, for example, by incorporation of a salvage receptor binding epitope into the antibody or antibody fragment by mutation of the appropriate region in the antibody or antibody fragment or by incorporating the epitope into a peptide tag that is then fused to the antibody or antibody fragment at either end or in the middle (e.g., by DNA or peptide synthesis), or by YTE mutation. Other methods to increase the serum half-life of an antibody or antigen-binding fragment thereof, e.g., conjugation to a heterologous molecule such as PEG are known in the art.

Heteroconjugate anti-HER3 antibodies and antigen-binding fragments thereof are also within the scope of the present invention. Heteroconjugate antibodies are composed of two covalently joined antibodies. Such antibodies have, for example, been proposed to target immune cells to unwanted cells (see, e.g., U.S. Pat. No. 4,676,980). It is contemplated that the heteroconjugate anti-HER3 antibodies and antigen-binding fragments thereof can be prepared in vitro using known methods in synthetic protein chemistry, including those involving crosslinking agents. For example, immunotoxins can be constructed using a disulfide exchange reaction or by forming a thioether bond. Examples of suitable reagents for this purpose include iminothiolate and methyl-4-mercaptobutyrimidate.

In certain aspects, the HER3-binding molecules of the invention, e.g., antibodies or antigen-binding fragments thereof can be combined with other therapeutic agents or conjugated to other therapeutic agents or toxins to form immunoconjugates and/or fusion proteins. Examples of such therapeutic agents and toxins include, but are not limited to cetuximab (Erbitux®), panitumumab (Vectibix®), lapatinib (Tykerb®/Tyverb®), and paclitaxel (Taxol®, Abraxane®) and derivatives (e.g., docetaxel).

In some aspects the HER3-binding molecules of the invention, e.g., antibodies or antigen-binding fragments thereof can be conjugated to antibodies or antibody fragments targeting epidermal growth factor receptor (EGFR). In other aspects, the HER3-binding molecules of the invention can be conjugated to tyrosine kinase inhibitors. In some specific aspects, the HER3-binding molecules of the invention can be conjugated to inhibitors of the tyrosine kinase activity associated with EGFR and/or HER2/neu. In some aspects, the HER3-binding molecules of the invention can be conjugated to antimitotic agents. In some specific aspects, the HER3-binding molecules of the invention can be conjugated to agents that stabilize the mitotic spindle microtubule assembly.

For the purposes of the present invention, it should be appreciated that modified anti-HER3 antibodies or antigen-binding fragments thereof can comprise any type of variable region that provides for the association of the antibody or polypeptide with HER3. In this regard, the variable region can comprise or be derived from any type of mammal that can be induced to mount a humoral response and generate immunoglobulins against the desired tumor associated antigen. As such, the variable region of the modified anti-HER3 antibodies or antigen-binding fragments thereof can be, for example, of human, murine, non-human primate (e.g., cynomolgus monkeys, macaques, etc.) or lupine origin. In some aspects both the variable and constant regions of the modified anti-HER3 antibodies or antigen-binding fragments thereof are human. In other aspects the variable regions of compatible antibodies (usually derived from a non-human source) can be engineered or specifically tailored to improve the binding properties or reduce the immunogenicity of the molecule. In this respect, variable regions useful in the present invention can be humanized or otherwise altered through the inclusion of imported amino acid sequences.

In certain aspects, the variable domains in both the heavy and light chains of an anti-HER3 antibody or antigen-binding fragment thereof are altered by at least partial replacement of one or more CDRs and, if necessary, by partial framework region replacement and sequence changing. Although the CDRs can be derived from an antibody of the same class or even subclass as the antibody from which the framework regions are derived, it is envisaged that the CDRs will be derived from an antibody of different class and in certain aspects from an antibody from a different species. It is not necessary to replace all of the CDRs with the complete CDRs from the donor variable region to transfer the antigen binding capacity of one variable domain to another. Rather, it is only necessary to transfer those residues that are necessary to maintain the activity of the antigen binding site. Given the explanations set forth in U.S. Pat. Nos. 5,585,089, 5,693,761 and 5,693,762, it will be well within the competence of those skilled in the art, either by carrying out routine experimentation or by trial and error testing to obtain a functional antibody with reduced immunogenicity.

Alterations to the variable region notwithstanding, those skilled in the art will appreciate that the modified anti-HER3 antibodies or antigen-binding fragments thereof of this invention will comprise antibodies (e.g., full-length antibodies or immunoreactive fragments thereof) in which at least a fraction of one or more of the constant region domains has been deleted or otherwise altered so as to provide desired biochemical characteristics such as increased tumor localization or reduced serum half-life when compared with an antibody of approximately the same immunogenicity comprising a native or unaltered constant region. In some aspects, the constant region of the modified antibodies will comprise a human constant region. Modifications to the constant region compatible with this invention comprise additions, deletions or substitutions of one or more amino acids in one or more domains. That is, the modified antibodies disclosed herein can comprise alterations or modifications to one or more of the three heavy chain constant domains (CH1 CH2 or CH3) and/or to the light chain constant domain (CL). In some aspects, modified constant regions wherein one or more domains are partially or entirely deleted are contemplated. In some aspects, the modified antibodies will comprise domain deleted constructs or variants wherein the entire CH2 domain has been removed (ΔCH2 constructs). In some aspects, the omitted constant region domain will be replaced by a short amino acid spacer (e.g., 10 residues) that provides some of the molecular flexibility typically imparted by the absent constant region.

Besides their configuration, it is known in the art that the constant region mediates several effector functions. For example, binding of the C1 component of complement to antibodies activates the complement system. Activation of complement is important in the opsonisation and lysis of cell pathogens. The activation of complement also stimulates the inflammatory response and can also be involved in autoimmune hypersensitivity. Further, antibodies bind to cells via the Fc region, with a Fc receptor site on the antibody Fc region binding to a Fc receptor (FcR) on a cell. There are a number of Fc receptors which are specific for different classes of antibody, including IgG (gamma receptors), IgE (eta receptors), IgA (alpha receptors) and IgM (mu receptors). Binding of antibody to Fc receptors on cell surfaces triggers a number of important and diverse biological responses including engulfment and destruction of antibody-coated particles, clearance of immune complexes, lysis of antibody-coated target cells by killer cells (called antibody-dependent cell-mediated cytotoxicity, or ADCC), release of inflammatory mediators, placental transfer and control of immunoglobulin production.

In certain aspects, a anti-HER3 antibody or an antigen-binding fragment thereof provides for altered effector functions that, in turn, affect the biological profile of the administered antibody or antigen-binding fragment thereof. For example, the deletion or inactivation (through point mutations or other means) of a constant region domain can reduce Fc receptor binding of the circulating modified antibody thereby increasing tumor localization. In other cases it can be that constant region modifications, consistent with this invention, moderate complement binding and thus reduce the serum half-life and nonspecific association of a conjugated cytotoxin. Yet other modifications of the constant region can be used to eliminate disulfide linkages or oligosaccharide moieties that allow for enhanced localization due to increased antigen specificity or antibody flexibility. Similarly, modifications to the constant region in accordance with this invention can easily be made using well known biochemical or molecular engineering techniques well within the purview of the skilled artisan.

In certain aspects, a HER3-binding molecule that is an antibody or antigen-binding fragment thereof does not have one or more effector functions. For instance, in some aspects, the antibody or antigen-binding fragment thereof has no antibody-dependent cellular cytotoxicity (ADCC) activity and/or no complement-dependent cytotoxicity (CDC) activity. In certain aspects, the anti-HER3 antibody or antigen binding fragment thereof does not bind to an Fc receptor and/or complement factors. In certain aspects, the antibody or antigen-binding fragment thereof has no effector function.

It will be noted that in certain aspects, the anti-HER3 modified antibodies or antigen-binding fragments thereof can be engineered to fuse the CH3 domain directly to the hinge region of the respective modified antibodies or fragments thereof. In other constructs it can be desirable to provide a peptide spacer between the hinge region and the modified CH2 and/or CH3 domains. For example, compatible constructs could be expressed wherein the CH2 domain has been deleted and the remaining CH3 domain (modified or unmodified) is joined to the hinge region with a 5-20 amino acid spacer. Such a spacer can be added, for instance, to ensure that the regulatory elements of the constant domain remain free and accessible or that the hinge region remains flexible. However, it should be noted that amino acid spacers can, in some cases, prove to be immunogenic and elicit an unwanted immune response against the construct. Accordingly, in certain aspects, any spacer added to the construct will be relatively non-immunogenic, or even omitted altogether, so as to maintain the desired biochemical qualities of the modified antibodies.

Besides the deletion of whole constant region domains, it will be appreciated that the anti-HER3 antibodies and antigen-binding fragments thereof of the present invention can be provided by the partial deletion or substitution of a few or even a single amino acid. For example, the mutation of a single amino acid in selected areas of the CH2 domain can be enough to substantially reduce Fc binding and thereby increase tumor localization. Similarly, it can be desirable to simply delete that part of one or more constant region domains that control the effector function (e.g., complement C1Q binding) to be modulated. Such partial deletions of the constant regions can improve selected characteristics of the antibody or antigen-binding fragment thereof (e.g., serum half-life) while leaving other desirable functions associated with the subject constant region domain intact. Moreover, as alluded to above, the constant regions of the disclosed anti-HER3 antibodies and antigen-binding fragments thereof can be modified through the mutation or substitution of one or more amino acids that enhances the profile of the resulting construct. In this respect it is possible to disrupt the activity provided by a conserved binding site (e.g., Fc binding) while substantially maintaining the configuration and immunogenic profile of the modified antibody or antigen-binding fragment thereof. Certain aspects can comprise the addition of one or more amino acids to the constant region to enhance desirable characteristics such as decreasing or increasing effector function or provide for more cytotoxin or carbohydrate attachment. In such aspects it can be desirable to insert or replicate specific sequences derived from selected constant region domains.

The present invention further embraces variants and equivalents which are substantially homologous to the chimeric, humanized and human anti-HER3 antibodies, or antigen-binding fragments thereof, set forth herein. These can contain, for example, conservative substitution mutations, i.e., the substitution of one or more amino acids by similar amino acids. For example, conservative substitution refers to the substitution of an amino acid with another within the same general class such as, for example, one acidic amino acid with another acidic amino acid, one basic amino acid with another basic amino acid or one neutral amino acid by another neutral amino acid. What is intended by a conservative amino acid substitution is well known in the art.

An anti-HER3 antibody or antigen-binding fragment thereof can be further modified to contain additional chemical moieties not normally part of the protein. Those derivatized moieties can improve the solubility, the biological half-life or absorption of the protein. The moieties can also reduce or eliminate any desirable side effects of the proteins and the like. An overview for those moieties can be found in Remington's Pharmaceutical Sciences, 20th ed., Mack Publishing Co., Easton, Pa. (2000).

VI. Polynucleotides Encoding HER3-Binding Molecules

In certain aspects, the invention encompasses polynucleotides comprising nucleic acid sequences that encode a polypeptide that specifically binds HER3 or an antigen-binding fragment thereof. For example, the invention provides a polynucleotide comprising a nucleic acid sequence that encodes an anti-HER3 antibody or encodes an antigen-binding fragment of such an antibody. The polynucleotides of the invention can be in the form of RNA or in the form of DNA. DNA includes cDNA, genomic DNA, and synthetic DNA;

and can be double-stranded or single-stranded, and if single stranded can be the coding strand or non-coding (anti-sense) strand.

In certain aspects, the polynucleotides are isolated. In certain aspects, the polynucleotides are substantially pure. In certain aspects the polynucleotides comprise the coding sequence for the mature polypeptide fused in the same reading frame to a polynucleotide which aids, for example, in expression and secretion of a polypeptide from a host cell (e.g., a leader sequence which functions as a secretory sequence for controlling transport of a polypeptide from the cell). The polypeptide having a leader sequence is a preprotein and can have the leader sequence cleaved by the host cell to form the mature form of the polypeptide. The polynucleotides can also encode for an HER3-binding proprotein which is the mature protein plus additional 5' amino acid residues.

In certain aspects the polynucleotides comprise the coding sequence for the mature HER3-binding polypeptide, e.g., an anti-HER3 antibody or an antigen-binding fragment thereof fused in the same reading frame to a marker sequence that allows, for example, for purification of the encoded polypeptide. For example, the marker sequence can be a hexa-histidine tag supplied by a pQE-9 vector to provide for purification of the mature polypeptide fused to the marker in the case of a bacterial host, or the marker sequence can be a hemagglutinin (HA) tag derived from the influenza hemagglutinin protein when a mammalian host (e.g., COS-7 cells) is used.

The present invention further relates to variants of the described polynucleotides encoding, for example, HER3-binding fragments, analogs, and derivatives of the HER3-binding molecules of the invention.

The polynucleotide variants can contain alterations in the coding regions, non-coding regions, or both. In some aspects the polynucleotide variants contain alterations which produce silent substitutions, additions, or deletions, but do not alter the properties or activities of the encoded polypeptide. In some aspects, nucleotide variants are produced by silent substitutions due to the degeneracy of the genetic code. Polynucleotide variants can be produced for a variety of reasons, e.g., to optimize codon expression for a particular host (change codons in the human mRNA to those preferred by a bacterial host such as *E. coli*). Vectors and cells comprising the polynucleotides described herein are also provided.

In some aspects a DNA sequence encoding a HER3-binding molecule, e.g., an anti-HER3 antibody or an antigen-binding fragment thereof can be constructed by chemical synthesis using an oligonucleotide synthesizer. Such oligonucleotides can be designed based on the amino acid sequence of the desired polypeptide and selecting those codons that are favored in the host cell in which the recombinant polypeptide of interest will be produced. Standard methods can be applied to synthesize an isolated polynucleotide sequence encoding an isolated polypeptide of interest. For example, a complete amino acid sequence can be used to construct a back-translated gene. Further, a DNA oligomer containing a nucleotide sequence coding for the particular isolated polypeptide can be synthesized. For example, several small oligonucleotides coding for portions of the desired polypeptide can be synthesized and then ligated. The individual oligonucleotides typically contain 5' or 3' overhangs for complementary assembly.

Once assembled (by synthesis, site-directed mutagenesis or another method), the polynucleotide sequences encoding a particular isolated polypeptide of interest will be inserted into an expression vector and operatively linked to an expression control sequence appropriate for expression of the protein in a desired host. Proper assembly can be confirmed by nucleotide sequencing, restriction mapping, and expression of a biologically active polypeptide in a suitable host. As is well known in the art, in order to obtain high expression levels of a transfected gene in a host, the gene must be operatively linked to transcriptional and translational expression control sequences that are functional in the chosen expression host.

In certain aspects, recombinant expression vectors are used to amplify and express DNA encoding anti-HER3 antibodies or antigen-binding fragments thereof. Recombinant expression vectors are replicable DNA constructs which have synthetic or cDNA-derived DNA fragments encoding a polypeptide chain of an anti-HER3 antibody or and antigen-binding fragment thereof, operatively linked to suitable transcriptional or translational regulatory elements derived from mammalian, microbial, viral or insect genes. A transcriptional unit generally comprises an assembly of (1) a genetic element or elements having a regulatory role in gene expression, for example, transcriptional promoters or enhancers, (2) a structural or coding sequence which is transcribed into mRNA and translated into protein, and (3) appropriate transcription and translation initiation and termination sequences, as described in detail below. Such regulatory elements can include an operator sequence to control transcription. The ability to replicate in a host, usually conferred by an origin of replication, and a selection gene to facilitate recognition of transformants can additionally be incorporated. DNA regions are operatively linked when they are functionally related to each other. For example, DNA for a signal peptide (secretory leader) is operatively linked to DNA for a polypeptide if it is expressed as a precursor which participates in the secretion of the polypeptide; a promoter is operatively linked to a coding sequence if it controls the transcription of the sequence; or a ribosome binding site is operatively linked to a coding sequence if it is positioned so as to permit translation. Structural elements intended for use in yeast expression systems include a leader sequence enabling extracellular secretion of translated protein by a host cell. Alternatively, where recombinant protein is expressed without a leader or transport sequence, it can include an N-terminal methionine residue. This residue can optionally be subsequently cleaved from the expressed recombinant protein to provide a final product.

The choice of expression control sequence and expression vector will depend upon the choice of host. A wide variety of expression host/vector combinations can be employed. Useful expression vectors for eukaryotic hosts, include, for example, vectors comprising expression control sequences from SV40, bovine papilloma virus, adenovirus and cytomegalovirus. Useful expression vectors for bacterial hosts include known bacterial plasmids, such as plasmids from *E. coli*, including pCR 1, pBR322, pMB9 and their derivatives, wider host range plasmids, such as M13 and filamentous single-stranded DNA phages.

Suitable host cells for expression of an HER3-binding molecule, e.g., an anti-HER3 antibody or antigen-binding fragment thereof include prokaryotes, yeast, insect or higher eukaryotic cells under the control of appropriate promoters. Prokaryotes include gram negative or gram positive organisms, for example *E. coli* or bacilli. Higher eukaryotic cells include established cell lines of mammalian origin as described below. Cell-free translation systems could also be employed. Appropriate cloning and expression vectors for use with bacterial, fungal, yeast, and mammalian cellular hosts are described by Pouwels et al. (Cloning Vectors: A Laboratory Manual, Elsevier, N.Y., 1985), the relevant disclosure of which is hereby incorporated by reference. Additional information regarding methods of protein production, including antibody production, can be found, e.g., in U.S. Patent Publication No. 2008/0187954, U.S. Pat. Nos. 6,413,746 and 6,660,501, and International Patent Publication No. WO 04009823, each of which is hereby incorporated by reference herein in its entirety.

Various mammalian or insect cell culture systems can also be advantageously employed to express recombinant HER3-binding molecules, e.g., anti-HER3 antibodies or antigen-binding fragments thereof. Expression of recombinant proteins in mammalian cells can be performed because such proteins are generally correctly folded, appropriately modified and completely functional. Examples of suitable mammalian host cell lines include HEK-293 and HEK-293T, the COS-7 lines of monkey kidney cells, described by Gluzman (Cell 23:175, 1981), and other cell lines including, for example, L cells, C127, 3T3, Chinese hamster ovary (CHO), NSO, HeLa and BHK cell lines. Mammalian expression vectors can comprise nontranscribed elements such as an origin of replication, a suitable promoter and enhancer linked to the gene to be expressed, and other 5' or 3' flanking nontranscribed sequences, and 5' or 3' nontranslated sequences, such as necessary ribosome binding sites, a polyadenylation site, splice donor and acceptor sites, and transcriptional termination sequences. Baculovirus systems for production of heterologous proteins in insect cells are reviewed by Luckow and Summers, BioTechnology 6:47 (1988).

HER3-binding molecules, e.g., anti-HER3 antibodies or antigen-binding fragments thereof produced by a transformed host can be purified according to any suitable method. Such standard methods include chromatography (e.g., ion exchange, affinity and sizing column chromatography), centrifugation, differential solubility, or by any other standard technique for protein purification. Affinity tags such as hexahistidine, maltose binding domain, influenza coat sequence and glutathione-S-transferase can be attached to the protein to allow easy purification by passage over an appropriate affinity column. Isolated proteins can also be physically characterized using such techniques as proteolysis, nuclear magnetic resonance and x-ray crystallography.

For example, supernatants from systems which secrete recombinant protein into culture media can be first concentrated using a commercially available protein concentration filter, for example, an Amicon or Millipore Pellicon ultrafiltration unit. Following the concentration step, the concentrate can be applied to a suitable purification matrix. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Finally, one or more reversed-phase high performance liquid chromatography (RP-HPLC) steps employing hydrophobic RP-HPLC media, e.g., silica gel having pendant methyl or other aliphatic groups, can be employed to further purify an HER3-binding molecule. Some or all of the foregoing purification steps, in various combinations, can also be employed to provide a homogeneous recombinant protein.

A recombinant HER3-binding protein, e.g., an anti-HER3 antibody or antigen-binding fragment thereof produced in bacterial culture can be isolated, for example, by initial extraction from cell pellets, followed by one or more concentration, salting-out, aqueous ion exchange or size exclusion chromatography steps. High performance liquid chromatography (HPLC) can be employed for final purification steps. Microbial cells employed in expression of a recombinant protein can be disrupted by any convenient method, including freeze-thaw cycling, sonication, mechanical disruption, or use of cell lysing agents.

Methods known in the art for purifying antibodies and other proteins also include, for example, those described in U.S. Patent Publication Nos. 2008/0312425, 2008/0177048, and 2009/0187005, each of which is hereby incorporated by reference herein in its entirety.

In certain aspects, the HER3-binding molecule is a polypeptide that is not an antibody. A variety of methods for identifying and producing non-antibody polypeptides that bind with high affinity to a protein target are known in the art. See, e.g., Skerra, Curr. Opin. Biotechnol., 18:295-304 (2007), Hosse et al., Protein Science, 15:14-27 (2006), Gill et al., Curr. Opin. Biotechnol., 17:653-658 (2006), Nygren, FEBS J., 275:2668-76 (2008), and Skerra, FEBS J., 275:2677-83 (2008), each of which is incorporated by reference herein in its entirety. In certain aspects, phage display technology can been used to identify/produce an HER3-binding polypeptide. In certain aspects, the polypeptide comprises a protein scaffold of a type selected from the group consisting of protein A, a lipocalin, a fibronectin domain, an ankyrin consensus repeat domain, and thioredoxin.

VI. Treatment Methods Using Therapeutic Anti-HER3 Antibodies

Methods of the invention are directed to the use of anti-HER3 binding molecules, e.g., antibodies, including antigen-binding fragments, variants, and derivatives thereof, to treat patients having a disease associated with HER3 expression or HER3-expressing cells. By "HER3-expressing cell" is meant a cell expressing HER3. Methods for detecting HER3 expression in cells are well known in the art and include, but are not limited to, PCR techniques, immunohistochemistry, flow cytometry, Western blot, ELISA, and the like.

Though the following discussion refers to diagnostic methods and treatment of various diseases and disorders with an HER3-binding molecule of the invention, the methods described herein are also applicable to anti-HER3 antibodies, and the antigen-binding fragments, variants, and derivatives of these anti-HER3 antibodies that retain the desired properties of the anti-HER3 antibodies of the invention, e.g., capable of specifically binding HER3 and neutralizing HER3 activity. In some aspects, HER3-binding molecules are human or humanized antibodies that do not mediate human ADCC, or are selected from known anti-HER3 antibodies that do not mediate ADCC, or are anti-HER3 antibodies that are engineered such that they do not mediate ADCC. In some aspects, the HER3-binding molecule is a clone 16 monoclonal antibody. In other aspects, the HER3-binding molecule is a clone 16 YTE mutant antibody. In some aspects the HER3-binding molecule is a P2B11 monoclonal antibody. In some aspects the HER3-binding molecule is a 1A4 monoclonal antibody. In some aspects the HER3-binding molecule is a 2C2 monoclonal antibody. In some aspects the HER3-binding molecule is a 2F10 monoclonal antibody. In some aspects the HER3-binding molecule is a 3E1 monoclonal antibody. In some aspects the HER3-binding molecule is a P2B11 monoclonal antibody engineered to extend serum half-life. In some aspects the HER3-binding molecule is a 1A4 monoclonal antibody engineered to extend serum half-life. In some aspects the HER3-binding molecule is a 2C2 monoclonal antibody engineered to extend serum half-life. In some aspects the HER3-binding molecule is a 2F10 monoclonal antibody engineered to extend serum half-life. In some aspects the HER3-binding molecule is a 3E1 monoclonal antibody engineered to extend serum half-life. In other aspects the HER3-binding molecule is a P2B11 YTE mutant antibody. In other aspects the HER3-binding molecule is a 1A4 YTE mutant antibody. In other aspects the HER3-binding molecule is a 2C2-YTE mutant antibody. In other aspects the HER3-binding molecule is a 2F10 YTE mutant antibody. In other aspects the HER3-binding molecule is a 3E1 YTE mutant antibody.

In one aspect, treatment includes the application or administration of an anti-HER3 binding molecule, e.g., an antibody or antigen binding fragment, variant, or derivative thereof of the current invention to a subject or patient, or application or administration of the anti-HER3 binding molecule to an isolated tissue or cell line from a subject or patient, where the subject or patient has a disease, a symptom of a disease, or a predisposition toward a disease. In another aspect, treatment is also intended to include the application or administration of a pharmaceutical composition comprising the anti-HER3 binding molecule, e.g., an antibody or antigen binding fragment, variant, or derivative thereof of the current invention to a subject or patient, or application or administration of a pharmaceutical composition comprising the anti-HER3 binding molecule to an isolated tissue or cell line from a subject or patient, who has a disease, a symptom of a disease, or a predisposition toward a disease.

The anti-HER3 binding molecules, e.g., antibodies or antigen-binding fragments, variants, or derivatives thereof of the present invention are useful for the treatment of various cancers. In one aspect, the invention relates to anti-HER binding molecules, e.g., antibodies or antigen-binding fragments, variants, or derivatives thereof for use as a medicament, in particular for use in the treatment or prophylaxis of cancer. Examples of cancer include, but are not limited to colon cancer, lung cancer, gastric cancer, head and neck squamous cells cancer, melanoma, pancreatic cancer, prostate cancer, and breast cancer.

In accordance with the methods of the present invention, at least one anti-HER3 binding molecule, e.g., an antibody or antigen binding fragment, variant, or derivative thereof as defined elsewhere herein is used to promote a positive therapeutic response with respect to cancer. The term "positive therapeutic response" with respect to cancer treatment refers to an improvement in the disease in association with the activity of these anti-HER3 binding molecules, e.g., antibodies or antigen-binding fragments, variants, or derivatives thereof, and/or an improvement in the symptoms associated with the disease. Thus, for example, an improvement in the disease can be characterized as a complete response. By "complete response" is intended an absence of clinically detectable disease with normalization of any previously test results. Alternatively, an improvement in the disease can be categorized as being a partial response. A "positive therapeutic response" encompasses a reduction or inhibition of the progression and/or duration of cancer, the reduction or amelioration of the severity of cancer, and/or the amelioration of one or more symptoms thereof resulting from the administration of an anti-HER3 binding molecule of the invention. In specific aspects, such terms refer to one, two or three or more results following the administration of anti-HER3 binding molecules of the invention: (1) a stabilization, reduction or elimination of the cancer cell population; (2) a stabilization or reduction in cancer growth; (3) an impairment in the formation of cancer; (4) eradication, removal, or control of primary, regional and/or metastatic cancer; (5) a reduction in mortality; (6) an increase in disease-free, relapse-free, progression-free, and/or overall survival, duration, or rate; (7) an increase in the response rate, the durability of response, or number of patients who respond or are in remission; (8) a decrease in hospitalization rate, (9) a decrease in hospitalization lengths, (10) the size of the cancer is maintained and does not increase or increases by less than 10%, preferably less than 5%, preferably less than 4%, preferably less than 2%, and (12) an increase in the number of patients in remission.

Clinical response can be assessed using screening techniques such as magnetic resonance imaging (MRI) scan, x-radiographic imaging, computed tomographic (CT) scan, flow cytometry or fluorescence-activated cell sorter (FACS) analysis, histology, gross pathology, and blood chemistry, including but not limited to changes detectable by ELISA, RIA, chromatography, and the like. In addition to these positive therapeutic responses, the subject undergoing therapy with the anti-HER3 binding molecule, e.g., an antibody or antigen-binding fragment, variant, or derivative thereof, can experience the beneficial effect of an improvement in the symptoms associated with the disease.

The anti-HER3 binding molecules, e.g., antibodies or antigen-binding fragments, variants, or derivatives thereof of the invention can be used in combination with any known therapies for cancer, including any agent or combination of agents that are known to be useful, or which have been used or are currently in use, for treatment of cancer, e.g., colon cancer, lung cancer, gastric cancer, head and neck squamous cells cancer, and breast cancer. The second agent or combination of agents of the pharmaceutical combination formulation or dosing regimen preferably has complementary activities to the antibody or polypeptide of the invention such that they do not adversely affect each other.

Anticancer agents include drugs used to treat malignancies, such as cancerous growths. Drug therapy can be used alone, or in combination with other treatments such as surgery or radiation therapy. Several classes of drugs can be used in cancer treatment, depending on the nature of the organ involved. For example, breast cancers are commonly stimulated by estrogens, and can be treated with drugs which inactive the sex hormones. Similarly, prostate cancer can be treated with drugs that inactivate androgens, the male sex hormone. Anti-cancer agents for use in certain methods of the present invention include, among others, antibodies (e.g., antibodies which bind IGF-1R, antibodies which bind EGFR, antibodies which bind HER2, antibodies which bind HER3, or antibodies which bind cMET), small molecules targeting IGF1R, small molecules targeting EGFR, small molecules targeting HER2, antimetabolites, alkylating agents, topoisomerase inhibitors, microtubule targeting agents, kinase inhibitors, protein synthesis inhibitors, immunotherapeutic agents, hormonal therapies, glucocorticoids, aromatase inhibitors, mTOR inhibitors, chemotherapeutic agents, Protein Kinase B inhibitors, Phosphatidylinositol 3-Kinase (PI3K) inhibitors, Cyclin Dependent Kinase (CDK) inhibitors, RLr9, CD289, enzyme inhibitors, anti-TRAIL, MEK inhibitors, etc.

In specific aspects the HER3-binding molecules of the invention, e.g., antibodies or antigen-binding fragments thereof, can be administered in combination with antibodies or antibody fragments targeting epidermal growth factor receptor (EGFR), e.g., cetuximab (Erbitux®, Imclone), panitumumab (Vectibix®, Amgen), matuzumab/EMD72000 (Merck Serono), MM-151 oligoclonal (Merrimack), nimotuzumab (TheraCIM, InnGene Kalbiotechy), GA201/RG7160 (Roche), Sym004 (Symphogen), MEHD-7945A (EGFR/HER3 dual specific, Genentech). In other specific aspects the HER3-binding molecules of the invention, e.g., antibodies or antigen-binding fragments thereof, can be administered in combination with antibodies or antibody fragments targeting HER2, e.g., pertuzumab (rhuMAb 2C4/Omnitarg®, Genentech), trastuzumab (Herceptin®, Genentech/Roche), MM-111 (HER2/HER3 bispecific antibody, Merrimack, e.g., WO 2009/126920). In still other specific aspects the HER3-binding molecules of the invention, e.g., antibodies or antigen-binding fragments thereof, can be administered in combination with antibodies or antibody fragments that also target HER3, e.g., MEHD-7945A/RG7597 (EGFR/HER3 dual specific, Genentech, e.g., WO 2010108127), MM-121 (Merrimack, e.g., WO 2008/100624), MM-111 (HER2/HER3 bispecific antibody, Merrimack, e.g., WO 2009/126920), AV-203 (Aveo, e.g., WO 2011/136911), AMG888 (Amgen, WO 2007/077028), HER3-8 (ImmunogGen, e.g., WO 2012/019024). In further specific aspects the HER3-binding molecules of the invention, e.g., antibodies or antigen-binding fragments thereof, can be administered in combination with antibodies or antibody fragments targeting HER4. In a specific aspect, the HER3-binding molecules of the invention can be administered in combination with an antibody that targets EGFR, or HER2 (e.g., cetuximab or trastuzumab). In a further specific aspect, the HER3-binding molecules of the invention can be administered in combination with antibody drug conjugates that targets HER2 (e.g., trastuzumab emtansine, Genentech/Roche). It is contemplated that the HER3-binding molecules of the invention enhance the internalization and degradation of a co-receptor induced by the binding of an antibody to the co-receptor and will thus, enhance the efficacy of an antibody and/or antibody drug conjugate that targets EGFR, HER2 and/or HER4.

In other aspects, the HER3-binding molecules of the invention can be administered in combination with tyrosine kinase inhibitors. In some other specific aspects, the HER3-binding molecules of the invention can be administered in combination with inhibitors of the tyrosine kinase activity associated with EGFR and/or HER2/neu, e.g., lapatinib. In specific aspects the HER3-binding molecules of the invention, can be administered in combination with small molecule inhibitors of the epidermal growth factor receptor(s) (e.g., EGFR, HER2, HER4) e.g., gefitinib (Lressa®, Astrazeneca); canertinib/CI-1033 (Pfizer); lapatinib (Tykerb®, GlaxoSmithKline), erlotinib (Tarceva®, OSI Pharma), afatinib (Tovok®/Tomtovok®, Boehringer Ingelheim), neratinib (HKI-272, Pfizer).

In some aspects, the HER3-binding molecules of the invention can be administered in combination with antimitotic agents. In some specific aspects, the HER3-binding molecules of the invention can be administered in combination with agents that stabilize the mitotic spindle microtubule assembly, e.g, paclitaxel or docetaxel.

In some aspects, the HER3-binding molecules of the invention can be administered in combination with MEK (mitogen-activated protein kinase (MAPK) kinase, also known as MAPKK) inhibitors, e.g., selumetinib (AZD6244, ARRY-142866, AstraZeneca), WX-554 (Wilex), trametinib (GlaxoSmithKline), refametinib (Ardea Biosciences), E-6201 (Eisai), MEK-162 (Novartis). In a particular aspect, the combination of a MEK inhibitor and a HER3-binding molecule of the invention is more efficacious than either agent alone. In a specific aspect, a HER3-binding molecule of the invention is administered in combination with selumetinib.

Where the combined therapies comprise administration of an anti-HER3 binding molecule in combination with administration of another therapeutic agent, the methods of the invention encompass coadministration, using separate formulations or a single pharmaceutical formulation, and consecutive administration in either order. In some aspects, the anti-HER3 antibodies described herein are administered in combination with other drugs, wherein the antibody or antigen-binding fragment, variant, or derivative thereof and the therapeutic agent(s) can be administered sequentially, in either order, or simultaneously (i.e., concurrently or within the same time frame).

The combination therapy can provide "synergy" and prove "synergistic", i.e., the effect achieved when the active ingredients used together is greater than the sum of the effects that results from using the compounds separately. A synergistic effect can be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect can be attained when the compounds are administered or delivered sequentially, e.g., by different injections in separate syringes. In general, during alternation therapy, an effective dosage of each active ingredient is administered sequentially, i.e., serially, whereas in combination therapy, effective dosages of two or more active ingredients are administered together.

In some aspects, the HER3-binding molecule, e.g., an anti-HER3 antibody or antigen binding fragment thereof of the invention can be administered in a synergistic combination with a epidermal growth factor receptor (EGFR) inhibitor. In some aspects, the EGFR inhibitor is an antibody. In specific aspects, the EGFR inhibitor antibody is Erbitux® (cetuximab) or panitumumab (Vectibix®). In specific aspects the HER3-binding molecules of the invention, e.g., antibodies or antigen-binding fragments thereof, can be administered in a synergistic combination with inhibitors of the tyrosine kinase activity associated with EGFR and/or HER2/neu, e.g., lapatinib. In some aspects, the HER3-binding molecule, e.g., an anti-HER3 antibody or antigen binding fragment thereof of the invention can be administered in a synergistic combination with a HER2 inhibitor. In some aspects, the HER2 inhibitor is an antibody. In specific aspects, the HER2 inhibitor antibody is pertuzumab (rhuMAb 2C4/Omnitarg®, Genentech), trastuzumab (Herceptin®, Genentech/Roche) or trastuzumab emtansine (Genentech/Roche). In specific aspects the HER3-binding molecules of the invention, e.g., antibodies or antigen-binding fragments thereof, can be administered in a synergistic combination with inhibitors of the tyrosine kinase activity associated with HER2/neu, e.g., lapatinib. In some aspects, the HER3-binding molecules of the invention can be administered in a synergistic combination with an antimitotic agent. In some specific aspects the antimitotic agent stabilizes the mitotic spindle microtubule assembly. In some specific aspects, the antimitotic agent is paclitaxel or docetaxel. In some specific embodiments, the 2C2 antibody can be administered in a synergistic combination with a growth factor receptor (EGFR) inhibitor. In some specific embodiments, the EGFR inhibitor is an antibody. In specific embodiments, the EGFR inhibitor antibody administered synergistically with the 2C2 antibody is Erbitux® (cetuximab). In specific embodiments the 2C2 antibody can be administered in a synergistic combination with inhibitors of the tyrosine kinase activity associated with EGFR and/or HER2/neu, e.g., lapatinib. In some embodiments, the 2C2 antibody can be administered in a synergistic combination with an antimitotic agent. In some specific embodiments, the antimitotic agent administered synergistically with the 2C2 antibody stabilizes the mitotic spindle microtubule assembly. In some specific embodiments, the antimitotic agent administered synergistically with the 2C2 antibody is paclitaxel.

In one aspect, the cancer comprises the KRAS mutation. In specific aspects, the KRAS mutation is located at codon 12 of a human KRAS gene. As demonstrated in the Examples section, anti-HER3 antibodies disclosed herein as capable on inhibiting the growth of tumor cells that comprise a KRAS mutation, either when used as a single agent (monotherapy) or in combination with another therapeutic agent.

A further aspect is the use of anti-HER3 binding molecules, e.g., antibodies or antigen-binding fragments, variants, or derivatives thereof, for diagnostic monitoring of protein levels in tissue as part of a clinical testing procedure, e.g., to determine the efficacy of a given treatment regimen. For example, detection can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}$I, $^{131}$I, $^{35}$S, or $^{3}$H.

VII. Pharmaceutical Compositions and Administration Methods

Methods of preparing and administering anti-HER3 binding molecules, e.g., antibodies, or antigen-binding fragments, variants, or derivatives thereof of the invention to a subject in need thereof are well known to or are readily determined by those skilled in the art. The route of administration of the anti-HER3 binding molecule, e.g, antibody, or antigen-binding fragment, variant, or derivative thereof can be, for example, oral, parenteral, by inhalation or topical. The term parenteral as used herein includes, e.g., intravenous, intraarterial, intraperitoneal, intramuscular, subcutaneous, rectal, or vaginal administration. However, in other methods compatible with the teachings herein, anti-HER3 binding molecules, e.g., antibodies, or antigen-binding fragments, variants, or derivatives thereof, of the invention can be delivered directly to the site of the adverse cellular population thereby increasing the exposure of the diseased tissue to the therapeutic agent.

As discussed herein, anti-HER3 binding molecules, e.g., antibodies, or antigen-binding fragments, variants, or derivatives thereof of the invention can be administered in a pharmaceutically effective amount for the in vivo treatment of HER3-expressing cell-mediated diseases such as certain types of cancers.

The pharmaceutical compositions used in this invention can comprise pharmaceutically acceptable carriers, including, e.g., water, ion exchangers, proteins, buffer substances, and salts. Preservatives and other additives can also be present. The carrier can be a solvent or dispersion medium. Suitable formulations for use in the therapeutic methods disclosed herein are described in Remington's Pharmaceutical Sciences (Mack Publishing Co.) 16th ed. (1980). In some aspects, the HER3-binding molecules of the invention are formulated in a refrigerator (2-8° C.) stable composition. In a particular aspect, the refrigerator stable composition comprises 25 mM histidine/histidine HCL, 205 mM sucrose, 0.02% polysorbate 80 at pH 6.0. In another particular aspect, the HER3-binding molecules of the invention are formulated at 25-100 mg/ml in the refrigerator stable composition.

In any case, sterile injectable solutions can be prepared by incorporating an active compound (e.g., an anti-HER3 antibody, or antigen-binding fragment, variant, or derivative thereof, by itself or in combination with other active agents) in the required amount in an appropriate solvent followed by filtered sterilization. Further, the preparations can be packaged and sold in the form of a kit. Such articles of manufacture can have labels or package inserts indicating that the associated compositions are useful for treating a subject suffering from, or predisposed to a disease or disorder.

Parenteral formulations can be a single bolus dose, an infusion or a loading bolus dose followed with a maintenance dose. These compositions can be administered at specific fixed or variable intervals, e.g., once a day, or on an "as needed" basis.

The composition can be administered as a single dose, multiple doses or over an established period of time in an infusion. Dosage regimens also can be adjusted to provide the optimum desired response (e.g., a therapeutic or prophylactic response).

Therapeutically effective doses of the compositions of the present invention, for treatment of HER3-expressing cell-mediated diseases such as certain types of cancers including e.g., colon cancer, lung cancer, gastric cancer, head and neck squamous cells cancer, melanoma, pancreatic cancer, prostate cancer, and breast cancer, vary depending upon many different factors, including means of administration, target site, physiological state of the patient, whether the patient is human or an animal, other medications administered, and whether treatment is prophylactic or therapeutic. Usually, the patient is a human, but non-human mammals including transgenic mammals can also be treated. Treatment dosages can be titrated using routine methods known to those of skill in the art to optimize safety and efficacy.

The amount of at least one anti-HER3 binding molecule, e.g., antibody or binding fragment, variant, or derivative thereof to be administered is readily determined by one of ordinary skill in the art without undue experimentation given the disclosure of the present invention. Factors influencing the mode of administration and the respective amount of at least one anti-HER3 binding molecule, e.g., antibody, antigen-binding fragment, variant or derivative thereof include, but are not limited to, the severity of the disease, the history of the disease, and the age, height, weight, health, and physical condition of the individual undergoing therapy. Similarly, the amount of anti-HER3 binding molecule, e.g., antibody, or fragment, variant, or derivative thereof, to be administered will be dependent upon the mode of administration and whether the subject will undergo a single dose or multiple doses of this agent.

The present invention also provides for the use of an anti-HER3 binding molecule, e.g., an antibody or antigen-binding fragment, variant, or derivative thereof, in the manufacture of a medicament for treating a type of cancer, including, e.g., colon cancer, lung cancer, gastric cancer, head and neck squamous cells cancer, melanoma, pancreatic cancer, prostate cancer, and breast cancer.

The invention also provides for the use of an anti-HER3 binding molecule, e.g., antibody of the invention, or antigen-binding fragment, variant, or derivative thereof, in the manufacture of a medicament for treating a subject for treating a type of cancer. In certain aspects, the medicament is used in a subject that has been pretreated with at least one other therapy. By "pretreated" or "pretreatment" is intended the subject has received one or more other therapies (e.g., been treated with at least one other anti-cancer therapy) prior to receiving the medicament comprising the anti-HER3 binding molecule, e.g., antibody or antigen-binding fragment, variant, or derivative thereof. It is not necessary that the subject was a responder to pretreatment with the prior therapy or therapies. Thus, the subject that receives the medicament comprising the anti-HER3 binding molecule, e.g., an antibody or antigen-binding fragment, variant, or derivative thereof could have responded, or could have failed to respond to pretreatment with the prior therapy, or to one or more of the prior therapies where pretreatment comprised multiple therapies.

The invention also provides for the co-administration of an anti-HER3 binding molecule, e.g., antibody of the invention, or antigen-binding fragment, variant, or derivative thereof and at least one other therapy. The anti-HER3 antibody and the at least one other therapy can be co-administered together in a single composition or can be co-administered together at the same time or overlapping times in separate compositions.

The invention also provides for the use of an anti-HER3 binding molecule, e.g., antibody of the invention, or antigen-binding fragment, variant, or derivative thereof, in the manufacture of a medicament for treating a subject for treating cancer, wherein the anti-HER3 binding molecule is administered before a subject has been treated with at least one other therapy.

VIII. Diagnostics

The invention further provides a diagnostic method useful during diagnosis of HER3-expressing cell-mediated diseases such as certain types of cancer including, e.g., colon cancer, lung cancer, gastric cancer, head and neck squamous cells cancer, melanoma, pancreatic cancer, prostate cancer, and breast cancer, which involves measuring the expression level of HER3 protein or transcript in tissue or other cells or body fluid from an individual and comparing the measured expression level with a standard HER3 expression level in normal tissue or body fluid, whereby an increase in the expression level compared to the standard is indicative of a disorder.

The anti-HER3 antibodies of the invention and antigen-binding fragments, variants, and derivatives thereof, can be used to assay HER3 protein levels in a biological sample using classical immunohistological methods known to those of skill in the art (e.g., see Jalkanen, et al., *J. Cell. Biol.* 101:976-985 (1985); Jalkanen et al., *J. Cell Biol.* 105:3087-3096 (1987)). Other antibody-based methods useful for detecting HER3 protein expression include immunoassays, such as the enzyme linked immunosorbent assay (ELISA), immunoprecipitation, or Western blotting. Suitable assays are described in more detail elsewhere herein.

By "assaying the expression level of HER3 polypeptide" is intended qualitatively or quantitatively measuring or estimating the level of HER3 polypeptide in a first biological sample either directly (e.g., by determining or estimating absolute protein level) or relatively (e.g., by comparing to the disease associated polypeptide level in a second biological sample). HER3 polypeptide expression level in the first biological sample can be measured or estimated and compared to a standard HER3 polypeptide level, the standard being taken from a second biological sample obtained from an individual not having the disorder or being determined by averaging levels from a population of individuals not having the disorder. As will be appreciated in the art, once the "standard" HER3 polypeptide level is known, it can be used repeatedly as a standard for comparison.

The invention further provides a diagnostic method useful during diagnosis of HER3-expressing cell-mediated diseases such as certain types of cancer including, e.g., colon cancer, lung cancer, gastric cancer, head and neck squamous cells cancer, melanoma, pancreatic cancer, prostate cancer, and breast cancer, which involves measuring the activity level of HER3 protein in tissue or other cells or body fluid from an individual and comparing the measured activity level with a standard HER3 activity level in normal tissue or body fluid, whereby an increase in the activity level compared to the standard is indicative of a disorder.

The invention further provides a diagnostic method useful during treatment of HER3-expressing cell-mediated diseases such as certain types of cancer including, e.g., colon cancer, lung cancer, gastric cancer, head and neck squamous cells cancer, melanoma, pancreatic cancer, prostate cancer, and breast cancer, which involves measuring the activity level of HER3 protein in tissue or other cells or body fluid from an individual during treatment of a HER3-expressing cell-mediated disease and comparing the measured activity level with a standard HER3 activity level in normal tissue or body fluid and/or comparing the measured activity level with a standard HER3 activity level in tissue or body fluid obtained from the individual prior to treatment, whereby a decrease in the activity level compared to the standard is indicative of an inhibition of HER3 activity.

By "assaying the activity level of HER3 protein" is intended qualitatively or quantitatively measuring or estimating the activity of HER3 protein in a first biological sample either directly (e.g., by determining or estimating absolute activity level) or relatively (e.g., by comparing to the activity level in a second biological sample). HER3 protein activity level in the first biological sample can be measured or estimated and compared to a standard HER3 protein activity, the standard being taken from a second biological sample obtained from an individual not having the disorder or being determined by averaging levels from a population of individuals not having the disorder or from an individual prior to treatment. As will be appreciated in the art, once the "standard" HER3 protein activity level is known, it can be used repeatedly as a standard for comparison. In certain aspects, the activity level of HER3 in a biological sample is measured or estimated or compared by detecting phosphorylated HER3 in a biological sample. In a specific aspect, the activity level of HER3 in a biological sample is measured or estimated or compared by detecting phosphorylated HER3 in a skin biopsy, wherein the skin is stimulated with HRG prior to or after biopsy.

By "biological sample" is intended any biological sample obtained from an individual, cell line, tissue culture, or other source of cells potentially expressing HER3. Methods for obtaining tissue biopsies and body fluids from mammals are well known in the art.

In some aspects, the bioactivity of a HER3 inhibitor (e.g., anti-HER3 antibody of the invention and antigen-binding fragments, variants and derivatives thereof) administered to a subject can be detected using an ex-vivo assay. In particular aspects the ex-vivo assay comprises detecting the level of phosphorylated HER3 in a skin biopsy, wherein the skin is stimulated with HRG prior to or after biopsy. In a specific aspect matched skin biopsies are taken from a subject that has been administered the HER3 inhibitor. In a specific aspect, HRG is injected under a first area of the skin and a control buffer is injected under a second area of the skin of a subject administered the HER3 inhibitor, wherein after a desired amount of time (e.g., 10-60 minutes) a biopsy is taken from the first and second areas of the skin. In an alternative aspect, a first skin biopsy is treated with HRG and a second skin biopsy is treated with a control buffer, wherein the first and the second biopsies are matched skin biopsies taken from a subject that has been administered the HER3 inhibitor. In another specific aspect, the level of phosphorylated HER3 is detected in the skin biopsies. In certain aspects, the difference in the level of phosphorylated HER3 between the first (HRG treated) and the second (control buffer treated) biopsy is determined. In certain aspects, the skin biopsy is homogenized and the level of phosphorylated HER3 is detected by ELISA. In still other aspects, the levels of phosphorylated HER3 in the skin biopsies from a subject that has been administered the HER3 inhibitor is compared to the levels of phosphorylated HER3 in skin biopsies from a control subject that has not been administered the HER3 inhibitor, wherein a reduction in the level of phosphorylated HER3 in the skin biopsies of the subject that has been administered the HER3 inhibitor is a measure of the bioactivity of the HER3 inhibitor. In alternative aspects, the levels of phosphorylated HER3 in the skin biopsies from a subject that has been administered the HER3 inhibitor is compared to the levels of phosphorylated HER3 in skin biopsies from the same subject taken prior to the administration of the HER3 inhibitor, wherein a reduction in the level of phosphorylated HER3 in the skin biopsies of the subject after administration of the HER3 inhibitor is a measure of bioactivity of the HER3 inhibitor. Other specific aspects of the methods are detailed in the Examples section 5.15.

IX. Kits Comprising HER3-Binding Molecules

The present invention provides kits that comprise the HER3-binding molecule, e.g., an anti-HER3 antibody or antigen binding fragment thereof of the invention described herein and that can be used to perform the methods described herein. In certain aspects, a kit comprises at least one purified anti-HER3 antibody or an antigen-binding fragment thereof in one or more containers. In some aspects, the kits contain all of the components necessary and/or sufficient to perform a detection assay, including all controls, directions for performing assays, and any necessary software for analysis and presentation of results. One skilled in the art will readily recognize that the disclosed HER3-binding molecule, e.g., an anti-HER3 antibody or antigen binding fragment thereof of the present invention can be readily incorporated into one of the established kit formats which are well known in the art.

X. Immunoassays

Anti-HER3 binding molecules, e.g., antibodies or antigen-binding fragments thereof, variants, or derivatives thereof of the molecules of the invention can be assayed for immunospecific binding by any method known in the art. The immunoassays that can be used include but are not limited to competitive and non-competitive assay systems using techniques such as Western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al., eds, (1994) Current Protocols in Molecular Biology (John Wiley & Sons, Inc., NY) Vol. 1, which is incorporated by reference herein in its entirety).

HER3-binding molecules, e.g., anti-HER3 antibodies or antigen-binding fragments thereof, variants, or derivatives thereof of the molecules of the invention, can be employed histologically, as in immunofluorescence, immunoelectron microscopy or non-immunological assays, for in situ detection of HER3 receptors or conserved variants or peptide fragments thereof. In situ detection can be accomplished by removing a histological specimen from a patient, and applying thereto a labeled HER3-binding molecule, e.g., an anti-HER3 antibody or antigen-binding fragment thereof, variant, or derivative thereof, preferably applied by overlaying the labeled HER3-binding molecule (e.g., and antibody or fragment) onto a biological sample. Through the use of such a procedure, it is possible to determine not only the presence of HER3, or conserved variants or peptide fragments, but also its distribution in the examined tissue. Using the present invention, those of ordinary skill will readily perceive that any of a wide variety of histological methods (such as staining procedures) can be modified in order to achieve such in situ detection.

The binding activity of a given lot of HER3-binding molecule, e.g., anti-HER3 antibody or antigen-binding fragment thereof, variant, or derivative thereof can be determined according to well-known methods. Those skilled in the art will be able to determine operative and optimal assay conditions for each determination by employing routine experimentation.

Methods and reagents suitable for determination of binding characteristics of an isolated HER3-binding molecule, e.g., anti-HER3 antibody or antigen-binding fragment thereof, variant, or an altered/mutant derivative thereof, are known in the art and/or are commercially available. Equipment and software designed for such kinetic analyses are commercially available (e.g., BIAcore, BIAevaluation software, GE Healthcare; KinExa Software, Sapidyne Instruments).

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Sambrook et al., ed. (1989) Molecular Cloning A Laboratory Manual (2nd ed.; Cold Spring Harbor Laboratory Press); Sambrook et al., ed. (1992) Molecular Cloning: A Laboratory Manual, (Cold Springs Harbor Laboratory, NY); D. N. Glover ed., (1985) DNA Cloning, Volumes I and II; Gait, ed. (1984) Oligonucleotide Synthesis; Mullis et al. U.S. Pat. No. 4,683,195; Hames and Higgins, eds. (1984) Nucleic Acid Hybridization; Hames and Higgins, eds. (1984) Transcription And Translation; Freshney (1987) Culture Of Animal Cells (Alan R. Liss, Inc.); Immobilized Cells And Enzymes (IRL Press) (1986); Perbal (1984) A Practical Guide To Molecular Cloning; the treatise, Methods In Enzymology (Academic Press, Inc., N.Y.); Miller and Calos eds. (1987) Gene Transfer Vectors For Mammalian Cells, (Cold Spring Harbor Laboratory); Wu et al., eds., Methods In Enzymology, Vols. 154 and 155; Mayer and Walker, eds. (1987) Immunochemical Methods In Cell And Molecular Biology (Academic Press, London); Weir and Blackwell, eds., (1986) Handbook Of Experimental Immunology, Volumes I-IV; Manipulating the Mouse Embryo, Cold Spring Harbor Laboratory Press, Cold Spring Harbor, N.Y., (1986); and in Ausubel et al. (1989) Current Protocols in Molecular Biology (John Wiley and Sons, Baltimore, Md.).

General principles of antibody engineering are set forth in Borrebaeck, ed. (1995) Antibody Engineering (2nd ed.; Oxford Univ. Press). General principles of protein engineering are set forth in Rickwood et al., eds. (1995) Protein Engineering, A Practical Approach (IRL Press at Oxford Univ. Press, Oxford, Eng.). General principles of antibodies and antibody-hapten binding are set forth in: Nisonoff (1984) Molecular Immunology (2nd ed.; Sinauer Associates, Sunderland, Mass.); and Steward (1984) Antibodies, Their Structure and Function (Chapman and Hall, New York, N.Y.). Additionally, standard methods in immunology known in the art and not specifically described are generally followed as in Current Protocols in Immunology, John Wiley & Sons, New York; Stites et al., eds. (1994) Basic and Clinical Immunology (8th ed; Appleton & Lange, Norwalk, Conn.) and Mishell and Shiigi (eds) (1980) Selected Methods in Cellular Immunology (W.H. Freeman and Co., NY).

Standard reference works setting forth general principles of immunology include Current Protocols in Immunology, John Wiley & Sons, New York; Klein (1982) J., Immunology: The Science of Self-Nonself Discrimination (John Wiley & Sons, NY); Kennett et al., eds. (1980) Monoclonal Antibodies, Hybridoma: A New Dimension in Biological Analyses (Plenum Press, NY); Campbell (1984) "Monoclonal Antibody Technology" in Laboratory Techniques in Biochemistry and Molecular Biology, ed. Burden et al., (Elsevere, Amsterdam); Goldsby et al., eds. (2000) Kuby Immunnology (4th ed.; H. Freemand & Co.); Roitt et al. (2001) Immunology (6th ed.; London: Mosby); Abbas et al. (2005) Cellular and Molecular Immunology (5th ed.; Elsevier Health Sciences Division); Kontermann and Dubel (2001) Antibody Engineering (Springer Verlan); Sambrook and Russell (2001) Molecular Cloning: A Laboratory Manual (Cold Spring Harbor Press); Lewin (2003) Genes VIII (Prentice Ha112003); Harlow and Lane (1988) Antibodies: A Laboratory Manual (Cold Spring Harbor Press); Dieffenbach and Dveksler (2003) PCR Primer (Cold Spring Harbor Press).

All of the references cited above, as well as all references cited herein, are incorporated herein by reference in their entireties.

The following examples are offered by way of illustration and not by way of limitation.

EXAMPLES

Aspects of the present disclosure can be further defined by reference to the following non-limiting examples, which describe in detail preparation of certain antibodies of the present disclosure and methods for using antibodies of the present disclosure. It will be apparent to those skilled in the art that many modifications, both to materials and methods, can be practiced without departing from the scope of the present disclosure.

Example 1

Methods for Isolation/Optimization of Anti-HER3 Monoclonal Antibodies 1.1. Antigens and Cell Lines Recombinant human Her1(ECD)/Fc chimera, human HER2(ECD)/Fc chimera, human HER3(ECD)/Fc chimera and human Her4(ECD)/Fc were all purchased from R&D Systems (Minneapolis, Minn.) and were fused to the C-terminal 6x Histidine-tag via a linker peptide. Recombinant mouse HER3(ECD)/Fc chimera was generated in house. Human KPL-4 breast cancer cells were cultured in DMEM supplemented with 5% fetal bovine serum (FBS).

1.2. Library Selection of HER3 Binders—Identification of Clone 16 Antibody (CL16)

The unlabeled and biotinylated HER3(ECD)/Fc were used as the targets for selection of HER3 binders from Dyax's Fab 310 human Fab phage display library (Dyax, Cambridge, Mass.). Two arms of panning were carried out: captured panning and in solution panning. For the captured panning, input phage were first incubated with polyclonal human IgG captured on immunotubes via immobilized recombinant Protein A/G, and then selected with unlabeled target captured on immunotubes via immobilized recombinant Protein A/G.

In the in solution panning, input phage were allowed to incubate with polyclonal human IgG, streptavidin-coated magnetic beads with quenched biotin for deselection and then selected with biotinylated target with subsequent incubation with streptavidin-coated magnetic beads to capture phage bound to the target. After removal of unbound phage by washing extensively with TPBS (1xPBS/0.1% Tween-20), the bound phage were eluted with 100 mM TEA (triethylamine). Eluted phage and the remaining phage on beads from in solution panning were subsequently amplified, and subjected to further rounds of selection. Three rounds of selection were carried out for each arm of selection.

The percentage of positive binding phages ranged from less than 1% using capture panning up to 68% using three rounds of in solution panning (TABLE 3).

TABLE 3

Screening of HER3 binders.

| Panning | Captured Panning | Second Round In Solution Panning | Third Round In Solution Panning |
| --- | --- | --- | --- |
| Total clones screened | 380 | 285 | 475 |
| Positive clones | 1 | 7 | 322 |
| Positive rate (%) | <1 | 2 | 68 |

1.3. Screening for Human and Mouse HER3 Binders by Phage ELISA

Phage enriched from the second and the third rounds of selection were screened by phage ELISA for human and mouse HER3 binding. 96-well half area plates were coated with 5 µg/ml, 50 µl per well of different antigens diluted in 1xPBS, pH 7.4 overnight at 4° C. The coated plates were blocked with 3% (w/v) non-fat milk in TPBS for 1 hour at room temperature, and washed two times with TPBS. The plates were then incubated for 1 h with overnight phage supernatant. After washing ten times with TPBS, the plates were incubated with horseradish peroxidase (HRP)-conjugated anti-M13 antibody for 1 hour, and washed ten times. Plates were developed with tetramethylbenzidine (TMB) peroxidase substrate solution, the reactions were stopped with 0.18M of $H_2SO_4$, and plates were read at 450 nm on an ELISA plate reader.

29 unique positive binders were identified that were cross reactive to murine HER3 (as a HER3-Fc fusion). None of the identified binders showed cross reactivity to HER2 or Her4 (data not shown).

1.4. Reformatting of Fabs into Whole IgG Antibodies and Expression

The immunoglobulin variable light chain (VL) and variable heavy chain (VH) from positive phage clones were generated by PCR and inserted into a human IgG1 expression vector containing the lambda light chain constant region and the CH1-hinge-CH2-CH3 IgG1 region. To express IgG1 antibodies, human embryonic kidney 293-F cells were transiently transfected with the reformatted IgG vectors using 293 Fectin™ reagent (Invitrogen, Carlsbad, Calif.). Conditioned media were harvested 10 days after transfection, pooled, and sterile-filtered. IgG1s were purified using protein A beads. The final eluted IgG1s were dialyzed against PBS, and IgG1 concentrations were determined by protein quantitation assay.

Clone 16 (CL16; SEQ ID NOs: 1 and 2, VL and VH amino acid sequences, respectively) was reformatted to human IgG1

1.5. Determination of Internalization of Clone 16 Antibody (CL16) by Immunofluorescence Human breast cancer KPL-4 cells were labeled with Clone 16 antibody (CL16). Incubation of the cells with CL16 lead to an increase in HER3 endocytosis, which prevented the receptor from forming active signaling complexes with HER2 at the cell surface.

Figure 1:
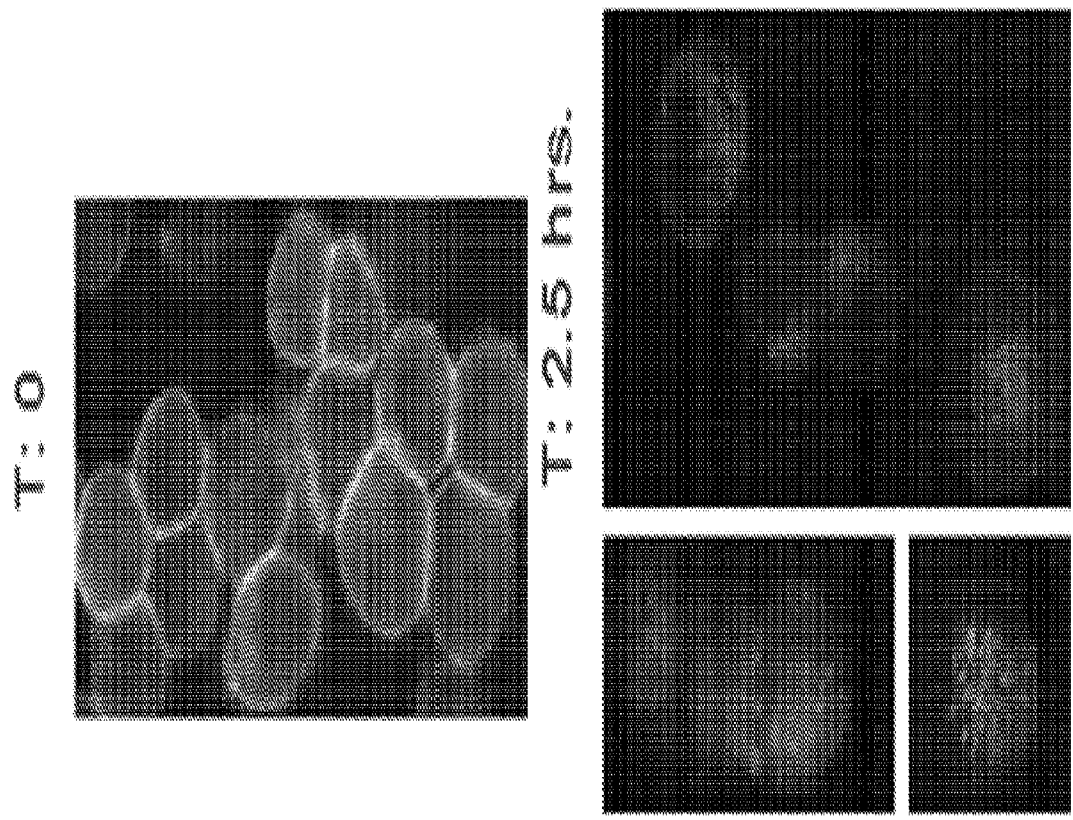

Cell surface attached CL16 antibodies were allowed to internalize by incubating the cells under growth conditions for either zero (non-internalized) or 2.5 hours (internalized) (FIG. 1). All cells were then fixed with 3.7% paraformaldehyde, washed in PBS, permeabilized with 0.5% Triton X-100 in PBS, and stained with 1 µg/ml Alexa Fluor® 488 goat anti-human IgG (Invitrogen) prior to addition of antifade mounting media and fluorescent microscopy examination. The CL16 antibody was found to internalize in KPL-4 cells. At time zero KPL-4 cells showed intense cell surface staining (FIG. 1, 0 hours, top panel), after incubation under growth conditions for 2.5 hours the cell surface staining was diminished and replaced by intracellular punctuate staining indicative of internalization (FIG. 1, 2.5 hours, bottom panels).

1.6. Construction of a Phage Vector Expressing Clone 16 Fab

DNA encoding the antigen binding fragment (Fab) of the antibody Clone 16 was cloned into a modified, M13-based phage expression vector previously described by Dall'Acqua et al. (Dall'Acqua et al., 2005, Methods. 36:43-60). In this modified vector, a human lambda (λ) constant region DNA was engineered in place of the human kappa (c) light chain. The expression of Fab fragment is under the control of the LacZ promoter and secretion of the Fab fragment is enabled by the phage P3 signal sequences fused to the N-termini of either the VH and the VL chains of the Fab fragment. The cloning was carried out by hybridization mutagenesis as described by Kunkel (Kunkel, T. A., 1985, Proc. Natl. Acad. Sci. USA; 82:488-492) and Wu (Wu, H., 2003, Methods Mol. Biol. 207:197-212).

Briefly, the variable regions of clone 16 IgG were amplified by polymerase chain reaction (PCR). By hybridization followed by DNA polymerization reaction, the clone 16 variable light region was integrated in frame with the human lambda constant region, and the variable heavy region was cloned in frame with the human heavy chain constant region 1 (CH1), respectively. The phage vector containing the Clone 16 Fab fragment was then grown in *Escherichia coli* CJ236 strain to produce uridine (U) containing single stranded DNA (ssDNA) as described by Wu and An (Wu, H. and An, LL., 2003, Methods Mol. Biol. 207:213-33). The uridine containing ssDNA was used as the template to introduce designed mutations for improving binding affinity to HER3.

1.7. Germlining of Clone 16 (CL16)

Sequence analysis shows that the VH frameworks of Clone 16 (CL16) shares 100% sequence identity with VH germline gene 3-23 while VL frameworks differ at 6 positions from its closest germline gene 47*01. Site direct mutagenesis to change each and all of the amino acids that differ from the germline gene 47*01 was performed. Specifically, six point mutations were introduced into the light chain variable regions as follows: Y2S, E3V, S18R, M21I, H38Q and S50Y where the first letter represents the one letter amino acid code of the original Clone 16, the number represents the framework residue number (as per Kabat), and the second letter represents the one letter amino acid code of the germline sequence. See sequences in FIG. 2A and FIG. 2C, corresponding to the original VL CL16 and germlined (GL) VL CL16, respectively. The resultant variants were expressed as Fab and their binding to the recombinant HER3 protein was determined by ELISA.

The binding results showed that the H38Q amino acid mutation in framework 2 improved binding over the parental Clone 16 as measured by ELISA. In contrast, the S49Y mutation in the same framework had negative impact on binding. Other point mutations showed no impact on HER3 binding. The fully germlined mutant with all 6 non-germline amino acids mutated showed a similar degree of reduced binding as the S50Y point mutation, indicating that amino acid S50 participates in binding. Further testing of the clone with all the germline point mutations except S50Y retained and/or increased binding to HER3 comparing to the parental clone 16. This partially germlined clone, Clone 16 (GL) (also referred to here as "GL-P6"), was used as the template for further affinity optimization.

1.8. Affinity Optimization of Clone 16 (CL16)

Each amino acid of all 6 complementary-determining regions (CDRs) of germlined clone GL-P6 was individually mutated to other 20 amino acids using a hybridization mutagenesis method (Kunkel, 1985). Two sets of DNA primers, one containing a NSS codon encoding 8 amino acids and the other containing a NWS codon encoding 12 different amino acids, were used to introduce mutations to each targeted CDR position. The individual degenerate primers were used in hybridization mutagenesis reactions. Briefly, each degenerate primer was phosphorylated, then used in a 10:1 ratio with the uridinylated GL-16 Fab ssDNA. The mixture was heated to 95° C. then cooled down to 55° C. over 1 hour. Thereafter, T4 ligase and T7 DNA polymerase were added and the mix was incubated for 1.5 hours at 37° C. Synthesis products for VH and VL CDRs were pooled respectively; however, NSS and NWS libraries were kept separate and screened independently. Typically, 1 µL of the pooled library DNA was electroporated into XL1-Blue for plaque formation on XL1-Blue bacterial lawn or for production of Fab fragments (Wu and An, 2003).

1.9. Primary Screening of the Fab Library

The primary screen consisted of a single point ELISA (SPE) assay which was carried out using culture supernatant of bacteria grown in 96-well plates (deep well) and infected with individual recombinant M13 clones as described elsewhere (Wu and An, 2003). Briefly, this capture ELISA involved coating individual wells of a 96-well Maxisorp Immunoplate with approximately 50 ng of a sheep anti-human Fd antibody (Biodesign International, ME) in a carbonate buffer at pH 8.5 overnight at 4° C. The next day, the plate was blocked with 3% BSA in PBS buffer for 1 h at room temperature. Fab supernatant was then added to the plate and incubated at room temperature for 1 hr. After washing, 0.1 µg of biotinylated HER3 protein was added to the well and the mixture was incubated for 1.5 h at room temperature. This was followed by incubation with neutravidin-horseradish peroxidase (HRP) conjugate (Pierce, Ill.) for approximately 40 min at room temperature. HRP activity was detected with tetra-methyl-benzidine (TMB) substrate and the reaction quenched with 0.2 M $H_2SO_4$. Plates were read at 450 nm.

Clones exhibiting an optical density (OD) signal at 450 nm greater than the parental clone GL-P6 Fab were picked and regrown (15 mL) (Wu and An, 2003) and re-assayed by ELISA (as described above) in duplicate to confirm positive results. Clones that repeatedly exhibited a signal greater than that of the GL-P6 Fab were sequenced. The Fab protein concentration of each clone that had a CDR change was then determined by a quantitative Fab ELISA, where a Fab with known concentration was used as a reference. The Fab concentration was determined by comparing the ELISA signals with the signals generated by the reference Fab. The binding assay was repeated once more for all positive variants under normalized Fab concentrations in order to determine the relative binding affinity of the mutant Fabs and the parental GL-P6 Fab.

The binding ELISA showed that two VH variants, designated clone 14C7 and clone 15D12, which contained the Y50I or Y50V point mutations, respectively, in CDR2 displayed approximately a 5-fold improvement in HER3 binding over the parental, germlined clone GL-P6. In the VL mutagenesis campaign, several single mutations either in CDR1, e.g., clone 4H6 (comprising the S24R point mutation), clone 6E3 (comprising the S27L point mutation) or in CDR3, e.g., clone 5H6 (comprising the S94G point mutation), clone 8A3 (comprising the S96aI point mutation), clone 4C4 (comprising the S96aR point mutation), clone 2B11 (comprising the S96aP point mutation) and clone 2D1 (comprising the V97A mutation) displaying improved binding were identified.

Most notably, the substitution of amino acid S96a of VL-CDR3 with either Isoleucine (I), Arginine (R) or Proline (P) resulted in a 3.5-fold, 8.6-fold and 32-fold binding improvement, respectively.

1.10. Combinatorial Screening of the Fab Library

The point mutations in VH and VL determined to be beneficial for binding to HER3 were further combined to gain additional binding synergy. The combinatorial mutants were expressed as Fab and screened using the HER3 binding ELISA. While combining either one of the Y50I or Y50V point mutation in the VH chain of the Fab fragment with the VL mutations appeared to have no beneficial but reduced binding to HER3, combining several VL mutations further improved binding. These combination of VL mutations include the combinations in clone 1A4 (comprising the L96P, S97P and V100A point mutations), clone 2C2 (comprising the S26L, L96P, S97P and V100A point mutations), clone 2F10 (comprising the S97P and V100A mutations) and clone 3E1 (comprising the S23R, L96P, S97P and V100A point mutations).

1.11. Conversion of the Affinity-Optimized Fab Variants to IgG Format and Antibody Expression of Singe mutant and combination mutant variants displaying improved binding were converted into IgG format for further characterization. The variable regions of each variant were amplified by PCR using primers that encoded restriction sites to facilitate cloning into an IgG mammalian expression vector for expression using HEK 293F cells. The secreted, soluble human IgG1 proteins were purified from the conditioned media directly on 1 mL HiTrap protein A columns (GE Healthcare, NJ) according to the manufacturer's instructions. Purified human IgG1 samples (typically >95% homogeneity, as judged by sodium dodecyl sulphate-polyacrylamine gel electrophoresis) were dialyzed against PBS, flash frozen, and stored at −70° C.

Binding of the purified IgGs was examined using a HER3 binding ELISA. The combination mutant IgGs showed improved binding as determined by the total binding signal, with 2C2 showing the most significant binding improvement over the parental Clone 16 and other combination mutant variants. Binding of the IgGs to murine and cynomolgus HER3 were also tested by ELISA. The results showed improved binding of the combination mutants to these paralogous HER3 species.

Alignment of the amino acid sequences of the light and heavy chain variable regions for each of the identified single mutations is shown in FIG. 2A and FIG. 2B, respectively. TABLE 4 provides the SEQ ID NOs for each clone. An alignment of the light chain variable regions for each of the combination clones is provided in FIG. 2C.

TABLE 4

| SEQ ID | DESCRIPTION |
|---|---|
| 17 | Clone 16 $V_L$ aa |
| 1 | Clone 16-germlined $V_L$ aa |
| 2 | Clone 16 $V_H$ aa |
| 18 | Clone 16 $V_L$ CDR1 aa |
| 21 | Clone 16 $V_L$ CDR2 aa |
| 22 | Clone 16 $V_L$ CDR3 aa |
| 31 | Clone 16 $V_H$ CDR1 aa |
| 32 | Clone 16 $V_H$ CDR2 aa |
| 35 | Clone 16 $V_H$ CDR3 aa |
| 8 | Clone 2B11 $V_L$ aa |
| 18 | Clone 2B11 $V_L$ CDR1 aa |
| 21 | Clone 2B11 $V_L$ CDR2 aa |
| 25 | Clone 2B11 $V_L$ CDR3 aa |
| 14 | Clone 1A4 $V_L$ aa |
| 18 | Clone 1A4 $V_L$ CDR1 aa |
| 21 | Clone 1A4 $V_L$ CDR2 aa |
| 22 | Clone 1A4 $V_L$ CDR3 aa |
| 3 | Clone 2C2 $V_L$ aa |
| 19 | Clone 2C2 $V_L$ CDR1 aa |
| 21 | Clone 2C2 $V_L$ CDR2 aa |
| 23 | Clone 2C2 $V_L$ CDR3 aa |
| 16 | Clone 2F10 $V_L$ aa |
| 18 | Clone 2F10 $V_L$ CDR1 aa |
| 21 | Clone 2F10 $V_L$ CDR2 aa |
| 24 | Clone 2F10 $V_L$ CDR3 aa |
| 15 | Clone 3E.1 $V_L$ aa |
| 20 | Clone 3E.1 $V_L$ CDR1 aa |
| 21 | Clone 3E.1 $V_L$ CDR2 aa |
| 23 | Clone 3E.1 $V_L$ CDR3 aa |
| 4 | Clone 5H6 $V_L$ aa |
| 18 | Clone 5H6 $V_L$ CDR1 aa |
| 21 | Clone 5H6 $V_L$ CDR2 aa |
| 26 | Clone 5H6 $V_L$ CDR3 aa |

TABLE 4 -continued

| SEQ ID | DESCRIPTION |
|---|---|
| 5 | Clone 8A3 $V_L$ aa |
| 18 | Clone 8A3 $V_L$ CDR1 aa |
| 21 | Clone 8A3 $V_L$ CDR2 aa |
| 27 | Clone 8A3 $V_L$ CDR3 aa |
| 6 | Clone 4H6 $V_L$ aa |
| 20 | Clone 4H6 $V_L$ CDR1 aa |
| 21 | Clone 4H6 $V_L$ CDR2 aa |
| 22 | Clone 4H6 $V_L$ CDR3 aa |
| 7 | Clone 6E.3 $V_L$ aa |
| 19 | Clone 6E.3 $V_L$ CDR1 aa |
| 21 | Clone 6E.3 $V_L$ CDR2 aa |
| 22 | Clone 6E.3 $V_L$ CDR3 aa |
| 9 | Clone 2D1 $V_L$ aa |
| 18 | Clone 2D1 $V_L$ CDR1 aa |
| 21 | Clone 2D1 $V_L$ CDR2 aa |
| 28 | Clone 2D1 $V_L$ CDR3 aa |
| 10 | Clone 3A6 $V_L$ aa |
| 18 | Clone 3A6 $V_L$ CDR1 aa |
| 21 | Clone 3A6 $V_L$ CDR2 aa |
| 29 | Clone 3A6 $V_L$ CDR3 aa |
| 11 | Clone 4C4 $V_L$ aa |
| 18 | Clone 4C4 $V_L$ CDR1 aa |
| 21 | Clone 4C4 $V_L$ CDR2 aa |
| 30 | Clone 4C4 $V_L$ CDR3 aa |
| 12 | Clone 15D12.1 $V_H$ aa |
| 31 | Clone 15D12.1 $V_H$ CDR1 aa |
| 33 | Clone 15D12.1 $V_H$ CDR2 aa |
| 35 | Clone 15D12.1 $V_H$ CDR3 aa |
| 13 | Clone 15D12.2 $V_H$ aa |
| 31 | Clone 15D12.2 $V_H$ CDR1 aa |
| 34 | Clone 15D12.2 $V_H$ CDR2 aa |
| 35 | Clone 15D12.2 $V_H$ CDR3 aa |
| 36 | $V_H$ FW1 aa |
| 37 | $V_H$ FW2 aa |
| 38 | $V_H$ FW3 aa |
| 39 | $V_H$ FW4 aa |
| 40 | $V_L$ FW1 germlined aa |
| 41 | $V_L$ FW2 aa |
| 42 | $V_L$ FW3 aa |
| 43 | $V_L$ FW4 aa |
| 44 | $V_L$ FW1 original aa |
| 45 | IgG1 constant region* |
| 46 | IgG1 constant region*-YTE |
| 47 | Clone 16 $V_L$ nt |
| 48 | Clone 16 $V_H$ nt |

*allotype differences are provided $V_L$ aa consensus: [FW$_1$]X$_1$GSX$_2$SNIGLNYVS (SEQ ID NO: 49) [FW$_2$]RNNQRPS (SEQ ID NO: 21) [FW$_3$]AAWDDX$_3$X$_4$X$_5$GEX$_6$ (SEQ ID NO: 50) [FW$_4$]
wherein [FW$_1$], [FW$_2$], [FW$_3$] and [FW$_4$] represent VL framework regions,
wherein
(a) X$_1$ represents amino acid residues Arginine (R) or Serine (S),
(b) X$_2$ represents amino acid residues Serine (S) or Leucine (L),
(c) X$_3$ represents amino acid residues Serine (S) or Glycine (G),
(d) X$_4$ represents amino acid residues Leucine (L) or Proline (P),
(e) X$_5$ represents amino acid residues Arginine (R), Isoleucine (I), Proline (P) or Serine (S), and
(f) X$_6$ represents amino acid residues Valine (V) or Alanine (A).

$V_H$ aa consensus: [FW$_5$]YYYMQ (SEQ ID NO: 31) [FW$_6$]X$_7$IGSSGGVTNYADSVKG (SEQ ID NO: 51)[FW$_7$]VGLGDAFDI (SEQ ID NO: 35) [FW$_8$]
wherein [FW$_5$], [FW$_6$], [FW$_7$] and [FW$_8$] represent VH framework regions,
wherein X$_7$ represents amino acid residues Tyrosine (Y), Isoleucine (I) or Valine (V)

1.12. Anti-HER3 Monoclonal Antibody Binding Studies

The kinetic rate ($k_{on}$, $k_{off}$) and equilibrium dissociation constants ($K_D$) for the binding of the anti-HER3 IgGs to the extracellular domain of human HER3 protein were determined using BIAcore™ surface plasmon resonance technology by measuring the binding of human HER3 extracellular domain (hu HER3(ECD)) to IgG captured onto a sensor chip surface. Individual association ($k_{on}$) and dissociation ($k_{off}$) rate constants were then calculated from the resulting binding curves using the BIAevaluation software available through the vendor. Data were fit to a 1:1 binding model, which included a term to correct for mass transport limited binding, should it be detected. From these rate constants, the apparent dissociation binding constant ($K_D$) for the interaction of IgG with the human HER3 extracellular domain protein is then calculated from the quotient of $k_{off}/k_{on}$.

From high-resolution BIAcore plots, the association and dissociation rate constants for the binding parental IgG, Clone 16, to human HER3 extracellular domain were $5.29 \times 10^5$/Ms and $73.0 \times 10^{-4}$/s, respectively, yielding an apparent $K_D$ of 14 nM. In comparison, the association rate constants for the binding of the affinity-improved IgG variants to human HER3 extracellular domain were similar to those measured for the parental IgG, ranging from $3.41 \times 10^5$ to $4.32 \times 10^5$/Ms. These same plots were also used to determine the corresponding dissociation rate constants for the Clone 16 variants, which ranged from $1.60 \times 10^{-4}$ to $6.21 \times 10^{-4}$/s. The apparent $K_D$s for the Clone 16 variants were calculated as described above, and ranged from 0.429 nM (2C2 clone variant) to 1.44 nM. (P2B11 clone variant). Individual errors for $k_{on}$ and $k_{off}$ were low ($\leq \sim 2\%$ of the calculated parameter), and the overall fits to the kinetic data indicated that the use of the 1:1 interaction model was appropriate. Also, the evaluation did not indicate the binding was mass transport-limited.

TABLE 5 summarizes the biophysical attributes of the combination monoclonal clones provided in FIG. 2C, including $K_{on}$, $K_{off}$ and $K_D$ values, as well as expression levels and yields.

The 2C2 monoclonal antibody, comprising the 2C2 VL (SEQ ID NO: 3) and the original C16 VH (SEQ ID NO: 2) was the most affinity-improved lead with a $K_D$ of 0.4 nM, representing a 32-fold improvement from the parental Clone 16 monoclonal antibody. The $K_D$ improvement was mostly a result of decreased off-rate. The expression level and production yields were also assessed. All of the monoclonal antibody clones were well expressed in a 5 day transient transfection study, with the 2C2 monoclonal antibody showing the highest level of expression in this study. All affinity optimized leads showed different extents of affinity improvement but the 1A4 antibody dropped out due to lower expression efficiency.

Figure 3:
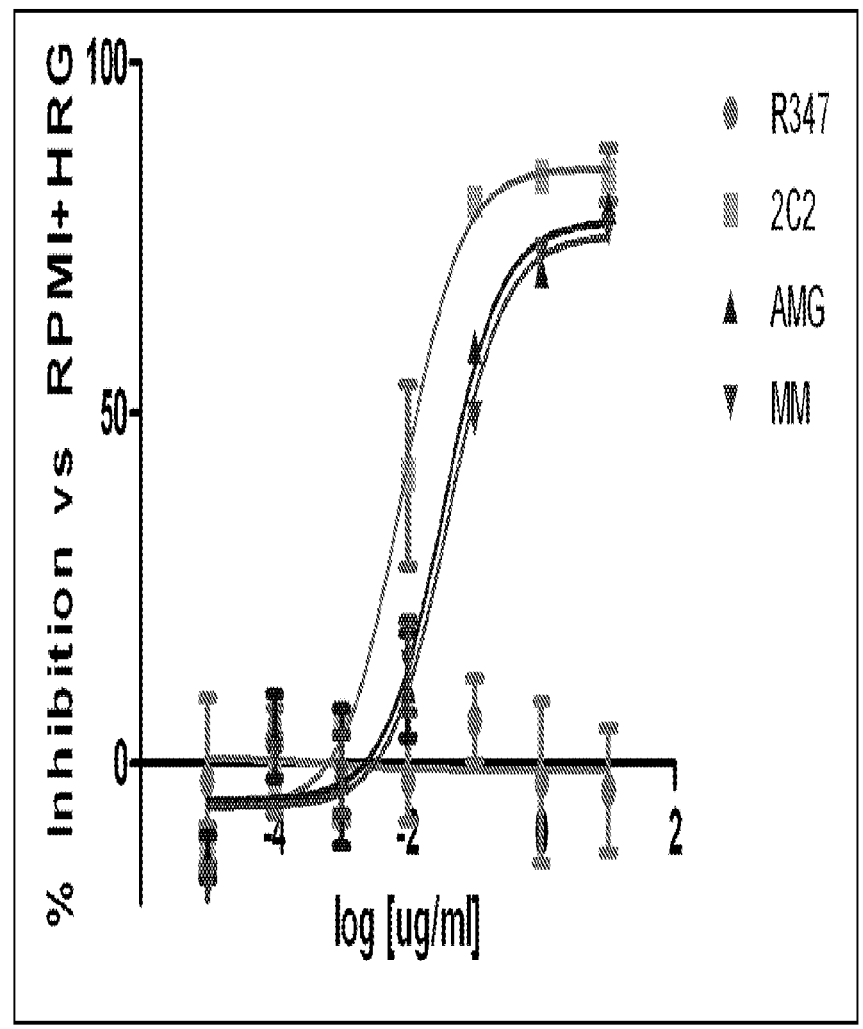
Figure 4:
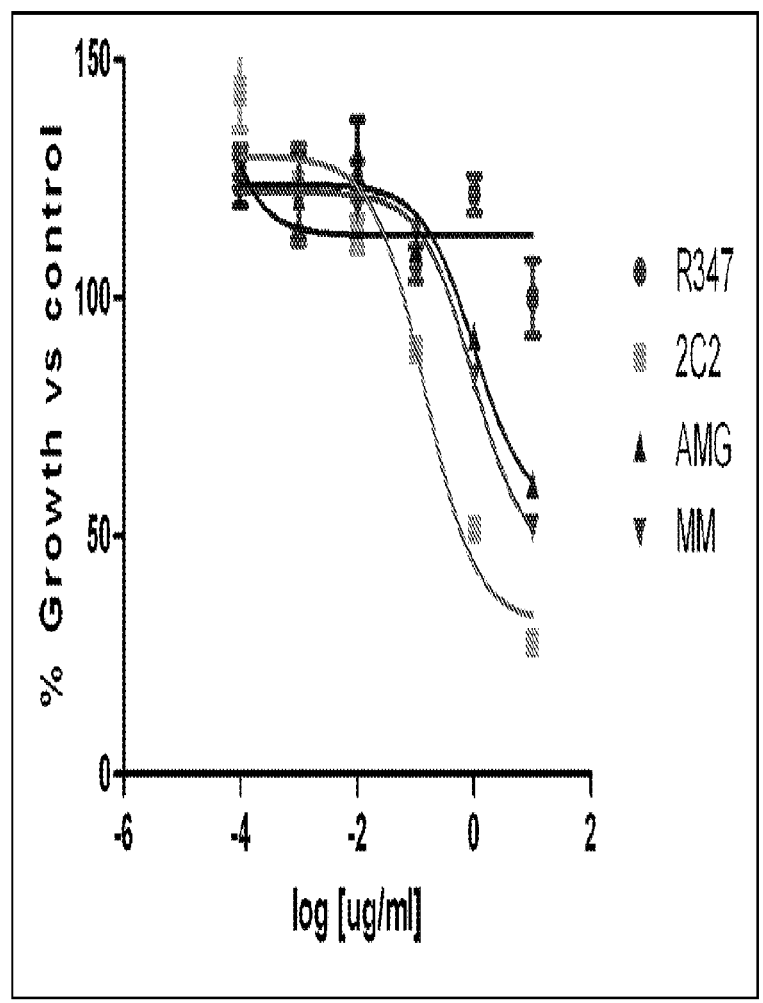

The BT-474 6-day growth assay was performed essentially as used for FIG. 4 (see Section 2.2 in Example 2, infra). The BT-474 pAKT assay was performed essentially as used for FIG. 10 (see Section 2.6.1 in Example 2, infra). The T-47D HRG inducible pHER3 assay was performed essentially as used for FIG. 3 (see Section 2.1 in Example 2, infra), and the T-47D FACS binding and internalization assay was performed using the same protocol used for FIG. 16A (see Section 3.3.1 in Example 3, infra).

The $IC_{50}$ values and maximal inhibition levels were compiled for comparison purposes. As shown in TABLE 6, the affinity improved leads displayed a consistent 2-3-fold

TABLE 5

Summary of biophysical properties of the various affinity-optimized leads in comparison with the parental CL16 (Clone 16) antibody.

| Clone name | Calculated pI | Kon (1/Ms) (xE+5) | Koff (1/s) (xE−4) | Biacore KD (nM, IgG down) | Biacore KD (nM, Her3 down) | Expression Level on Day 5 (transient) | Yield (mg/volume, ml) |
|---|---|---|---|---|---|---|---|
| P2B11 | 8.21 | 4.32 | 6.21 | 1.53 (9x) | 0.74 (2.4x) | 159 ug/ml | 70/500 |
| 1A4 | 8.2 | 3.41 | 2.86 | 0.838 (17x) | 0.493 (3.6x) | 60 ug/ml | 53/1200 |
| 2C2 | 8.2 | 3.73 | 1.60 | 0.434 (32x) | 0.093 (19x) | 148 ug/ml | 71/600 |
| 2F10 | 8.2 | 3.54 | 2.90 | 0.818 (17x) | 0.326 (5x) | 130 ug/ml | 66/600 |
| 3E 1 | 8.32 | 3.43 | 1.78 | 0.52 (26x) | 0.286 (6.2x) | 125 ug/ml | 59/600 |
| Clone 16 | 7.83 | 5.29 | 73.0 | 14 | 1.77 | ND | ND |

Note:
Each affinity-optimized lead comprises the clone name VL chain and the original C16 VH Various cell-based assays were performed to assess the functional improvement of the various affinity optimized leads over clone 16 across ligand-independent (human breast cancer cell line BT-474, ATCC No. HTB-20™) as well as ligand-dependent (human breast cancer cell line T-47D, ATCC No. HTB-133) models (both cell lines obtained from ATCC), including inhibition of HER3 signaling pathway (pHER3 and pAKT), suppression of cell growth (short-term 6-day growth assay and long-term clonogenic assay), and abrogation of HRG-induced pHER3 in T-47D cells (T-47 differentiated epithelial substrain).

Clonogenic assays were performed as follows. BT-474 cells were plated at a density of 1,000 cells/well into 6-well plates. After overnight attachment, cells were treated with isotype control IgG or the indicated HER3 monoclonal antibodies following a concentration dose curve. The medium with the proper doses of monoclonal antibodies was refreshed once a week for three weeks. At the end of day 21, cells were processed for Cell-titer-Glo (CTG) assay to assess the inhibition of colony formation by the various monoclonal antibodies (using control IgG as base-line). $IC_{50}$ values were derived from Prizm analysis.

increased potency across most of the assays. The parental Clone 16 and/or a representative optimized clone, e.g., Clone 2C2 antibody (also referred to simply as 2C2, or 2C2 monoclonal antibody) were further characterized in a number of in vitro and in vivo assays as described below.

In addition, mutations were introduced into the Fc region of the optimized clone 2C2 to extend half-life. Specifically, M252Y, S254T, T256E, numbered according to the EU index as in Kabat. This half-life-optimized molecule is referred to as 2C2-YTE. It will be understood that other mutations could be introduced instead of, or in combination with these three, see, e.g., U.S. Pat. No. 7,083,784; International Appl. Pub. No. WO2009058492; Dall'Acqua et al., 2002 J. Immunol. 169:5171-80; Zalevsky et al., 2010, Nature Biotech. 28:157-9). 2C2-YTE was show to inhibit BT-474 cell proliferation and colony growth to the same extent as 2C2 (data not shown).

A refrigerator (2-8° C.) stable composition was obtained by formulating the antibodies (e.g., 50 mg/ml) in 25 mM histidine/histine HCL, 205 mM sucrose, 0.02% polysorbate 80 at pH 6.0.

TABLE 6

Summary of the biological properties of the affinity optimized leads in comparison with parental CL16 monoclonal antibody.

| Clone name | BT474 clonogenic asssay | | BT474 6-day growth | | BT474 pAKT assay | | T47D HRG inducible pHer3 | | T47D FACS binding | |
|---|---|---|---|---|---|---|---|---|---|---|
| | IC50 (pM) | % Max inhibition | Inflection point (pM) | % Max inhibition | Inflection point (pM) | % Max inhibition | IC50 (PM) | % Max inhibition | Kd (pM) | Max GMFI |
| P2B11 | 26.9 | 87.1 | 98 | 47.5 | 23.6 | 62 | 79.8 | 85 | 199 | 1441 |
| 1A4 | 30.7 | 81.3 | 133.3 | 54.5 | 28.5 | 62 | 133 | 84 | 281 | 1577 |
| 2C2 | 31.9 | 87.2 | 62.7 | 48.3 | 42.6 | 61 | 130.3 | 85 | 316 | 1583 |
| 2F10 | 31.2 | 80.4 | 66.7 | 49 | 46.4 | 62 | 127.2 | 86 | 306 | 1527 |

TABLE 6-continued

Summary of the biological properties of the affinity optimized
leads in comparison with parental CL16 monoclonal antibody.

| Clone name | BT474 clonogenic assay | | BT474 6-day growth | | BT474 pAKT assay | | T47D HRG inducible pHer3 | | T47D FACS binding | |
|---|---|---|---|---|---|---|---|---|---|---|
| | IC50 (pM) | % Max inhibition | Inflection point (pM) | % Max inhibition | Inflection point (pM) | % Max inhibition | IC50 (PM) | % Max inhibition | Kd (pM) | Max GMFI |
| 3E 1 | 20.8 | 79.2 | 85.3 | 48.1 | 26.2 | 66 | 59.2 | 86 | 447 | 1644 |
| Clone 16-PA | 64.5 | 79.8 | 280 | 46 | 73.1 | 64 | 104.4 | 75 | 112 | 1055 |

Example 2

Characterization of Anti-HER3 Monoclonal Antibodies 2.1. HRG-Induced HER3 Phosphorylation (pHER3) Assay in MCF-7 Cells MCF-7 (ATCC No. HTB-22™) is a human breast cancer cell line with HER3 expression but no endogenous HRG expression. MCF-7 cells were plated at a density of 30,000 cells/well in a 96-well plate and were allowed to attach overnight. The cells were then serum-starved for 24 hours before treatment. Following serum-starvation, media was removed and replaced with serum-free media containing test and control antibodies, and the cells incubated at 37° C. for 1 hour. Test antibodies used in this example, and in the additional examples provided below, include the anti-HER3 antibodies provided herein such as, Clone 16, 2C2, 2C2-YTE; and anti-HER3 antibodies known in the art, in particular U1-59 (International Patent Publication WO 2007077028) and Ab#6 (Patent Publication WO 2008/100624) designated herein as AMG and MM, respectively. Meanwhile, heregulin (HRGβ1, R&D Systems, Minneapolis, Minn.) stock was prepared at 4× (80 ng/ml) in serum-free growth media. At the end of the 1 hour incubation period, HRGβ1 was spiked into wells (20 ng/ml final concentration) and incubated at 37° C. for 20 minutes. At the end of treatment, media was removed and cells were washed with PBS. Cells were lysed in 80 μl Triton X lysis buffer (Boston Bioproducts, Ashland, Mass.) with protease and phosphatase inhibitors (Calbiochem, La Jolla, Calif.) and were stored at −20° C. until analysis. pHER3 ELISA was then performed following manufacturer's protocol (R&D Systems, DYC1769) using half-volume 96-well Corning® Costar® 3690 ELISA plates (Corning Life Science, Lowell, Mass.) and 50 μl of cell lysate per well.

HER3 activation, reflected by HER3 phosphorylation (abbreviated as pHER3), was stimulated by cells treatment with HRGβ1. Pre-treatment with anti-HER3 2C2 mAb caused a dose-dependent suppression of the pHER3 signal in the pHER3 ELISA assay (FIG. 3, top). The published anti-HER3 monoclonal antibodies MM and AMG were also active in this assay, however, 2C2 was approximately 5-fold more potent as determined by $IC_{50}$ measurements (FIG. 3, bottom). Similar results were seen for 2C2-YTE (data not shown).

2.2. Growth Suppression of MDA-MB-175 Breast Cancer Cells

MDA-MB-175 (ATCC No. HTB-25™) is an established HRG-expressing (γ-isoform) breast cancer cell-line that depends on HRG-HER3 signaling pathway for growth and survival. Cells were plated at a density of 2,000 cells/well in a 96-well white-walled plate and were allowed to attach overnight. The following day, media was removed and replaced with 100 μl/well fresh complete growth medium containing test and control antibodies. Plates were then incubated for a total of 6 days. To calculate relative cell number, CellTiter-Glo™ (Promega, Madison, Wis.) was used according to manufacturer's protocol. After CellTiter-Glo™ addition, plates were incubated at room temperature for 10 minutes and luminescence was measured using a microplate reader.

The growth assay was carried out with 2C2, MM, or AMG anti-HER3 monoclonal antibodies. As shown in FIG. 4, all three antibodies achieved anti-proliferation effect to various extents, with 2C2 showing higher potency ($IC_{50}$=0.14 μg/ml) (FIG. 4, top) and higher growth suppression (72%) (FIG. 4, bottom).

2.3. Growth Suppression of HMCB Melanoma Cells

HMCB (ATCC No. CRL-9607™) is an established HRG-expressing (1β-isoform) melanoma model driven by HRG-induced HER2-HER3 heterodimerization. HMCB cells were plated at a density of 750 per well in 100 μl of complete medium containing 10% heat-inactivated FBS in 96 well plates (Costar®). The next day, antibody treatments were prepared in complete medium. The starting concentration for all anti-HER3 monoclonal antibodies and control IgG was 10 μg/ml, and serial dilutions were prepared in complete medium. The plating medium was removed and treatments were added in 100 μl per well in triplicates.

Plates were then incubated in 5% $CO_2$ at 37° C. for 6 days. Equal volumes of CellTiter-Glo™ reagent were added to each well. Plates were rocked on a plate shaker for 10 minutes at room temperature to ensure complete cell lysis. Luminescence was measured using a 2104 EnVision® Multilabel Reader (PerkinElmer, Waltham, Mass.).

Figure 5:
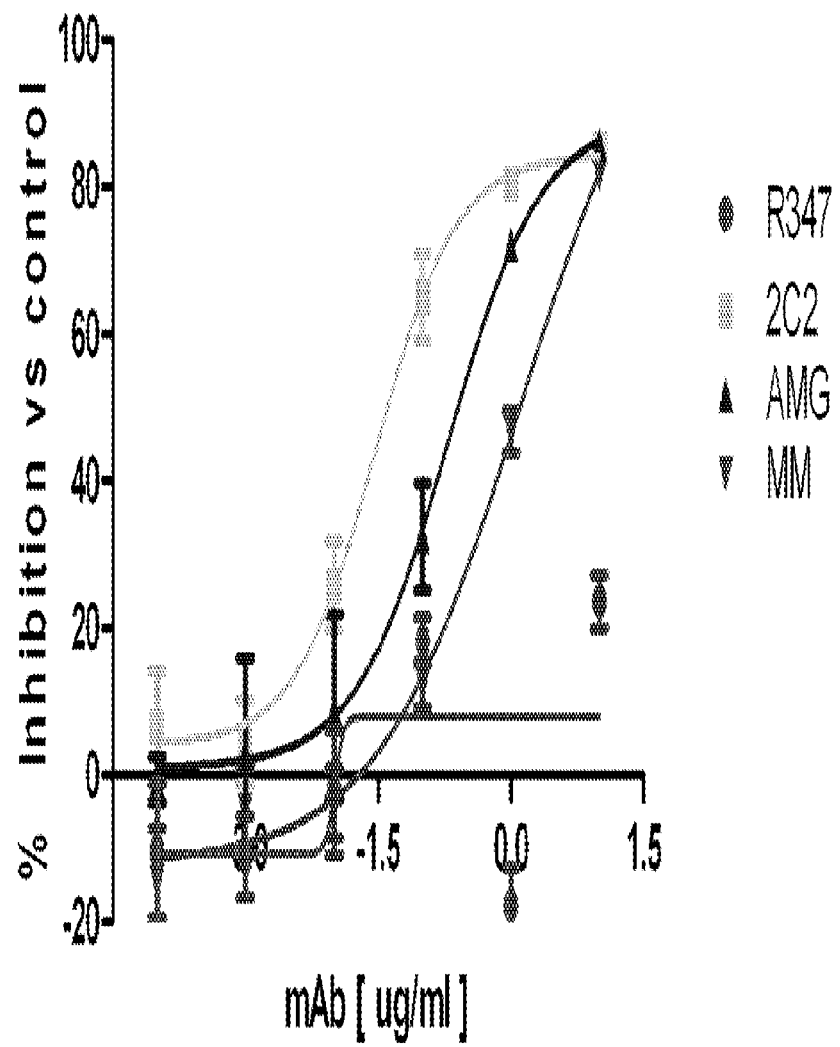
FIG. 5 shows growth suppression in HMCB cells, an established HRG-autocrine loop driven model wherein endogenous HRG drives HER3 activity and cell growth. The 2C2 anti-HER3 monoclonal, published anti-HER3 monoclonal antibodies AMG and MM, and R347 control antibody were assayed. $IC_{50}$'s are presented.

As shown in FIG. 5, 2C2 was again more potent than existing antibodies. 2C2 was 8-30 fold more potent than the published anti-HER3 monoclonal antibodies AMG and MM in inhibiting cell growth of the HMCB melanoma cell line.

2.4. HER3 and AKT Activity Assays in HMCB Melanoma Cells and A549 NSCLC Cells

The ability of the HER3 leads to suppress the HER3 signaling pathway in the HRG-autocrine HMCB (ATCC No. CRL-9607™) and A549 (ATCC No. CCL-185) models were assessed. HMCB cells were plated at $10^5$ per well in 24-well plates and in medium containing 10% heat-inactivated FBS and allowed to reach a confluency of 80% or more prior to antibody treatment. The plating medium was removed and the cells were subjected to incubation with the antibodies. Anti-HER3 monoclonal antibodies and a control IgG were prepared in complete medium. The starting concentration for all anti-HER3 antibodies was 10 μg/ml and serial dilutions were performed. The control IgG was only used at a concentration of 10 μg/ml. Treatments were applied following removal of plating medium. After an incubation of 6 hours (HMCB cells) or 72 hours (A549 cells) in 5% $CO_2$ at 37° C., cells were washed once with ice-cold PBS and then lysed by adding Laemmli Reducing buffer (Boston BioProducts, Ashland, Mass.).

After a brief incubation, cell lysates were collected, equal amounts were loaded onto Bis NuPAGE® Novex® Bis-Tris gels (Invitrogen, Carlsbad, Calif.) and proteins transferred to PVDF membranes (Invitrogen, Carlsbad, Calif.). Membranes were blocked with 5% nonfat dry milk and 0.1% Tween 20 (Sigma, St. Louis, Mo.) in TBS (pH 7.4) and incubated overnight at 4° C. with antibodies to HER3 (sc-285 antibody, Cell Signaling Technology, Beverly, Mass.), pHER3 (4791 antibody, Cell Signaling Technology, Beverly, Mass.), AKT (9272 antibody, Cell Signaling, Technology, Beverly, Mass.), pAKT (4060 antibody, Cell Signaling Technology, Beverly, Mass.), neuregulin-1/HRG (NRG1/HRG) antibody (sc-348, Santa Cruz) and GAPDH (G8795 antibody, Sigma, St. Louis, Mo.).

Membranes were washed in 0.1% Tween 20 in TBS and then incubated for 1 hour in horseradish peroxidase-conjugated streptavidin secondary antibodies (GE Healthcare). After washing, protein bands were detected in X-ray film by using SuperSignal® West Femto Chemiluminescent Substrate and SuperSignal® West Pico Chemiluminescent Substrate (Pierce/Thermo Scientific, Rockford, Ill.).

Figure 6:
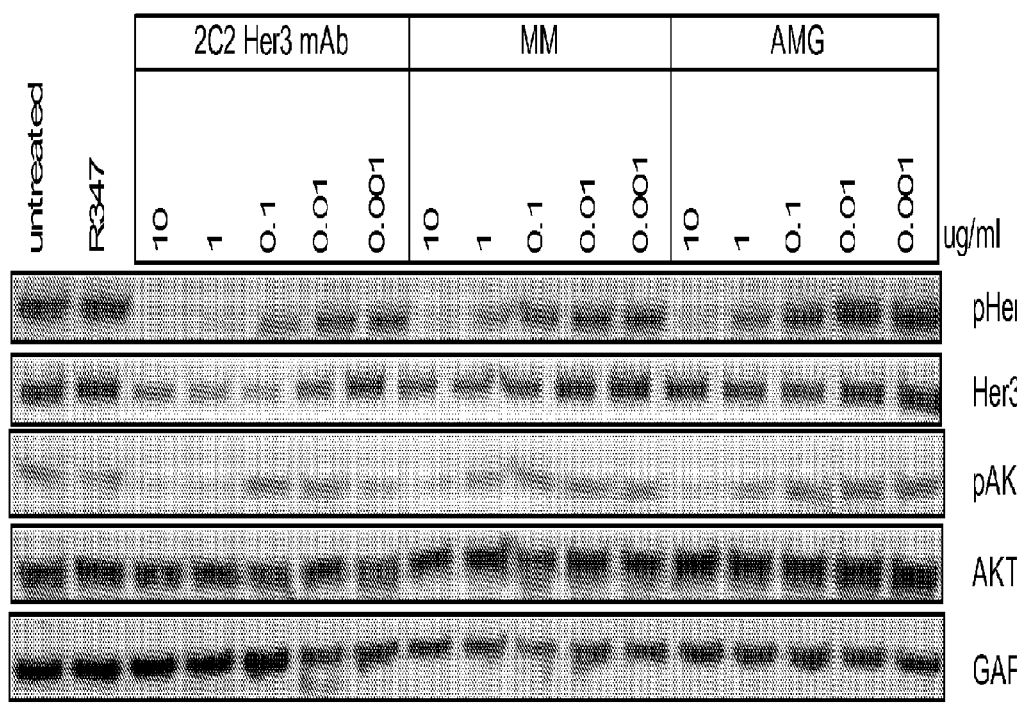
FIG. 6 shows that 2C2 not only inhibited HMCB cell growth but also suppressed HER3 phosphorylation (pHER3) and AKT phosphorylation (pAKT) in this ligand dependent melanoma.
Figure 7:
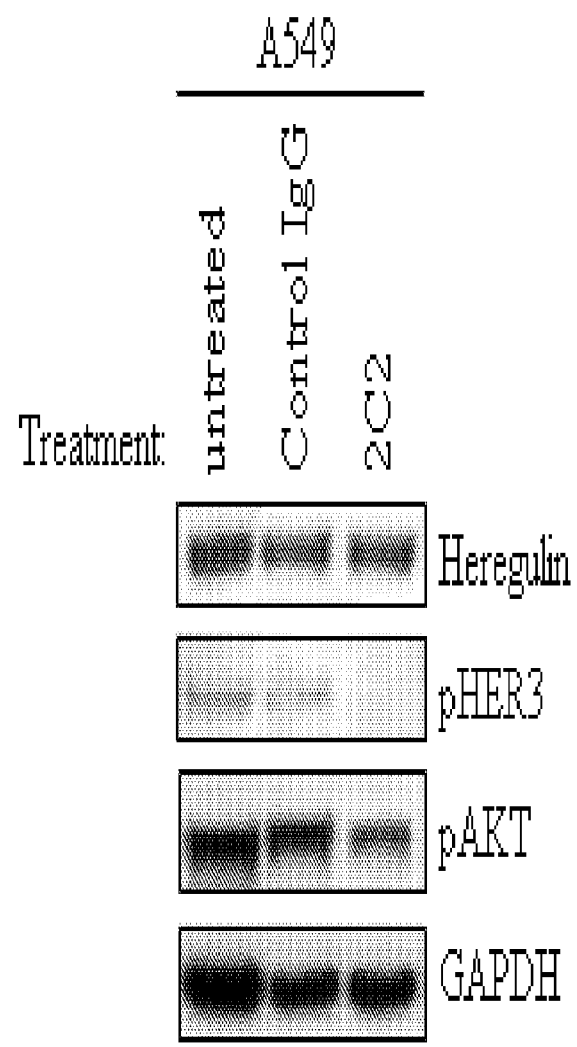
FIG. 7 shows that 2C2 suppressed HER3 phosphorylation (pHER3) and AKT phosphorylation (pAKT) in the ligand dependent A549 NSCLC.

As shown in FIGS. 6 and 7, the 2C2 antibody abrogated the HER3 signaling pathway in both HMCB and A549 cells. 2C2 efficiently suppressed pHER3 and its downstream effector molecule pAKT in a dose-dependent manner and was more potent than either of the published anti-HER3 monoclonal antibodies AMG or the MM in HMCB cells. The 2C2 antibody also surpressed pHER3 and its downstream effector molecule pAKT in A549 cells.

2.5. Assay for HER3 Phosphorylation (pHER3) in Cell Models for Lung, Gastric, and Breast Cancer 2.5.1. pHER3 Cell Assay Cells (HCC827 NSCLC cells, Gefitinib-resistant HCC827 NSCLC cells, MKN45 gastric cancer cells, Kato III gastric cancer cells, or BT-474 HER2-amplified breast cancer cells) were plated at a density of 30,000 cells/well in a 96-well plate and were allowed to attach overnight. The cells were then treated with test or control antibodies at the indicated dose-curve at 37° C. for 4 hours. At the end of treatment, media was removed and cells were washed with PBS. Cells were lysed in 80 µl Triton X lysis buffer (Boston BioProducts, Ashland, Mass.) with protease and phosphatase inhibitors (Calbiochem, La Jolla, Calif.) and were stored at −20° C. until analysis. pHER3 ELISA was then performed following manufacturer's protocol (R&D Systems, DYC1769, Minneapolis, Minn.) using half-volume 96-well ELISA plates (Costar 3690) and 50 µl of cell lysate per well.

2.5.2. Suppression of pHER3 Activity in HCC827 Cells

Figure 8A:
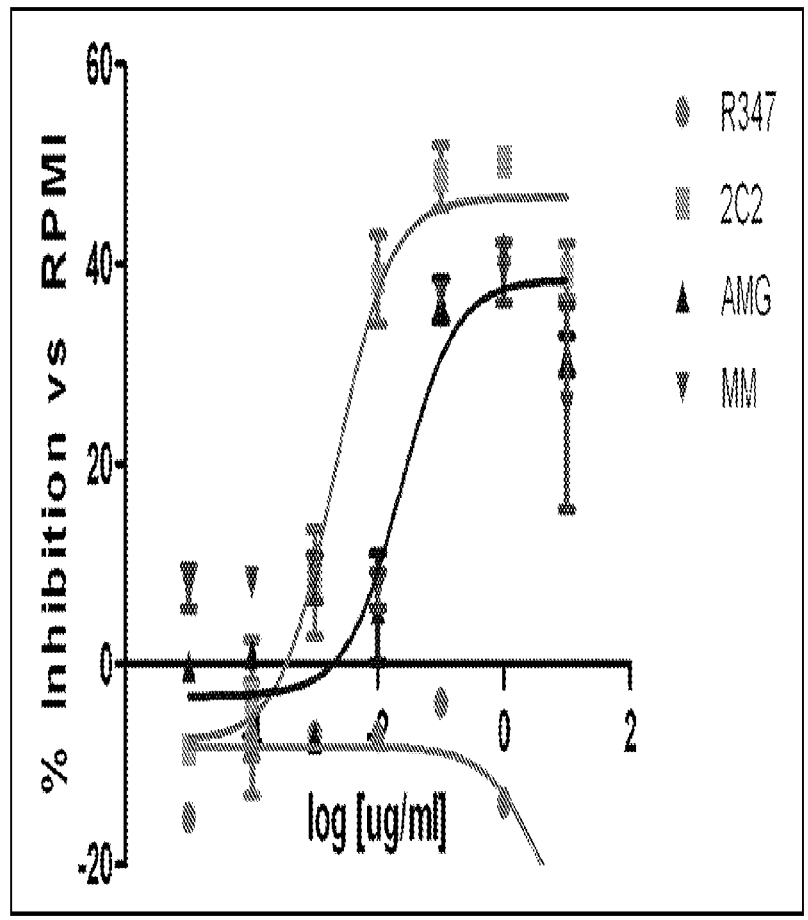

HCC827 cells (ATCC CRL-2868™), a mutant EGFR-driven non-small cell lung cancer (NSCLC) model, were treated with test or control antibodies as described above in Example section 2.5.1 (see above). As shown in FIG. 8A, the 2C2 antibody was able to partially inhibit pHER3 signal, whereas the published anti-HER3 monoclonal antibodies AMG and MM were less effective and 10-fold less potent than 2C2.

2.5.3. Suppression of pHER3 Activity in Gefitinib-Resistant HCC827 Cells

Figure 8B:
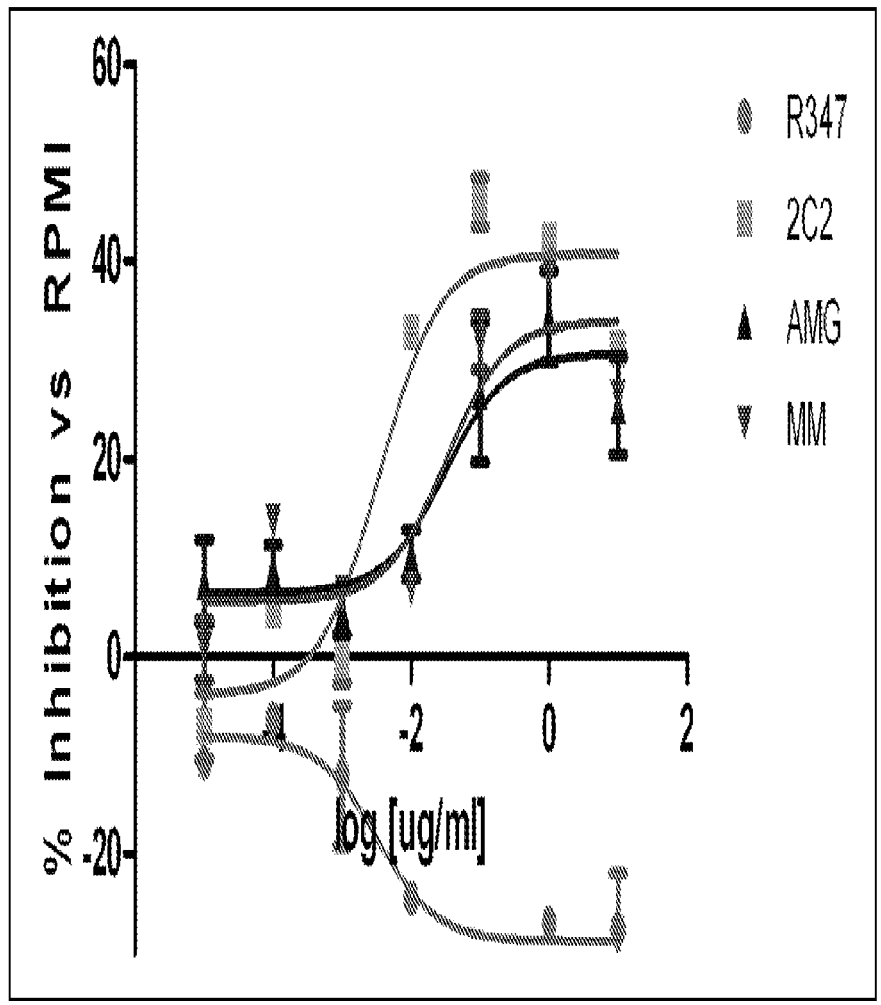

HCC827 harbors and is driven by mutant-EGFR, which makes it highly sensitive to EGFR tyrosine kinase inhibitors (TKIs) such as gefitinib. Parental HCC827 cells were exposed to a constant toxic dose of gefitinib and resistant clones were isolated that were shown to harbor amplified cMET, a known mechanism for cancers to escape TKI therapy. TKI-resistant HCC827 cells were treated with the anti-HER3 monoclonal antibodies as described above in Examples section 2.5.1 (see above). As shown in FIG. 8B, the anti-HER3 monoclonal antibody 2C2 suppressed HER3 activity in the mutant HCC827 made resistant to gefitinib. Similar to the results seen for the parental cell line, 2C2 displayed higher potency than the AMG and MM antibodies (about 10-fold better potency) in the TKI-resistant HCC827 cell line.

2.5.4. Suppression of pHER3 Activity in MKN45 Cells

Figure 8C:
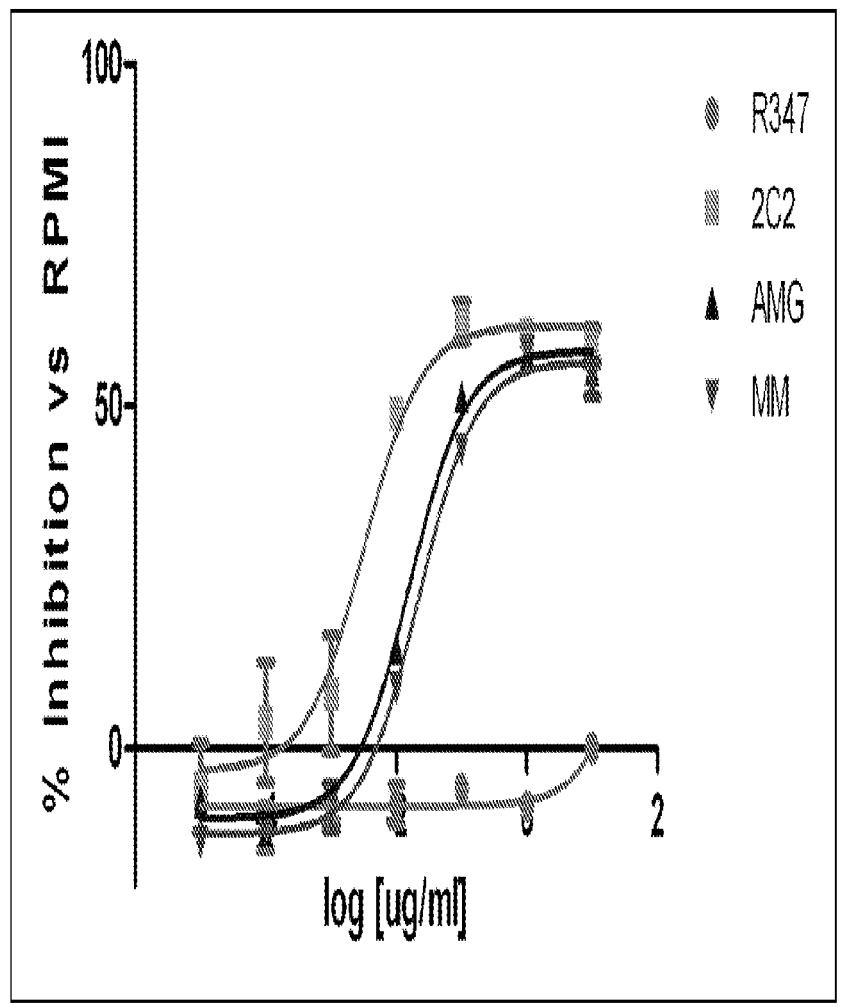

Even though cMET is not a member of the Her-family, it has been shown to be capable of forming dimers with HER3. The MKN45 cMET-amplified gastric cancer model cell line was used to assess whether anti-HER3 antibodies could antagonize cMET-driven HER3 activation. MKN45 cells were treated with the anti-HER3 monoclonal antibodies as described above in Examples section 2.5.1. As shown in FIG. 8C, all three anti-HER3 monoclonal antibodies (2C2, AMG and MM) were able to suppress pHER3 in MKN45 cells, but 2C2 displayed higher potency than the AMG and MM antibodies (approximately 5-7-fold better potency).

2.5.5. Suppression of pHER3 Activity in Kato III Cells

Figure 8D:
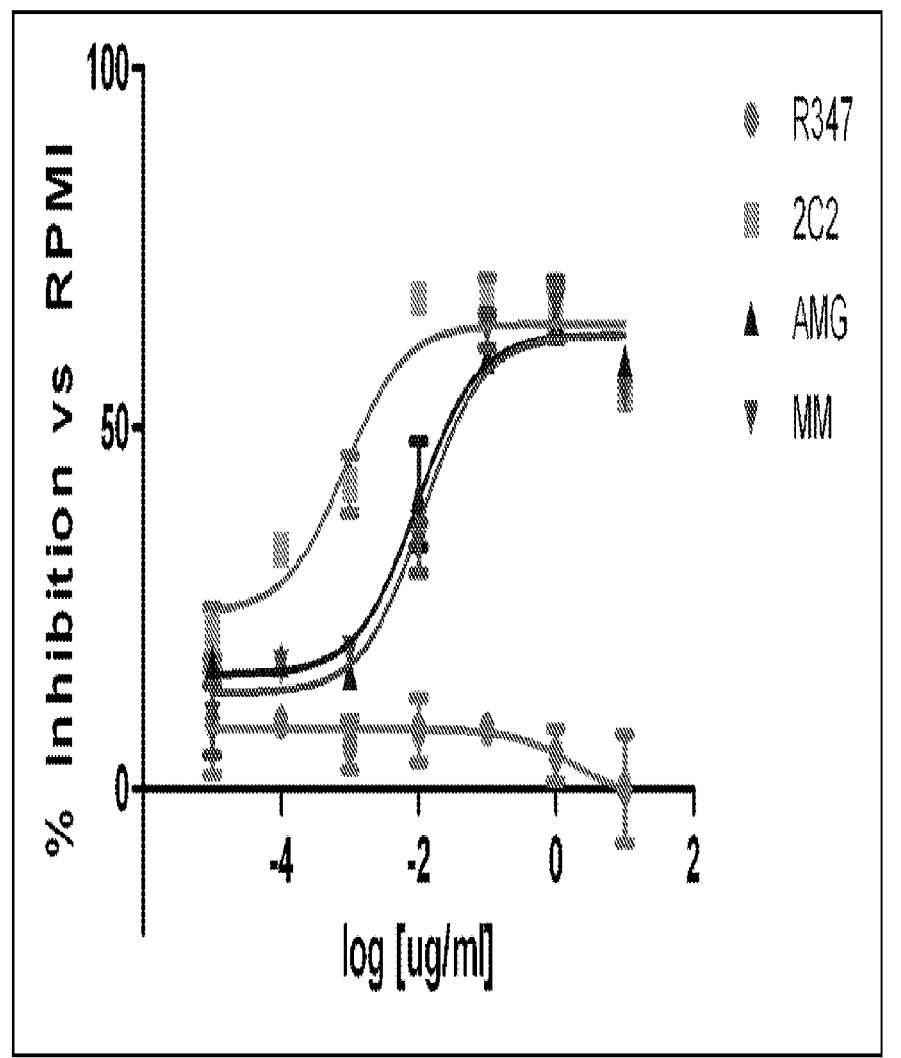

Besides coupling with EGFR, HER2 and cMET, HER3 dimerizes with FGFR2 to facilitate its transforming potential. The Kato III (ATCC No. HTB-103™) cell line, a FGFR2-amplified gastric cancer model, was used to assess whether anti-HER3 antibodies could suppress FGFR2-driven HER3 activation. Kato III cells were treated with the anti-HER3 monoclonal antibodies as described above in Examples section 2.5.1 (see above). In this model, all three anti-HER3 monoclonal antibodies (2C2, AMG, and MM) achieved similar maximal extents of pHER3 suppression (~60%), but as measured by $IC_{50}$, 2C2 was 15-20-fold more potent than the AMG and MM antibodies, respectively (FIG. 8D).

2.5.6. Suppression of pHER3 Activity in BT-474 Cells

Figure 8E:
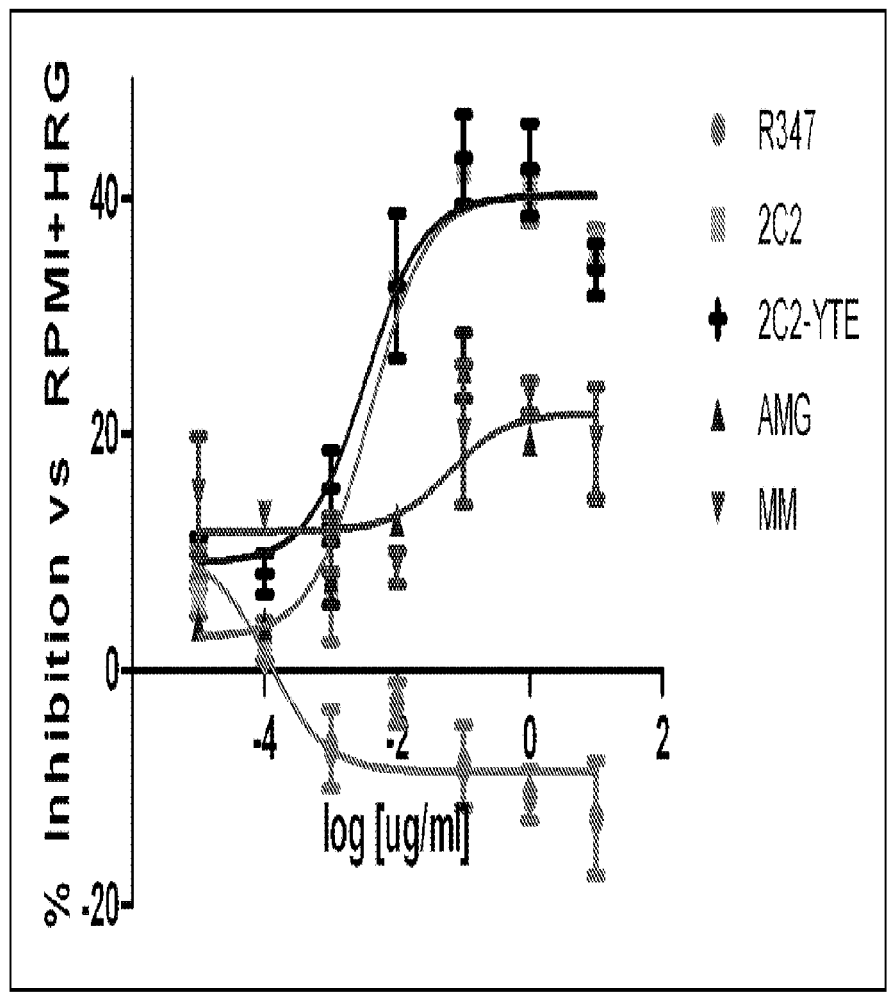

HER2-HER3 dimers have been shown to be one of the most transforming oncogenic entities in cancer. Accordingly, we investigated the anti-HER3 monoclonal antibodies in the BT-474 cell-line (ATCC NO. HTB-20™), a well-established HER2-amplified breast cancer model that does not express the ligand and is expected to be driven by ligand-independent HER2-HER3 dimerization. BT-474 cells were treated with the three anti-HER3 monoclonal antibodies and also 2C2-YTE, as described above in Examples section 2.5.1. Unlike the models where all three anti-HER3 monoclonal antibodies tested were active, such as HCC827 cells, Gefitinib-resistant HCC827 cells, MKN45 cells, and Kato III cells, 2C2 (both parent 2C2 and 2C2-YTE mutant) was the only one among the anti-HER3 monoclonal antibodies tested showing substantial activity suppressing pHER3 (FIG. 8E). These results indicated that 2C2 (both parent 2C2 form and 2C2-YTE mutant) was functional in a ligand-independent model and demonstrated the bi-functionality of 2C2 in both ligand-dependent and ligand-independent settings.

2.6. Assay for AKT Phosphorylation (pAKT) in Cell Models for Gastric, and Breast Cancer 2.6.1. pAKT Cell Assay Cells (MKN45 gastric cancer cells, Kato III gastric cancer cells, or BT-474 HER2-amplified breast cancer cells) were plated at a density of 30,000 cells/well in 96-well plates and were allowed to attach overnight. The cells were then treated with test or control antibodies at the indicated dose-curve at 37° C. for 4 hours. At the end of treatment, media was removed and cells were washed with PBS. Cells were lysed in 80 µl of Triton X lysis buffer (Boston BioProducts, Ashland, Mass.) with protease and phosphatase inhibitors (Calbiochem, La Jolla, Calif.), and were stored at −20° C. until analysis. AKT/pAKT were analyzed based on the manufacturer's protocol included in the Phospho (Ser473)/Total AKT Whole Cell Lysate Kit (Cat. No. K15100D, Meso-Scale Discovery, Gaithersburg, Md.) to determine pAKT content.

2.6.2. Suppression of pAKT Activity in MKN45 Cells

Figure 9A:
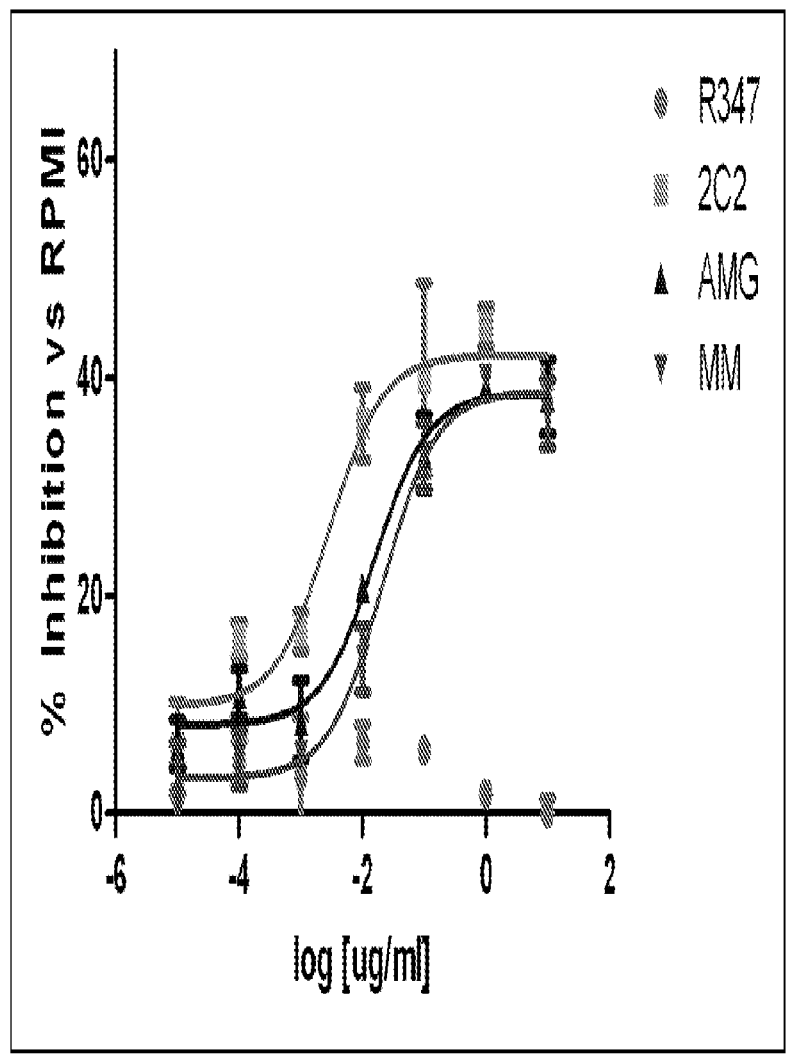

To ascertain if 2C2 could suppress HER3 downstream signaling pathway in addition to pHER3, we additionally assessed its ability to suppress AKT phosphorylation in the amplified cMET-driven gastric cancer model MKN45. MKN45 cells were treated with anti-HER3 monoclonal antibodies as described above in Examples section 2.6.1. In this model system, the 2C2 monoclonal antibody achieved partial pAKT inhibition with higher potency (approximately 5-7-fold higher) than the AMG, and MM anti-HER3 monoclonal antibodies (FIG. 9A). This demonstrated that 2C2 not only inhibits HER3 activity but also suppresses downstream effector molecules of HER3 such as pAKT.

2.6.3. Suppression of pAKT Activity in Kato III Cells

Figure 9B:
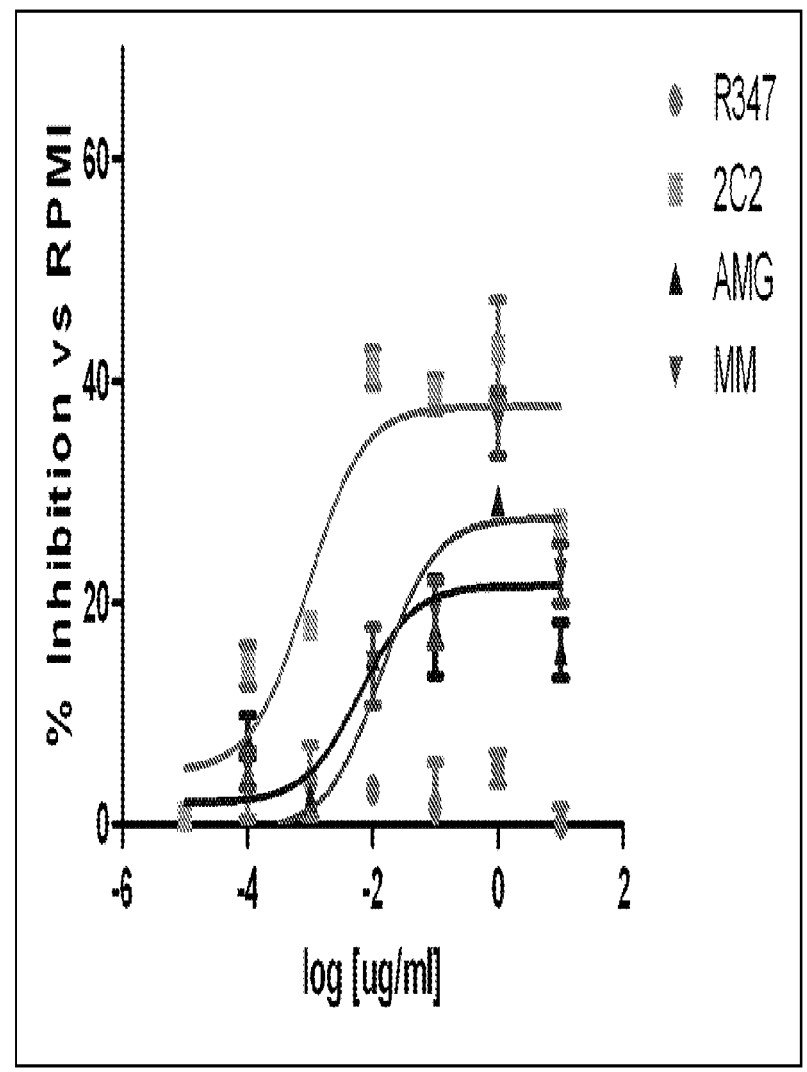

To investigate whether this activity translated into a better potency suppressing pAKT, the effector of HER3, we analyzed pAKT inhibition by various anti-HER3 monoclonal antibodies using in this cell-line a Meso-Scale Discovery assay as described above in Examples section 2.6.1. As shown in FIG. 9B, consistent with the pHER3 data, 2C2 suppressed pAKT in amplified FGFR2-driven gastric cancer model Kato III cells. 2C2 again achieved higher potency (as measured by $IC_{50}$) and maximal response in pAKT inhibition than the AMG and MM antibodies.

2.6.4. Suppression of pAKT Activity in BT-474 Cells

Figure 9C:
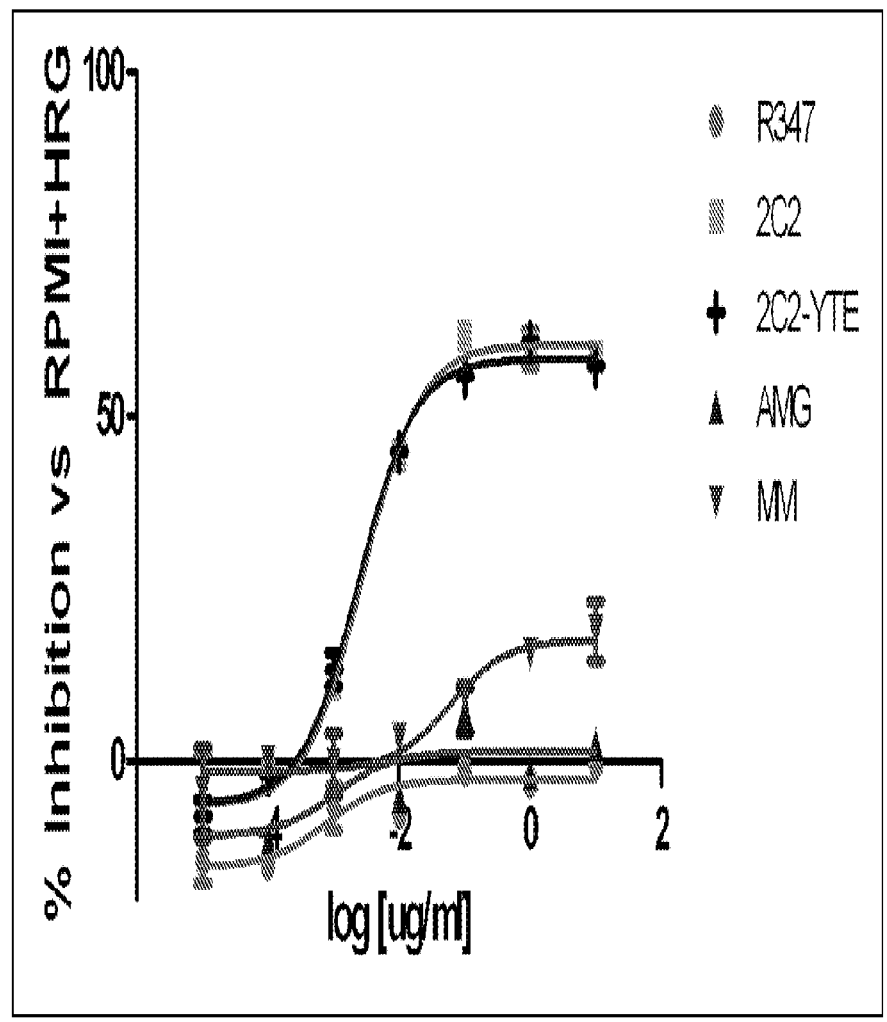

HER2-HER3 dimers have been shown to be one of the most transforming oncogenic entities in cancer. Accordingly, we investigated the activity of anti-HER3 monoclonal antibodies in the BT-474 cell-line. BT-474 cells were treated with the anti-HER3 monoclonal antibodies as described above in Examples section 2.6.1, supra, and also with the YTE mutant form of 2C2. Unlike the models where all three anti-HER3 monoclonal antibodies tested (2C2, AMG and MM) were active, such as MKN45 and KatoIII cells, 2C2 (both parent 2C2 form and 2C2-YTE mutant) was the only one among the anti-HER3 monoclonal antibodies tested that showed substantial activity suppressing pAKT (FIG. 9C). These results indicated that 2C2 (both parent 2C2 form and 2C2-YTE mutant) was functional in a ligand-independent model and demonstrated the bi-functionality of 2C2 (both parent 2C2 form and 2C2-YTE mutant) in both ligand-dependent and ligand-independent settings.

2.7. Suppression of HER3 Signaling and Cell Proliferation in MDA-MB-361 Cells.

To characterize the activity of 2C2-YTE in HER2-amplified breast cancer cells that are not highly responsive to trastuzumab, we focused on MDA-MB-361 (ATCC No. HTB-27), a breast cancer model that harbors the activating mutation in PIK3CA (E545K), which may contribute to its resistance to trastuzumab due to intrinsic activation of the PI3K pathway (Junttila et al, 2009, Cancer Cell. 15:429-40). We determined the effects of 2C2 on HER3 signaling and cell proliferation in this model.

To assess signaling the human breast cell line MDA-MB-361 was plated in 24-well plates at a density of 150,000 cells per well in RPMI (Invitrogen) supplemented with 10% heat-inactivated fetal bovine serum (FBS) (Invitrogen). The next day, the plating medium was removed and cells were subjected to incubation with the anti-HER3 antibody 2C2 or a control antibody, in complete medium at a final concentration of 30 µg/mL. After an incubation of 6 hours in 5% $CO_2$ at 37° C., cells were washed once with ice-cold PBS and then lysed by adding Laemmli Reducing buffer (Boston BioProducts, Ashland, Mass.). After a brief incubation, cell lysates were collected, equal amounts were loaded onto Bis NuPAGE® Novex® Bis-Tris gels (Invitrogen, Carlsbad, Calif.) and proteins transferred to PVDF membranes (Invitrogen, Carlsbad, Calif.). Membranes were blocked with 5% nonfat dry milk and 0.1% Tween 20 (Sigma, St. Louis, Mo.) in TBS (pH 7.4) and incubated overnight at 4° C. with antibodies to HER3 (sc-285 antibody, Cell Signaling Technology, Beverly, Mass.) and pHER3 (4791 antibody, Cell Signaling Technology, Beverly, Mass.). Membranes were washed in 0.1% Tween 20 in TBS and then incubated for 1 hour in horseradish peroxidase-conjugated streptavidin secondary antibodies (GE Healthcare). After washing, protein bands were detected in X-ray film by using SuperSignal® West Femto Chemiluminescent Substrate and SuperSignal® West Pico Chemiluminescent Substrate (Pierce/Thermo Scientific, Rockford, Ill.).

To access cell proliferation MDA-MB-361 cells were seeded at a density of 2,000 cells in 100 µL of medium containing 10% heat-inactivated FBS; Costar white polystyrene tissue-culture treated 96-well plates with flat bottoms (Corning) were used. The next day, the plating medium was removed and antibodies were added in complete medium to a final volume of 100 µL per well. Plates were then incubated in 5% CO2 at 37° C. for 6 or 14 days. For the 14-day assay, fresh antibodies were applied at Day 7. Equal volumes of CellTiter-GloR reagent (Promega) were added to each well at the end of each time point. Plates were rocked on a plate shaker for 10 minutes at room temperature to ensure complete cell lysis. Luminescence was measured using an EnVision 2104 Multilabel Reader (PerkinElmer).

2C2 reduced pHER3 levels (FIG. 10A) and suppressed cell growth (FIG. 10B) of this cell line, suggesting 2C2-YTE not only is active in trastuzumab-sensitive cancers with HER2-amplification, but also active in HER2-amplified cancers that are less sensitive to trastuzumab due to mutations on PIK3CA.

2.8. Identification of Novel HRG-dependent Cancer Types

To identify additional novel HRG-dependent cancer times multiple lung squamous cell carcinoma (SCC) cell lines were screened for HER3 signaling activity and HRG expression. HARA-B (JCRB No. JCRB1080.1) and KNS-62 (JCRB No. IFO50358) cell lines expressed significant levels of HER3, HRG as well as pHER3 (data not shown). Accordingly, we investigated the activity of 2C2 in the HARA-B and KNS-62 cell-lines. The cells were treated with the anti-HER3 monoclonal antibodies essentially as described above in Examples section 2.4 supra, 2C2 was able to reduce pHER3 levels in the HARA-B cell line (FIG. 11) and the KNS-62 cell line (data not shown). As shown below (Examples, section 5.4), 2C2-YTE demonstrated dose-dependent anti-tumor efficacy in the human squamous HARA-B NSCLC xenograft model. Thus, these criteria (i.e., expression of HER3, HRG as well as pHER3) may be useful screening tools to identify additional cancer types responsive to anti-HER3 antibodies, including for example 2C2, AMG, MM as described herein and others known in the art (see for example International Patent Publications WO2011/136911, WO2012/019024, WO2010/022814).

2.9. HER2 is a Major Driver in Certain HRG-dependent Cancer Types

In the presence of the HER3 ligand heregulin (HRG), HER3 heterodimerizes with EGFR or HER2, which leads to phosphorylation of HER3 and transmission of an oncogenic signal via phosphoinositide 3 kinase (PI3K) and protein kinase B (PKB), also known as AKT. A collection of CRC models were characterized to determine which receptor tyrosine kinase, EGFR or HER2, is the major driver of signaling through HER3. Specifically, six different CRC tumor cell lines, SW620 (ATCC No. CCL-227), SW480 (ATCC No. CCL-228), Colo205 (ATCC No. CCL-222), LOVO (ATCC No. CCL-229), HCT15 (ATCC No. CCL-225), and Caco-2 (ATCC No. HTB-37), were treated with antagonists of HER2 or EGFR alone or in combination with the HER3 antagonist 2C2. Briefly, cells were seeded into 24-well plates at a density of $1.5 \times 10^5$ cells per well. The next day, 2 identical sets of cells were treated with the 10 µg/mL of the following antibodies: 2C2 anti-HER3 antibody, the R347 control IgG antibody, the anti-HER2 antibody 2C4 (e.g., Patent Publication WO2001/00245), the anti-EGFR antibody cetuximab or the EGFR tyrosine kinase inhibitor gefitinib at 5 µM. After 5-6 hours of incubation at 37° C., HRG was added at 50 ng/mL into one set of cells for 15 minutes at 37° C. All cells were then washed with cold PBS and lysed by the addition of 60 µL of 2×SDS (sodium dodecyl sulfate) sample buffer (Invitrogen). Lysates were transferred to 1.5 mL tubes and boiled for 5 minutes followed by chilling on ice for 2 minutes. Equal volumes (20 µL) of protein samples were resolved in NuPAGE Novex Bis-Tris gels (Invitrogen) before transfer to polyvinylidene fluoride (PVDF) membranes (Invitrogen). Membranes were washed in Tris-buffered saline (KPL) containing 0.1% Tween 20 (Sigma) and incubated overnight at 4° C. with antibodies to HER3 (Santa Cruz Biotechnology), pHER3-Tyr1289 (Cell Signaling Technology), phosphorylated AKT (protein kinase B (pAKT)) (Cell Signaling Technology), phosphorylated ERK (mitogen-activated protein kinase/extracellular signal-regulated kinase (pERK)) (Cell Signaling Technology), and glyceraldehyde 3-phosphate dehydrogenase (GAPDH) (Sigma). Membranes were washed in Tris-buffered saline (KPL) containing 0.1% Tween 20 (Sigma) and then incubated for 1 hour in horseradish peroxidase-conjugated secondary antibodies (GE HealthCare). After washing, protein bands were detected on X-ray film by using SuperSignal West Pico Chemiluminescent Substrate (Pierce/Thermo Scientific).

As seen in FIG. 12, both the anti-HER3 and the anti-HER2 antibodies reduced the levels of HER3, pHER3 and pAKT in ligand stimulated cells while EGFR antagonist such as cetuximab and gefitinib treatment had no effect on these signaling molecules. These data demonstrate that HER2 is the major driver of HRG-induced HER3 signaling in all the cancer models tested.

Example 3

Mechanism of Action Studies for Anti-HER3 Monoclonal Antibodies 3.1. Clone 16 Partially Blocked Ligand-Binding to HER3

The efficacy of anti-HER3 monoclonal antibodies to block ligand-induced HER3 activity can be due to their ability to directly block off ligand-binding. To investigate this scenario, we established an in vitro HRG-HER3 binding assay by coating a plate with heregulin (HRG) and binding labeled recombinant HER3 protein to it.

3.1.1. HRG-HER3 Binding Assay

Microplate wells were coated with 10 ng/ml heregulin (HRGβ1, Cat. No. 377-HB, R&D Systems, Minneapolis, Minn.) overnight at 4° C. The next day, plates were washed 4 times with PBST (PBS+0.05% Tween 20) and blocked in PBS+1 µg/ml BSA at room temperature for 1 hour. During blocking, serial dilutions of test antibodies (Clone 16, AMG, MM and a positive control anti-HER3 ligand blocking monoclonal antibody) were prepared in a separate plate in PBSTB (PBS+0.05% Tween 20+0.1% BSA) and combined with 5 µg/ml of recombinant HER3 (Cat. No. 348-RB, R&D Systems, Minneapolis, Minn.) at room temperature for 30 minutes. ELISA plates were then washed 4× with PBST before addition of antibody-HER3 mixture. Plates were incubated at room temperature for 1 hour and were subsequently washed 4 times with PBST. Anti-His HRP (Cat. No. 34460, Qiagen, Valencia, Calif.) was added at room temperature for 1 hour. Plates were washed 4 times with PBST followed by detection with TMB. Plates were read at 450 nm using a microplate reader. Representative results are shown in FIG. 13.

3.1.2. Results

The ability of several monoclonal antibodies (Clone 16, AMG, MM and a positive control anti-HER3 ligand blocking monoclonal antibody) to interfere with the binding of HRG to HER3 was tested. The positive control HER3 ligand-blocking monoclonal antibody, efficiently and completely suppressed the HER3 binding to HRG. In contrast, Clone 16 (the parental lead for 2C2, see "Affinity Optimization" Examples section 1.6 above) was only partially effective in disrupting this binding (approximately 30% maximum inhibition). The AMG and MM monoclonal antibodies showed similar weak, partial blocking effect (FIG. 13). These findings showed that Clone 16 was unlikely to function as a direct ligand-blocking monoclonal antibody.

3.2. 2C2 Disrupts HER2-HER3 Dimerization

Due to its kinase-deficient nature, HER3 monomer is not active and it needs to form heterodimers with other RTKs to be active. The HER2:HER3 dimer has been shown to be the most oncogenic signaling species in both ligand-dependent and independent settings (Junttila et al, 2009, Cancer Cell. 15:429-40). The disruption of HER2-HER3 dimerization by 2C2 was assessed using an HRG-induced HER2-HER3 dimer formation assay in T-47D cells, a ligand-dependent breast cancer model showing HRG-induced HER3-HER2 dimer formation, and in ligand-independent BT-474 cells. The assay was based on HER3-HER2 co-immunoprecipitation.

3.2.1. Ligand-induced HER2-HER3 Dimerization Assay

T-47D cells (ATCC Cat. No. HTB-133™) were seeded at $1 \times 10^6$/well in 6 well plates overnight. Next morning, cells were treated with 2C2, CL16, AMG and MM monoclonal antibodies at a concentration of 5 µg/ml in full serum for 2 hours at 37° C. Controls included no antibody treatment, or treatment with control R347 IgG1. Treatment was followed by 50 ng/ml HRG treatment for 10 minutes at 37° C. (including a control not treated with HRG). Cells were washed 3 times with cold PBS before adding 500 µl of cell lysis buffer, including protease and phosphatase inhibitors (Sigma, St. Louis, Mo.). Cells were lysed on ice for at least 30 minutes. Lysates were harvested with a cell scraper. 50 µl of a protein A beads solution containing 25 µl protein A beads conjugated with 1 µg of anti-HER3 mAb (Cat. No. MAB3481, R&D Systems, Minneapolis, Minn.) were added to 500 µl of cell lysate and transferred to immunoprecipitation (IP) columns. The IP columns were rotated overnight at 4° C. Subsequently, the IP columns were spun down to remove the lysates, and the beads were washed with cold cell lysis buffer. 50 µl of 2×SDS sample buffer containing 50 mM DTT were added to each IP column, and columns were boiled for 4 minutes. The bottom tip of each column was removed, and columns were spun down to collect the eluates. 20 µl of eluate were separated using SDS-PAGE. Western blotting was performed for both HER2 and HER3 (with anti-HER2 antibody Cat. No. OP15L, CalBiochem, La Jolla, Calif.; and anti-HER3 antibody Cat. No. SC-285, Santa Cruz Biotechnology, Inc., Santa Cruz, Calif.).

3.2.2. Ligand-Independent HER2-HER3 Dimerization Assay

BT-474 cells (ATCC Cat. No. HTB-20™) were plated at a density of 1×106 cells per well in a 6-well plate in complete RPMI 1640 cell culture media with 10% heat-inactivated FBS. The next day, plating medium was removed and replaced with fresh complete RPMI 1640 containing saturating dose of testing antibodies. In this experiment, CL16, the precursor lower affinity version of 2C2, 2C2, and R347, a control IgG, were tested at a concentration of 5 µg/mL. Cells were incubated with antibodies for 2 hours at 37° C. Then the medium was removed, and cells were washed once with cold PBS. The crosslinker 3,3'-dithiobis [sulfosuccinimidylpropionate] (DTSSP) was added at a concentration of 2 mM in 1 mL cold PBS. Cells were incubated for at least 1 hour on ice. Cells were then washed 3 times with cold PBS. Cell lysis buffer (500 µL) containing protease and phosphatase inhibitors was added and the cells were placed on ice for at least 30 minutes to allow for lysis before harvesting with a cell scraper. HER2 and HER3 were immunoprecipitated from cell lysates. Cell lysates (500 µL) were combined with 50 µL protein A sepharose beads (50% slurry; Invitrogen) pre-conjugated to 1 µg of HER3 MAb (MAB3481, R&D Systems) in a SigmaPrep spin column (Sigma). The mixture was incubated with rotation at 4° C. overnight. The next day, beads were separated from the cell lysate by centrifugation. Beads in the columns were washed four times with cold cell lysis buffer (Cell Signaling Technologies) containing protease (Sigma) and phosphatase inhibitors (EMD Millipore). After the wash procedure, 50 µL 2×SDS (sodium dodecyl sulfate) sample buffer containing 50 mM dithiothreitol (DTT; EMD Chemicals) was added into the spin columns. The columns were then boiled for 4 minutes. Proteins were eluted by centrifugation and used immediately for immunoblotting (as done in section 2.4).

3.2.3. Results

Figure 14A:
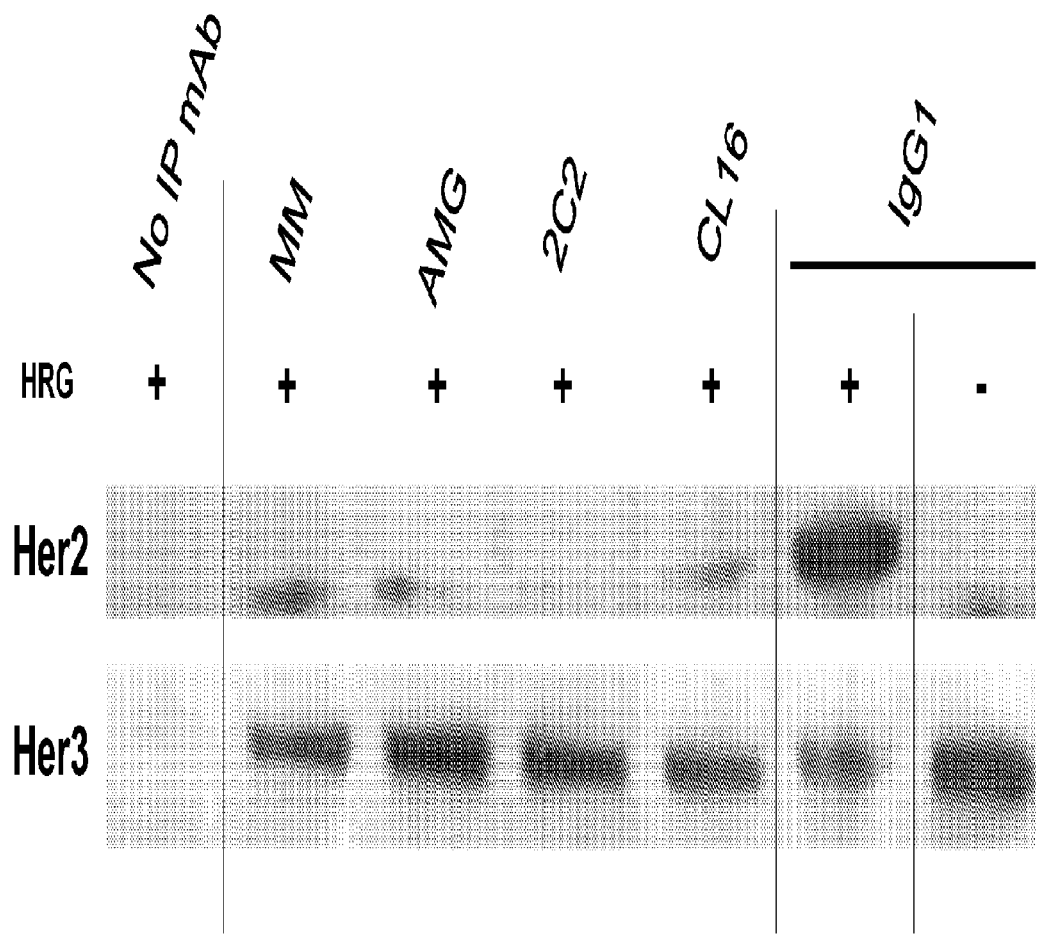
Figure 14B:
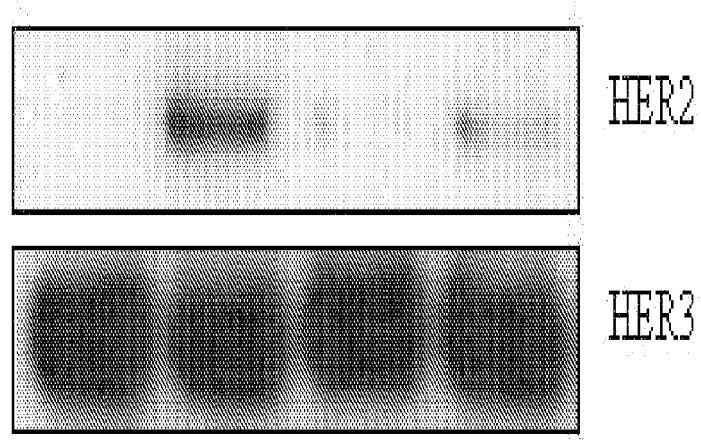

T-47D cells treated or not treated with HRG were lysed. HER3 was precipitated with anti-HER3 monoclonal antibody, then the proteins in the pellet were resolved on SDS-PAGE and blotted for the presence of HER2 as signs of HER2-HER3 interaction. The model was ligand-inducible since the dimer only occurred after ligand-stimulation. A pre-treatment with 2C2 efficiently prevented dimer formation, demonstrating its ability to impede ligand-induced HER2-HER3 dimer formation. Other anti-HER3 monoclonal antibodies including MM, AMG, and the parental Clone 16, were also found to be effective (FIG. 14A). When the crosslinker DTSSP was used to biochemically stabilize protein complexes, constitutive HER2:HER3 heterodimer was captured in the absence of HRG in BT-474 cells, indicating a ligand-independent heterodimer formation. Pretreatment of cells with 2C2 or CL16 effectively disrupted this heterodimer formation (FIG. 14B).

3.3. HER3 Internalization and Degradation Induced by 2C2

Target internalization and degradation are two common mechanisms by which monoclonal antibodies inhibit their target functions. First, we assessed the 2C2-mediated HER3 internalization in the BT-474 breast cancer cells. Next, we ascertained if this rapid 2C2-induced HER3 internalization could be followed by target degradation.

3.3.1. HER3 Internalization Assay

HER3 internalization was determined using a Fluorescence Activated Cell Sorting (FACS) assay. BT-474 cells were detached with Accutase enzyme and suspend the cells in PBS containing 1% BSA (FACS buffer) to a cell density of $10 \times 10^6$ cells/ml. 50 µl of cells were added to each cell of a U-bottom 96 well plate. 50 µl of anti-HER3 monoclonal antibodies plus Isotope control (at 20 µg/ml) were added into each well to achieve a 10 µg/ml final concentration. The plate was incubated at 37° C. for 0.5 hours, 2 hours and 4.5 hours, respectively. Cells were washed with cold FACS buffer twice (cells were pelleted by centrifugation at 1,500 rpm for 2 minutes). Cells were resuspended with cold FACS buffer containing mouse anti-human HER3 monoclonal antibody (Cat. No. MAB3481, R&D Systems, Minneapolis, Minn.) at 1 µg/ml or 10 µg/ml.

Figure 15A:
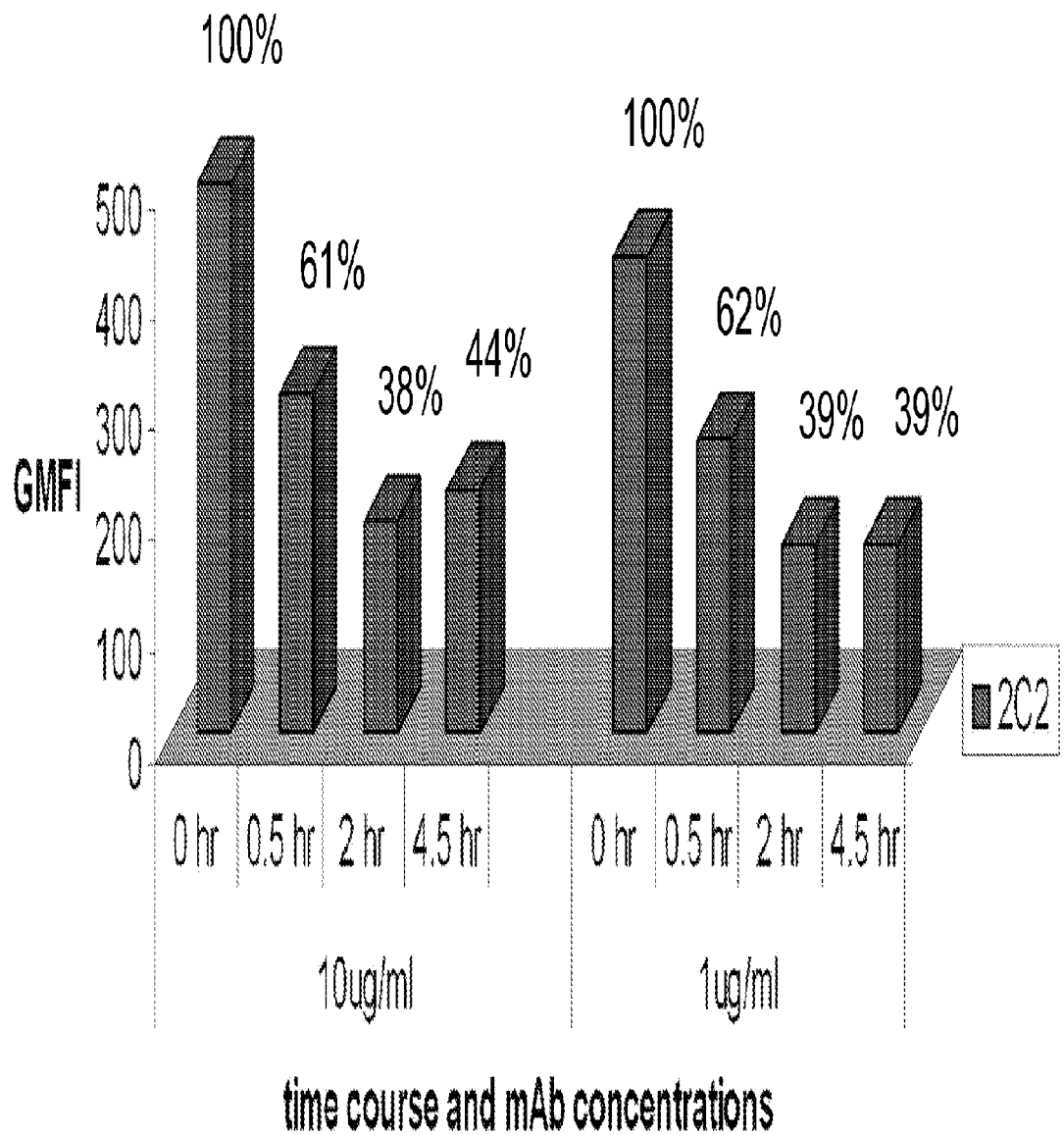
Figure 15B:
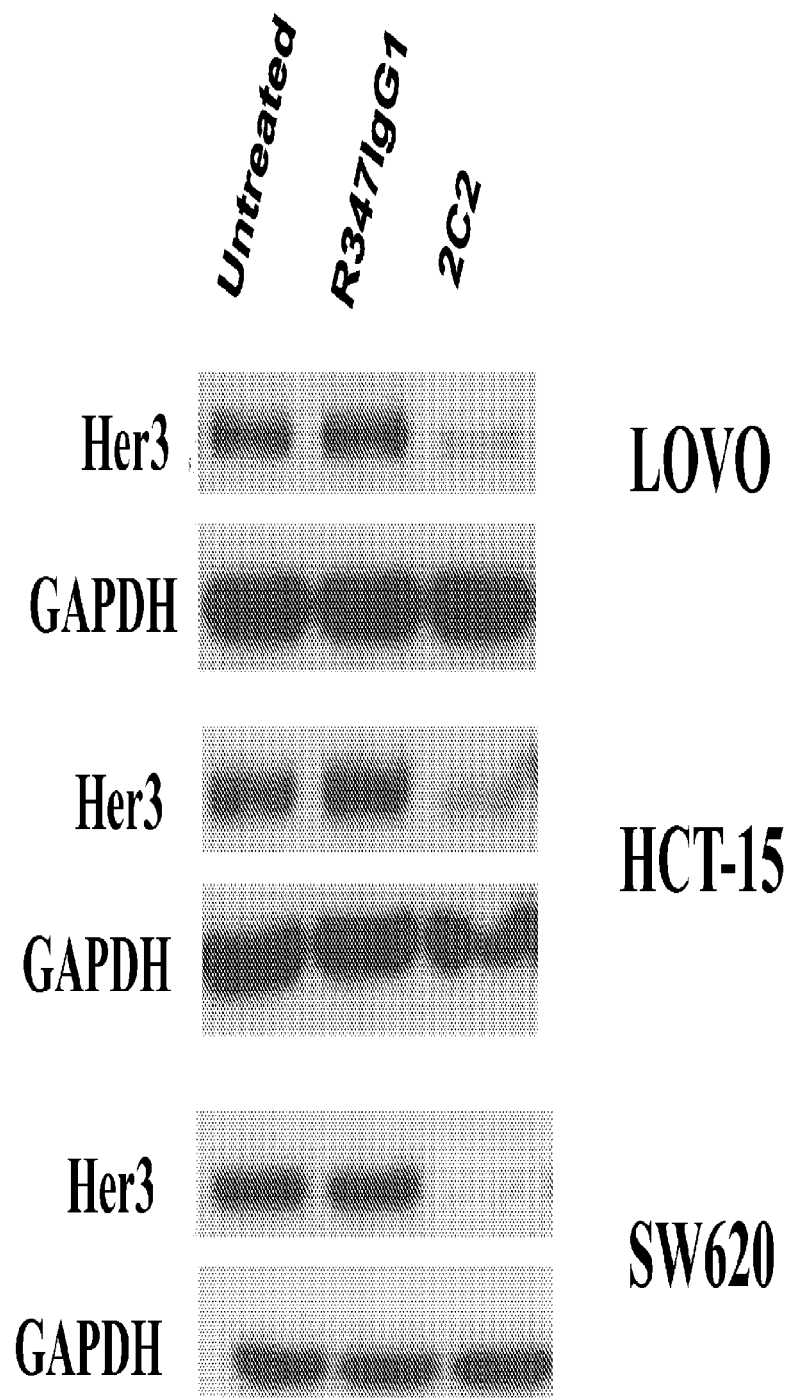

Cells and anti-human HER3 were incubated on ice for 1 hour. Cells were then washed twice with cold FACS buffer. Cells were subsequently resuspended with cold FACS buffer containing an Alexa Fluor® 488-labeled secondary antibody (Invitrogen) (1:200 v/v), and incubated on ice for 30-45 minutes. Cells were then washed with cold FACS buffer twice and resuspended with 100 µl of cold FACS buffer. At this point, FACS was performed. Absolute Geometric Mean of Fluorescence Intensities (GMFI) were obtained by subtracting the GMFI from controls including only the secondary antibody. Relative HER3 surface clearance was calculated by comparing with results obtained using an IgG control monoclonal antibody. Representative results are shown in FIG. 15A.

3.3.2. HER3 Protein Degradation Assay

Lovo, HCT15 and SW620 colorectal model cancer cells (ATCC Nos. CCL-229, CCL-225 and CCL-227, respectively) were seeded at $1.5 \times 10^5$/well in 24 well plates. After overnight attachment, the cells were treated with 2C2 and control monoclonal antibody for 3-4 hours. Cells were washed with cold PBS once, directly lysed with 50-60 µl of 2×SDS sample buffer and boiled at 100° C. for 10 minutes. 20 µl of samples were loaded into SDS-PAGE gels, electrophoretically separated, and Western blotted with antibody against HER3 (Santa Cruz Biotech) to quantitate total HER3 protein levels. Antibodies against GAPDH (Sigma) were also used to quantitate GAPDH levels as a general protein loading control.

3.3.3. Results

As shown in FIG. 15A, both doses of 2C2 had a very similar impact. A 30-minute treatment caused a 39% loss of surface HER3 population (61% remaining), whereas a 2-hour treatment caused a 62% loss (38% remaining), suggesting a rapid target internalization by 2C2. Additionally, when the three different colorectal cancer models were incubated with 2C2, complete HER3 degradation was observed in SW620 cells, whereas nearly complete degradation was observed in the other two cell-lines (FIG. 15B), demonstrating that 2C2 was capable of strong target degradation capacity.

3.4. Effector Functions: Antibody-Dependent Cell-Mediated Cytotoxicity (ADCC) and Complement-Dependent Cytotoxicity (CDC)

ADCC is one recognized way through which a monoclonal antibody can confer its anti-tumor efficacy in vivo. To assess the ADCC activity of Clone 16, we used an in vitro PBMC-enabled ADCC assay in two HER2-amplified breast cancer models: BT-474 and SkBR3. Herceptin/Trastuzumab was used as positive control since it has been shown to confer ADCC effect in these type of cancers. In both models we observed significant tumor-killing effects from Herceptin, but the remaining monoclonal antibodies tested, Clone 16, AMG and MM, were largely inactive, indicating that they lacked appreciable ADCC effect (data not shown). 2C2-YTE was tested in CDC assays using human serum as a source of complement. In addition, the anti-HER2 antibody trastuzumab and the anti-CD20 antibody rituximab, were included as controls. None of the antibodies including 2C2-YTE showed any detectable CDC activity at any concentration (data not shown). SkBR3 cells do not express CD20. As a positive control, rituximab demonstrated substantial cell-kill activity in a similar CDC assay against Daudi cells, which express CD20 (data not shown).

3.5. Cell-Cycle Arrest 3.5.1. Cell-cycle Arrest Assay in SkBR3 Breast Cancer Cells BioSantecells (ATCC No. HTB-30) were plated at a density of 150,000 cells/well in a 6-well plate and allowed to attach overnight. The following day, media was removed and replaced with fresh growth medium containing test and control antibodies. Cells were then incubated at 37° C. for 48 hours. At the end of the treatment, cells were trypsinized, pooled into a 15 ml conical tube, and centrifuged at 1500 rpm for 5 minutes. Cell were then washed once with PBS and fixed in ice cold 70% ethanol at −20° C. overnight.

Following fixation, cells were centrifuged as described above, washed once in PBS, and resuspended in staining solution (PBS+0.1% Triton X-100, 0.2 mg/ml DNAse-free RNAse A, and 20 µg/ml propidium iodide). Cells were stained for 30 minutes at room temperature in the dark, and analyzed using an LSRII Flow Cytometer System (BD Biosciences). Propidium iodide was detected using the Texas Red channel; data was analyzed using the FlowJo flow cytometry analysis package (Tree Star, Inc., OR) using the Dean/Jett/Fox Model.

3.5.2. Results

The FACS-based cell-cycle analysis showed that in SkBR3 cells, a HER2-amplified breast cancer cell-line similar to BT-474, both Herceptin and Clone 16 (parental lead for 2C2) caused cell-cycle arrest at G1-phase (increased G1-population by decreasing S/G2 populations as shown in FIG. 16).

3.6. Anti-Angiogenic Effects by Blocking HRG-Induced VEGF Secretion

HRG has been shown to drive secretion of VEGF, a major pro-angiogenic cytokine, in various cancer models. Therefore we assessed the inhibitory effects of 2C2 in suppressing HRG-induced VEGF secretion in two breast cancer models: MCF-7 and BT-474.

3.6.1. HRG-Induced VEGF Secretion Assay

MCF-7 cells and BT-474 cells were plated at a density of 100,000 cells/well in a 24-well plate, and were allowed to rest for 2 days. Media was then removed and replaced with 500 µl of fresh growth medium containing 2% FBS and control and test antibodies. Following 24 hour incubation, cell culture media was collected and VEGF levels were determined using a VEGF ELISA Kit (R&D Systems DY293B). Relative cell number in each well was determined by adding fresh media to the cells along with Cell Titer Glo (Promega, 1:1 ratio) and incubating plates for 10 minutes at room temperature. Luminescence was read using a plate reader, and these values were used for normalization of the data.

3.6.2. Results

HRG treatment induced dramatic increases in VEGF secretion in the BT-474 (FIG. 17A) and MCF-7 (FIG. 17B) both breast cancer model cell-lines ranging from 6.5-fold to 8-fold. CL16 (Clone 16), and MM monoclonal antibodies were able to suppress most of the increases, suggesting that these anti-HER3 monoclonal antibodies can confer additional vascular modulation effects.

Example 4

Cross Reactivity with Cynomolgus Monkey and Mouse HER3

4.1. 2C2 Binds to Cynomolgus and Mouse HER3 with Similar Affinity as to Human HER3

Biacore assays were performed essentially as described above to compare the affinity of 2C2 to human, cynomolgus monkey (cyno) and mouse HER3 to enable relevant toxicity species selection (top portion of Table 7.) Additional Biacore assays were performed for 2C2-YTE using a higher resolution BIAcore instrument, an alternative Fc capture reagent and a refined injection protocol to correct for background binding. Briefly, Protein A capture reagent was immobilized onto two adjacent flow cells connected in series on the same CM5 sensor chip, using a standard amine protocol as outlined by the instrument's manufacturer. One of these Protein A surfaces was used as a reference surface for this experiment, while the other served as the active surface used to record IgG capture and subsequent HER3 (ECD) binding. The final Protein A densities on the reference and active flow cell surfaces were recorded as 1986 RUs and 1979 RUs, respectively. As configured, the method was set up such that 2C2-YTE IgG was first captured onto only the active Protein A surface, followed by an injection of a HER3 protein solution over both the active and reference flow cell surfaces. In so doing, this strategy corrects the binding curve for any non-specific binding of the HER3 analyte to the Protein A capture surface. For the IgG capture step, 2C2-YTE IgG was prepared at 10 nM in HBS-EP+ instrument buffer (0.01 M HEPES, pH 7.4, 0.15 M NaCl, 3 mM EDTA, and 0.05% P20), then injected over the active Protein A flow cell surface for 30 seconds at a flow rate of 10 µL/min. Human, cyno, and murine HER3 protein were then initially prepared at 500 nM stock solutions in instrument buffer, then two-fold serial dilution series of each were generated to provide a final concentration of 0.39 nM. The HER3 protein was then injected over both the active and reference cell Protein A surfaces for 120 seconds, at a flow rate of 75 µL/min. Dissociation data was collected for 15 minutes, followed by two 60-second pulses with 10 mM Gly buffer, pH 1.7, between injections to regenerate the flow cells back to the Protein A capture surfaces. Several buffer injections were also interspersed throughout the injection series. Select buffer injections were subsequently used along with the reference cell data to correct the raw data sets for injection artifacts and/or non-specific binding interactions, a technique commonly referred to as "double-referencing" (Myszka, 1999). Fully corrected binding data were then globally fit to a 1:1 binding model (BIAevaluation 4.1 software) that included a term to correct for mass transport-limited binding, should it be detected. This analysis determined the kinetic rate (kon, koff) constants, from which the apparent KD was then calculated as koff/kon (bottom of Table 7). The variation in the $K_{on}$ and $K_{off}$ values between the two sets of experiments are likely due to the differences between the two protocols as detailed above and were generally within the accepted two fold error range for measuring these kinetic parameters. As shown in TABLE 7, the affinity of 2C2, and 2C2-YTE to cyno HER3 was virtually identical with that to human HER3. The affinity for mouse HER3 was within 3-fold of the affinity for human HER3.

TABLE 7

Biacore binding assay showing 2C2's affinity to human, cyno, and mouse HER3.

| IgG Capture | 2C2 (exp34c, 34d, 43b) | 2C2 (exp43d) | 2C2 (exp43f) |
|---|---|---|---|
| Receptor Format | huHER3 (ECD)-His IgG (Fc) capture | muHER3-His IgG (Fc) capture | Cyno HER3-His IgG (Fc) capture |
| $K_{on}$ (1/Ms) (×10$^5$) | 4.27 (+/− 0.45) | 3.26 | 4.66 |
| $K_{off}$ (1/s) (×10$^{-4}$) | 1.71 (+/− 0.18) | 3.78 | 1.81 |

TABLE 7-continued

Biacore binding assay showing 2C2's affinity to human, cyno, and mouse HER3.

| $K_D$ (nM) | 0.402 (+/− 0.029) | 1.16 | 0.389 |
|---|---|---|---|
| IgG Capture | 2C2-YTE | 2C2-YTE | 2C2-YTE |
| Receptor Format | huHER3 (ECD)-His IgG (Fc) capture | muHER3-His IgG (Fc) capture | Cyno HER3-His IgG (Fc) capture |
| $K_{on}$ (1/Ms) (×10$^5$) | 1.61 | 1.11 | 1.52 |
| $K_{off}$ (1/s) (×10$^{-4}$) | 0.743 | 1.91 | 0.734 |
| $K_D$ (nM) | 0.461 | 1.721 | 0.483 |

4.2. Assay for HRG-Induced Phosphorylation of Cynomolgus HER3

Ad293 cells (Stratagene No. 240085) were transiently transfected with full length cynoHER3-expression vector following protocol provided with the Lipofectamine 2000 reagent (Invitrogen). Cells were allowed to incubate at 37° C. for 48 hours before treatment. Antibodies were added at 10 µg/ml in complete growth medium for 1 hour followed by stimulation with 20 ng/ml HRGβ1 (R&D Systems) for 10 minutes at 37° C. At the end of treatment, media was removed and cells were washed once with PBS. Cells were lysed with 2× Novex Tris-glycine sample buffer (Invitrogen) and the levels of pHER3 and total HER3 were determined by immunoblotting (Cell Signaling antibody #4791 and Santa Cruz antibody #285, respectively). Densitometry of bands was accomplished using ImageJ software (NIH, imagej.nih.gov/ij/).

4.3. Results

Figure 18A:
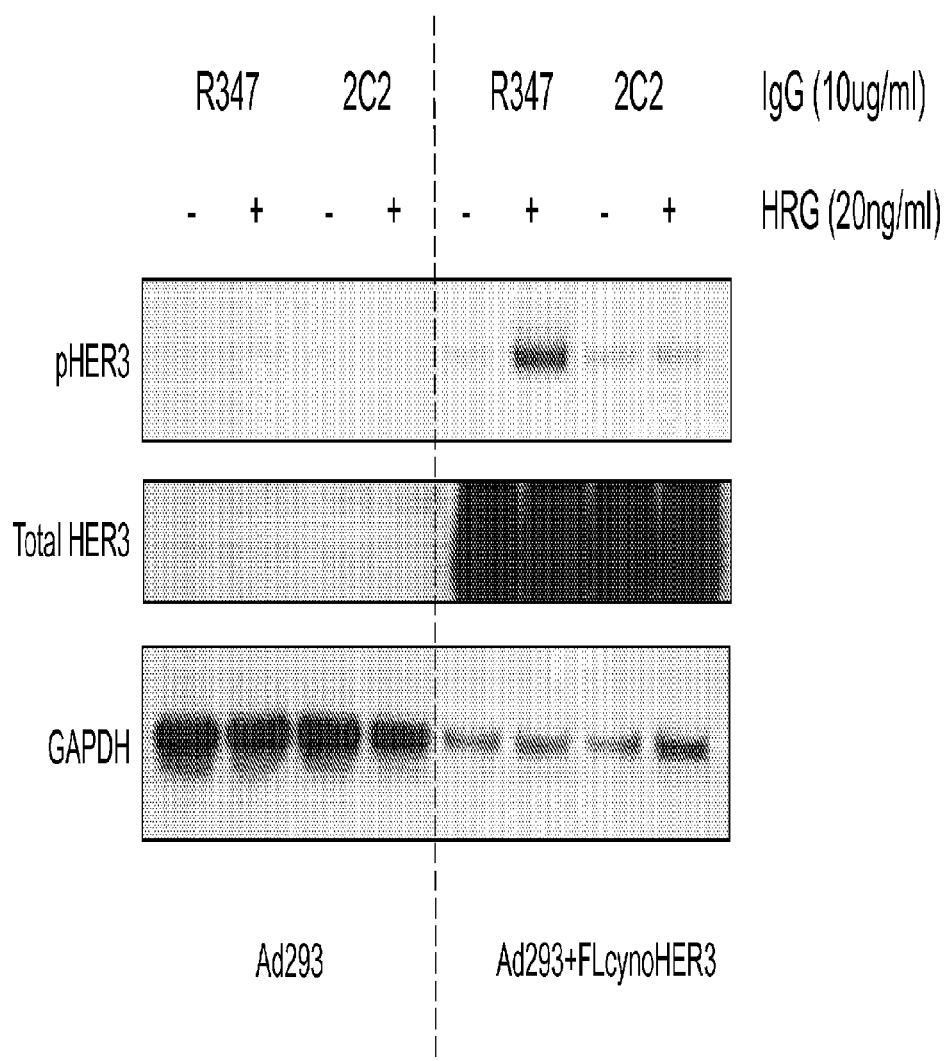
Figure 18B:
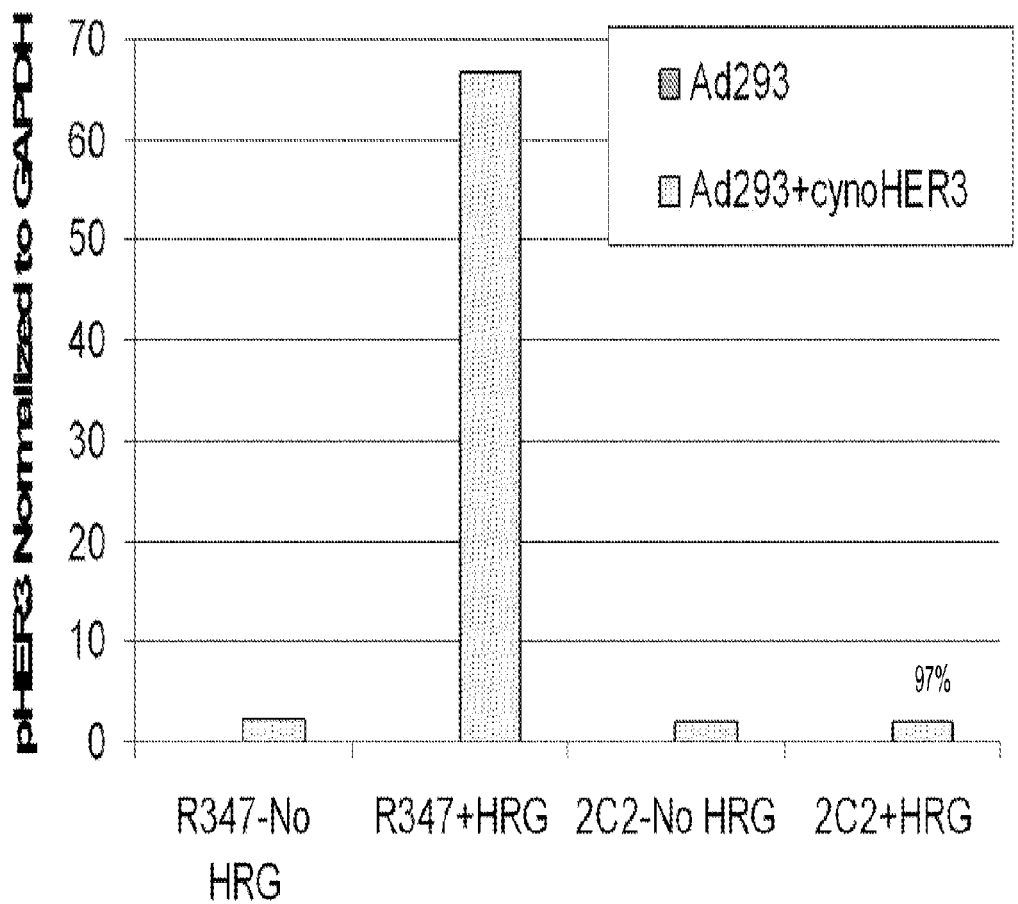

To fully establish the binding and cross-modulation of cyno HER3 by 2C2, a stable Ad293 cell-line ectopically expressing full-length cyno HER3 was established, as demonstrated by Western Blot (FIG. 18A). When treated with HRG, the cyno HER3 underwent robust activation as evidenced by the induction of pHER3 signal (FIG. 18B). When cells were co-treated with 2C2 but not when they were treated with the R347 control antibody, pHER3 induction was completely abrogated, demonstrating that 2C2 was not only able to bind to cyno HER3 on cell-surface, but also able to efficiently ablate its activation (FIG. 18B). Combined with the above Biacore affinity measurement data showing that 2C2 displayed identical affinity to cyno HER3 as to human HER3, these results validated cyno as a relevant toxicity species for 2C2 trials.

In Vivo Studies for Anti-HER3 Monoclonal Antibodies 4.4. Subcutaneous Human FADU Head and Neck Xenograft Model Studies 4.4.1. Method Human FADU Head and Neck cells (ATCC No. HTB-43) were maintained at 37° C. in a 5% CO$_2$ incubator in RPMI 1640 medium containing 4.5 g/L glucose, L-glutamine, sodium pyruvate and 10% fetal bovine serum. Xenografts were established by subcutaneously injecting 5×10$^6$ cells per mouse (suspended in 50% matrigel) into the right flanks of 4- to 6-week-old athymic nu/nu mice. Tumors were allowed to grow up to 200 mm$^3$ before randomization for efficacy studies. 2C2, 2C2-YTE, cetuximab, control IgG1 or the combination of 2C2 with cetuximab monoclonal antibodies were administered intraperitoneally. For dose dependency studies the 2C2 was adminstered at 3, 5, 7, and 10 mg per kilogram body weight (mg/kg), the control at 10 mg/kg. For the combination studies 2C2 was administered at 3 mg/kg, cetuximab at 30 mg/kg and the control antibody at 6 mg/kg. Caliper measurements were used to calculate tumor volumes using the formula:

tumor volume=π÷6(length×width×width)

for tumors grown in mice. Antitumor effects are expressed as percent delta tumor growth inhibition (TGI), which was calculated as follows:

percent delta TGI=1−(dT÷dC)×100, where dT=change in mean tumor volume in treatment group compared to the value at staging, and dC=change in mean tumor volume in control group compared to the value at staging.

At the conclusion of the efficacy studies with 2C2, mice were treated with 2C2 a final time as indicated to determine pharmacokinetic values. Cardiac puncture was performed to collect blood into Microtainer Serum Separator Tubes (SST). Tubes with blood were vortexed gently for 10 seconds and kept at room temperature for 20 minutes to allow the serum to clot. Samples were centrifuged at 1000×g for 10 minutes, and the serum samples were carefully transferred into new tubes and stored at −80° C.

An indirect Enzyme-Linked Immunosorbent Assay (ELISA) format was used for the quantitative determination of 2C2 in mouse serum. Standards, quality controls, and mouse serum samples were incubated with goat anti-human IgG antibodies which were immobilized on a 96-well microtiter plate. After incubation, unbound materials were removed by a wash step and 2C2 was detected using a goat anti-human IgG with horseradish-peroxidase conjugate. An acidic stopping solution was added and the degree of enzymatic turnover of substrate was determined by measuring absorbance at 450 nm. The absorbance measured was directly proportional to the concentration of 2C2 present in the mouse serum. A 2C2 standard curve for the assay was used to interpolate the concentration of the serum samples.

4.4.2. Results.

Figure 19A:
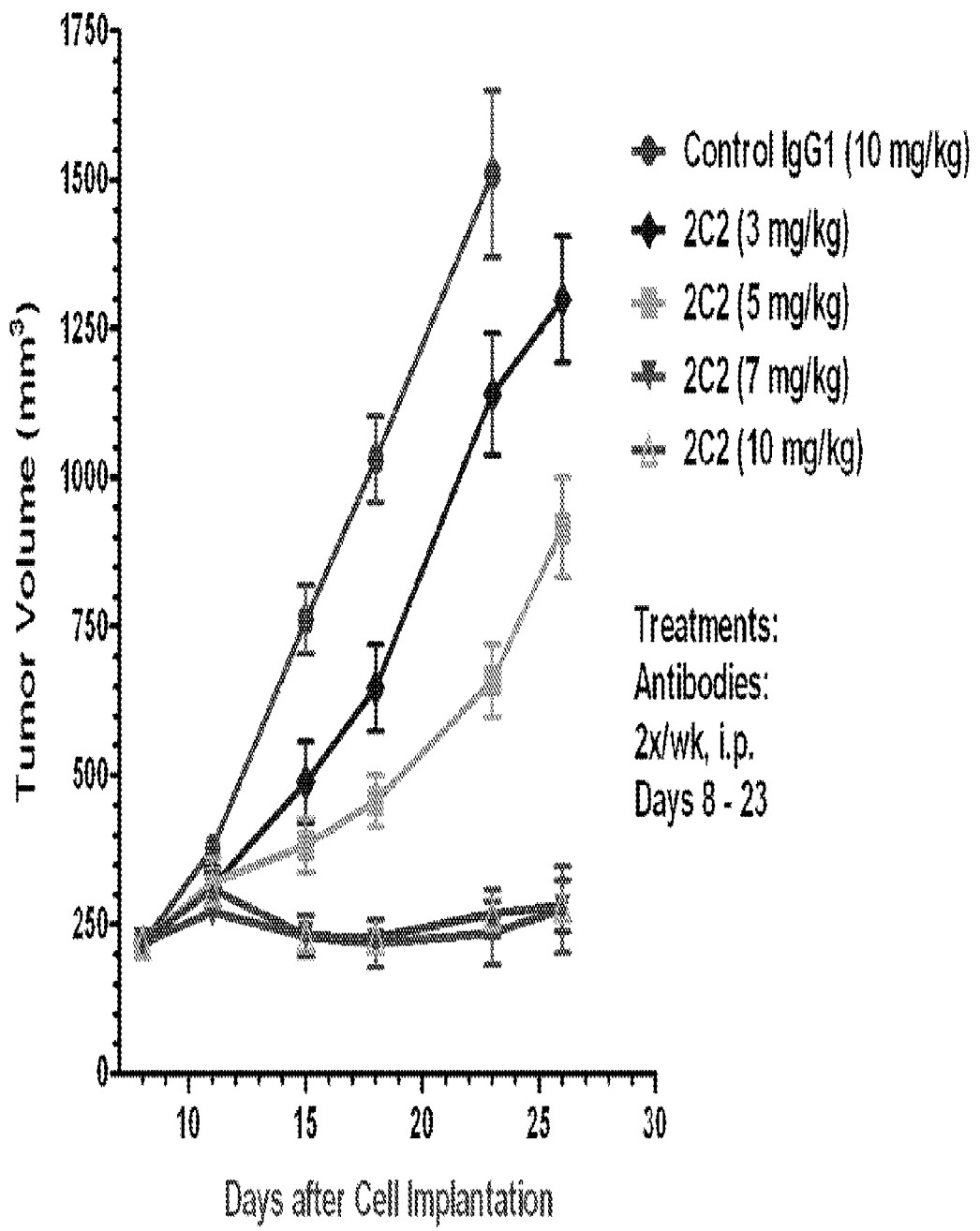

Utilizing a human FADU Head and Neck xenograft model grown subcutaneously in female nude mice, 2C2 demonstrated dose-dependent anti-tumor efficacy. Maximal efficacy at 99% tumor growth inhibition (dTGI) was observed with 7 mg/kg administered twice per week for the duration of the study (FIG. 19A).

Figure 19B:
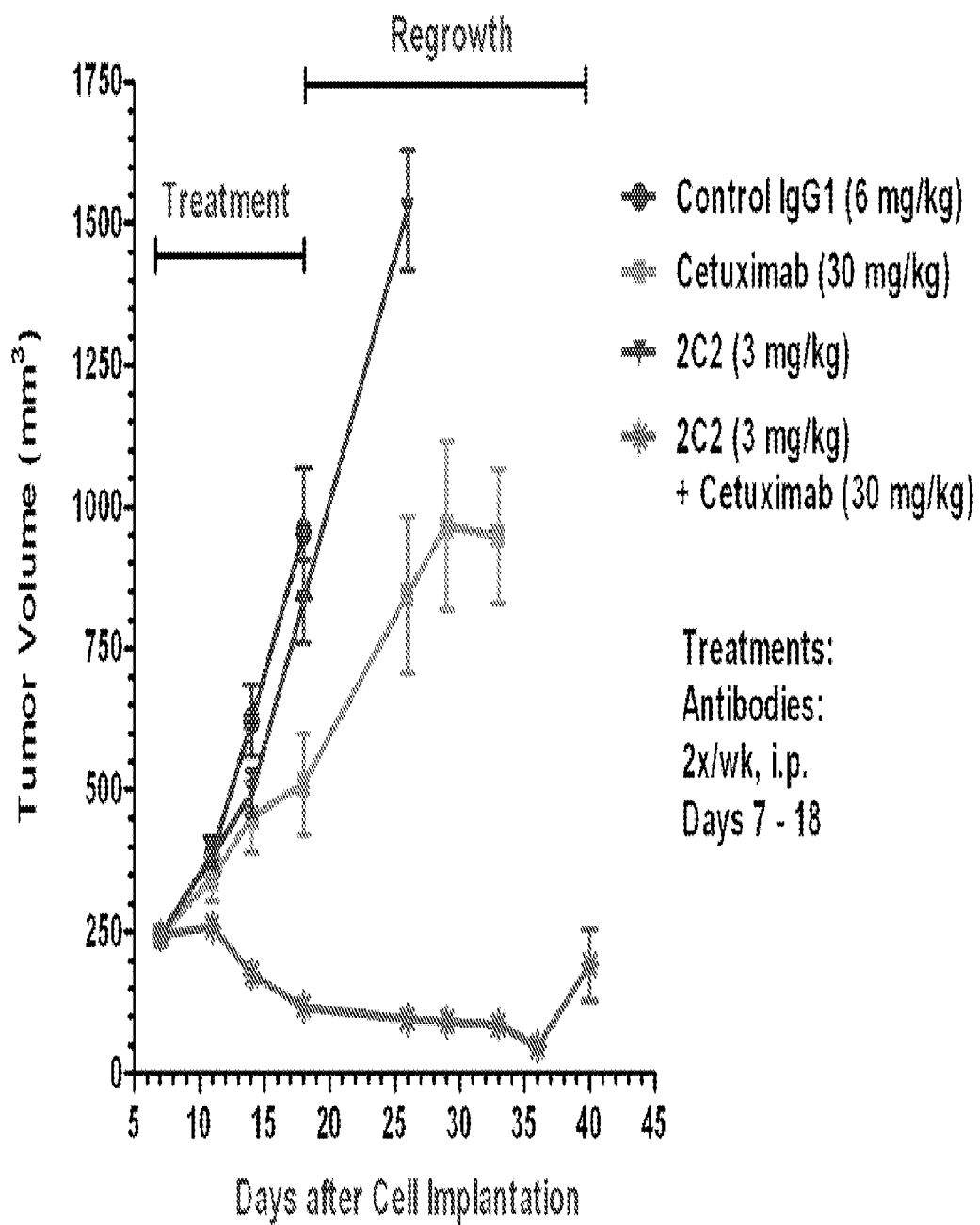

Combined administration of 3 mg/kg of 2C2 with 30 mg/kg of cetuximab administered two times per week during the treatment phase (days 7-18) showed clear synergistic anti-tumor efficacy in the FADU xenograft model (FIG. 19B). This effect was long lasting and the tumors only started to grow back at the end of the regrowth phase at day 40. The combination treatment produced 7 out of 10 partial regressions and 2/10 complete regressions.

2C2 cross-reacted with mouse HER3 and it is well established that HER3 is expressed in many non-diseased mouse tissues. Therefore, host HER3 could serve as a sink to absorb the 2C2 monoclonal antibody before it gets to the tumor tissue. Using tumor-bearing female nude mice, 2C2 at 5 mg/kg was administered either once or three times to these mice and the exposure levels of 2C2 were followed over time. 2C2 was only detectable 1 day after the last dose of 5 mg/kg of 2C2 and became undetectable after 3 days after the last treatment (FIG. 36). On the other hand, dosing with 30 mg/kg of 2C2 using the same schedules as for 5 mg/kg led to a much more prolonged window where 2C2 could be measured in mouse serum. These findings demonstrated non-linear pharmacokinetics for 2C2 after single dose and repeat-dose administration of 5 mg/kg or 30 mg/kg to tumor-bearing mice. The data showed that mouse HER3 can act as a sink to bind 2C2 administered to the mice and that 30 mg/kg as a single dose was sufficient to saturate the sink.

The existence of a HER3 sink in mice for 2C2 was confirmed functionally by administering a high loading dose of 2C2 follow by a low maintenance dose in mice with FADU xenograft tumors. The anti-tumor efficacy of a 10 mg/kg loading dose and a 3 mg/kg maintenance dose of 2C2 was demonstrated in the FADU tumor model. 10 mg/kg of 2C2 as a single dose had only transient anti-tumor efficacy. 2C2 given at 3 mg/kg twice per week had modest but continuous efficacy. The combination of the 10 mg/kg loading dose with the 3 mg/kg maintenance dose of 2C2 was more efficacious in blocking tumor growth compared to either treatment schedule alone (FIG. 21).

The ability of 2C2 to modulate the pharmacodynamic markers pHER3 and pAKT was tested in FADU xenograft tumor extracts. 2C2 was administered twice at 30 mg/kg within 48 hours to mice bearing human FADU xenograft tumors and extracts were analyzed 24 hours later. Briefly, athymic nude mice were implanted subcutaneously with FADU head and neck cancer cells. Animals were administered 2C2 at 30 mg/kg twice within 48 hours. Extracts were prepared 24 hours later for analysis of pHER3, pAKT and total HER3 (FIG. 22, top, middle and bottom panels, respectively). R347 was used as the control IgG1 antibody. There were 6 animals per treatment group. Data are presented as the mean±standard deviation. Here, 2C2 inhibited phosphorylation of both HER3 and AKT by 59.5% and 51.7%, respectively, compared to tumors from control IgG1-treated mice (FIG. 22, top and middle panels). No modulation of total HER3 was observed by 2C2 (FIG. 22, bottom panel).

4.5. Subcutaneous Human Detroit562 Head and Neck Xenograft Model Studies 4.5.1. Method.

Human Detroit562 Head and Neck cells (ATCC No. CCL-138) were maintained at 37° C. in a 5% $CO_2$ incubator in RPMI 1640 medium containing 4.5 g/L glucose, L-glutamine, sodium pyruvate and 10% fetal bovine serum. Xenografts were established by subcutaneously injecting $5 \times 10^6$ cells per mouse into the right flanks of 4- to 6-week-old athymic nu/nu mice. Tumors were allowed to grow up to 200 $mm^3$ before randomization for efficacy studies. 2C2, 2C2-YTE, cetuximab, control IgG1 or the combination of 2C2 with cetuximab monoclonal antibodies were administered intraperitoneally. For dose dependency studies the 2C2 was administered at, 1, 3, 10, and 30 mg per kilogram body weight (mg/kg). For the combination studies 2C2 was administered at 3 mg/kg, cetuximab at 30 mg/kg and the control antibody at 10 mg/kg. Caliper measurements were used to calculate tumor volumes using the formula:

tumor volume=π÷6(length×width×width)

for tumors grown in mice. Antitumor effects are expressed as percent delta tumor growth inhibition (TGI), which was calculated as follows:

percent delta TGI=1−(dT÷dC)×100, where dT=change in mean tumor volume in treatment group compared to the value at staging, and dC=change in mean tumor volume in control group compared to the value at staging.

At the conclusion of the efficacy studies with 2C2, mice were treated with 2C2 a final time as indicated to determine pharmacokinetic values. Cardiac puncture was performed to collect blood into SST microtainer tubes. Tubes with blood were vortexed gently for 10 seconds and kept at room temperature for 20 minutes to allow the serum to clot. Samples were centrifuged at 1000×g for 10 minutes, and the serum samples were carefully transferred into new tubes and stored at −80° C.

An indirect Enzyme-Linked Immunosorbent Assay (ELISA) format was used for the quantitative determination of 2C2 in mouse serum. Standards, quality controls, and mouse serum samples were incubated with goat anti-human IgG antibodies which were immobilized on a 96-well microtiter plate. After incubation, unbound materials were removed by a wash step and 2C2 was detected using a goat anti-human IgG with horseradish-peroxidase conjugate. An acidic stopping solution was added and the degree of enzymatic turnover of substrate was determined by measuring absorbance at 450 nm. The absorbance measured was directly proportional to the concentration of 2C2 present in the mouse serum. A 2C2 standard curve for the assay was used to interpolate the concentration of the serum samples.

4.5.2. Results

Figure 23A:
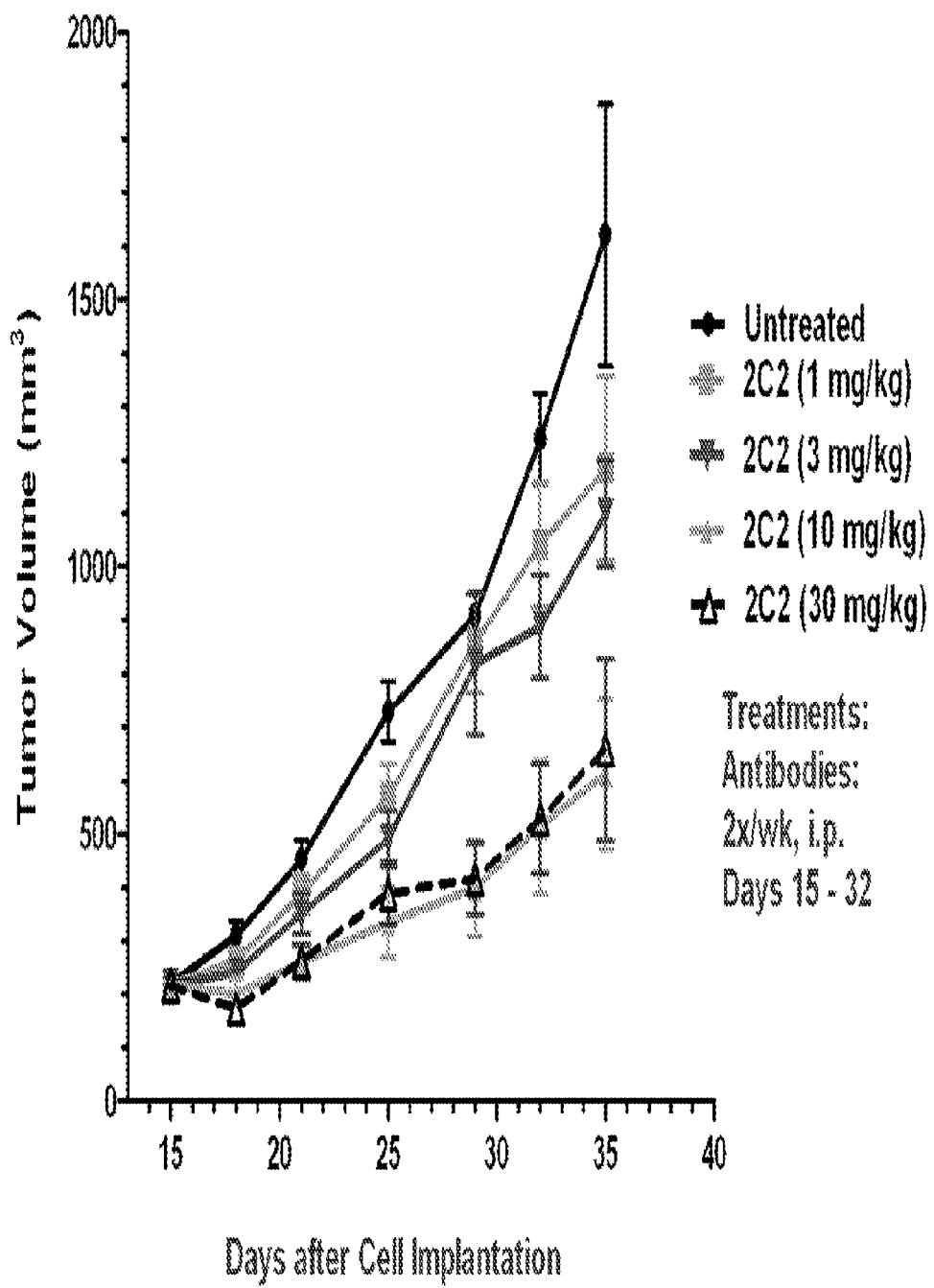

2C2 showed anti-tumor efficacy in the human Detroit562 Head and Neck xenograft model grown subcutaneously in female nude mice. 10 mg/kg of 2C2 administered twice per week was maximally efficacious at 72% dTGI (FIG. 23A). The Detroit562 model contains a PIK3CA mutation.

Figure 23B:
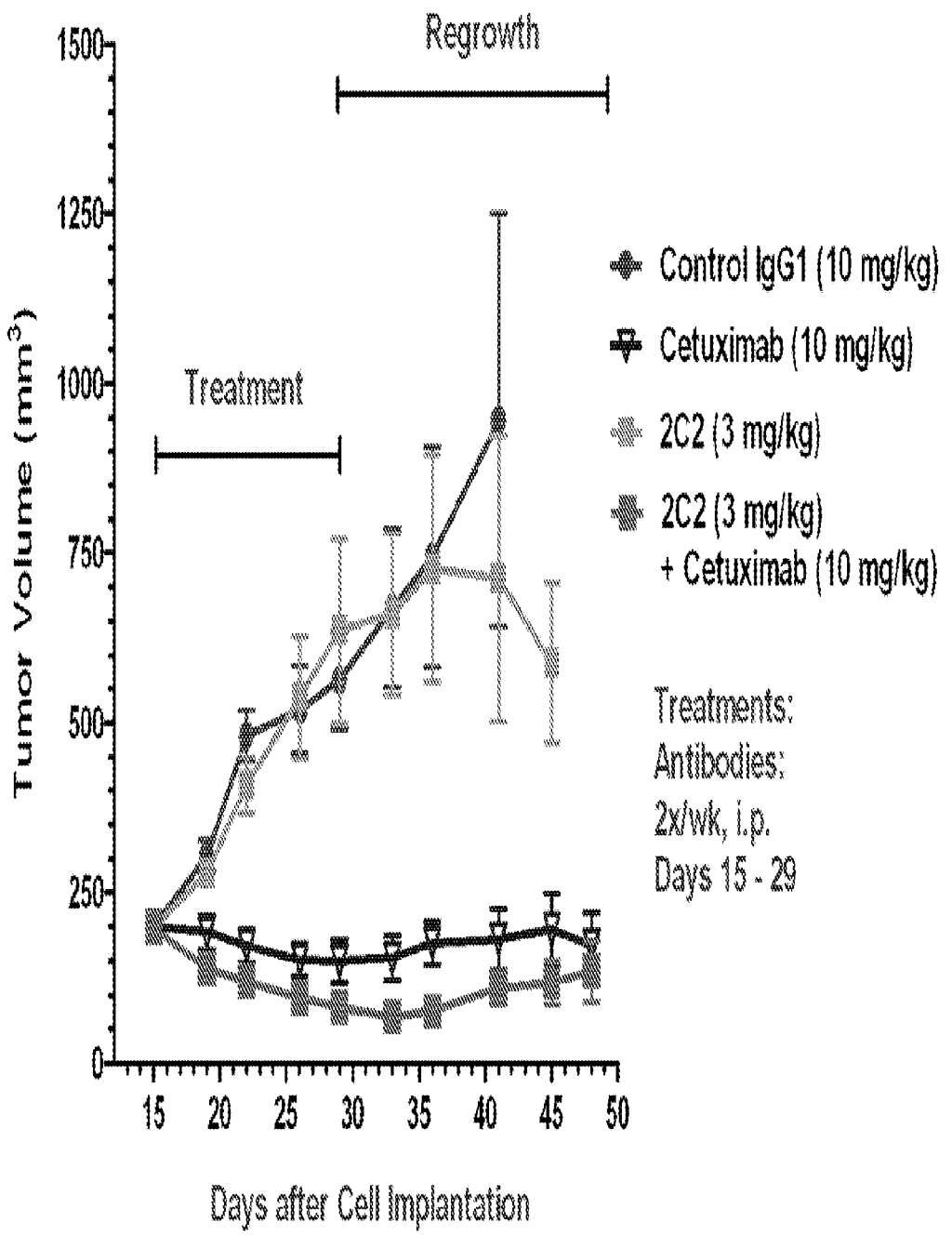

The Detroit562 tumor model was sensitive to the anti-EGFR monoclonal antibody cetuximab which caused tumor growth inhibition at 10 mg/kg administered twice per week. The combination of 3 mg/kg of 2C2 with 10 mg/kg of cetuximab added to the anti-tumor efficacy of cetuximab and resulted in 9 out of 10 partial regressions while cetuximab alone produced 5/10 partial regressions (FIG. 23B).

4.6. Subcutaneous Human CAL27 Head and Neck Xenograft Model Studies 4.6.1. Method.

Human CAL27 Head and Neck cells (ATCC No. CRL-2095) were maintained at 37° C. in a 5% $CO_2$ incubator in RPMI 1640 medium containing 4.5 g/L glucose, L-glutamine, sodium pyruvate and 10% fetal bovine serum. Xenografts were established by subcutaneously injecting $5 \times 10^6$ cells per mouse into the right flanks of 4- to 6-week-old athymic nu/nu mice. Tumors were allowed to grow up to 200 $mm^3$ before randomization for efficacy studies. 2C2-YTE, cetuximab or control IgG1 were administered intraperitoneally. For dose dependency studies the 2C2-YTE was administered at 3, 10, and 30 mg per kilogram body weight (mg/kg). Caliper measurements were used to calculate tumor volumes using the formula:

tumor volume=π÷6(length×width×width)

for tumors grown in mice. Antitumor effects are expressed as percent delta tumor growth inhibition (TGI), which was calculated as follows:

percent delta TGI=1−(dT÷dC)×100, where dT=change in mean tumor volume in treatment group compared to the value at staging, and dC=change in mean tumor volume in control group compared to the value at staging.

4.6.2. Results.

Dose-dependent activity of 2C2-YTE was confirmed in a third head and neck tumor model, CAL27, using 2C2-YTE. 2C2-YTE at 3, 10 or 30 mg/kg administered twice per week showed TGI with 26.4%, 55.2%, or 68.8%, respectively, compared to control IgG1-treated animals (FIG. 24).

The CAL27 tumor model was sensitive to the anti-EGFR monoclonal antibody cetuximab which caused tumor growth inhibition at 30 mg/kg administered twice per week with TGI of 75.0% (FIG. 24).

4.7. Subcutaneous Human KRAS Mutated A549 NSCLC Xenograft Model Studies

4.7.1. Method

Human A549 NSCLC cells (ATCC No. CCL-185) which contain a mutation in codon 12 of the KRAS gene (were maintained at 37° C. in a 5% $CO_2$ incubator in HAM'S F12K medium containing 4.5 g/L glucose, L-glutamine, sodium pyruvate and 10% fetal bovine serum. Xenografts were established by subcutaneously injecting $5 \times 10^6$ cells per mouse (suspended in 50% matrigel) into the right flanks of 4- to 6-week-old athymic nu/nu mice. Tumors were allowed to grow up to 200 mm³ before randomization for efficacy studies. 2C2, 2C2-YTE, cetuximab, control IgG1 or the combination of 2C2 with cetuximab monoclonal antibodies were administered intraperitoneally. For dose dependency studies the 2C2 was adminstered at, 3, 10 and 30 mg per kilogram body weight (mg/kg) and 2C2-YTE at 10 mg/kg. For the combination studies 2C2 and cetuximab were each administered at 10 mg/kg. Caliper measurements were used to calculate tumor volumes using the formula:

$$\text{tumor volume} = \pi \div 6 (\text{length} \times \text{width} \times \text{width})$$

for tumors grown in mice. Antitumor effects are expressed as percent delta tumor growth inhibition (TGI), which was calculated as follows:

$$\text{percent delta TGI} = 1 - (dT \div dC) \times 100,$$

where dT=change in mean tumor volume in treatment group compared to the value at staging, and dC=change in mean tumor volume in control group compared to the value at staging.

4.7.2. Results.

2C2 demonstrated dose-dependent anti-tumor efficacy in the human A549 NSCLC xenograft model grown subcutaneously in female nude mice. Maximal efficacy of 91% dTGI was achieved with 30 mg/kg of 2C2 administered twice per week until day 33 (FIG. 25A). 2C2 and 2C2-YTE given at 10 mg/kg displayed similar anti-tumor efficacy in this A549 tumor model. Once the treatment was stopped the tumors started to grow at the same rate as tumors in control-treated mice. The A549 xenograft model contains a KRAS mutation and a LKB-1 deletion.

Figure 25B:
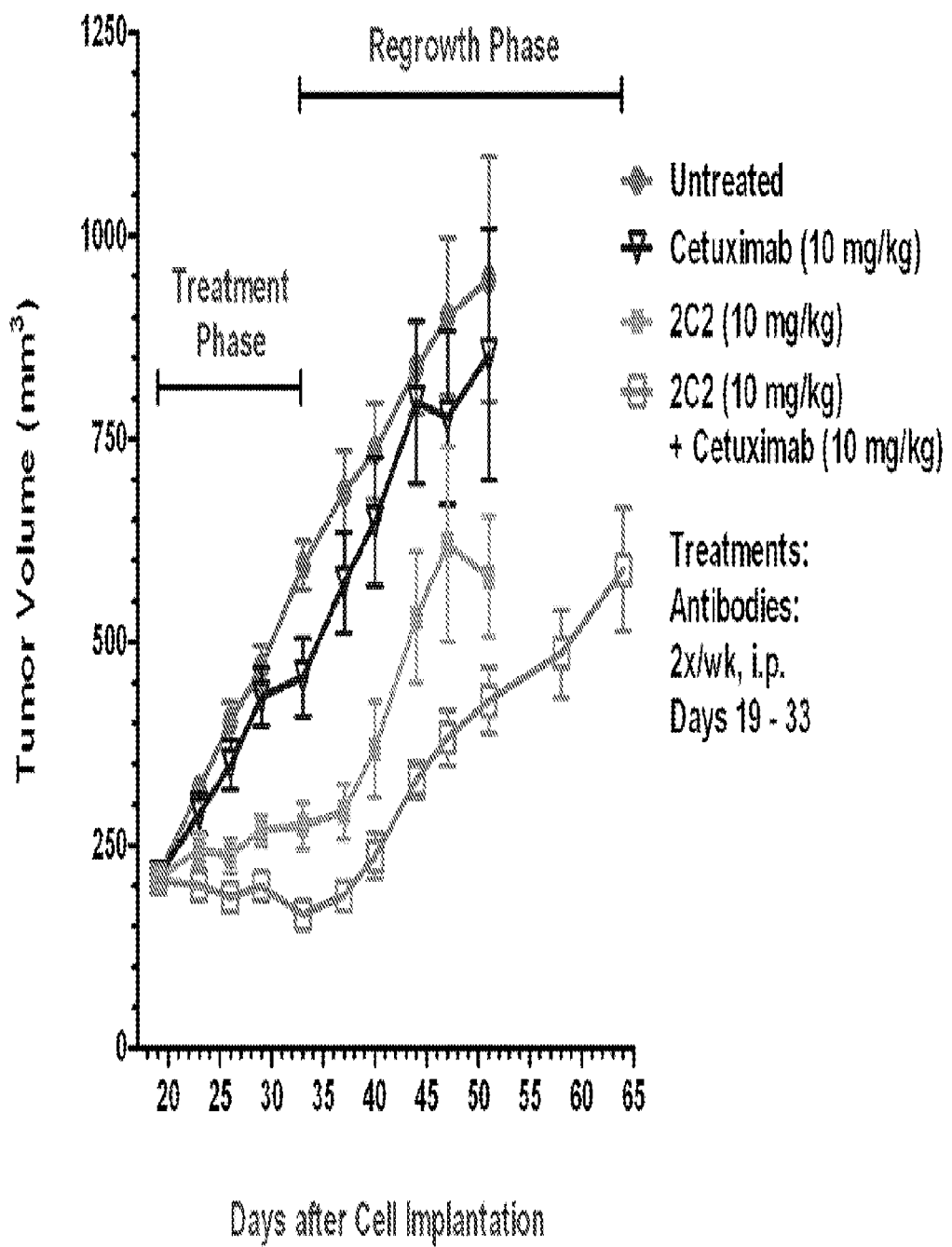

Cetuximab at 10 mg/kg alone was not efficacious in this A549 tumor model. However, the addition of cetuximab at 10 mg/kg to 2C2 also at 10 mg/kg resulted in additive anti-tumor efficacy during the treatment phase compared to 2C2 alone. In addition, the combination treatment group showed a slower regrowth rate of the tumors after cessation of treatment (FIG. 25B).

4.8. Subcutaneous Human HARA-B Squamous NSCLC Xenograft Model Studies

4.8.1. Method

Human squamous HARA-B NSCLC cells which express the wild-type RAS gene, HRG and pHER3 were maintained at 37° C. in a 5% $CO_2$ incubator in RPMI 1640 medium containing 4.5 g/L D. glucose, 2.383 g/L HEPES Buffer, L. Glutamine, 1.5 g/L Sodium Bicarbinate, 110 mg/L sodium pyruvate and 10% fetal bovine serum. Xenografts were established by subcutaneously injecting $5 \times 10^6$ cells per mouse (suspended in 50% matrigel) into the right flanks of 4- to 6-week-old athymic nu/nu mice. Tumors were allowed to grow up to 227 mm³ before randomization for efficacy studies. 2C2-YTE were administered intraperitoneally at 3, 10 and 30 mg per kilogram body weight (mg/kg), the control was at 30 mg/kg. Caliper measurements were used to calculate tumor volumes using the formula:

$$\text{tumor volume} = \pi \div 6 (\text{length} \times \text{width} \times \text{width})$$

for tumors grown in mice. Antitumor effects are expressed as percent delta tumor growth inhibition (TGI), which was calculated as follows:

$$\text{percent delta TGI} = 1 - (dT \div dC) \times 100,$$

where dT=change in mean tumor volume in treatment group compared to the value at staging, and dC=change in mean tumor volume in control group compared to the value at staging.

4.8.2. Results.

2C2-YTE demonstrated dose-dependent anti-tumor efficacy in the human squamous HARA-B NSCLC xenograft model grown subcutaneously in female nude mice. Maximal efficacy of 64.6% dTGI was achieved with 30 mg/kg of 2C2-YTE administered twice per week until day 29 (FIG. 26). 2C2-YTE given at 10 mg/kg displayed similar anti-tumor efficacy as 30 mg/kg; however, 2C2-YTE at 3 mg/kg was not efficacious in this HARA-B tumor model. The HARA-B xenograft model contains a wild-type RAS allele.

4.9. Subcutaneous Human HT-29 CRC Xenograft Model Studies

4.9.1. Method

Human HT-29 colorectal carcinoma cells (ATCC No. HTB-38) were maintained at 37° C. in a 5% $CO_2$ incubator in RPMI 1640 medium containing 4.5 g/L glucose, L-glutamine, sodium pyruvate and 10% fetal bovine serum. Xenografts were established by subcutaneously injecting $5 \times 10^6$ cells per mouse into the right flanks of 4- to 6-week-old athymic nu/nu mice. Tumors were allowed to grow up to 200 mm³ before randomization for efficacy studies. 2C2, 2C2-YTE and control IgG1 monoclonal antibodies were administered intraperitoneally. 2C2 was administered at 2, 10 and 30 mg per kilogram body weight (mg/kg), while 2C2-YTE was at 30 mg/kg. Caliper measurements were used to calculate tumor volumes using the formula:

$$\text{tumor volume} = \pi \div 6 (\text{length} \times \text{width} \times \text{width})$$

for tumors grown in mice. Antitumor effects are expressed as percent delta tumor growth inhibition (TGI), which was calculated as follows:

$$\text{percent delta TGI} = 1 - (dT \div dC) \times 100,$$

where dT=change in mean tumor volume in treatment group compared to the value at staging, and dC=change in mean tumor volume in control group compared to the value at staging.

4.9.2. Results.

2C2 showed dose-dependent anti-tumor efficacy using the human HT-29 colorectal xenograft model subcutaneously injected into female nude mice. 30 mg/kg of 2C2 administered twice per week was maximally efficacious at 56% dTGI during the treatment phase (FIG. 27). 2C2-YTE displayed the same efficacy as 2C2 both given at 30 mg/kg. Once the treatment was stopped the tumors grew at the same rate as the control tumors. The HT-29 xenograft model contains a BRAF mutation. Cetuximab at 10 mg/kg alone had no measurable anti-tumor activity in this model. The activity of 2C2 30 mg/kg in combination with cetuximab at 10 mg/kg was indistinguishable from the activity of 2C2 30 mg/kg alone at the end of treatment phase (data not shown). This indicates that this EGFR-expressing CRC tumor model, which responds well to 2C2, was not further inhibited by the addition of 2C2-YTE to cetuximab.

4.10. Subcutaneous Human HCT-116 CRC Xenograft Model Studies

4.10.1. Method

Human HCT-116 colorectal carcinoma cells were maintained at 37° C. in a 5% $CO_2$ incubator in RPMI 1640 medium containing 4.5 g/L glucose, L-glutamine, sodium pyruvate and 10% fetal bovine serum. Xenografts were established by subcutaneously injecting $5 \times 10^6$ cells per mouse into the right flanks of 4- to 6-week-old athymic nu/nu mice. Tumors were allowed to grow up to 200 $mm^3$ before randomization for efficacy studies. 2C2, 2C2-YTE, cetuximab and control IgG1 monoclonal antibodies were administered intraperitoneally. 2C2 was administered at 3, 10 and 30 mg per kilogram body weight (mg/kg) while 2C2-YTE was at 30 mg/kg. Caliper measurements were used to calculate tumor volumes using the formula:

$$\text{tumor volume} = \pi \div 6 (\text{length} \times \text{width} \times \text{width})$$

for tumors grown in mice. Antitumor effects are expressed as percent delta tumor growth inhibition (TGI), which was calculated as follows:

$$\text{percent delta TGI} = 1 - (dT \div dC) \times 100,$$

where dT=change in mean tumor volume in treatment group compared to the value at staging, and dC=change in mean tumor volume in control group compared to the value at staging.

4.10.2. Results.

2C2 at several different concentrations and 2C2-YTE at 10 mg/kg administered twice per week displayed modest anti-tumor efficacy in the human HCT-116 colorectal xenograft model injected subcutaneously into female nude mice (FIG. 28). Maximal efficacy was noted at 43% dTGI for 2C2 at 10 mg/kg. The anti-EGFR monoclonal antibody cetuximab had no efficacy at 10 mg/kg. The HCT-116 xenograft model contains a KRAS mutation.

4.11. Subcutaneous Human LOVO CRC Xenograft Model Studies

4.11.1. Method.

Human LOVO colorectal carcinoma cells (ATCC No. CCL-229) were maintained at 37° C. in a 5% $CO_2$ incubator in HAM'S F12K medium containing 4.5 g/L glucose, L-glutamine, sodium pyruvate and 10% fetal bovine serum. Xenografts were established by subcutaneously injecting $5 \times 10^6$ cells per mouse into the right flanks of 4- to 6-week-old athymic nu/nu mice. Tumors were allowed to grow up to 200 $mm^3$ before randomization for efficacy studies. 2C2, 2C2-YTE, cetuximab and control IgG1 monoclonal antibodies were administered intraperitoneally. 2C2 was administered at 10 or 30 mg per kilogram body weight (mg/kg), 2C2-YTE and cetuximab were administered at 10 mg/kg and the control at 30 mg/kg. Caliper measurements were used to calculate tumor volumes using the formula:

$$\text{tumor volume} = \pi \div 6 (\text{length} \times \text{width} \times \text{width})$$

for tumors grown in mice. Antitumor effects are expressed as percent delta tumor growth inhibition (TGI), which was calculated as follows:

$$\text{percent delta TGI} = 1 - (dT \div dC) \times 100,$$

where dT=change in mean tumor volume in treatment group compared to the value at staging, and dC=change in mean tumor volume in control group compared to the value at staging.

4.11.2. Results

2C2 at 30 mg/kg administered twice per week achieved anti-tumor efficacy of 48% dTGI in the human LOVO colorectal xenograft model grown subcutaneously in female nude mice (FIG. 29). 2C2, 2C2-YTE and cetuximab all at 10 mg/kg had comparable efficacy. The LOVO xenograft model contains a KRAS mutation.

4.12. Subcutaneous Human DU145 Prostate Carcinoma Xenograft Model Studies

4.12.1. Method.

Human DU145 prostate carcinoma cells (ATCC No. HTB-81) were maintained at 37° C. in a 5% $CO_2$ incubator in MEM medium containing Earle's salts, 1-glutamine and 10% fetal bovine serum. Xenografts were established by subcutaneously injecting $5 \times 10^6$ cells per mouse (suspended in 50% matrigel) into the right flanks of 4- to 6-week-old athymic nu/nu mice. Tumors were allowed to grow up to 200 $mm^3$ before randomization for efficacy studies. 2C2, MM and AMG monoclonal antibodies were administered intraperitoneally at 30 mg per kilogram body weight. Caliper measurements were used to calculate tumor volumes using the formula:

$$\text{tumor volume} = \pi \div 6 (\text{length} \times \text{width} \times \text{width})$$

for tumors grown in mice. Antitumor effects are expressed as percent delta tumor growth inhibition (TGI), which was calculated as follows:

$$\text{percent delta TGI} = 1 - (dT \div dC) \times 100,$$

where dT=change in mean tumor volume in treatment group compared to the value at staging, and dC=change in mean tumor volume in control group compared to the value at staging.

4.12.2. Results

Using a human DU145 prostate cancer xenograft model grown subcutaneously in male nude mice 2C2 at 30 mg/kg administered twice per week demonstrated anti-tumor efficacy of 77% dTGI in this tumor model (FIG. 30). The DU145 xenograft model contains a LKB-1 deletion. The anti-HER3 monoclonal antibodies AMG and MM used at 30 mg/kg demonstrated anti-tumor efficacy but they were less effective than 2C2 at the same dose of 30 mg/kg.

4.13. Orthotopic Human BT-474 Breast Cancer Xenograft Model Studies

4.13.1. Method.

Human BT-474 breast cancer cells were maintained at 37° C. in a 5% $CO_2$ incubator in RPMI 1640 medium containing 4.5 g/L glucose, L-glutamine, sodium pyruvate and 10% fetal bovine serum. Orthotopic xenografts were established by injecting $1 \times 10^7$ cells per mouse (suspended in 50% matrigel) into the mammary fat pad on the right flank of 4 to 6-week-old athymic nu/nu mice. Estrogen pellets (0.36 mg) were placed under the skin of the left flank 1-2 days before cell injection. Tumors were allowed to grow up to 200 $mm^3$ before randomization for efficacy studies. 2C2, 2C2-YTE, and or anti-HER2 antibodies known in the art: MM, AMG and trastuzumab (trade name Herceptin®; e.g., U.S. Pat. No. 5,821,337) were administered intraperitoneally at 30 mg per kilogram body weight. Lapatinib was administered by oral gavaging at 100 mg per kilogram body weight. Caliper measurements were used to calculate tumor volumes using the formula:

$$\text{tumor volume} = \pi \div 6 (\text{length} \times \text{width} \times \text{width})$$

for tumors grown in mice. Antitumor effects are expressed as percent delta tumor growth inhibition (TGI), which was calculated as follows:

$$\text{percent delta TGI} = 1 - (dT \div dC) \times 100,$$

where dT=change in mean tumor volume in treatment group compared to the value at staging, and dC=change in mean tumor volume in control group compared to the value at staging.

4.13.2. Results

Figure 31A:
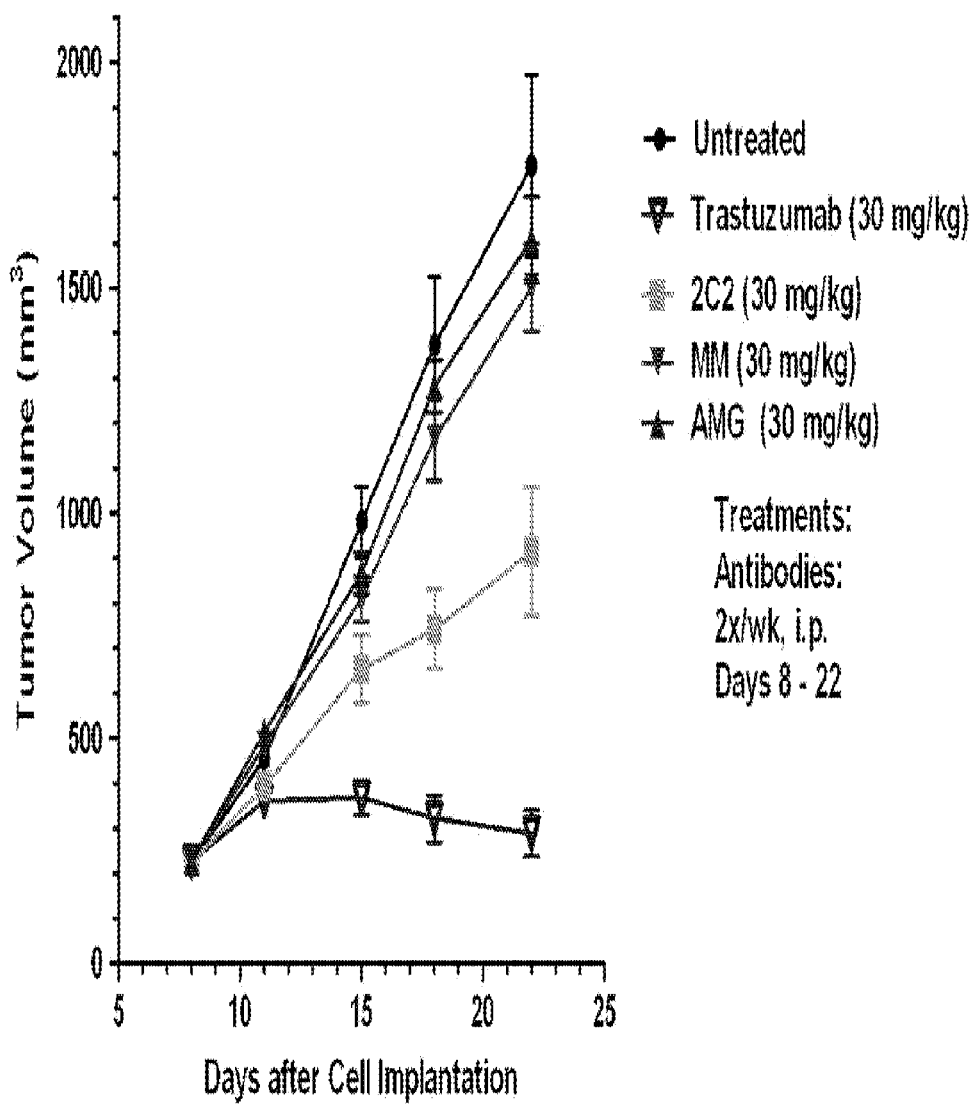

Using a HER2-driven human breast cancer model, BT-474, injected orthotopically into the mammary fat pad of female nude mice administration of 2C2 at 30 mg/kg injected twice per week led to a 55% dTGI in BT-474 xenografts (FIG. 31A). BT-474 express HER2 at very high levels of 3+ characterized by HercepTest. AMG and MM both administered at 30 mg/kg did not show anti-tumor efficacy in this HER2-driven model.

Figure 31B:
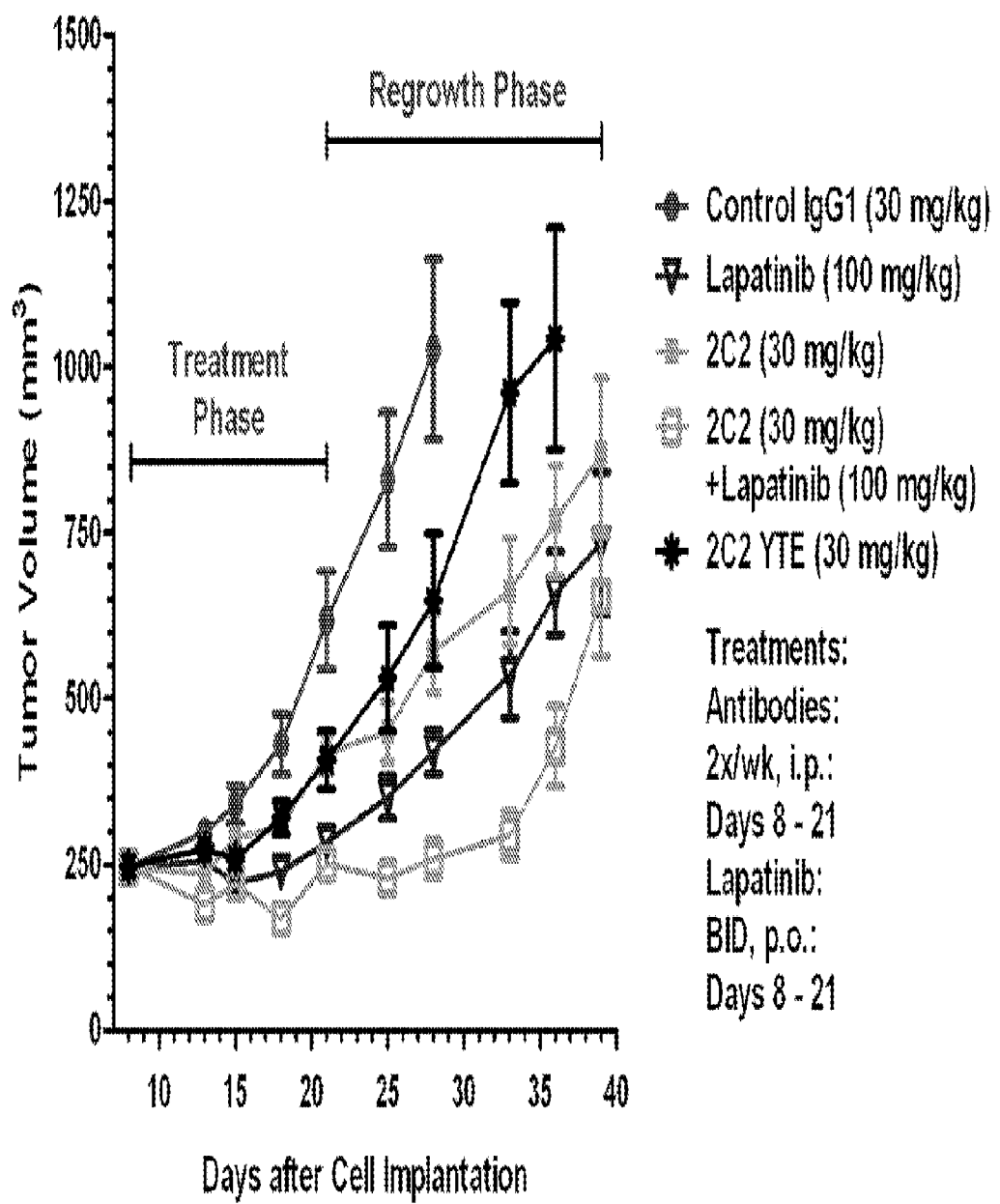
Figure 31C:
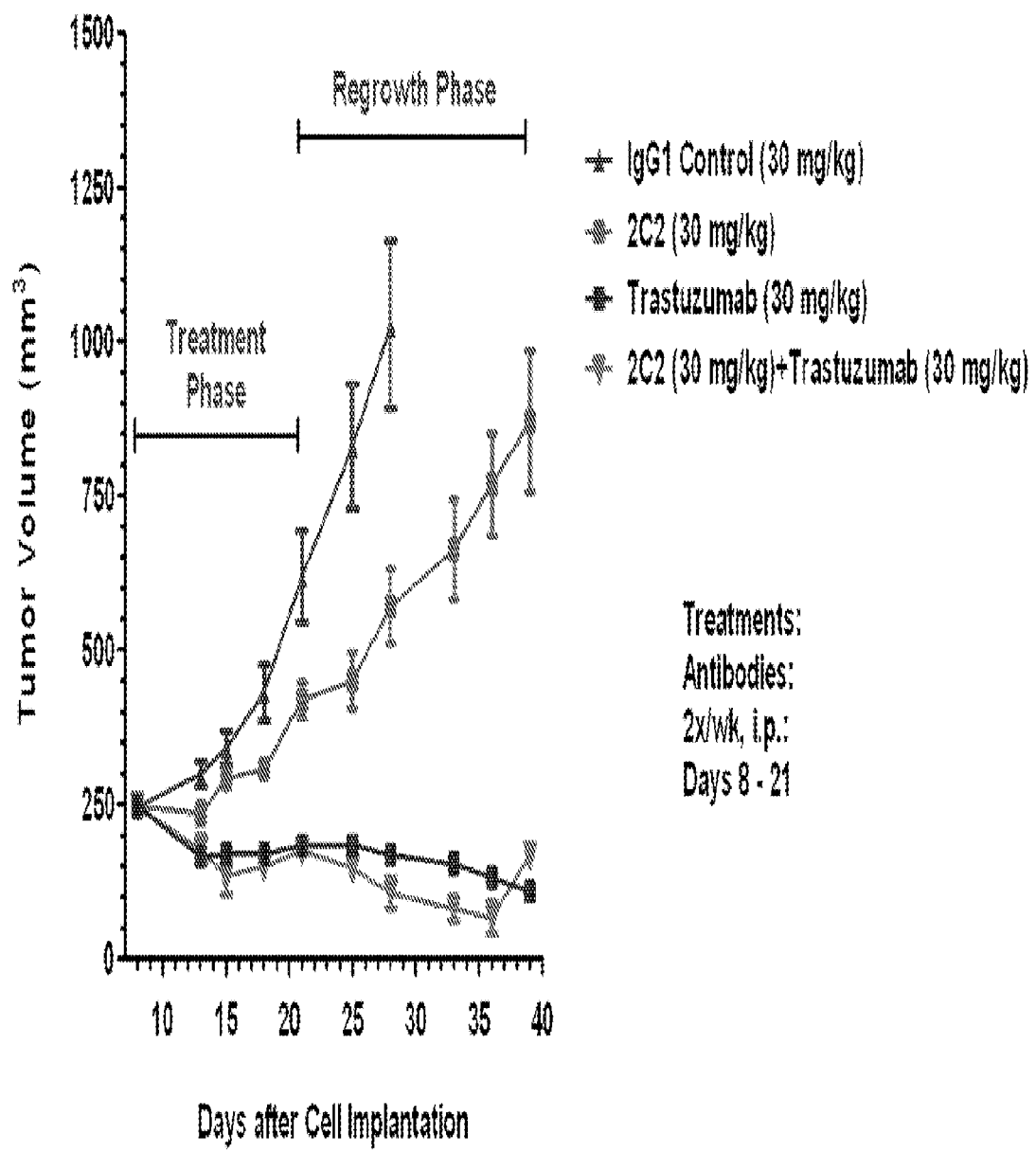

Lapatinib is a small molecule drug inhibiting EGFR and HER2. Since BT-474 tumors are driven by HER2, lapatinib was tested in this model and found to cause tumor stasis in the BT-474 tumor model. The combination treatment of 30 mg/kg of 2C2 with 100 mg/kg of lapatinib resulted in improved anti-tumor efficacy of lapatinib alone which was most clearly visible in a delay in regrowth of the tumors in the absence of additional treatments (FIG. 31B). The anti-tumor activity of 2C2-YTE was similar to that of 2C2. The anti-HER2 antibody trastuzumab was also was tested in this model and shown to be very active in this HER2-driven xenograph model with a dTGI of 111.6%. There was little further enhancement in the activity of trastuzumab at 30 mg/kg by the addition of 30 mg/kg of 2C2 which showed a dTGI of 118.5% (FIG. 31C).

The ability of clone 16 (the parental clone from which 2C2 was derived) to modulate the pharmacodynamic markers pHER3 and pAKT was tested in BT-474 xenograft tumor extracts. Briefly, female athymic nude mice were implanted orthotopically with high HER2-expressing BT-474 breast cancer cells. Animals were administered Clone 16 at 30 mg/kg twice within 48 hours. Extracts were prepared 24 hours later for analysis of pHER3, pAKT, and total HER3 (tHER3). The results are normalized for PBS-treated control animals. There were three animals per treatment group. As shown in FIG. 32, Clone 16 inhibited phosphorylation of both HER3 and AKT by 50.0% and 46.1%, respectively, compared to tumors from PBS-treated mice and no modulation of total HER3 was observed by Clone 16.

4.14. Orthotopic Human MCF-7 Breast Cancer Xenograft Model Studies 4.14.1. Method.

Human MCF-7 breast cancer cells were maintained at 37° C. in a 5% $CO_2$ incubator in Optimem medium containing glutamax, 2.4/L sodium bicarbonate, Hepes and 5% fetal bovine serum. Orthotopic xenografts were established by injecting $5 \times 10^6$ cells per mouse (suspended in 50% matrigel) into the mammary fat pad on the right flank of 4 to 6-week-old athymic nu/nu mice. Estrogen pellets (0.36 mg) were placed under the skin of the left flank 1-2 days before cell injection. Tumors were allowed to grow up to 200 mm³ before randomization for efficacy studies. 2C2, 2C2-YTE and trastuzumab monoclonal antibodies were administered intraperitoneally. 2C2 was administered at 10 or 30 mg per kilogram body weight (mg/kg) 2c2-YTE and trastuzumab at 10 mg/kg. Paclitaxel was administered intravenously at 10 mg per kilogram body weight. Caliper measurements were used to calculate tumor volumes using the formula:

tumor volume=π÷6(length×width×width)

for tumors grown in mice. Antitumor effects are expressed as percent delta tumor growth inhibition (TGI), which was calculated as follows:

percent delta TGI=1−(dT÷dC)×100, where dT=change in mean tumor volume in treatment group compared to the value at staging, and dC=change in mean tumor volume in control group compared to the value at staging.

4.14.2. Results

Figure 33A:
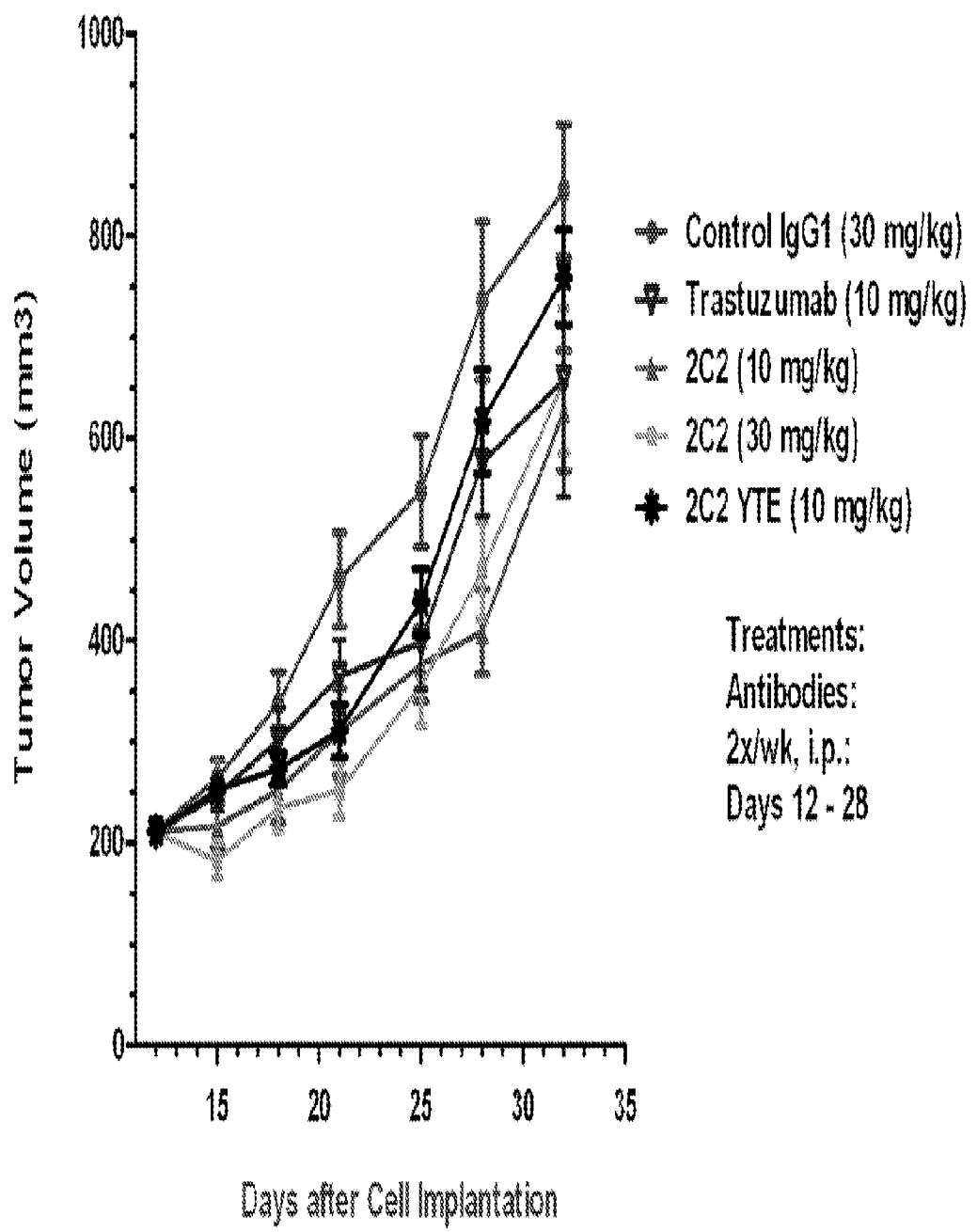

2C2 at either 10 mg/kg or 30 mg/kg showed modest anti-tumor efficacy of 34% dTGI in a human MCF-7 breast cancer xenograft model injected orthotopically into the mammary fat pad of female nude mice. 2C2-YTE at 10 mg/kg had similar efficacy as 2C2 at the same concentration (FIG. 33A). Trastuzumab did not demonstrate efficacy in this HER2 expressing model which indicated that HER2 is not sufficient to drive tumor growth. MCF-7 tumors expressed low levels of HER2 (1+) measured by HercepTest.

Figure 33B:
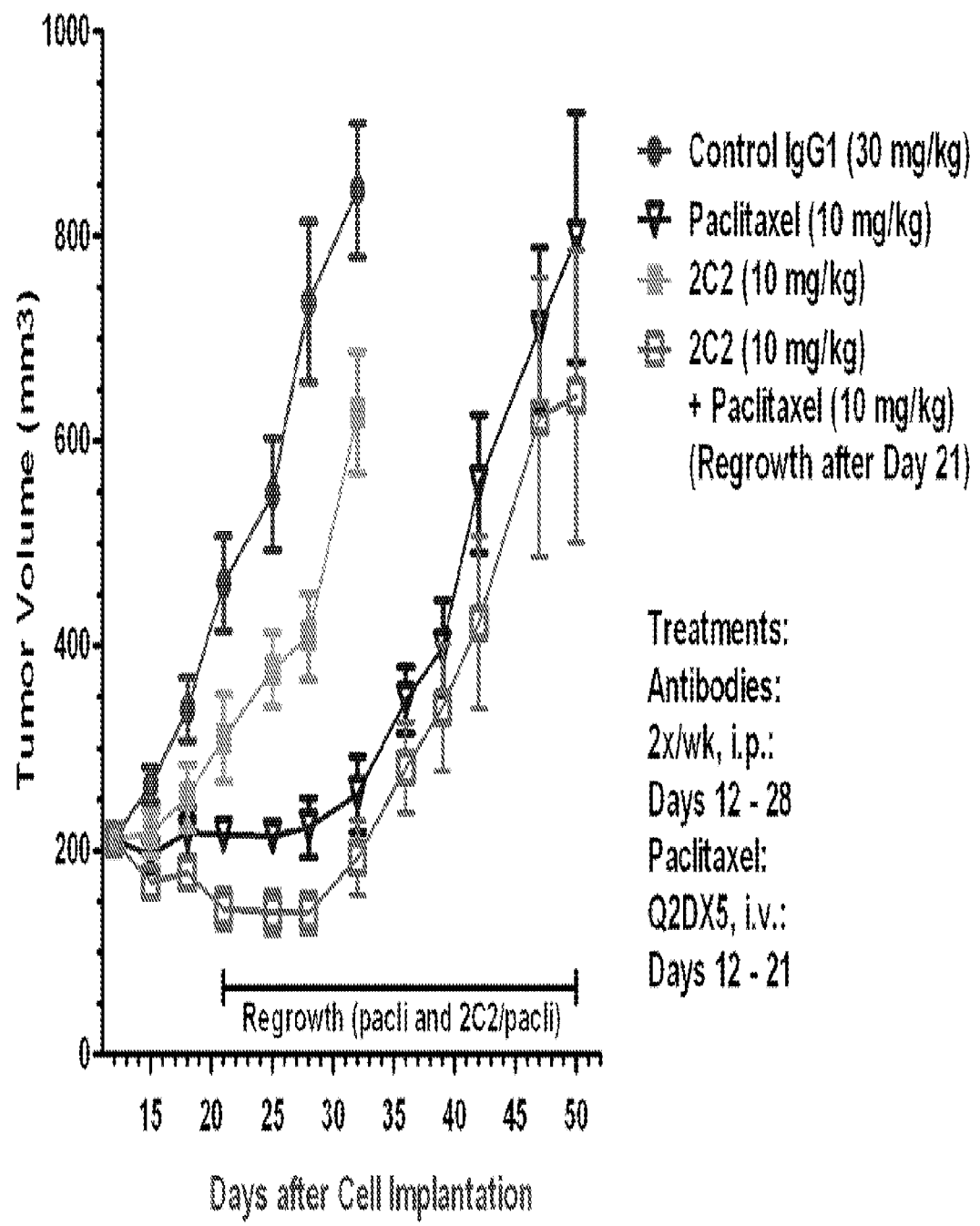

Paclitaxel showed clear anti-tumor efficacy in the MCF-7 orthotopic breast cancer model when dosed at 10 mg/kg every second day for ten days. The addition of 10 mg/kg of 2C2 to the paclitaxel treatment increased the anti-tumor efficacy of paclitaxel alone at the end of the treatment phase (FIG. 33B). The tumors regrew at the same rate as the paclitaxel treated tumors after the treatment was stopped.

4.15. Orthotopic Human MDA-MB-361 Breast Cancer Xenograft Model Studies 4.15.1. Method.

Human MDA-MB-361 breast cancer cells were maintained at 37° C. in a 5% $CO_2$ incubator in RPMI 1640 medium containing 4.5 g/L glucose, L-glutamine, sodium pyruvate and 10% fetal bovine serum. Orthotopic xenografts were established by injecting $5 \times 10^6$ cells per mouse (suspended in 50% matrigel) into the mammary fat pad on the right flank of 4 to 6-week-old athymic nu/nu mice. Estrogen pellets (0.36 mg) were placed under the skin of the left flank 1-2 days before cell injection. Tumors were allowed to grow up to 230 mm³ before randomization for efficacy studies. 2C2-YTE, and/or anti-HER2 antibodies known in the art, in particular trastuzumab (trade name Herceptin®; e.g., U.S. Pat. No. 5,821,337) and RhuMAb 2C4 (e.g., Patent Publication WO2001/00245) designated herein as trastuzumab and 2C4, respectively. Trastuzumab, and 2C4 monoclonal antibodies were administered intraperitoneally at 30 mg per kilogram body weight (2C2-YTE) or at 10 mg per kilogram body weight (trastuzumab and 2C4). Lapatinib was administered by oral gavaging at 100 mg per kilogram body weight. Caliper measurements were used to calculate tumor volumes using the formula:

tumor volume=π÷6(length×width×width)

for tumors grown in mice. Antitumor effects are expressed as percent delta tumor growth inhibition (TGI), which was calculated as follows:

percent delta TGI=1−(dT÷dC)×100, where dT=change in mean tumor volume in treatment group compared to the value at staging, and dC=change in mean tumor volume in control group compared to the value at staging.

4.15.2. Results

Figure 34A:
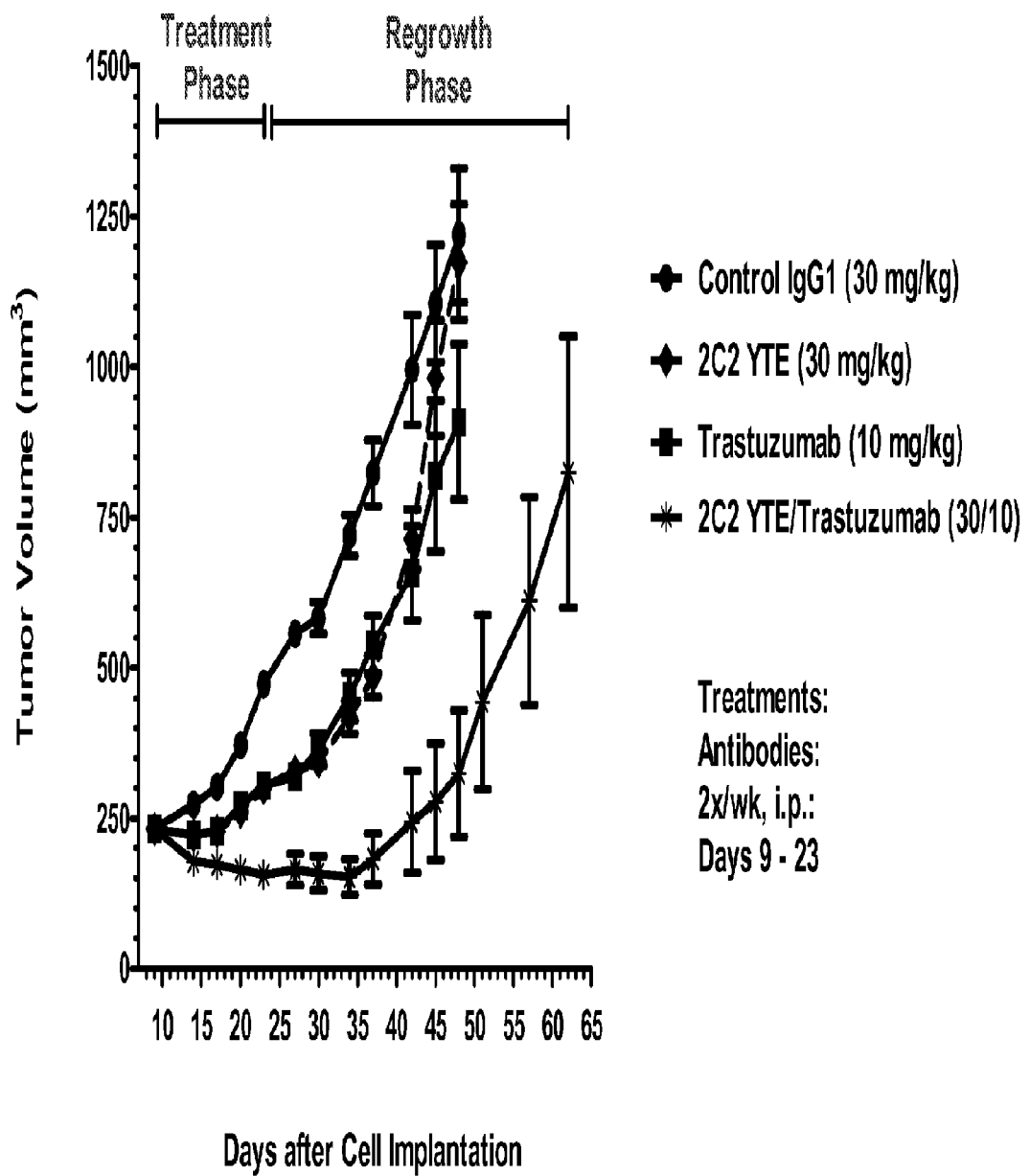
Figure 34B:
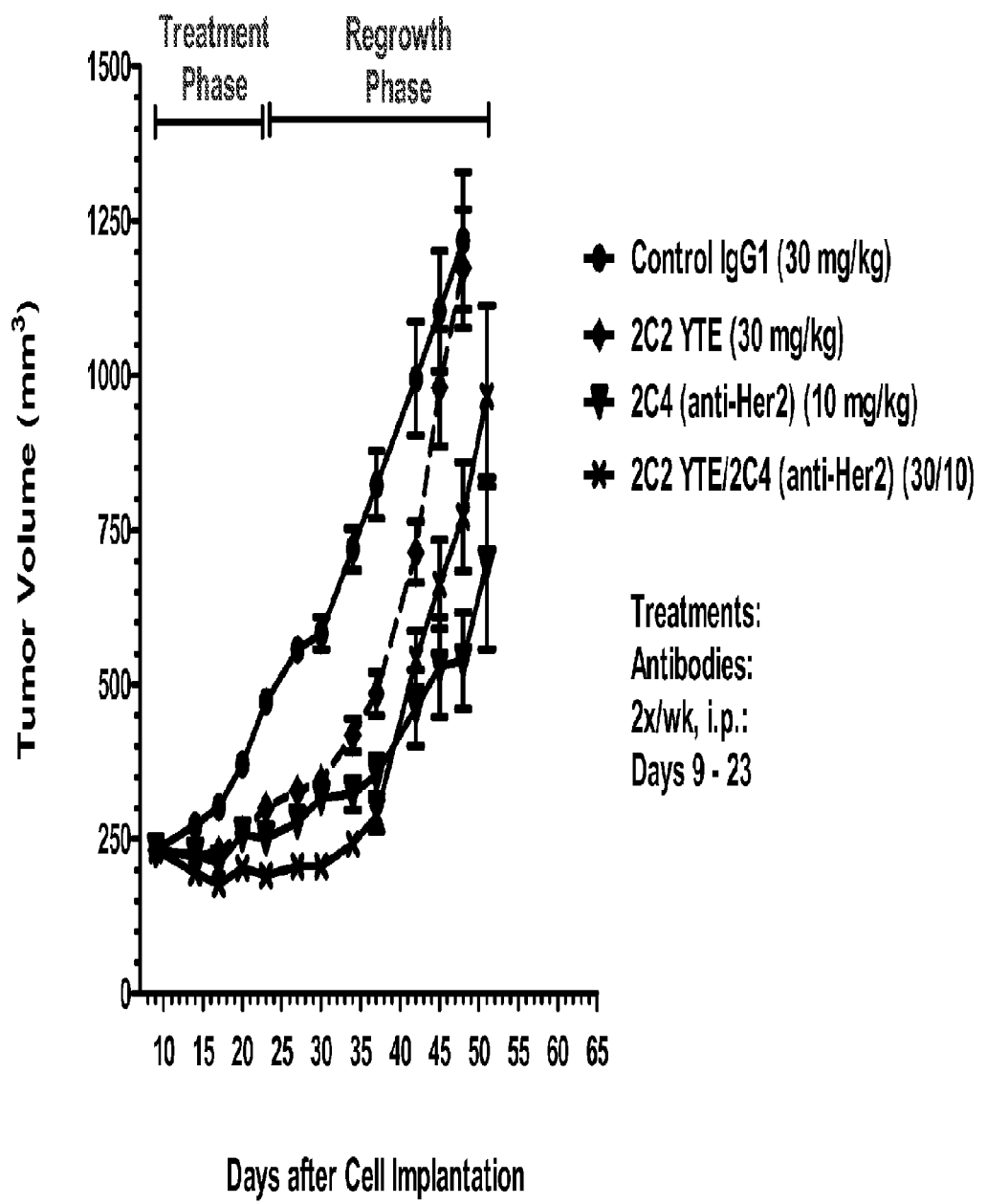
Figure 34C:
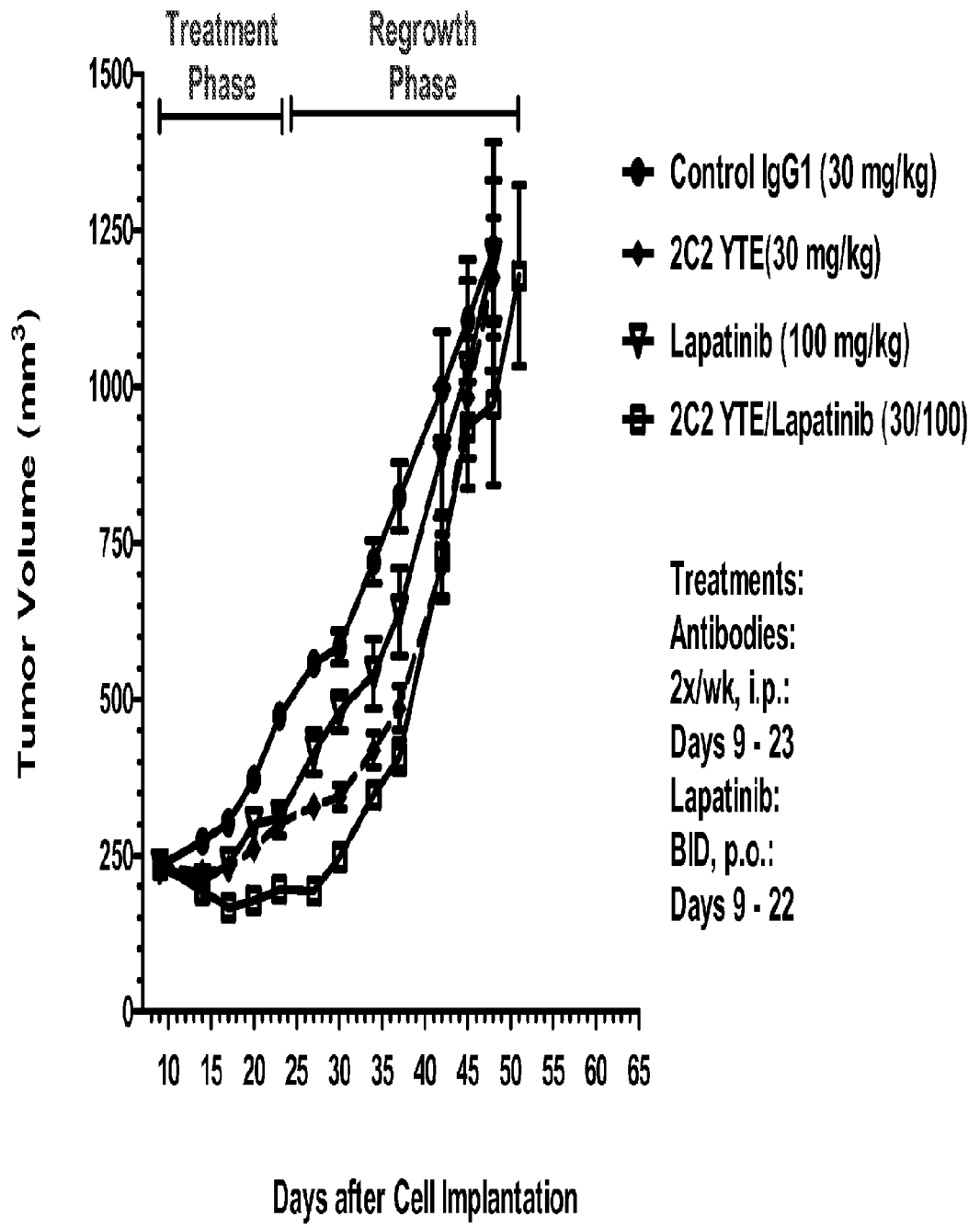

Using a HER2-driven human breast cancer model, MDA-MB-361 (Hercept test +2), injected orthotopically into the mammary fat pad of female nude mice, administration of 2C2-YTE at 30 mg/kg injected twice per week for five doses led to a 70.1% dTGI in MDA-MB-361 xenografts (FIG. 34A-C). MDA-MB-361 cells express HER2 at medium levels of 2+ characterized by HercepTest and score positive by FISH analysis (fluorescent in situ hybridization analysis). Trastuzumab and rhuMAb 2C4 both administered at 10 mg/kg and lapatinib at 100 mg/kg administered twice daily also showed anti-tumor efficacy in the MDA-MB-361 tumor model.

Since MDA-MB-361 tumors are driven by HER2, 2C2-YTE was combined with drugs that target HER2 such as trastuzumab, rhuMAb 2C4 or lapatinib. The combination treatment of 30 mg/kg of 2C2-YTE with 10 mg/kg of trastuzumab resulted in additive anti-tumor efficacy compared to trastuzumab alone. An additive effect was also visible in a delay in regrowth of the tumors in the absence of additional treatments (FIG. 34A). The combination of 2C2-YTE with trastuzumab was better compared to combinations of 2C2-YTE with either rhuMAb 2C4 (FIG. 34B) or lapatinib (FIG. 34C) in this model.

4.16. Transgenic Mice Expressing Human FcRn Receptor to Study Exposure of Antibodies with the YTE Modification.

4.16.1. Method.

Transgenic female SCID mice expressing the human FcRn receptor were given a single dose of 60 mg/kg of Clone 16-GL, 2C2 or 2C2-YTE via the intravenous route. Serum was collected from these mice at several time points after dosing by cardiac puncture and the blood was collected into SST microtainer tubes. The tubes were vortexed gently for 10 seconds and kept at room temperature for 20 minutes to allow the serum to clot. Samples were centrifuged at 1000×g for 10 minutes, and the serum samples were carefully transferred into new tubes and stored at −80° C. An indirect Enzyme-Linked Immunosorbent Assay (ELISA) format was used for the quantitative determination of 2C2 in mouse serum. Standards, quality controls, and mouse serum samples were incubated with goat anti-human IgG antibodies which were immobilized on a 96-well microtiter plate. After incubation, unbound materials were removed by a wash step and 2C2 was detected using a goat anti-human IgG with horseradish-peroxidase conjugate. An acidic stopping solution was added and the degree of enzymatic turnover of substrate was determined by measuring absorbance at 450 nm. The absorbance measured was directly proportional to the concentration of 2C2 or 2C2-YTE present in the mouse serum. A 2C2 or 2C2-YTE standard curve for the assay was used to interpolate the concentration of the serum samples.

4.16.2. Results.

2C2-YTE, which contains the YTE mutation on the 2C2 backbone, showed higher exposure levels over time compared to 2C2 or Clone 16-GL (FIG. 35). Fourteen days after the single dose of antibody to these mice the serum exposure level of 2C2-YTE was above 100 µg/ml while both 2C2 and Clone 16-GL were below 1 µg/ml. This finding demonstrated that YTE could extend the half-life of 2C2-YTE compared to its parental antibody 2C2.

4.17. MEK Inhibitor Induces HER3 Expression and in Combination with Anti-HER3 Antibody Shows Additive Anti-Tumor Efficacy.

KRAS (V-Ki-ras2 Kirsten rat sarcoma viral oncogene) and BRAF (v-raf murine sarcoma viral oncogene B1) mutations lead to the constitutive activation of EGFR signaling through the oncogenic Ras/Raf/Mek/Erk pathway. Kras mutation is among the most-frequently occurring mutation events in many solid tumors, especially colorectal (CRC, 30-40%) and lung cancers (LC, 20-25%). Braf mutation also occurs at relatively high frequency in CRC (~15%). Due to their ability to constitutively activate the ERK pathway, mutant Kras and Braf have been shown to confer tumor resistance to RTK therapies, especially EGFR mAbs such as Cetuximab and Panitumumab. The effect of inhibiting mitogen-activated protein kinase (MEK) on the HER3 pathway in CRC and LC models was examined using the MEK inhibitor selumetinib (AstraZeneca, see for e.g., WO03/077914 and WO2007/076245) alone or in combination with 2C2 (or 2C2-YTE). A number of CRC and LC models were examined including those harboring a mut-Kras (e.g. A549, LOVO) or mut-Braf (e.g., HT-29, Colo205) or a wild type RAS (e.g., HARA-B, KNS-62).

4.17.1. Methods.

Cell culture studies: cells were plated at $10^5$ per well in 24-well plates and in medium containing 10% heat-inactivated FBS and allowed to reach a confluency of 80% or more prior to treatment. 2C2 (10 µg/mL) or control antibody, MEK inhibitor selumetinib (1 or 10 µM) or a combination of 2C2 (10 µg/mL) and selumetinib (10 µM) were prepared in complete medium. Treatments were applied following removal of plating medium. After an incubation of 24 hours in 5% $CO_2$ at 37° C., cells were washed once with ice-cold PBS and then lysed by adding 60 µL of 2× sodium dodecyl sulfate (SDS) sample buffer (Invitrogen). The samples were heated for 5 minutes and then chilled on ice for 2 minutes. The samples were analyzed by Western blotting essentially as described above (see Examples, section 2.4).

Xenograft studies: Human A549 NSCLC cells (ATCC No. CCL-185) which contain a mutation in codon 12 of the KRAS gene (were maintained at 37° C. in a 5% $CO_2$ incubator in HAM'S F12K medium containing 4.5 g/L glucose, L-glutamine, sodium pyruvate and 10% fetal bovine serum. Xenografts were established by subcutaneously injecting $5 \times 10^6$ cells per mouse (suspended in 50% matrigel) into the right flanks of 4- to 6-week-old athymic nu/nu mice. Human HT-29 colorectal carcinoma cells (ATCC No. HTB-38) were maintained at 37° C. in a 5% $CO_2$ incubator in RPMI 1640 medium containing 4.5 g/L glucose, L-glutamine, sodium pyruvate and 10% fetal bovine serum. Xenografts were established by subcutaneously injecting $5 \times 10^6$ cells per mouse into the right flanks of 4- to 6-week-old athymic nu/nu mice. Human LOVO colorectal carcinoma cells (ATCC No. CCL-229) were maintained at 37° C. in a 5% $CO_2$ incubator in HAM'S F12K medium containing 4.5 g/L glucose, L-glutamine, sodium pyruvate and 10% fetal bovine serum. Xenografts were established by subcutaneously injecting $5 \times 10^6$ cells per mouse into the right flanks of 4- to 6-week-old athymic nu/nu mice. For all three tumor models, tumors were allowed to grow up to 200 $mm^3$ before randomization for efficacy studies. 2C2-YTE or control IgG1 were administered intraperitoneally. selumetinib was administered orally. For the combination studies 2C2-YTE and selumetinib were administered at 30 mg/kg or 75 mg/kg, respectively. Caliper measurements were used to calculate tumor volumes using the formula:

$$\text{tumor volume} = \pi \div 6 (\text{length} \times \text{width} \times \text{width})$$

for tumors grown in mice. Antitumor effects are expressed as percent delta tumor growth inhibition (TGI), which was calculated as follows:

$$\text{percent delta TGI} = 1 - (dT \div dC) \times 100,$$

where dT=change in mean tumor volume in treatment group compared to the value at staging, and dC=change in mean tumor volume in control group compared to the value at staging.

Preparation of lysates from frozen tumors: Mice were humanely euthanized by $CO_2$ asphyxiation in accordance with our in vivo protocol and tumors were excised and transferred to Lysing Matrix A tubes. RIPA lysis buffer (500 µL) containing protease inhibitor cocktail and phosphatase inhibitor cocktail set I and II was added, the samples were then homogenized using a Fast Prep machine. Samples were chilled on ice for 30 minutes and underwent an additional homogenization cycle before clarification by centrifugation at 14,000 rpm for 10 minutes at 4° C. Clarified lysates were transferred to fresh 1.5 mL tubes and protein content was measured. Lysates were then stored at −80° C. until analysis. The samples were analyzed by Western blotting essentially as described above (see Examples, section 2.4).

4.17.2. Results.

As shown in FIG. 36, both total and pHER3 protein levels increased following treatment with the MEK inhibitor selumetinib in HT-29 colorectal cancer cells grown in culture which express mutant BRAF and in LOVO cells which express a mutant KRAS (FIG. 36, left and middle blots respectively). An increase of HER3 was also observed in Colo205 cells which express mut-BRAF and in DLD-1 and HCT cells, which express mutant KRAS (FIG. 36, right blot, and data not shown), following selumetinib treatment. The increases occurred at both the 1 µM and 10 µM doses of selumetinib. Activity of selumetinib was confirmed by reduction in pERK in all cell lines at both 1 µM and 10 µM doses. Inhibition of MEK results in an inhibition of ERK phosphorylation. The anti-HER3 antibody, 2C2, inhibited both total and pHER3 in HT-29 and LOVO cells. 2C2 also lowered HER3 in Colo205 and DLD-1 cells. In addition, co-treatment of 2C2 with selumetinib blocked the induction of total HER3 and pHER3 by selumetinib in HT-29, LOVO and DLD-1 cells (FIG. 36, and data not shown). No detectable HER3 or pHER3 could be observed in SW480 colorectal cancer cells, which express mutant KRAS, in either untreated or selumetinib-treated cells.

As shown in FIG. 37A, the combination treatment of 30 mg/kg of 2C2-YTE with 75 mg/kg of selumetinib resulted in additive anti-tumor efficacy in A549 NSCLC xenografts compared to selumetinib alone. An additive effect was also visible in a delay in regrowth of the tumors in the absence of additional treatments (top panel). Western blot analysis of tumor lysates from mice treated with the combination of 30 mg/kg of 2C2-YTE with 75 mg/kg of selumetinib over a 4 day period showed that phospho-HER3 and phospho-ERK were completely inhibited. Both markers serve as pharmacodynamic read-outs for the action of 2C2-YTE and selumetinib. Similar findings were made with the CRC xenograft models HT-29 (FIG. 37 B, upper and lower panel) and LoVo (FIG. 37 C, upper and lower panel). In addition, phospho-AKT was found to be reduced in HT-29 tumor lysates treated with the combination of 30 mg/kg of 2C2-YTE with 75 mg/kg of selumetinib compared to single treatments (FIG. 37B, lower panel). Treatment with selumetinib alone at 75 mg/kg lead to an increase in phospho-HER3 in the LoVo tumor extracts which was prevented in tumors treated with the combination of 2C2-YTE and selumetinib (FIG. 37C, lower panel). Similar results were seen in HARA-B (data not shown).

In cell culture the levels of HER3 protein were seen to increase in response to MEK inhibitor across most models examined, indicating that the HER3 pathway may play a role in resistance to MEK inhibitors. In a number of orthotopic CRC and LC xenograft model studies the combination of 2C2-YTE and selumetinib was seen to increase the anti-tumor efficacy of either agent alone. These data support the use of 2C2 in combination with a MEK inhibitor like selumetinib to enhance anti-tumor activity and prevent resistance.

4.18. Toxicology Studies in Cynomolgus Monkey 4.18.1. Method

Twenty Male cynomolgus monkeys (Macaca fascicularis) were assigned to four groups (5 animals per group) and a total of five doses of vehicle control or 2C2-YTE at 10, 30 or 120 mg/kg were administered. Animals were dosed once weekly via 5-minute IV infusion at a dose volume of 5 mL/kg. Three animals per group were necropsied on Day 32 (three days after the final dose administration on Day 29 of the dosing phase) and two animals per group were necropsied on Day 43 of the recovery phase (forty-five days after the final dose administration on Day 29 of the dosing phase). Assessment of toxicity was based on a number of factors including mortality, clinical observations, body weights, dose site irritation scoring, clinical and anatomic pathology evaluations.

Cynomolgus monkey plasma samples were isolated and analyzed for soluble HER3 (sHER3) levels using an anti-HER3 sandwich format with an electrochemiluminescence (ECL) detection system for quantitation of free sHER3. Meso Scale Discovery (MSD) bare 96-well plates (MSD, catalog number L15XA-6/L11XA-6) were coated with 0.5 ug/ml of 2C2-YTE overnight at 2 to 8° C. and subsequently blocked with MSD Blocker A (MSD, catalog number R93BA-1). Reference Standard and Quality controls (QC), and cynomolgus monkey plasma undiluted test samples were added to blocked plates for 1 hour at room temperature. Biotinylated anti-hErbB3/HER3 antibody (R&D Systems, catalog number BAM348) followed by addition of Sulfo-TAG (MSD, catalog number R32AD-1) resulted in light emission when electrochemically stimulated. The ECL signal was captured and recorded on a MSD Sector Imager 2400. The amount of light generated directly correlated with the amount of sHER3 in the cynomolgus monkey plasma samples. The raw data (ECL counts) were exported into SOFTmax® PRO. The standard curve for recombinant human HER3 standards was fitted using a 5-parameter fit program. Cynomolgus monkey plasma HER3 concentrations were calculated based on the standard curve using the statistical function of SOFTmax PRO.

In addition, skin biopsy samples were collected for bioanalysis. Briefly, matched 10 mm circles are drawn on the skin on the animal and ~100 µL of PBS or HRG at 0.1 mg/mL was injected intradermally into the center of each circle. Approximately 20 minutes later a skin sample was collected from each injection site and flash frozen. Alternatively, matched biopsy samples are collected (without prior intradermal injection) from each and incubated for approximately 30 min at room temperature in culture media with or without 100 µg/mL HRG followed by two washes with ice-cold PBS. The washed sample is then flash-frozen. The tissues were then homogenized in Lysing Matrix A tubes (MP Biomedicals) containing RIPA lysis buffer and protease inhibitor cocktail (Sigma-Aldrich) and phosphatase inhibitor cocktail set I and II (EMD-Millipore) using a Fast Prep machine (MP Biomedicals). Samples were then subjected to a freeze-thaw cycle and an additional homogenization cycle before clarification by centrifugation at 14,000 rpm for 5 minutes at 4° C. Clarified lysates were transferred to fresh 1.5 mL tubes and protein content was measured. The levels of total HER3 and pHER3 are determined using a sandwich ELISA assay.

4.18.2. Results

A non-GLP, 1-month, repeat-dose toxicity study of 2C2-YTE with a six-week recovery phase was performed in cynomolgus monkeys to evaluate the toxicity and activity of 2C2-YTE, when administered once weekly via an IV infusion to cynomolgus monkeys for at least 1-month (5 total doses) and to assess the reversibility, persistence, or delayed occurrence of any effects after a 6-week recovery period. No adverse effects were noted following once weekly IV administration (5 minute infusion) of up to 120 mg/kg/dose of 2C2-YTE, for 5 weeks (5 total doses), in male cynomolgus monkeys.

The ability of 2C2-YTE to block HRG-induced pHER3 in the skin of cynomolgus monkeys was confirmed by in vivo and ex vivo evaluations. Complete suppression of circulating soluble HER3 was observed in all animals receiving intravenous 2C2-YTE. Ex-vivo stimulation of skin biopsies with HRG resulted in an increase in the pHER3:tHER3 ratio, demonstrating that HER3 present in the skin of cynomolgus monkeys can be activated by HRG, the predominant ligand for HER3. Complete suppression of HRG-induced pHER3 was achieved in all 2C2-YTE treated groups at the end of the dosing phase (data not shown). Thus, 2C2-YTE blocked in vivo and ex vivo HRG-induced HER3 phosphorylation in cynomolgus monkey skin biopsy samples.

INCORPORATION BY REFERENCE

All publications and patents mentioned herein are hereby incorporated by reference in their entirety as if each individual publication or patent was specifically and individually indicated to be incorporated by reference. In addition, U.S. Provisional Application Nos. 61/563,092 filed Nov. 23, 2011; 61/656,670 filed Jun. 7, 2012; and 61/722,558 filed Nov. 5, 2012, are incorporated by reference in their entirety for all purposes.

The preceding description of the specific aspects will so fully reveal the general nature of the invention that others can, by applying knowledge within the skill of the art, readily modify and/or adapt for various applications such specific aspects, without undue experimentation, without departing from the general concept of the present invention. Therefore, such adaptations and modifications are intended to be within the meaning and range of equivalents of the disclosed aspects, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

What is claimed is:

1. An isolated antibody or an antigen-binding fragment thereof, which specifically binds to HER3, comprising an antibody variable light chain region (VL) and an antibody variable heavy chain region (VH), wherein the VL comprises the amino acid sequence:

|  |  |
|---|---|
| [FW1]SGSLSNIGLNYVS | (SEQ ID NO: 19) |
| [FW2]RNNQRPS | (SEQ ID NO: 21) |
| [FW3]AAWDDSPPGEA | (SEQ ID NO: 23) |
| [FW4] | | wherein [FW1], [FW2], [FW3] and [FW4] represent VL framework regions, and
wherein the VH comprises the amino acid sequence:

|  |  |
|---|---|
| [FW5]YYYMQ | (SEQ ID NO: 31) |
| [FW6]YIGSSGGVTNYADSVKG | (SEQ ID NO: 32) |
| [FW7]VGLGDAFDI | (SEQ ID NO: 35) |
| [FW8] | | wherein [FW5], [FW6], [FW7] and [FW8] represent VH framework regions.

2. The antibody or antigen-binding fragment of claim 1, wherein the VL comprises an amino acid sequence at least 80% identical to the amino acid sequence of SEQ ID NO: 3, and wherein the VH comprises an amino acid sequence at least 80% identical to the amino acid sequence of SEQ ID NO: 2.

3. The antibody or antigen-binding fragment of claim 1, wherein the VL comprises an amino acid sequence at least 90% identical to the amino acid sequence of SEQ ID NO: 3, and wherein the VH comprises an amino acid sequence at least 90% identical to the amino acid sequence of SEQ ID NO: 2.

4. The antibody or antigen-binding fragment of claim 1, wherein the VL comprises an amino acid sequence at least 95% identical to the amino acid sequence of SEQ ID NO: 3, and wherein the VH comprises an amino acid sequence at least 95% identical to the amino acid sequence of SEQ ID NO: 2.

5. The antibody or antigen-binding fragment thereof of claim 1, wherein FW1 comprises SEQ ID NO: 40 or 44, FW2 comprises SEQ ID NO: 41, FW3 comprises SEQ ID NO: 42, FW4 comprises SEQ ID NO: 43, FW5 comprises SEQ ID NO: 36, FW6 comprises SEQ ID NO: 37, FW7 comprises SEQ ID NO: 38 and FW8 comprises SEQ ID NO: 39.

6. The antibody or antigen-binding fragment thereof of claim 1, which comprises a VL comprising SEQ ID NO: 3 and a VH comprising SEQ ID NO: 2.

7. The antibody or antigen-binding fragment thereof of claim 1, which comprises a heavy chain constant region.

8. The antibody or antigen-binding fragment thereof of claim 7, wherein the heavy chain constant region is a human IgG constant region.

9. The antibody or antigen-binding fragment thereof of claim 8, wherein the human IgG constant region is an IgG1 constant region.

10. The antibody or antigen-binding fragment of claim 8,
(i) wherein the human IgG constant region comprises amino acid substitutions relative to a wild-type human IgG constant domain at positions 252, 254, and 256, wherein the numbering is according to the EU index as set forth in Kabat, and wherein
(a) the amino acid at position 252 Methionine) is substituted with Tyrosine (Y),
(b) the amino acid at position 254 (Serine) is substituted with Threonine (T), and
(c) the amino acid at position 256 (Threonine) is substituted with Glutamic acid (E).

11. The antibody or antigen-binding fragment thereof of claim 9, which comprises a light chain constant region selected from the group consisting of a human kappa constant region and a human lambda constant region.

12. The antibody or antigen-binding fragment thereof of claim 11, which comprises a human lambda constant region.

13. The antibody or antigen-binding fragment thereof of claim 1, which comprises a light chain constant region selected from the group consisting of a human kappa constant region and a human lambda constant region.

14. The antibody or antigen-binding fragment of claim 1, wherein the antibody is a human antibody, a humanized antibody, a chimeric antibody, a recombinant antibody, a multispecific antibody, or an antigen-binding fragment thereof; wherein the antigen-binding fragment is an Fv, Fab, F(ab')2, Fab', dsFv, scFv, or sc(Fv)2; or wherein the antibody or antigen-binding fragment thereof is conjugated to at least one heterologous agent.

15. The antibody or antigen-binding fragment of claim 1, wherein the antibody is a monoclonal antibody.

16. The antibody or antigen-binding fragment thereof of claim 1, comprising (i) an antibody light chain comprising an antibody VL comprising SEQ ID NO: 3 and a human lambda light chain constant region, and (ii) an antibody heavy chain comprising an antibody VH comprising SEQ ID NO: 2 and a human IgG1 heavy chain constant region, wherein the human IgG1 constant region comprises amino acid substitutions relative to a wild-type human IgG1 constant domain at positions 252, 254, and 256, wherein the numbering is according to the EU index as set forth in Kabat, and wherein
  (a) the amino acid at position 252 (Methionine) is substituted with Tyrosine (Y),
  (b) the amino acid at position 254 (Serine) is substituted with Threonine (T), and
  (c) the amino acid at position 256 (Threonine) is substituted with Glutamic acid (E).

17. The antibody of claim 16, wherein the antibody is a monoclonal antibody.

18. The antibody of claim 14, wherein the antibody is a human antibody.

19. The antibody of claim 16, wherein the antibody is a human antibody.

20. The antibody of claim 17, wherein the antibody is a human antibody.

21. A composition comprising the antibody or antigen-binding fragment thereof of claim 1, and a pharmaceutically acceptable carrier.

22. The composition of claim 21, wherein the composition is refrigerator stable, wherein the antibody or antigen-binding fragment thereof is at a concentration of 25-100 mg/mL, and wherein the composition further comprises 25 mM histidine/histidine HCl, 205 mM sucrose, and 0.02% polysorbate 80 at pH 6.0.

23. A composition comprising the antibody of claim 16, and a pharmaceutically acceptable carrier.

24. A kit comprising the antibody or antigen-binding fragment thereof of claim 1 for use in inhibiting the proliferation of a cell expressing HER3, wherein said cell is a human head and neck tumor cell, a human non-small cell lung cancer cell, a human colorectal tumor cell, a human prostate tumor cell, or a human breast cancer cell.

25. An isolated nucleic acid comprising a sequence encoding the antibody or antigen-binding fragment according to claim 1.

26. An isolated vector comprising a nucleic acid according to claim 25.

27. An in vitro host cell comprising a nucleic acid sequence according to claim 25.

28. A method of making an antibody or antigen-binding fragment thereof, comprising (a) culturing a cell comprising the nucleic acid of claim 25; and (b) isolating the antibody or antigen-binding fragment thereof.

29. A method of inhibiting the proliferation of a cell expressing HER3, said method comprising contacting the cell with the antibody or antigen-binding fragment of claim 1, wherein said cell is a human head and neck tumor cell, a human non-small cell lung cancer cell, a human colorectal tumor cell, a human prostate tumor cell, or a human breast cancer cell.

30. The method of claim 29, wherein the inhibition of cell proliferation occurs in vivo.

31. A method of inhibiting the in vivo proliferation of a cell expressing HER3, said method comprising contacting the cell with the antibody or antigen-binding fragment of claim 6, wherein said cell is a human head and neck tumor cell, a human non-small cell lung cancer cell, a human colorectal tumor cell, a human prostate tumor cell, or a human breast cancer cell.

32. A method of inhibiting the in vivo proliferation of a cell expressing HER3, said method comprising contacting the cell with the antibody or antigen-binding fragment of claim 11, wherein said cell is a human head and neck tumor cell, a human non-small cell lung cancer cell, a human colorectal tumor cell, a human prostate tumor cell, or a human breast cancer cell.

33. A method of inhibiting the in vivo proliferation of a cell expressing HER3, said method comprising contacting the cell with the antibody or antigen-binding fragment of claim 10, wherein said cell is a human head and neck tumor cell, a human non-small cell lung cancer cell, a human colorectal tumor cell, a human prostate tumor cell, or a human breast cancer cell.

34. A method of inhibiting the proliferation of a cell expressing HER3, said method comprising contacting the cell with the antibody or antigen-binding fragment of claim 16, wherein said cell is a human head and neck tumor cell, a human non-small cell lung cancer cell, a human colorectal tumor cell, a human prostate tumor cell, or a human breast cancer cell.

35. The method of claim 34, wherein the inhibition of cell proliferation occurs in vivo.

36. A method of inhibiting the proliferation of a cell expressing HER3, said method comprising contacting the cell with the antibody or antigen-binding fragment of claim 17, wherein said cell is a human head and neck tumor cell, a human non-small cell lung cancer cell, a human colorectal tumor cell, a human prostate tumor cell, or a human breast cancer cell.

37. The method of claim 36, wherein the inhibition of cell proliferation occurs in vivo.

38. A method of inhibiting the proliferation of a cell expressing HER3, said method comprising contacting the cell with the antibody or antigen-binding fragment of claim 20, wherein said cell is a human head and neck tumor cell, a human non-small cell lung cancer cell, a human colorectal tumor cell, a human prostate tumor cell, or a human breast cancer cell.

39. The method of claim 38, wherein the inhibition of cell proliferation occurs in vivo.

* * * * *

UNITED STATES PATENT AND TRADEMARK OFFICE
CERTIFICATE OF CORRECTION

PATENT NO. : 9,220,775 B2  Page 1 of 1
APPLICATION NO. : 14/359864
DATED : December 29, 2015
INVENTOR(S) : Chowdhury et al.

It is certified that error appears in the above-identified patent and that said Letters Patent is hereby corrected as shown below:

In the Specification

Column 3, line 34, "[FW1]X1GSX2SNIGLNYVS" should read --[FW1]$X_1$GS$X_2$SNIGLNYVS--.

In the Claims

CLAIM 10: Column 124, line 34, "252 Methionine)" should read --252 (Methionine)--.

Signed and Sealed this
Nineteenth Day of July, 2016

Michelle K. Lee
*Director of the United States Patent and Trademark Office*

SEQUENCE LISTING

```
<160> NUMBER OF SEQ ID NOS: 51

<210> SEQ ID NO 1
<211> LENGTH: 110
<212> TYPE: PRT
<213> ORGANISM: Artificial Sequence
<220> FEATURE:
<223> OTHER INFORMATION: Synthetic sequence

<400> SEQUENCE: 1

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Leu Asn
            20                  25                  30

Tyr Val Ser Trp Tyr Gln Gln Leu Pro Gly Thr Ala Pro Lys Leu Leu
        35                  40                  45

Ile Ser Arg Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Gly Glu Val Phe Gly Gly Gly Thr Lys Leu Thr Val Leu
            100                 105                 110

<210> SEQ ID NO 2
<211> LENGTH: 118
<212> TYPE: PRT
<213> ORGANISM: Artificial Sequence
<220> FEATURE:
<223> OTHER INFORMATION: Synthetic sequence

<400> SEQUENCE: 2

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Tyr Tyr
            20                  25                  30

Tyr Met Gln Trp Val Arg Gln Ala Pro Gly Lys Gly Leu Glu Trp Val
        35                  40                  45

Ser Tyr Ile Gly Ser Ser Gly Gly Val Thr Asn Tyr Ala Asp Ser Val
    50                  55                  60

Lys Gly Arg Phe Thr Ile Ser Arg Asp Asn Ser Lys Asn Thr Leu Tyr
```

```
            65                  70                  75                  80
Leu Gln Met Asn Ser Leu Arg Ala Glu Asp Thr Ala Val Tyr Tyr Cys
                    85                  90                  95

Ala Arg Val Gly Leu Gly Asp Ala Phe Asp Ile Trp Gly Gln Gly Thr
                100                 105                 110

Met Val Thr Val Ser Ser
            115

<210> SEQ ID NO 3
<211> LENGTH: 110
<212> TYPE: PRT
<213> ORGANISM: Artificial Sequence
<220> FEATURE:
<223> OTHER INFORMATION: Synthetic sequence

<400> SEQUENCE: 3

Gln Ser Val Leu Thr Gln Pro Pro Ser Ala Ser Gly Thr Pro Gly Gln
1               5                   10                  15

Arg Val Thr Ile Ser Cys Ser Gly Ser Leu Ser Asn Ile Gly Leu Asn
                20                  25                  30

Tyr Val Ser Trp Tyr Gln Gln Leu Pro Gly Thr Ala Pro Lys Leu Leu
            35                  40                  45

Ile Ser Arg Asn Asn Gln Arg Pro Ser Gly Val Pro Asp Arg Phe Ser
        50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Pro
                85                  90                  95

Pro Gly Glu Ala Phe Gly Gly Gly Thr Lys Leu Thr Val Leu
                100                 105                 110

<210> SEQ ID NO 4
<211> LENGTH: 110
<212> TYPE: PRT
<213> ORGANISM: Artificial Sequence
<220> FEATURE:
<223> OTHER INFORMATION: Synthetic sequence

<400> SEQUENCE: 4

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Leu Asn
                20                  25                  30

Tyr Val Ser Trp Tyr Gln Gln Leu Pro Gly Thr Ala Pro Lys Leu Leu
            35                  40                  45

Ile Ser Arg Asn Asn Gln Arg Pro Ser Gly Val Pro Asp Arg Phe Ser
        50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Gly Leu
                85                  90                  95

Pro Gly Glu Val Phe Gly Gly Gly Thr Lys Leu Thr Val Leu
                100                 105                 110

<210> SEQ ID NO 5
<211> LENGTH: 110
<212> TYPE: PRT
<213> ORGANISM: Artificial Sequence
<220> FEATURE:
```

<223> OTHER INFORMATION: Synthetic sequence

<400> SEQUENCE: 5

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Leu Asn
            20                  25                  30

Tyr Val Ser Trp Tyr Gln Gln Leu Pro Gly Thr Ala Pro Lys Leu Leu
        35                  40                  45

Ile Ser Arg Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ile Gly Glu Val Phe Gly Gly Gly Thr Lys Leu Thr Val Leu
            100                 105                 110

<210> SEQ ID NO 6
<211> LENGTH: 110
<212> TYPE: PRT
<213> ORGANISM: Artificial Sequence
<220> FEATURE:
<223> OTHER INFORMATION: Synthetic sequence

<400> SEQUENCE: 6

Gln Ser Val Leu Thr Gln Pro Pro Ser Ala Ser Gly Thr Pro Gly Gln
1               5                   10                  15

Arg Val Thr Ile Ser Cys Arg Gly Ser Ser Asn Ile Gly Leu Asn
            20                  25                  30

Tyr Val Ser Trp Tyr Gln Gln Leu Pro Gly Thr Ala Pro Lys Leu Leu
        35                  40                  45

Ile Ser Arg Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Gly Glu Val Phe Gly Gly Gly Thr Lys Leu Thr Val Leu
            100                 105                 110

<210> SEQ ID NO 7
<211> LENGTH: 110
<212> TYPE: PRT
<213> ORGANISM: Artificial Sequence
<220> FEATURE:
<223> OTHER INFORMATION: Synthetic sequence

<400> SEQUENCE: 7

Gln Ser Val Leu Thr Gln Pro Pro Ser Ala Ser Gly Thr Pro Gly Gln
1               5                   10                  15

Arg Val Thr Ile Ser Cys Ser Gly Ser Leu Ser Asn Ile Gly Leu Asn
            20                  25                  30

Tyr Val Ser Trp Tyr Gln Gln Leu Pro Gly Thr Ala Pro Lys Leu Leu
        35                  40                  45

Ile Ser Arg Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg

```
                65                  70                  75                  80
Ser Glu Asp Glu Ala Asp Tyr Tyr Cys Ala Ala Trp Asp Asp Ser Leu
                    85                  90                  95

Ser Gly Glu Val Phe Gly Gly Gly Thr Lys Leu Thr Val Leu
                100                 105                 110
```

<210> SEQ ID NO 8
<211> LENGTH: 110
<212> TYPE: PRT
<213> ORGANISM: Artificial Sequence
<220> FEATURE:
<223> OTHER INFORMATION: Synthetic sequence

<400> SEQUENCE: 8

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Leu Asn
            20                  25                  30

Tyr Val Ser Trp Tyr Gln Gln Leu Pro Gly Thr Ala Pro Lys Leu Leu
        35                  40                  45

Ile Ser Arg Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                    85                  90                  95

Pro Gly Glu Val Phe Gly Gly Gly Thr Lys Leu Thr Val Leu
                100                 105                 110
```

<210> SEQ ID NO 9
<211> LENGTH: 110
<212> TYPE: PRT
<213> ORGANISM: Artificial Sequence
<220> FEATURE:
<223> OTHER INFORMATION: Synthetic sequence

<400> SEQUENCE: 9

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Leu Asn
            20                  25                  30

Tyr Val Ser Trp Tyr Gln Gln Leu Pro Gly Thr Ala Pro Lys Leu Leu
        35                  40                  45

Ile Ser Arg Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                    85                  90                  95

Ser Gly Glu Ala Phe Gly Gly Gly Thr Lys Leu Thr Val Leu
                100                 105                 110
```

<210> SEQ ID NO 10
<211> LENGTH: 110
<212> TYPE: PRT
<213> ORGANISM: Artificial Sequence
<220> FEATURE:
<223> OTHER INFORMATION: Synthetic sequence

<400> SEQUENCE: 10

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Leu Asn
            20                  25                  30

Tyr Val Ser Trp Tyr Gln Gln Leu Pro Gly Thr Ala Pro Lys Leu Leu
            35                  40                  45

Ile Ser Arg Asn Asn Gln Arg Pro Ser Gly Val Pro Asp Arg Phe Ser
        50                  55                  60

Gly Ser Lys Ser Gly Thr Ser Ala Ser Leu Ala Ile Ser Gly Leu Arg
65              70                  75                  80

Ser Glu Asp Glu Ala Asp Tyr Tyr Cys Ala Ala Trp Asp Asp Ser Pro
            85                  90                  95

Ser Gly Glu Val Phe Gly Gly Gly Thr Lys Leu Thr Val Leu
            100                 105                 110

<210> SEQ ID NO 11
<211> LENGTH: 110
<212> TYPE: PRT
<213> ORGANISM: Artificial Sequence
<220> FEATURE:
<223> OTHER INFORMATION: Synthetic sequence

<400> SEQUENCE: 11

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Leu Asn
            20                  25                  30

Tyr Val Ser Trp Tyr Gln Gln Leu Pro Gly Thr Ala Pro Lys Leu Leu
            35                  40                  45

Ile Ser Arg Asn Asn Gln Arg Pro Ser Gly Val Pro Asp Arg Phe Ser
        50                  55                  60

Gly Ser Lys Ser Gly Thr Ser Ala Ser Leu Ala Ile Ser Gly Leu Arg
65              70                  75                  80

Ser Glu Asp Glu Ala Asp Tyr Tyr Cys Ala Ala Trp Asp Asp Ser Leu
            85                  90                  95

Arg Gly Glu Val Phe Gly Gly Gly Thr Lys Leu Thr Val Leu
            100                 105                 110

<210> SEQ ID NO 12
<211> LENGTH: 118
<212> TYPE: PRT
<213> ORGANISM: Artificial Sequence
<220> FEATURE:
<223> OTHER INFORMATION: Synthetic sequence

<400> SEQUENCE: 12

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Tyr Tyr
            20                  25                  30

Tyr Met Gln Trp Val Arg Gln Ala Pro Gly Lys Gly Leu Glu Trp Val
            35                  40                  45

Ser Ile Ile Gly Ser Ser Gly Val Thr Asn Tyr Ala Asp Ser Val
        50                  55                  60

Lys Gly Arg Phe Thr Ile Ser Arg Asp Asn Ser Lys Asn Thr Leu Tyr
65              70                  75                  80

Leu Gln Met Asn Ser Leu Arg Ala Glu Asp Thr Ala Val Tyr Tyr Cys

```
                    85                  90                  95
Ala Arg Val Gly Leu Gly Asp Ala Phe Asp Ile Trp Gly Gln Gly Thr
            100                 105                 110

Met Val Thr Val Ser Ser
        115

<210> SEQ ID NO 13
<211> LENGTH: 118
<212> TYPE: PRT
<213> ORGANISM: Artificial Sequence
<220> FEATURE:
<223> OTHER INFORMATION: Synthetic sequence

<400> SEQUENCE: 13

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Tyr Tyr
            20                  25                  30

Tyr Met Gln Trp Val Arg Gln Ala Pro Gly Lys Gly Leu Glu Trp Val
        35                  40                  45

Ser Val Ile Gly Ser Ser Gly Gly Val Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Gly Leu Gly Asp Ala Phe Asp Ile Trp Gly Gln Gly Thr
            100                 105                 110

Met Val Thr Val Ser Ser
        115

<210> SEQ ID NO 14
<211> LENGTH: 110
<212> TYPE: PRT
<213> ORGANISM: Artificial Sequence
<220> FEATURE:
<223> OTHER INFORMATION: Synthetic sequence

<400> SEQUENCE: 14

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Leu Asn
            20                  25                  30

Tyr Val Ser Trp Tyr Gln Gln Leu Pro Gly Thr Ala Pro Lys Leu Leu
        35                  40                  45

Ile Ser Arg Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Pro
                85                  90                  95

Pro Gly Glu Ala Phe Gly Gly Gly Thr Lys Leu Thr Val Leu
            100                 105                 110

<210> SEQ ID NO 15
<211> LENGTH: 110
<212> TYPE: PRT
<213> ORGANISM: Artificial Sequence
<220> FEATURE:
```

<223> OTHER INFORMATION: Synthetic sequence

<400> SEQUENCE: 15

Gln Ser Val Leu Thr Gln Pro Pro Ser Ala Ser Gly Thr Pro Gly Gln
1               5                   10                  15

Arg Val Thr Ile Ser Cys Arg Gly Ser Ser Ser Asn Ile Gly Leu Asn
            20                  25                  30

Tyr Val Ser Trp Tyr Gln Gln Leu Pro Gly Thr Ala Pro Lys Leu Leu
        35                  40                  45

Ile Ser Arg Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Pro
                85                  90                  95

Pro Gly Glu Ala Phe Gly Gly Gly Thr Lys Leu Thr Val Leu
            100                 105                 110

<210> SEQ ID NO 16
<211> LENGTH: 110
<212> TYPE: PRT
<213> ORGANISM: Artificial Sequence
<220> FEATURE:
<223> OTHER INFORMATION: Synthetic sequence

<400> SEQUENCE: 16

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Leu Asn
            20                  25                  30

Tyr Val Ser Trp Tyr Gln Gln Leu Pro Gly Thr Ala Pro Lys Leu Leu
        35                  40                  45

Ile Ser Arg Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Pro
                85                  90                  95

Ser Gly Glu Ala Phe Gly Gly Gly Thr Lys Leu Thr Val Leu
            100                 105                 110

<210> SEQ ID NO 17
<211> LENGTH: 110
<212> TYPE: PRT
<213> ORGANISM: Artificial Sequence
<220> FEATURE:
<223> OTHER INFORMATION: Synthetic sequence

<400> SEQUENCE: 17

Gln Tyr Glu Leu Thr Gln Pro Pro Ser Ala Ser Gly Thr Pro Gly Gln
1               5                   10                  15

Arg Val Thr Met Ser Cys Ser Gly Ser Ser Ser Asn Ile Gly Leu Asn
            20                  25                  30

Tyr Val Ser Trp Tyr Gln Gln Leu Pro Gly Thr Ala Pro Lys Leu Leu
        35                  40                  45

Ile Ser Arg Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg

```
                65                  70                  75                  80
Ser Glu Asp Glu Ala Asp Tyr Tyr Cys Ala Ala Trp Asp Asp Ser Leu
                    85                  90                  95
Ser Gly Glu Val Phe Gly Gly Gly Thr Lys Leu Thr Val Leu
            100                 105                 110

<210> SEQ ID NO 18
<211> LENGTH: 13
<212> TYPE: PRT
<213> ORGANISM: Artificial Sequence
<220> FEATURE:
<223> OTHER INFORMATION: Synthetic sequence

<400> SEQUENCE: 18

Ser Gly Ser Ser Ser Asn Ile Gly Leu Asn Tyr Val Ser
1               5                   10

<210> SEQ ID NO 19
<211> LENGTH: 13
<212> TYPE: PRT
<213> ORGANISM: Artificial Sequence
<220> FEATURE:
<223> OTHER INFORMATION: Synthetic sequence

<400> SEQUENCE: 19

Ser Gly Ser Leu Ser Asn Ile Gly Leu Asn Tyr Val Ser
1               5                   10

<210> SEQ ID NO 20
<211> LENGTH: 13
<212> TYPE: PRT
<213> ORGANISM: Artificial Sequence
<220> FEATURE:
<223> OTHER INFORMATION: Synthetic sequence

<400> SEQUENCE: 20

Arg Gly Ser Ser Ser Asn Ile Gly Leu Asn Tyr Val Ser
1               5                   10

<210> SEQ ID NO 21
<211> LENGTH: 7
<212> TYPE: PRT
<213> ORGANISM: Artificial Sequence
<220> FEATURE:
<223> OTHER INFORMATION: Synthetic sequence

<400> SEQUENCE: 21

Arg Asn Asn Gln Arg Pro Ser
1               5

<210> SEQ ID NO 22
<211> LENGTH: 11
<212> TYPE: PRT
<213> ORGANISM: Artificial Sequence
<220> FEATURE:
<223> OTHER INFORMATION: Synthetic sequence

<400> SEQUENCE: 22

Ala Ala Trp Asp Asp Ser Leu Ser Gly Glu Val
1               5                   10

<210> SEQ ID NO 23
<211> LENGTH: 11
<212> TYPE: PRT
<213> ORGANISM: Artificial Sequence
<220> FEATURE:
```

```
<223> OTHER INFORMATION: Synthetic sequence

<400> SEQUENCE: 23

Ala Ala Trp Asp Asp Ser Pro Pro Gly Glu Ala
1               5                   10

<210> SEQ ID NO 24
<211> LENGTH: 11
<212> TYPE: PRT
<213> ORGANISM: Artificial Sequence
<220> FEATURE:
<223> OTHER INFORMATION: Synthetic sequence

<400> SEQUENCE: 24

Ala Ala Trp Asp Asp Ser Pro Ser Gly Glu Ala
1               5                   10

<210> SEQ ID NO 25
<211> LENGTH: 11
<212> TYPE: PRT
<213> ORGANISM: Artificial Sequence
<220> FEATURE:
<223> OTHER INFORMATION: Synthetic sequence

<400> SEQUENCE: 25

Ala Ala Trp Asp Asp Ser Leu Pro Gly Glu Val
1               5                   10

<210> SEQ ID NO 26
<211> LENGTH: 11
<212> TYPE: PRT
<213> ORGANISM: Artificial Sequence
<220> FEATURE:
<223> OTHER INFORMATION: Synthetic sequence

<400> SEQUENCE: 26

Ala Ala Trp Asp Asp Gly Leu Pro Gly Glu Val
1               5                   10

<210> SEQ ID NO 27
<211> LENGTH: 11
<212> TYPE: PRT
<213> ORGANISM: Artificial Sequence
<220> FEATURE:
<223> OTHER INFORMATION: Synthetic sequence

<400> SEQUENCE: 27

Ala Ala Trp Asp Asp Ser Leu Ile Gly Glu Val
1               5                   10

<210> SEQ ID NO 28
<211> LENGTH: 11
<212> TYPE: PRT
<213> ORGANISM: Artificial Sequence
<220> FEATURE:
<223> OTHER INFORMATION: Synthetic sequence

<400> SEQUENCE: 28

Ala Ala Trp Asp Asp Ser Leu Ser Gly Glu Ala
1               5                   10

<210> SEQ ID NO 29
<211> LENGTH: 11
<212> TYPE: PRT
<213> ORGANISM: Artificial Sequence
<220> FEATURE:
<223> OTHER INFORMATION: Synthetic sequence
```

```
<400> SEQUENCE: 29

Ala Ala Trp Asp Asp Ser Pro Ser Gly Glu Val
1               5                   10

<210> SEQ ID NO 30
<211> LENGTH: 11
<212> TYPE: PRT
<213> ORGANISM: Artificial Sequence
<220> FEATURE:
<223> OTHER INFORMATION: Synthetic sequence

<400> SEQUENCE: 30

Ala Ala Trp Asp Asp Ser Leu Arg Gly Glu Val
1               5                   10

<210> SEQ ID NO 31
<211> LENGTH: 5
<212> TYPE: PRT
<213> ORGANISM: Artificial Sequence
<220> FEATURE:
<223> OTHER INFORMATION: Synthetic sequence

<400> SEQUENCE: 31

Tyr Tyr Tyr Met Gln
1               5

<210> SEQ ID NO 32
<211> LENGTH: 17
<212> TYPE: PRT
<213> ORGANISM: Artificial Sequence
<220> FEATURE:
<223> OTHER INFORMATION: Synthetic sequence

<400> SEQUENCE: 32

Tyr Ile Gly Ser Ser Gly Gly Val Thr Asn Tyr Ala Asp Ser Val Lys
1               5                   10                  15
Gly

<210> SEQ ID NO 33
<211> LENGTH: 17
<212> TYPE: PRT
<213> ORGANISM: Artificial Sequence
<220> FEATURE:
<223> OTHER INFORMATION: Synthetic sequence

<400> SEQUENCE: 33

Ile Ile Gly Ser Ser Gly Gly Val Thr Asn Tyr Ala Asp Ser Val Lys
1               5                   10                  15
Gly

<210> SEQ ID NO 34
<211> LENGTH: 17
<212> TYPE: PRT
<213> ORGANISM: Artificial Sequence
<220> FEATURE:
<223> OTHER INFORMATION: Synthetic sequence

<400> SEQUENCE: 34

Val Ile Gly Ser Ser Gly Gly Val Thr Asn Tyr Ala Asp Ser Val Lys
1               5                   10                  15
Gly

<210> SEQ ID NO 35
```

```
<211> LENGTH: 9
<212> TYPE: PRT
<213> ORGANISM: Artificial Sequence
<220> FEATURE:
<223> OTHER INFORMATION: Synthetic sequence

<400> SEQUENCE: 35

Val Gly Leu Gly Asp Ala Phe Asp Ile
1               5

<210> SEQ ID NO 36
<211> LENGTH: 30
<212> TYPE: PRT
<213> ORGANISM: Artificial Sequence
<220> FEATURE:
<223> OTHER INFORMATION: Synthetic sequence

<400> SEQUENCE: 36

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30

<210> SEQ ID NO 37
<211> LENGTH: 14
<212> TYPE: PRT
<213> ORGANISM: Artificial Sequence
<220> FEATURE:
<223> OTHER INFORMATION: Synthetic sequence

<400> SEQUENCE: 37

Trp Val Arg Gln Ala Pro Gly Lys Gly Leu Glu Trp Val Ser
1               5                   10

<210> SEQ ID NO 38
<211> LENGTH: 32
<212> TYPE: PRT
<213> ORGANISM: Artificial Sequence
<220> FEATURE:
<223> OTHER INFORMATION: Synthetic sequence

<400> SEQUENCE: 38

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 39
<211> LENGTH: 11
<212> TYPE: PRT
<213> ORGANISM: Artificial Sequence
<220> FEATURE:
<223> OTHER INFORMATION: Synthetic sequence

<400> SEQUENCE: 39

Trp Gly Gln Gly Thr Met Val Thr Val Ser Ser
1               5                   10

<210> SEQ ID NO 40
<211> LENGTH: 22
<212> TYPE: PRT
<213> ORGANISM: Artificial Sequence
<220> FEATURE:
<223> OTHER INFORMATION: Synthetic sequence

<400> SEQUENCE: 40
```

-continued

Gln Ser Val Leu Thr Gln Pro Pro Ser Ala Ser Gly Thr Pro Gly Gln
1               5                   10                  15

Arg Val Thr Ile Ser Cys
            20

<210> SEQ ID NO 41
<211> LENGTH: 15
<212> TYPE: PRT
<213> ORGANISM: Artificial Sequence
<220> FEATURE:
<223> OTHER INFORMATION: Synthetic sequence

<400> SEQUENCE: 41

Trp Tyr Gln Gln Leu Pro Gly Thr Ala Pro Lys Leu Leu Ile Ser
1               5                   10                  15

<210> SEQ ID NO 42
<211> LENGTH: 32
<212> TYPE: PRT
<213> ORGANISM: Artificial Sequence
<220> FEATURE:
<223> OTHER INFORMATION: Synthetic sequence

<400> SEQUENCE: 42

Gly Val Pro Asp Arg Phe Ser Gly Ser Lys Ser Gly Thr Ser Ala Ser
1               5                   10                  15

Leu Ala Ile Ser Gly Leu Arg Ser Glu Asp Glu Ala Asp Tyr Tyr Cys
            20                  25                  30

<210> SEQ ID NO 43
<211> LENGTH: 10
<212> TYPE: PRT
<213> ORGANISM: Artificial Sequence
<220> FEATURE:
<223> OTHER INFORMATION: Synthetic sequence

<400> SEQUENCE: 43

Phe Gly Gly Gly Thr Lys Leu Thr Val Leu
1               5                   10

<210> SEQ ID NO 44
<211> LENGTH: 22
<212> TYPE: PRT
<213> ORGANISM: Artificial Sequence
<220> FEATURE:
<223> OTHER INFORMATION: Synthetic sequence

<400> SEQUENCE: 44

Gln Tyr Glu Leu Thr Gln Pro Pro Ser Ala Ser Gly Thr Pro Gly Gln
1               5                   10                  15

Arg Val Thr Met Ser Cys
            20

<210> SEQ ID NO 45
<211> LENGTH: 330
<212> TYPE: PRT
<213> ORGANISM: Homo sapiens

<400> SEQUENCE: 45

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser

```
                35                  40                  45
Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
                115                 120                 125

Lys Pro Lys Asp Thr Leu Met Ile Ser Arg Thr Pro Glu Val Thr Cys
                130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
                195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
                275                 280                 285

Leu Tyr Ser Lys Leu Thr Val Asp Lys Ser Arg Trp Gln Gln Gly Asn
                290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 46
<211> LENGTH: 330
<212> TYPE: PRT
<213> ORGANISM: Artificial Sequence
<220> FEATURE:
<223> OTHER INFORMATION: Synthetic sequence

<400> SEQUENCE: 46

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
                35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Gln Thr
```

```
                65                  70                  75                  80
Tyr Ile Cys Asn Val Asn His Lys Pro Ser Asn Thr Lys Val Asp Lys
                    85                  90                  95

Lys Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
            115                 120                 125

Lys Pro Lys Asp Thr Leu Tyr Ile Thr Arg Glu Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 47
<211> LENGTH: 648
<212> TYPE: DNA
<213> ORGANISM: Artificial Sequence
<220> FEATURE:
<223> OTHER INFORMATION: Synthetic sequence

<400> SEQUENCE: 47
cagtacgaat tgactcagcc accctcagcg tctgggaccc ccggcagag tgtcaccatg      60 tcttgttctg ggagcagctc caatatcgga cttaattatg tatcctggta ccagcacctc    120
ccaggaacgg cccccaaact cctcatctct aggaataatc agcggccctc aggggtccct    180
gaccgattct ctggctccaa gtctggcacc tcagcctccc tggccatcag tgggctccgg    240
tccgaagatg aggctgatta ttattgtgca gcatgggatg acagcctgag tggtgaggta    300
ttcggcggag ggaccaagct gaccgtcctc ggtcagccca aggctgcccc ctcggtcact    360
ctgttcccgc cctcctctga ggagcttcaa gccaacaagg ccacactggt gtgtctcata    420
agtgacttct acccgggagc cgtgacagtg gcctggaagg cagatagcag ccccgtcaag    480
gcgggagtgg agaccaccac accctccaaa caaagcaaca caagtacgc ggccagcagc    540 tacctgagcc tgacgcctga gcagtggaag tcccacagaa gctacagctg ccaggtcacg    600
```

```
catgaaggga gcaccgtgga agacagtg gcccctgcag aatgctct                        648
```

```
<210> SEQ ID NO 48
<211> LENGTH: 356
<212> TYPE: DNA
<213> ORGANISM: Artificial Sequence
<220> FEATURE:
<223> OTHER INFORMATION: Synthetic sequence

<400> SEQUENCE: 48
gaagttcaat tgttagagtc tggtggcggt cttgttcagc ctggtggttc tttacgtctt          60
tcttgcgctg cttccggatt cactttctct tattactata tgcagtgggt tcgccaagct         120
cctggtaaag gtttggagtg ggtttcttat atcggttctt ctggtggcgt tactaattat         180
gctgactccg ttaaaggtcg cttcactatc tctagagaca actctaagaa tactctctac         240
ttgcagatga acagcttaag ggctgaggac acggccgtgt attactgtgc gagagtaggt         300
cttggggatg cttttgatat ctggggccaa gggacaatgg tcaccgtctc aagcgc            356
```

```
<210> SEQ ID NO 49
<211> LENGTH: 13
<212> TYPE: PRT
<213> ORGANISM: Artificial Sequence
<220> FEATURE:
<223> OTHER INFORMATION: consensus sequence of VL CDR1
<220> FEATURE:
<221> NAME/KEY: VARIANT
<222> LOCATION: (1)..(1)
<223> OTHER INFORMATION: Xaa = Arg or Ser
<220> FEATURE:
<221> NAME/KEY: VARIANT
<222> LOCATION: (4)..(4)
<223> OTHER INFORMATION: Xaa = Ser or Leu

<400> SEQUENCE: 49

Xaa Gly Ser Xaa Ser Asn Ile Gly Leu Asn Tyr Val Ser
1               5                   10
```

```
<210> SEQ ID NO 50
<211> LENGTH: 11
<212> TYPE: PRT
<213> ORGANISM: Artificial Sequence
<220> FEATURE:
<223> OTHER INFORMATION: consensus sequence of VL CDR3
<220> FEATURE:
<221> NAME/KEY: VARIANT
<222> LOCATION: (6)..(6)
<223> OTHER INFORMATION: Xaa = Ser or Gly
<220> FEATURE:
<221> NAME/KEY: VARIANT
<222> LOCATION: (7)..(7)
<223> OTHER INFORMATION: Xaa = Leu or Pro
<220> FEATURE:
<221> NAME/KEY: VARIANT
<222> LOCATION: (8)..(8)
<223> OTHER INFORMATION: Xaa = Arg, Ile, Pro or Ser
<220> FEATURE:
<221> NAME/KEY: VARIANT
<222> LOCATION: (11)..(11)
<223> OTHER INFORMATION: Xaa = Val or Ala

<400> SEQUENCE: 50

Ala Ala Trp Asp Asp Xaa Xaa Xaa Gly Glu Xaa
1               5                   10
```

```
<210> SEQ ID NO 51
<211> LENGTH: 17
<212> TYPE: PRT
```

```
<213> ORGANISM: Artificial Sequence
<220> FEATURE:
<223> OTHER INFORMATION: consensus sequence of VH CDR2
<220> FEATURE:
<221> NAME/KEY: VARIANT
<222> LOCATION: (1)..(1)
<223> OTHER INFORMATION: Xaa = Tyr, Ile or Val

<400> SEQUENCE: 51

Xaa Ile Gly Ser Ser Gly Gly Val Thr Asn Tyr Ala Asp Ser Val Lys
1               5                   10                  15

Gly
```